US011141413B2

(12) United States Patent
Aftab et al.

(10) Patent No.: US 11,141,413 B2
(45) Date of Patent: Oct. 12, 2021

(54) METHOD OF TREATING RENAL CELL CARCINOMA USING N-(4-(6,7-DIMETHOXY-QUINOLIN-4-YLOXY)PHENYL)-N'-(4-FLUOROPHENYL)CYCLOPROPANE-1,1-DICARBOXAMIDE, (2S)-HYDROXYBUTANEDIOATE

(71) Applicant: Exelixis, Inc., Alameda, CA (US)

(72) Inventors: Dana T. Aftab, San Rafael, CA (US); Gisela Schwab, Hayward, CA (US); Colin Hessel, Redwood City, CA (US); Christian Scheffold, Palo Alto, CA (US); Steven Lacy, San Mateo, CA (US); Dale Miles, Sunnyvale, CA (US); Alan Arroyo, Danville, CA (US); Mark Dean, San Francisco, CA (US)

(73) Assignee: Exelixis, Inc., Alameda, CA (US)

( * ) Notice: Subject to any disclaimer, the term of this patent is extended or adjusted under 35 U.S.C. 154(b) by 0 days.

(21) Appl. No.: 16/093,426

(22) PCT Filed: Apr. 17, 2017

(86) PCT No.: PCT/US2017/027965
§ 371 (c)(1),
(2) Date: Oct. 12, 2018

(87) PCT Pub. No.: WO2017/181187
PCT Pub. Date: Oct. 19, 2017

(65) Prior Publication Data
US 2019/0209547 A1 Jul. 11, 2019

Related U.S. Application Data

(60) Provisional application No. 62/323,536, filed on Apr. 15, 2016, provisional application No. 62/323,556, filed on Apr. 15, 2016, provisional application No. 62/323,548, filed on Apr. 15, 2016, provisional application No. 62/324,158, filed on Apr. 18, 2016, provisional application No. 62/324,157, filed on Apr. 18, 2016, provisional application No. 62/324,176, filed on Apr. 18, 2016, provisional application No. 62/338,240, filed on May 18, 2016, provisional application No. 62/338,267, filed on May 18, 2016, provisional application No. 62/338,154, filed on May 18, 2016, provisional application No. 62/338,195, filed on May 18, 2016, provisional application No. 62/345,652, filed on Jun. 3, 2016, provisional application No. 62/457,671, filed on Feb. 10, 2017, provisional application No. 62/457,613, filed on Feb. 10, 2017, provisional application No. 62/457,471, filed on Feb. 10, 2017.

(51) Int. Cl.
*A61K 31/47* (2006.01)
*A61K 31/16* (2006.01)
*A61P 35/00* (2006.01)
*A61K 9/20* (2006.01)
*A61K 9/28* (2006.01)

(52) U.S. Cl.
CPC ............ *A61K 31/47* (2013.01); *A61K 9/2009* (2013.01); *A61K 9/2018* (2013.01); *A61K 9/2054* (2013.01); *A61K 9/2866* (2013.01); *A61K 31/16* (2013.01); *A61P 35/00* (2018.01)

(58) Field of Classification Search
CPC ............................... A61K 31/47; A61P 35/00
USPC ....................................................... 514/312
See application file for complete search history.

(56) References Cited

U.S. PATENT DOCUMENTS

| | | | |
|---|---|---|---|
| 7,579,473 B2 | 8/2009 | Bannen et al. | |
| 7,977,345 B2 | 7/2011 | Bannen et al. | |
| 7,999,006 B2 | 8/2011 | Lamb | |
| 8,067,436 B2 | 11/2011 | Bannen et al. | |
| 8,178,532 B2 | 5/2012 | Bannen et al. | |
| 8,314,232 B2 | 11/2012 | Deschamps et al. | |
| 8,476,298 B2 | 7/2013 | Bannen et al. | |
| 8,497,284 B2 | 7/2013 | Bannen et al. | |
| 8,673,912 B2 | 3/2014 | Cannon et al. | |
| 8,877,776 B2 | 11/2014 | Brown et al. | |
| 9,174,947 B2 | 11/2015 | Bannen et al. | |
| 9,365,516 B2 | 6/2016 | Wilson et al. | |
| 9,717,720 B2 | 8/2017 | Wilson et al. | |
| 9,724,342 B2 | 8/2017 | Wilson et al. | |
| 9,809,549 B2 | 11/2017 | Brown et al. | |
| 9,861,624 B2 | 1/2018 | Aftab et al. | |
| 9,969,692 B2 | 5/2018 | Wilson et al. | |
| 10,034,873 B2 | 7/2018 | Wilson et al. | |
| 10,039,757 B2 | 9/2018 | Wilson et al. | |
| 10,159,666 B2 | 12/2018 | Aftab et al. | |
| 10,166,225 B2 | 1/2019 | Aftab et al. | |
| 10,273,211 B2 | 4/2019 | Aftab et al. | |
| 2008/0161305 A1 | 7/2008 | Forsyth et al. | |

(Continued)

FOREIGN PATENT DOCUMENTS

WO 2005030140 4/2005
WO WO-2010083414 A1 * 7/2010 ............... A61P 5/14

(Continued)

OTHER PUBLICATIONS

Osterweil, Neil, "Cabozantinib versus everolimus in advanced RCC with bone mets", Oncology Practice, Feb. 10, 2017, retrieved from the internet at www.mdedge.com/oncologypractice/article/131183/renal-cell-carcinoma/cabozantinib-versus-everolimus-advanced-rcc on Jun. 30, 2017.

(Continued)

*Primary Examiner* — Kevin E Weddington
(74) *Attorney, Agent, or Firm* — Honigman LLP; Heidi M. Berven

(57) ABSTRACT

The present disclosure relates to a method of treating advanced renal cell carcinoma (RCC) in human patients who have received prior anti-angiogenic therapy using CABOMETYX, a kinase inhibitor.

21 Claims, 56 Drawing Sheets

(56) References Cited

U.S. PATENT DOCUMENTS

| | | |
|---|---|---|
| 2009/0274693 A1 | 11/2009 | Gilmer et al. |
| 2011/0077233 A1 | 3/2011 | Bannen et al. |
| 2012/0070368 A1 | 3/2012 | Bannen et al. |
| 2012/0184523 A1 | 7/2012 | Bannen et al. |
| 2012/0252840 A1 | 10/2012 | Aftab et al. |
| 2012/0282179 A1 | 11/2012 | Aftab et al. |
| 2013/0030172 A1 | 1/2013 | Wilson et al. |
| 2013/0142790 A1 | 6/2013 | Gilmer et al. |
| 2013/0143881 A1 | 6/2013 | Cannon et al. |
| 2013/0150363 A1 | 6/2013 | Gilmer et al. |
| 2013/0197230 A1 | 8/2013 | Wilson et al. |
| 2013/0252940 A1 | 9/2013 | Bannen et al. |
| 2013/0252956 A1 | 9/2013 | Kallender et al. |
| 2013/0330377 A1 | 12/2013 | Wilson |
| 2014/0057908 A1 | 2/2014 | Smith et al. |
| 2014/0057943 A1 | 2/2014 | Smith et al. |
| 2014/0066444 A1 | 3/2014 | Smith et al. |
| 2014/0121239 A1 | 5/2014 | Aftab |
| 2014/0155396 A1 | 6/2014 | Bannen et al. |
| 2014/0179736 A1 | 6/2014 | Schwab et al. |
| 2014/0221372 A1 | 8/2014 | Kulkarni et al. |
| 2014/0228401 A1 | 8/2014 | Aftab et al. |
| 2014/0302012 A1 | 10/2014 | Aftab et al. |
| 2014/0323522 A1 | 10/2014 | Aftab et al. |
| 2015/0057310 A1 | 2/2015 | Brown et al. |
| 2015/0196545 A1 | 7/2015 | Aftab et al. |
| 2015/0202196 A1 | 7/2015 | Bannen et al. |
| 2015/0238477 A1 | 8/2015 | Aftab |
| 2015/0376133 A1 | 12/2015 | Bannen et al. |
| 2016/0000772 A1 | 1/2016 | Aftab et al. |
| 2016/0022662 A1 | 1/2016 | Decillis et al. |
| 2016/0031818 A1 | 2/2016 | Aftab et al. |
| 2016/0051532 A1 | 2/2016 | Aftab et al. |
| 2016/0082019 A1 | 3/2016 | Sweeney et al. |
| 2016/0185725 A1 | 6/2016 | Bannen et al. |
| 2016/0220554 A1 | 8/2016 | Smith et al. |
| 2017/0042880 A1 | 2/2017 | Aftab et al. |
| 2017/0044106 A1 | 2/2017 | Aftab et al. |
| 2017/0057921 A1 | 3/2017 | Wilson et al. |
| 2017/0087143 A1 | 3/2017 | Aftab et al. |
| 2017/0217896 A1 | 8/2017 | Donnelly et al. |
| 2017/0224670 A1 | 8/2017 | Smalley |
| 2017/0224672 A1 | 8/2017 | Aftab et al. |
| 2017/0275251 A1 | 9/2017 | Brown et al. |
| 2017/0355678 A1 | 12/2017 | Bannen et al. |
| 2018/0002289 A1 | 1/2018 | Brown et al. |
| 2018/0037552 A1 | 2/2018 | Brown et al. |
| 2018/0230100 A1 | 8/2018 | Wilson et al. |
| 2018/0311229 A1 | 11/2018 | Wilson et al. |
| 2019/0030021 A1 | 1/2019 | Wilson et al. |
| 2019/0076420 A1 | 3/2019 | Aftab et al. |
| 2019/0091215 A1 | 3/2019 | Aftab et al. |
| 2019/0151302 A1 | 5/2019 | Aftab et al. |
| 2019/0209547 A1 | 7/2019 | Aftab et al. |
| 2019/0218182 A1 | 7/2019 | Aftab et al. |
| 2019/0352403 A1 | 11/2019 | Schwab et al. |
| 2020/0330450 A1 | 10/2020 | Smith et al. |

FOREIGN PATENT DOCUMENTS

| | | |
|---|---|---|
| WO | 2012009722 | 1/2012 |
| WO | 2017181187 | 10/2017 |

OTHER PUBLICATIONS

International Search Report for PCT/US2017/027965, dated Sep. 19, 2017.

Toni K. Choueiri er al: "Cabozantinib versus Everolimus in Advanced Renal-Cell Carcinoma", New England Journal of Medicine, THE-NEJM—, vol. 373, No. 19, Nov. 5, 2015 (Nov. 5, 2015), pp. 1814-1823.

Cerbone, et al. (2014) Pharmacotherapy options for advanced renal cell carcinoma, Expert Opinion on Orphan Drugs 2:7, 643-652.

Decision T 023916, application No. 05012711.7, publication No. 1591122, Sep. 13, 2017.

\* cited by examiner

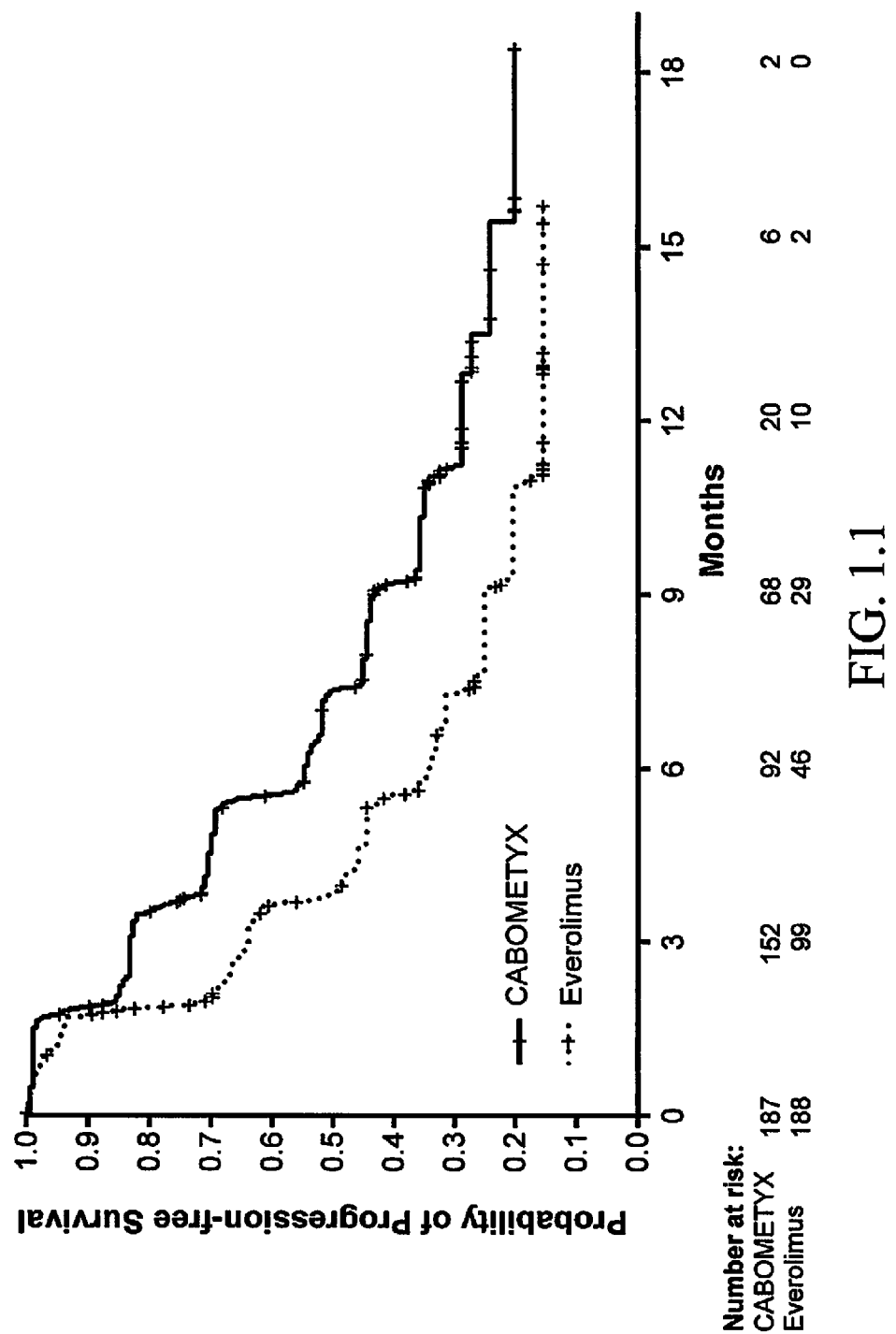
FIG. 1.1

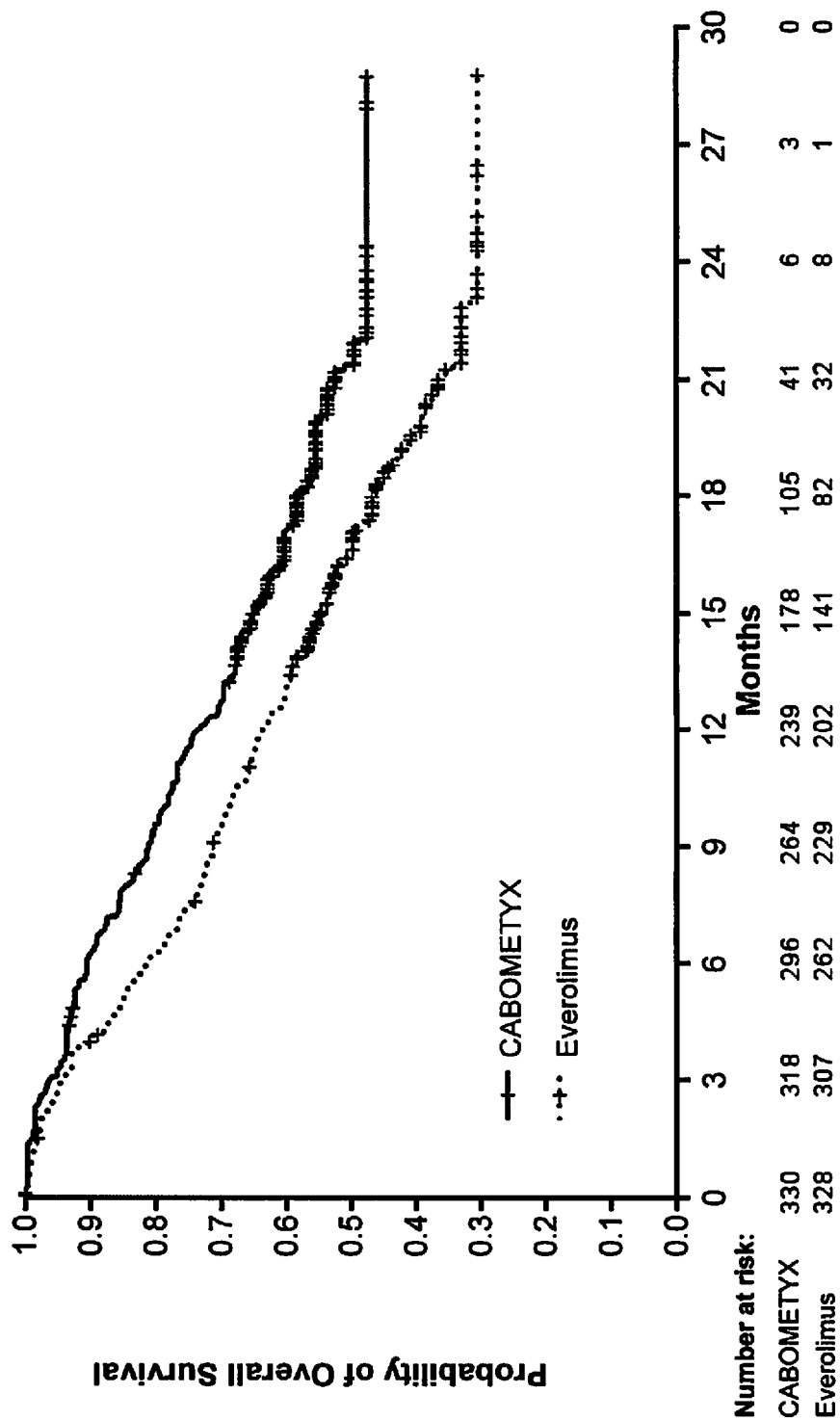
FIG. 1.2

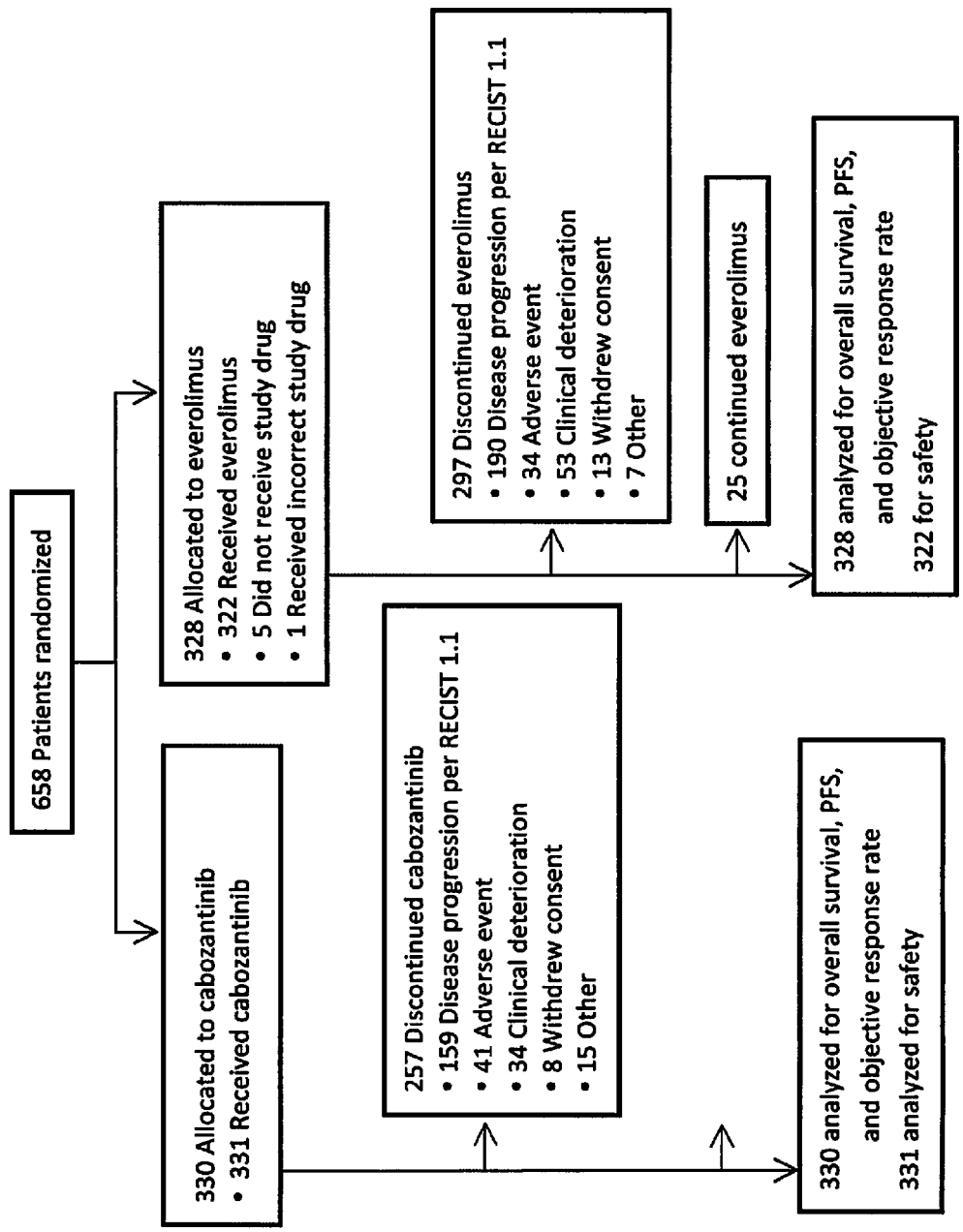
FIG. 1.3

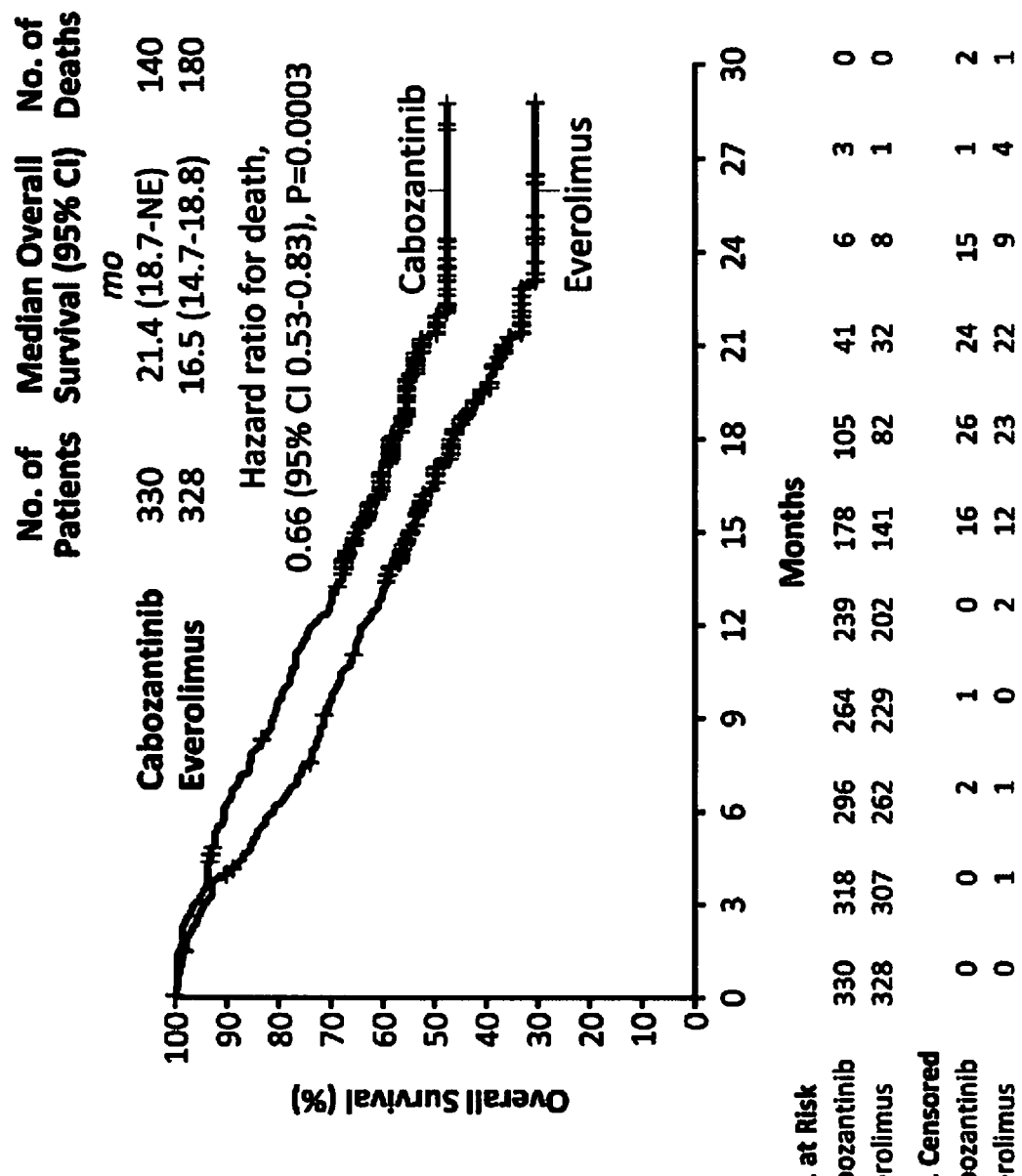
FIG. 1.4

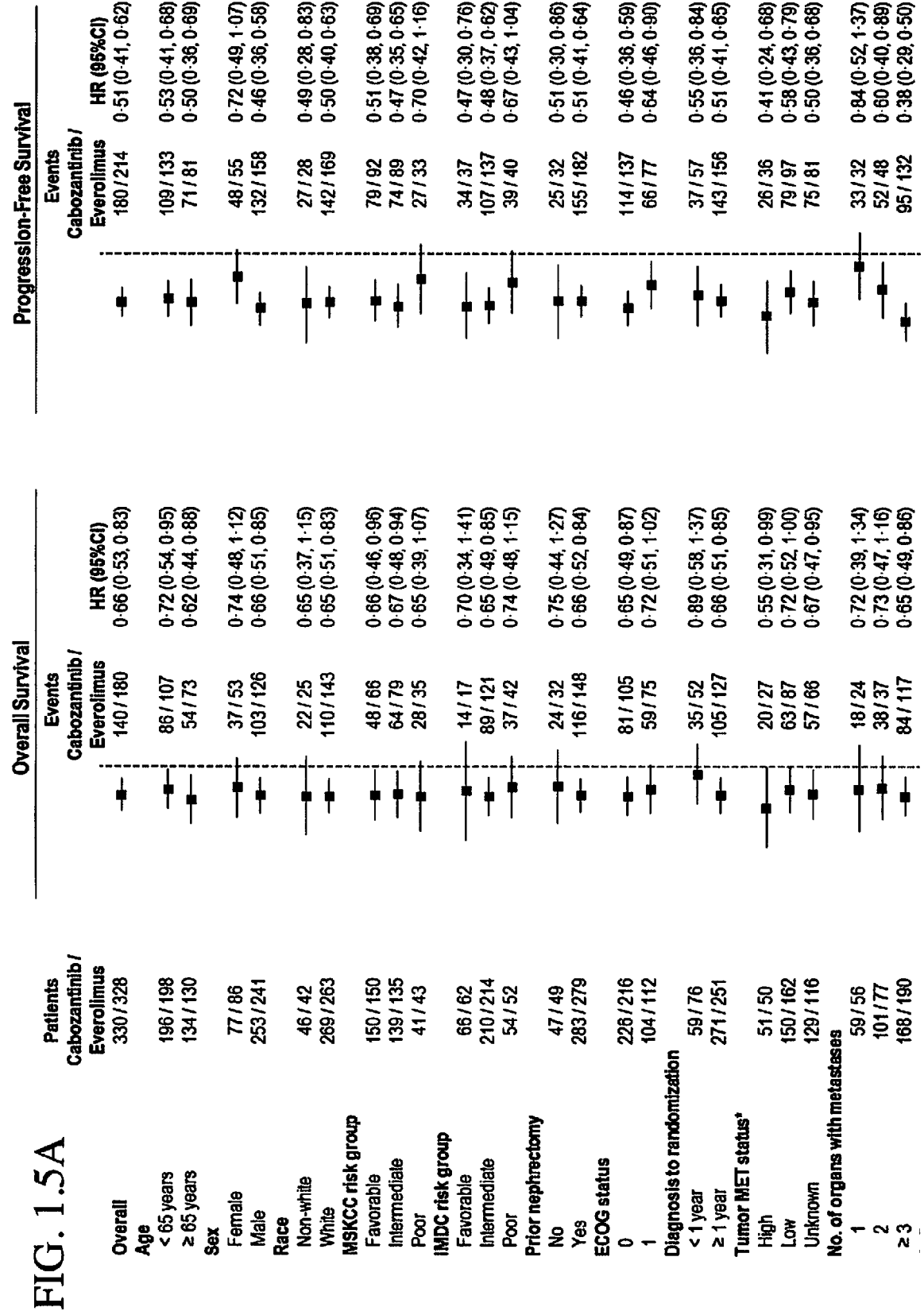
FIG. 1.5A

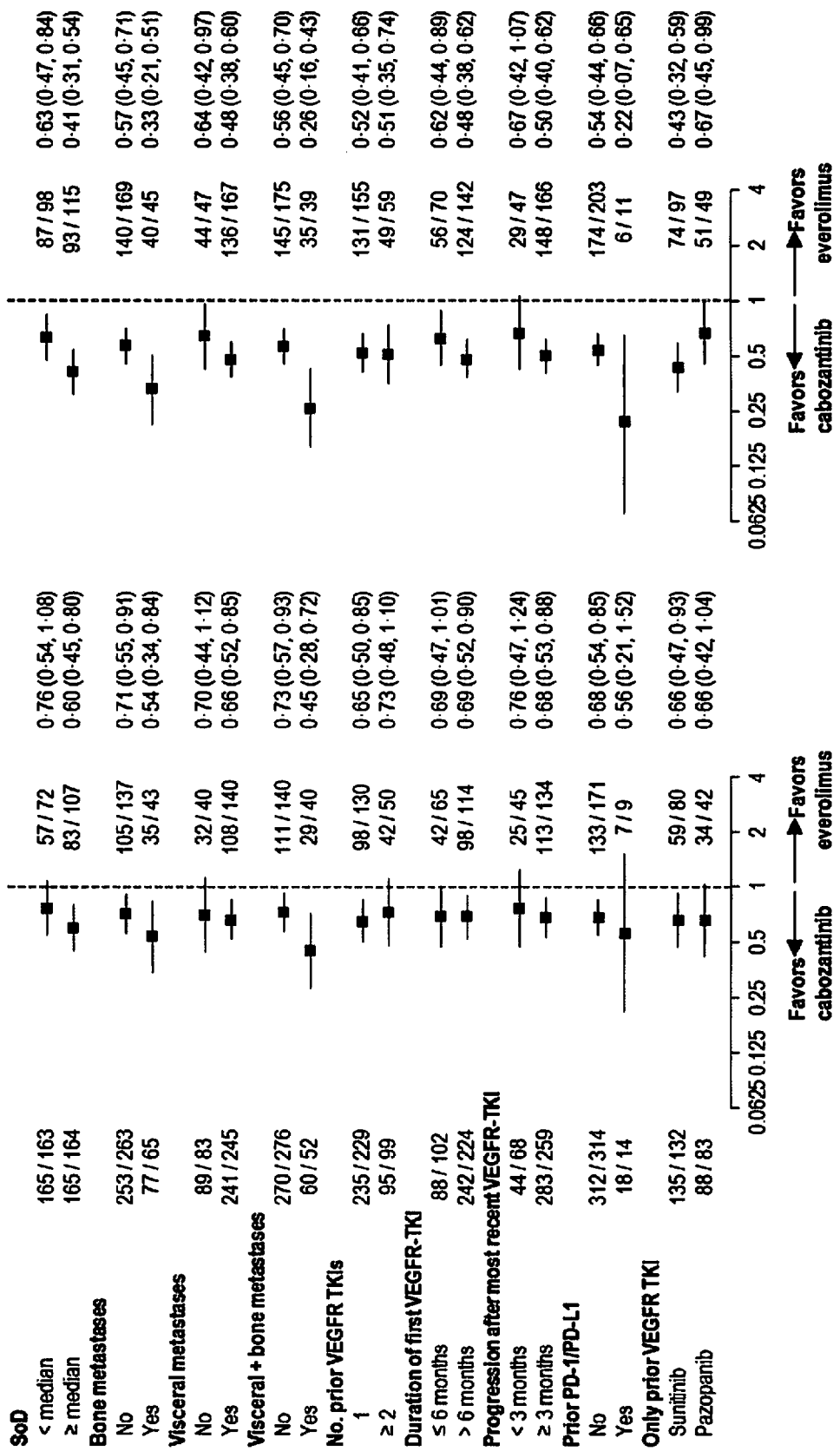
FIG. 1.5B

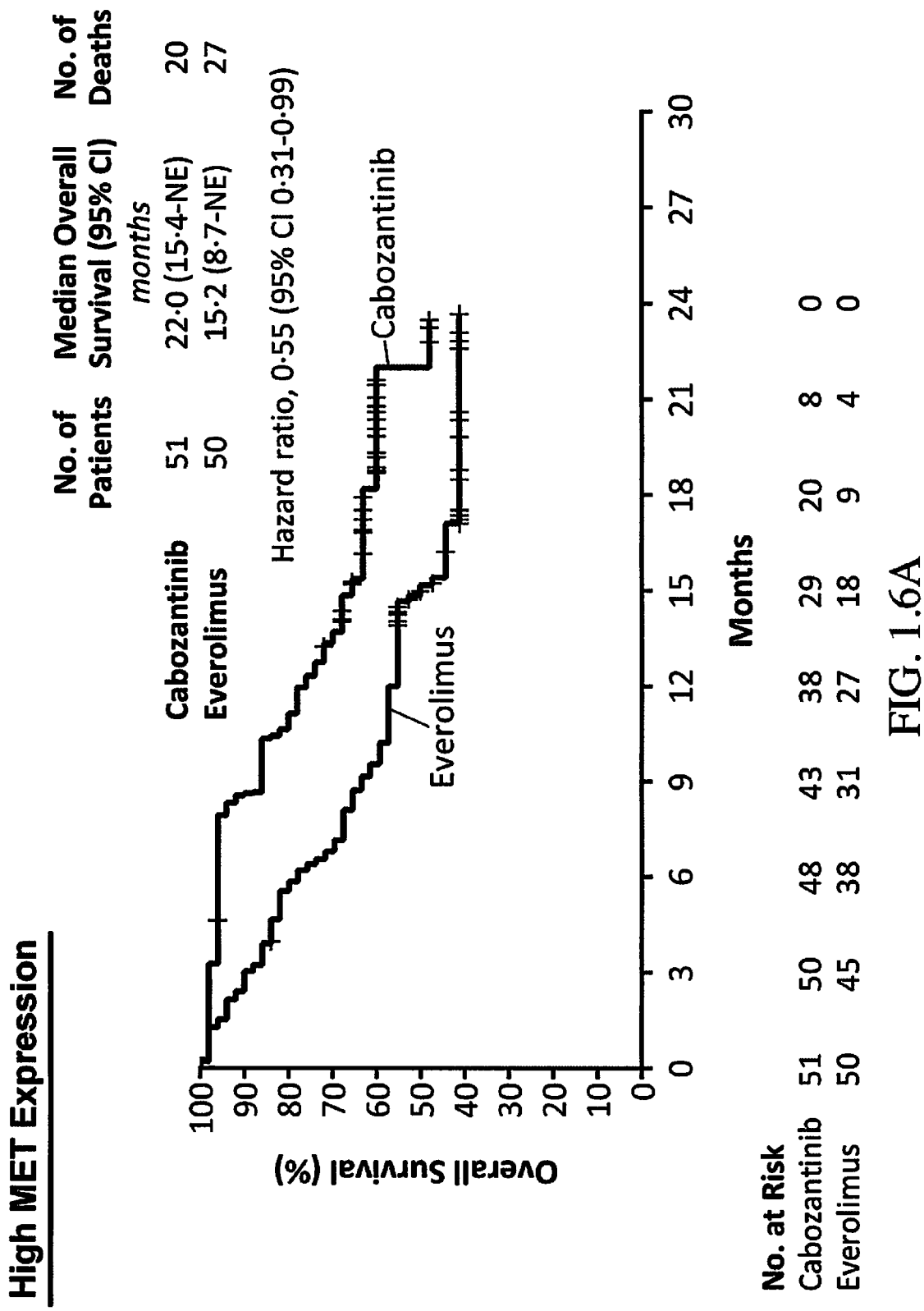
FIG. 1.6A

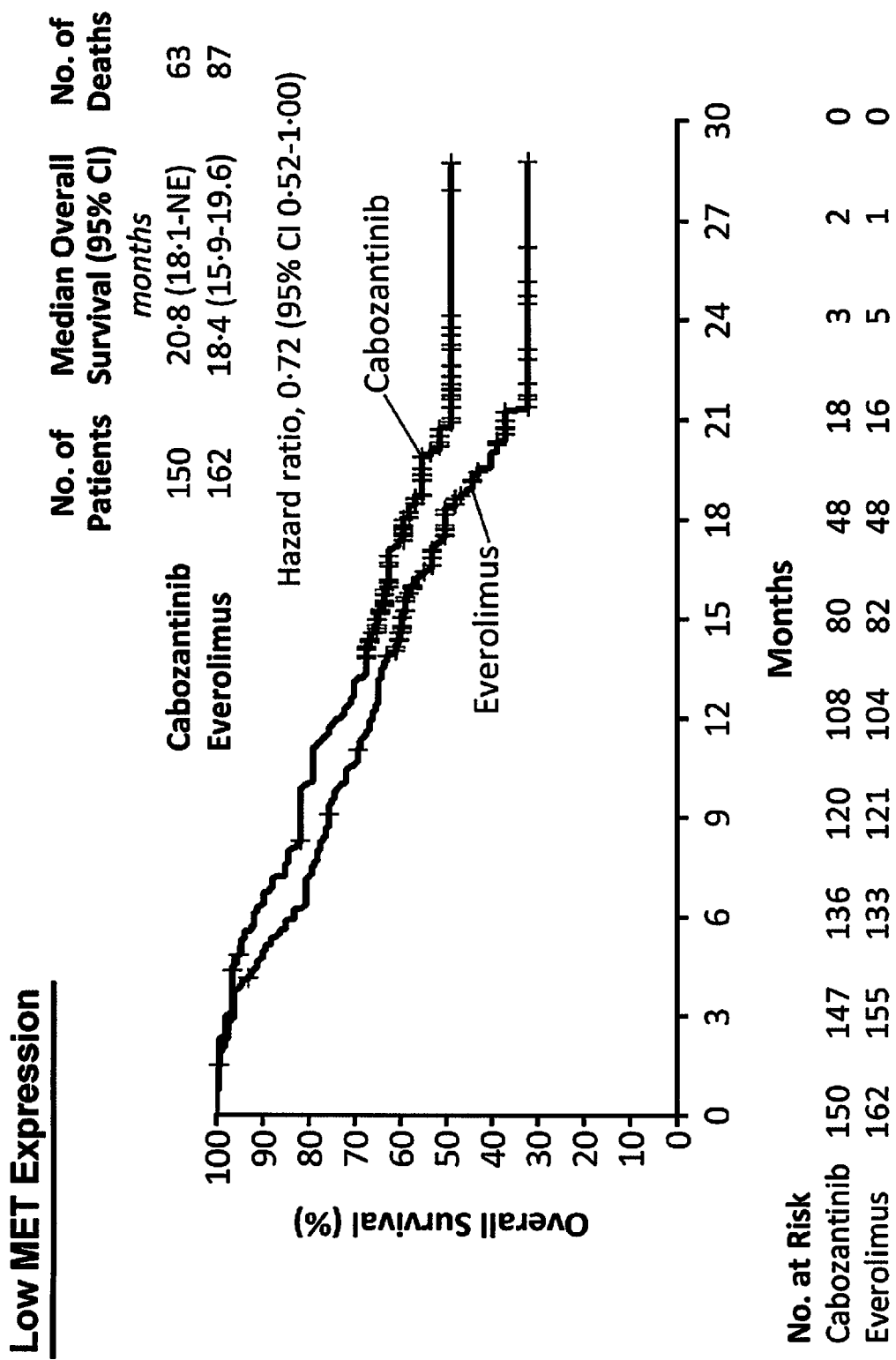
FIG. 1.6B

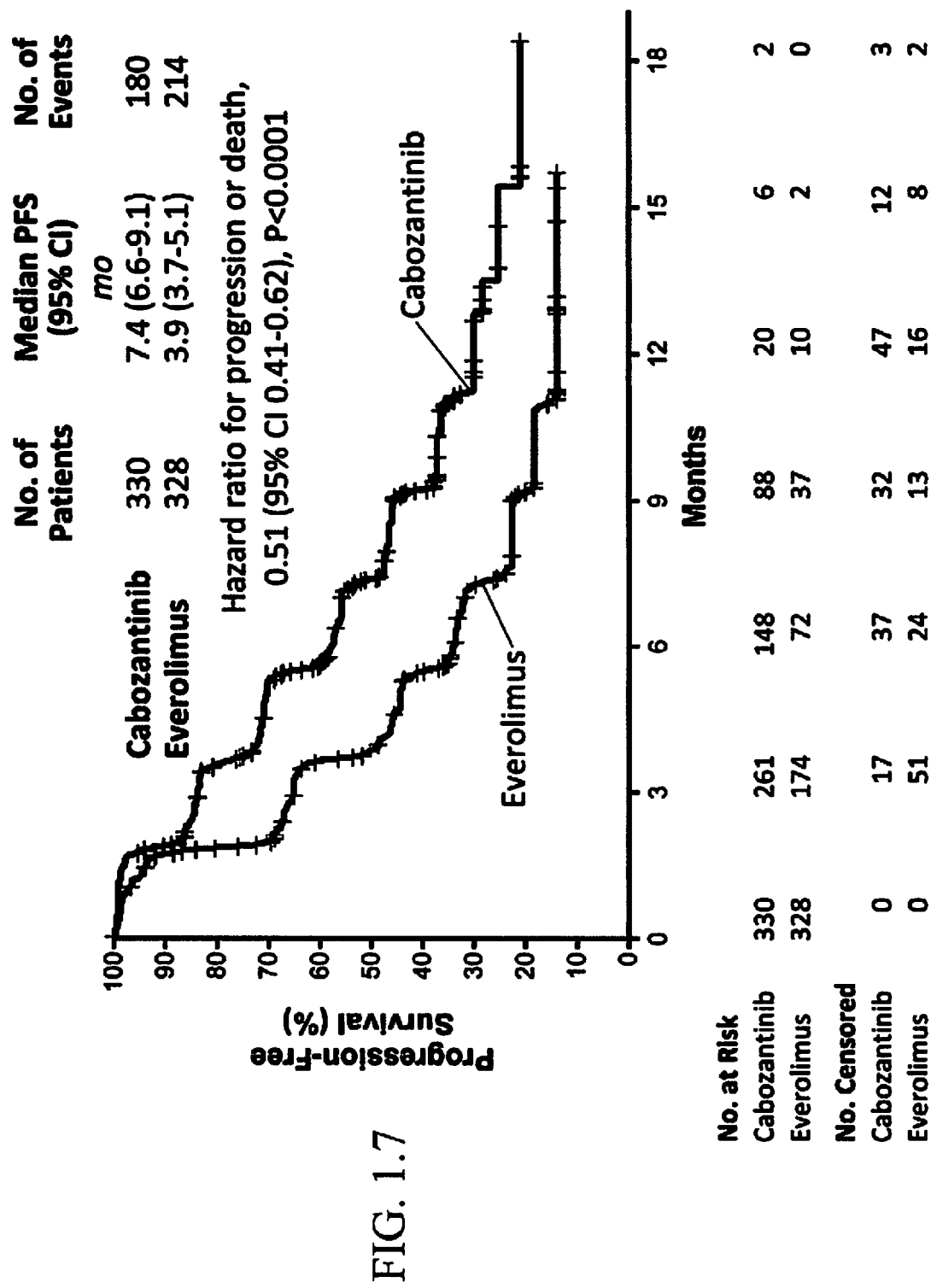
FIG. 1.7

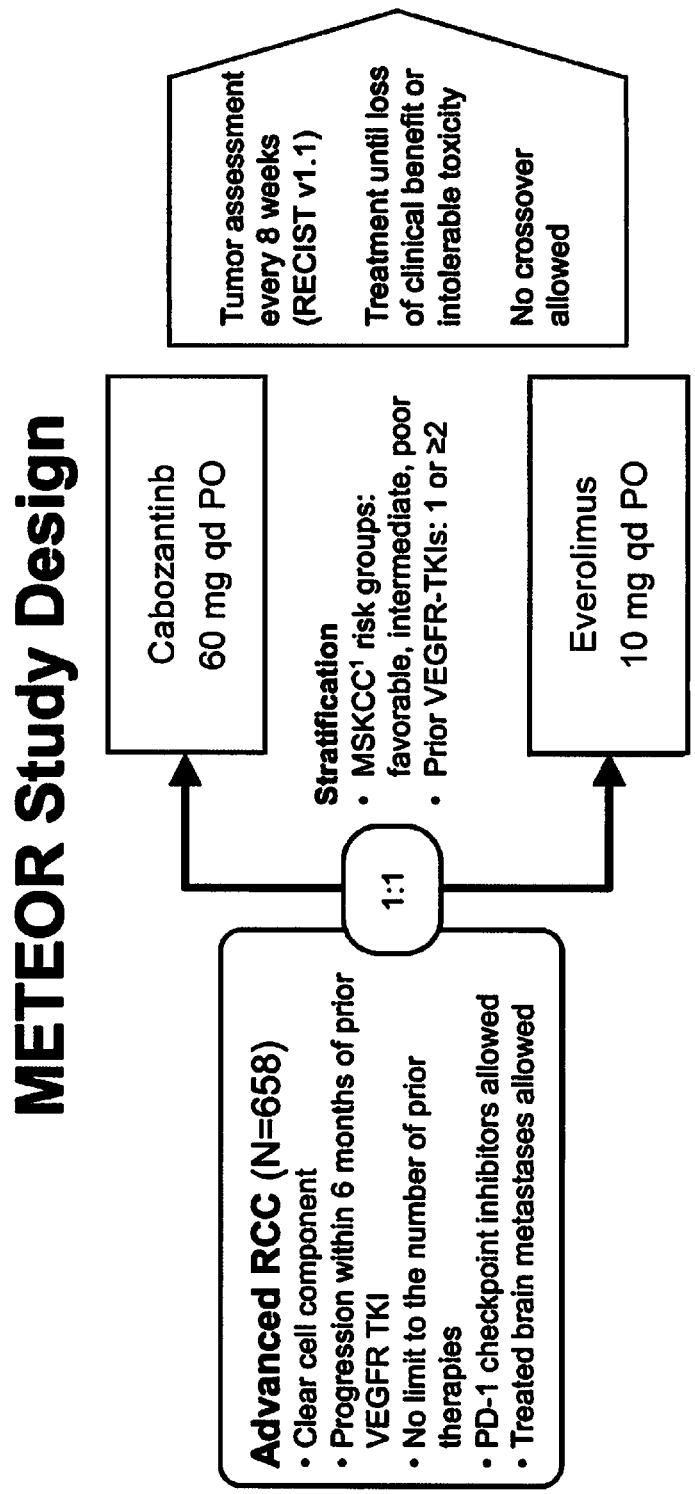
FIG. 1.8

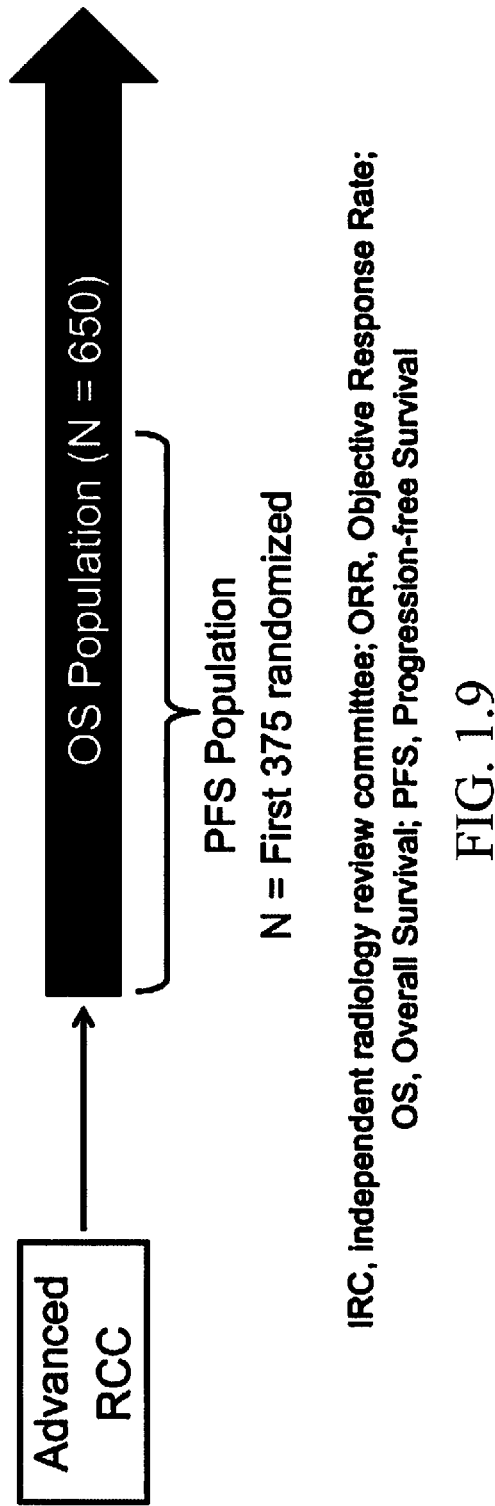
FIG. 1.9

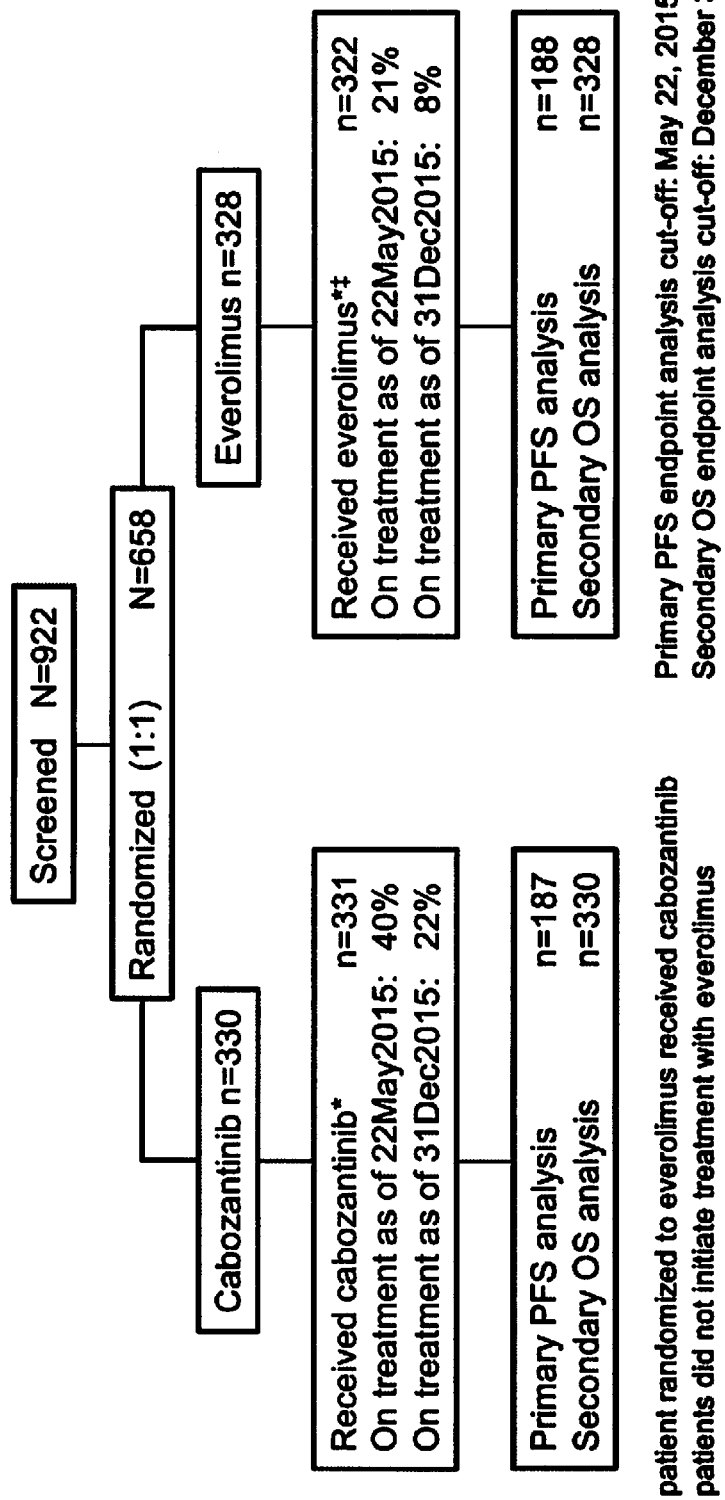
FIG. 1.10

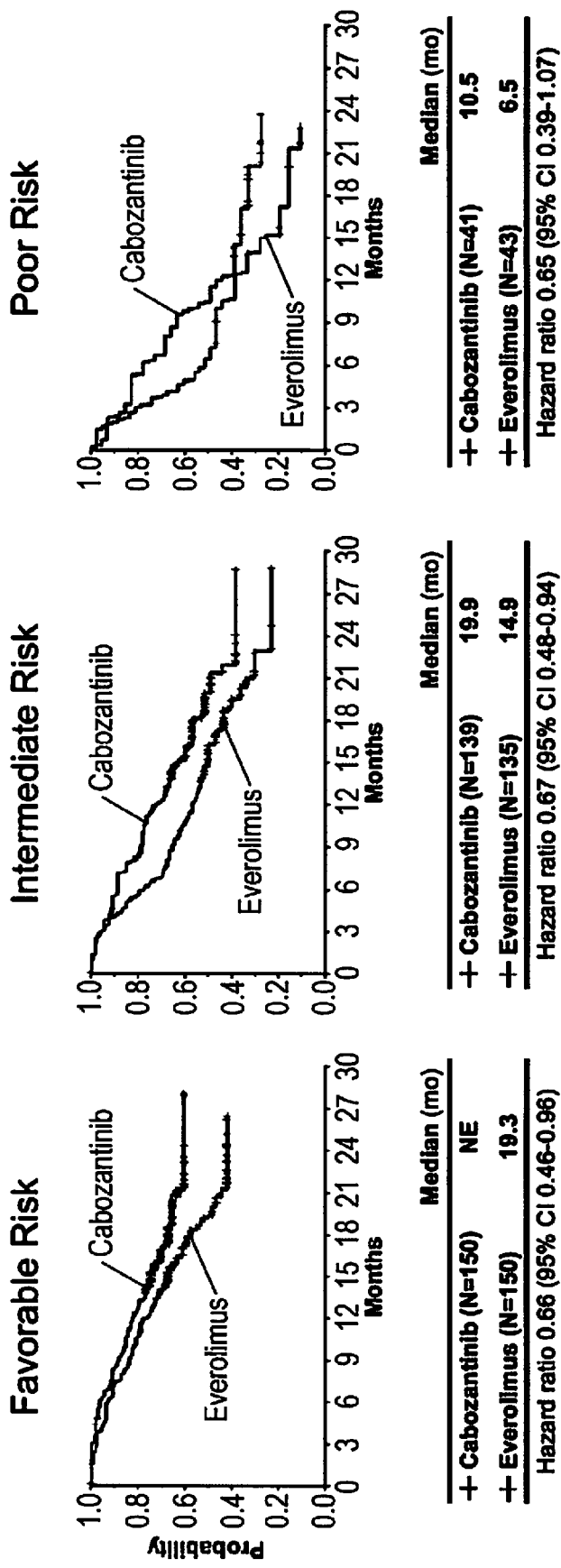
FIG. 1.11

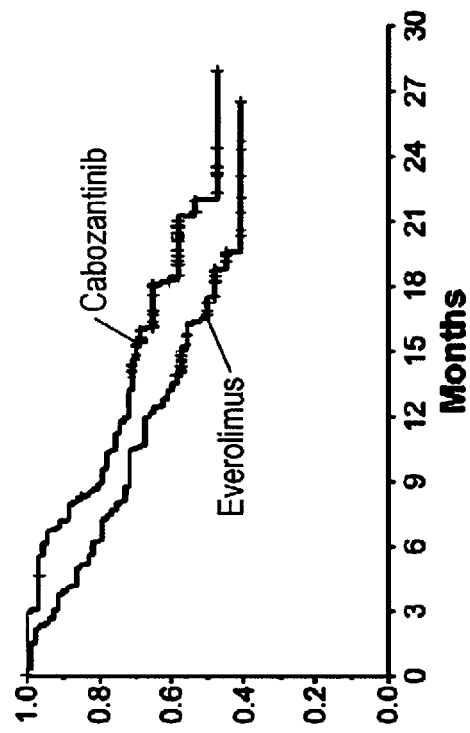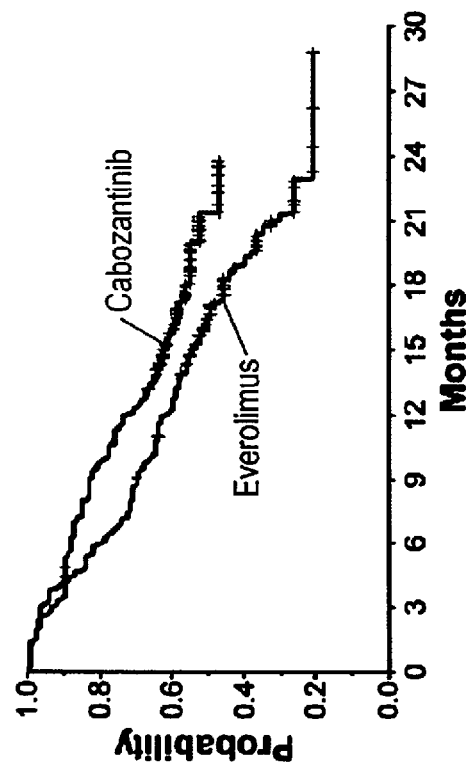
FIG. 1.12

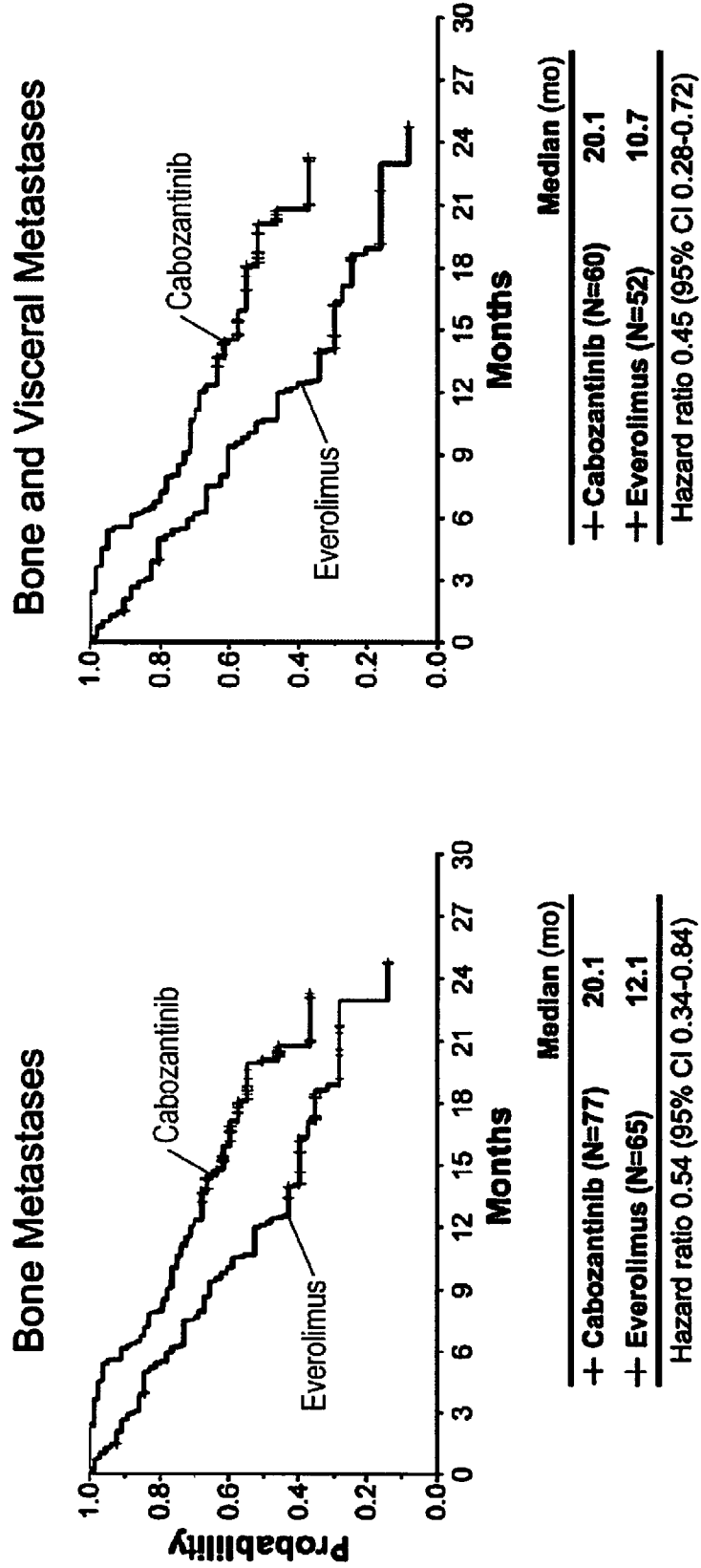
FIG. 1.13

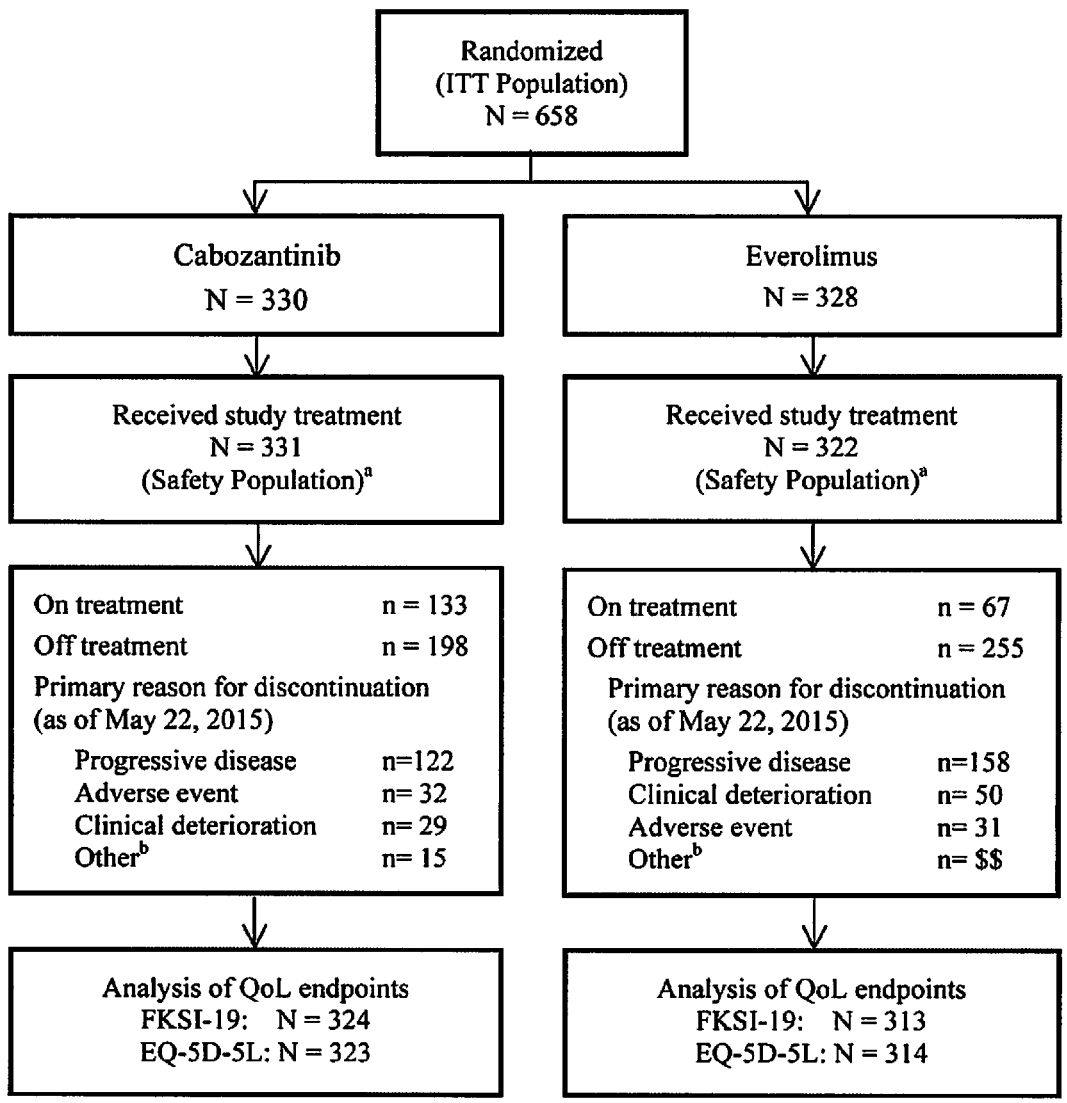
FIG. 1.14

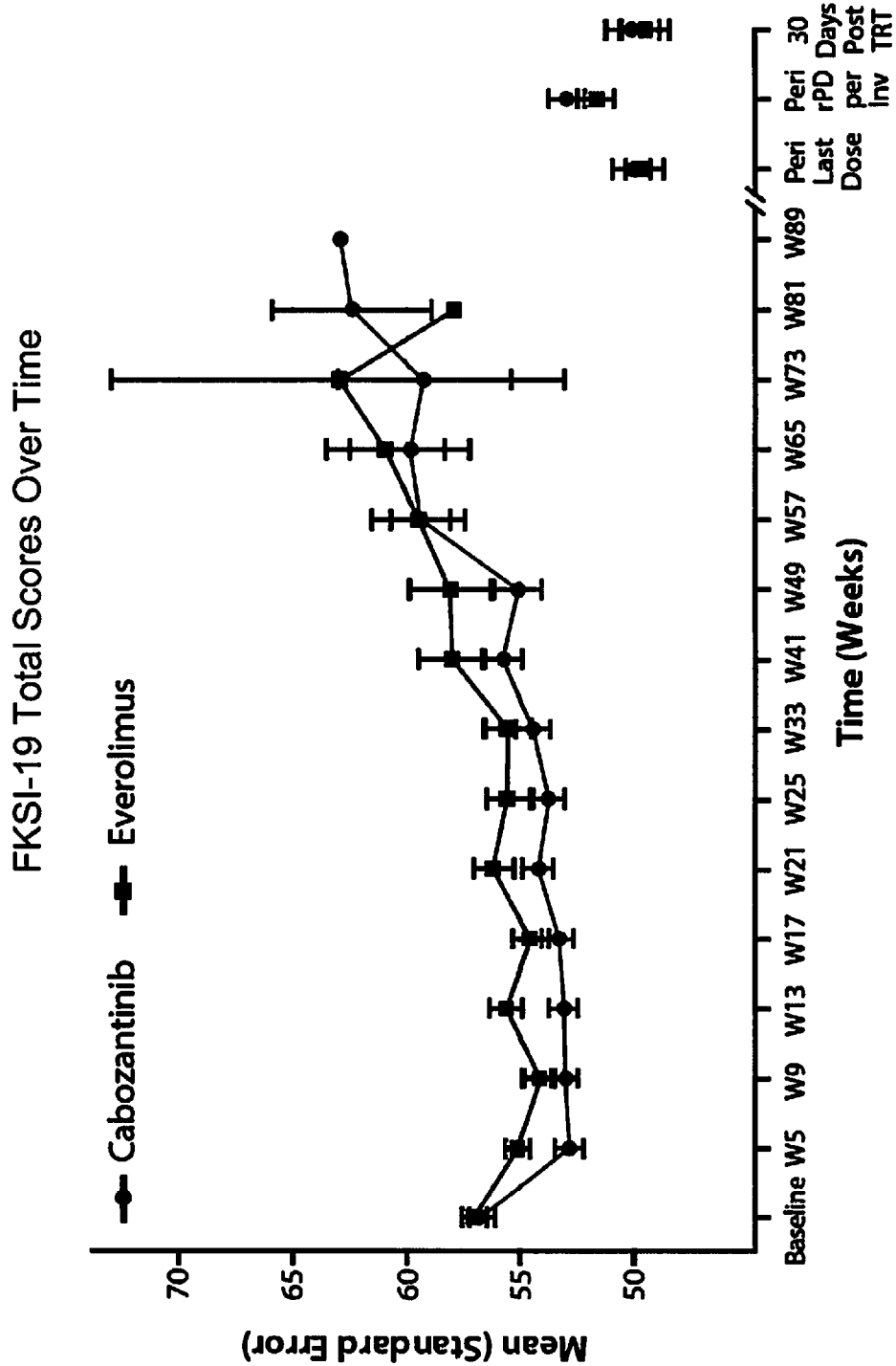
FIG. 1.15A

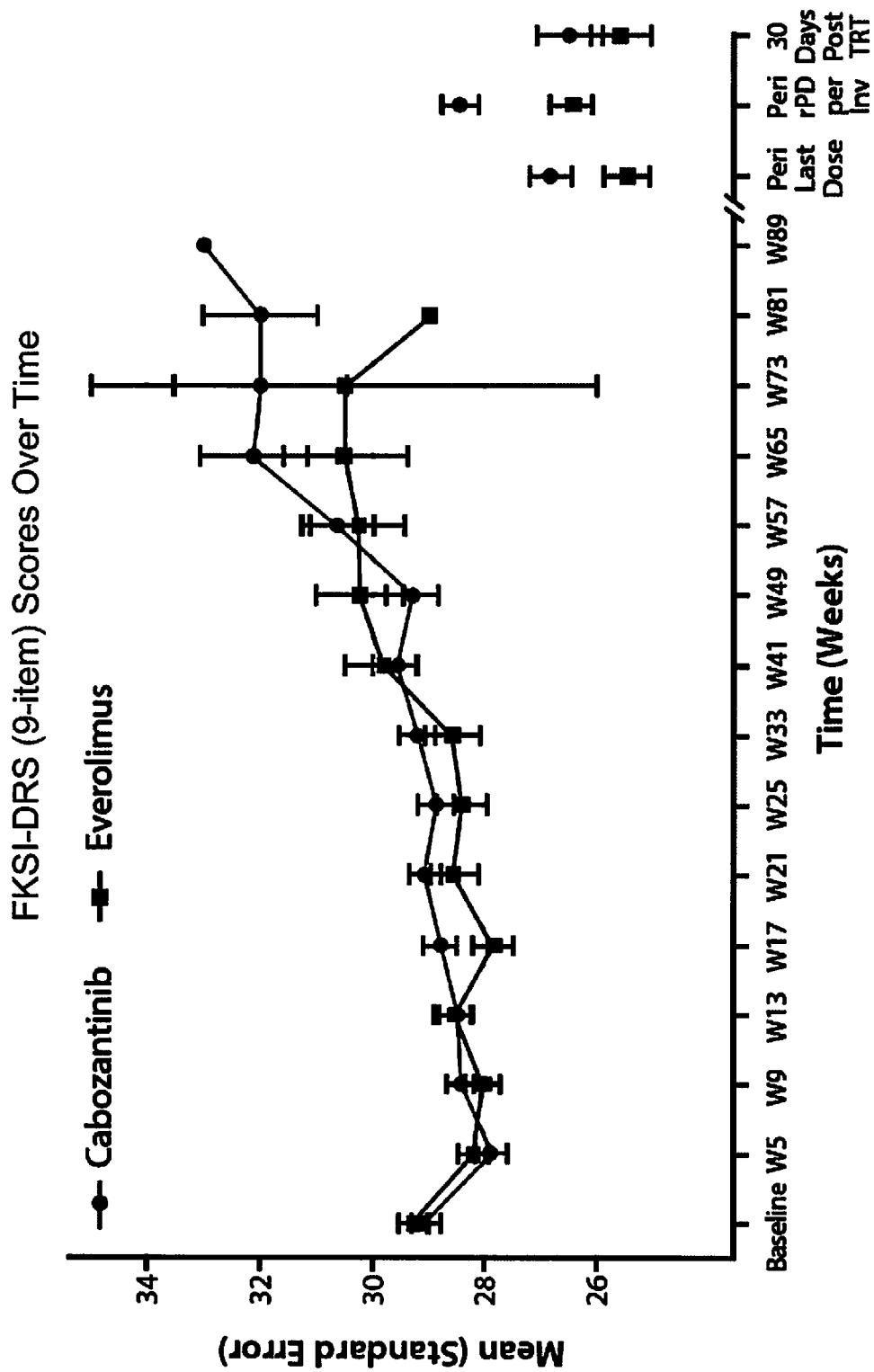
FIG. 1.15B

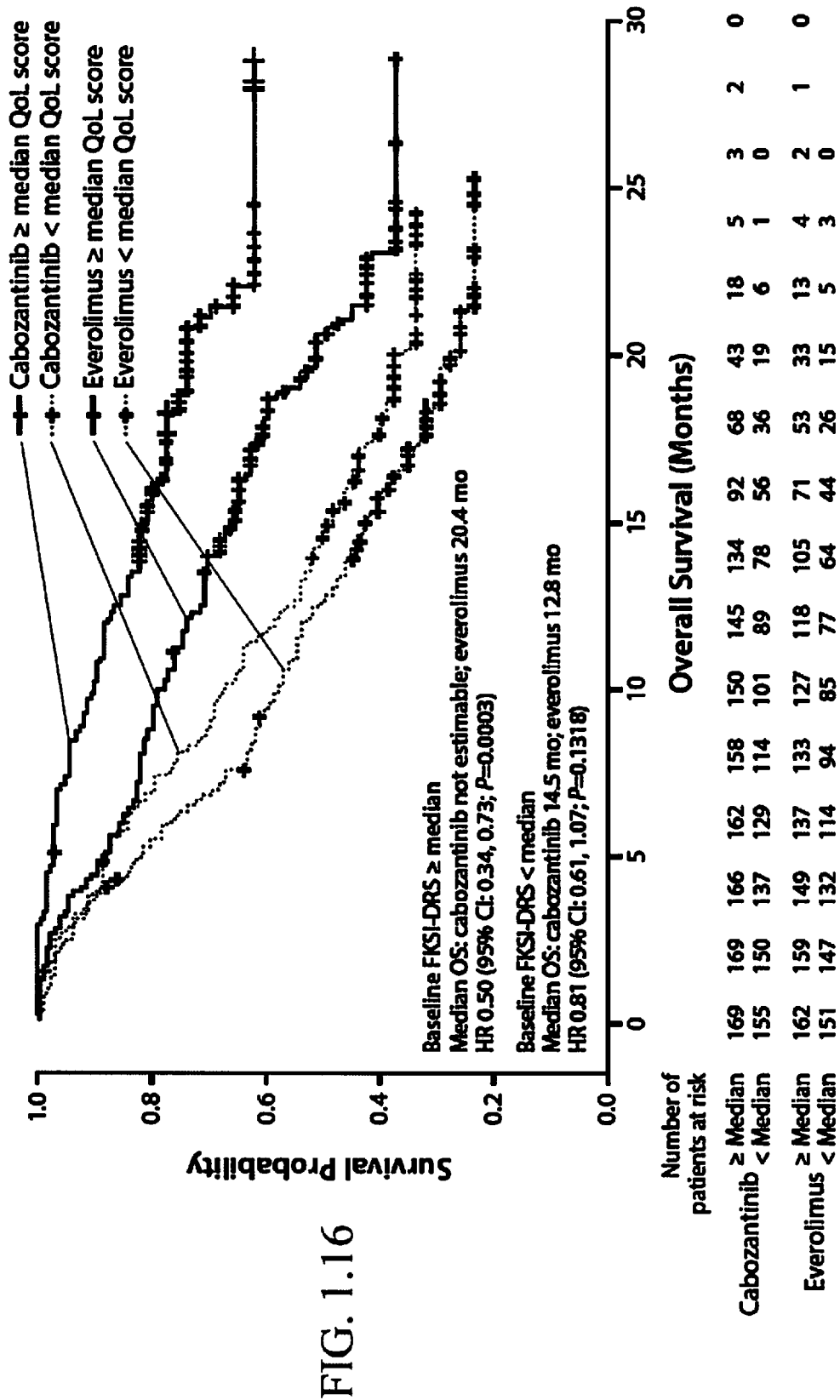
FIG. 1.16

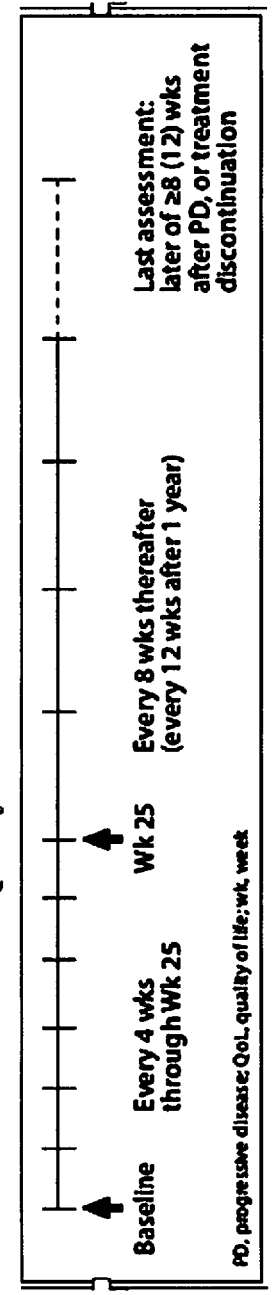
FIG. 2.1

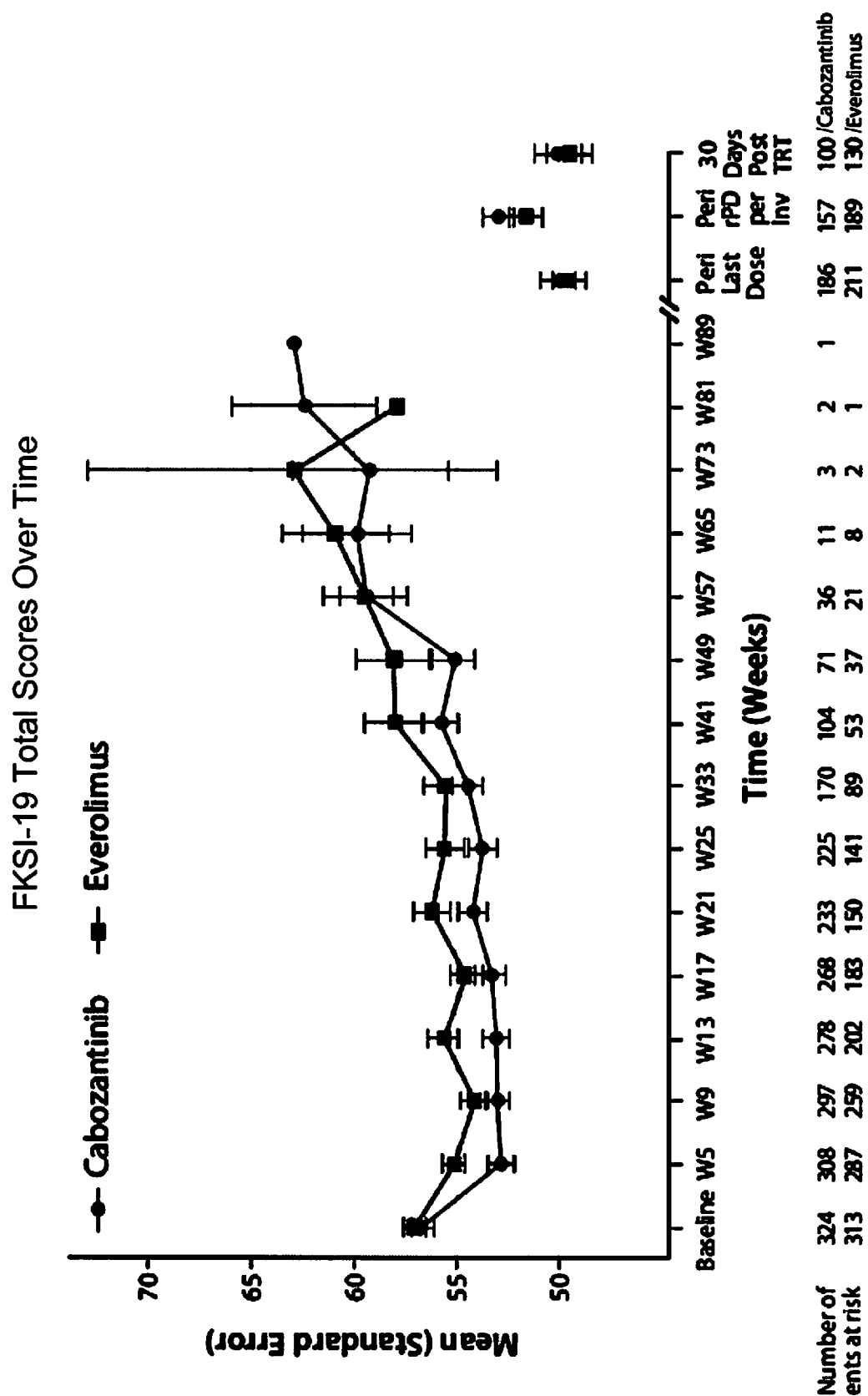
FIG. 2.2A

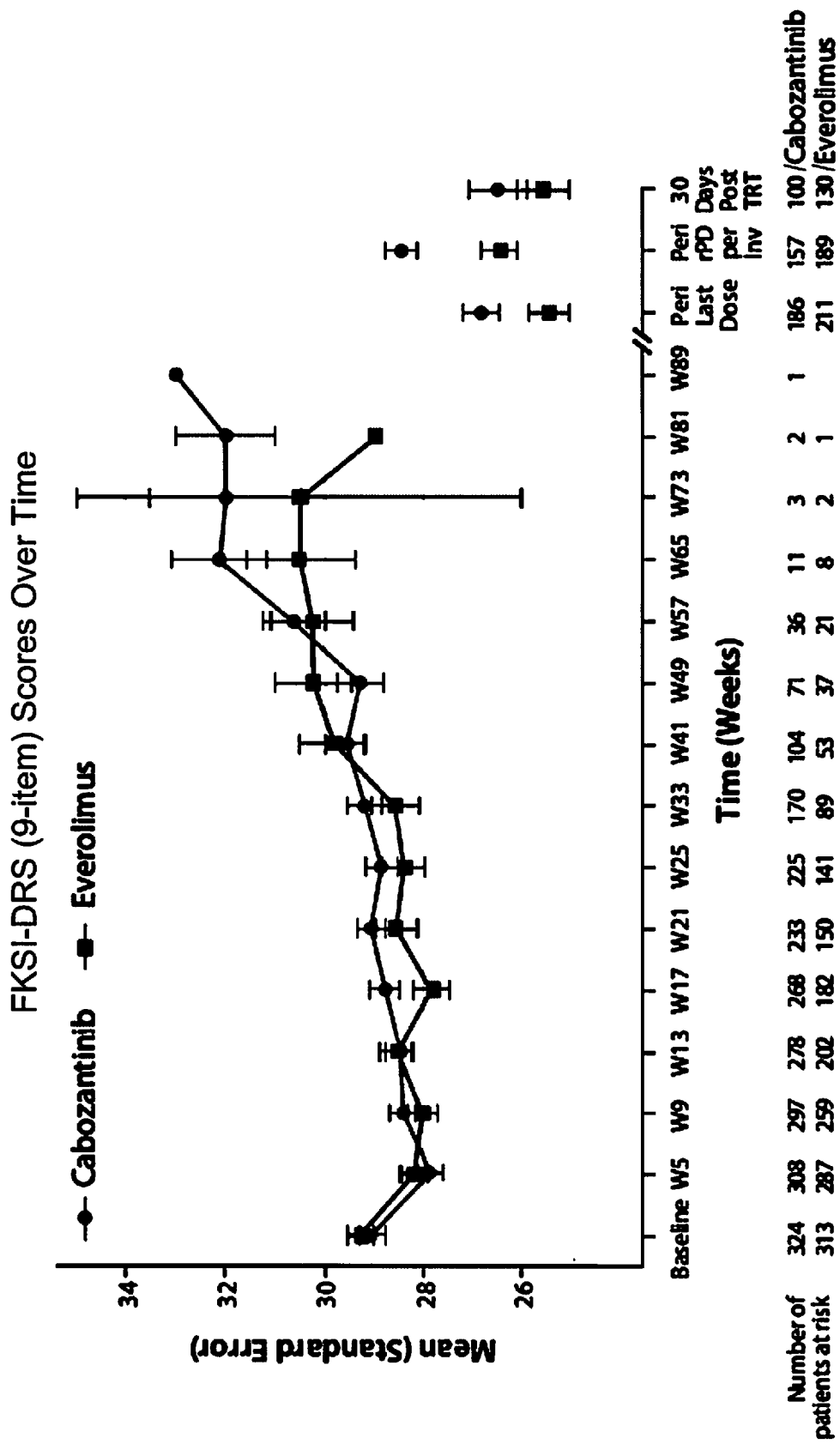
FIG. 2.2B

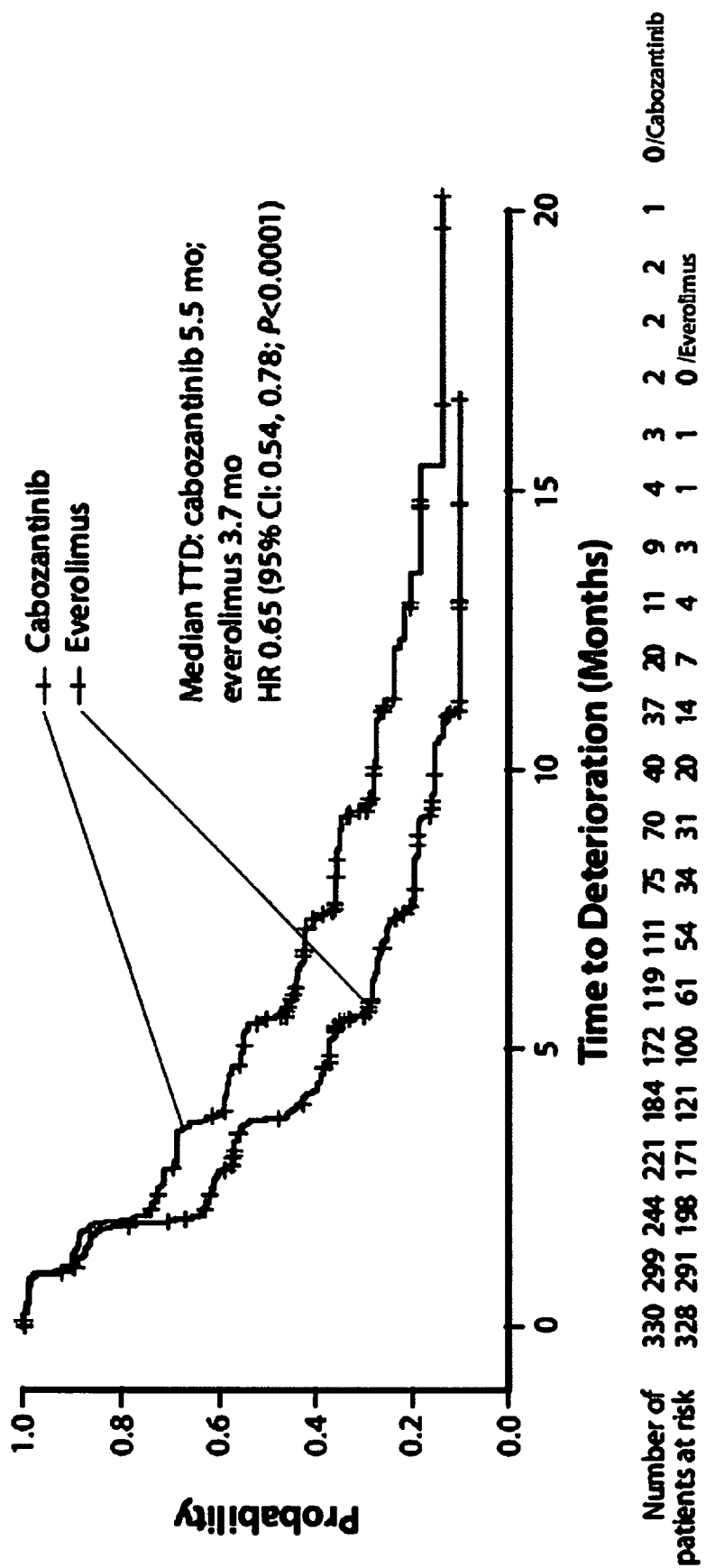
FIG. 2.3

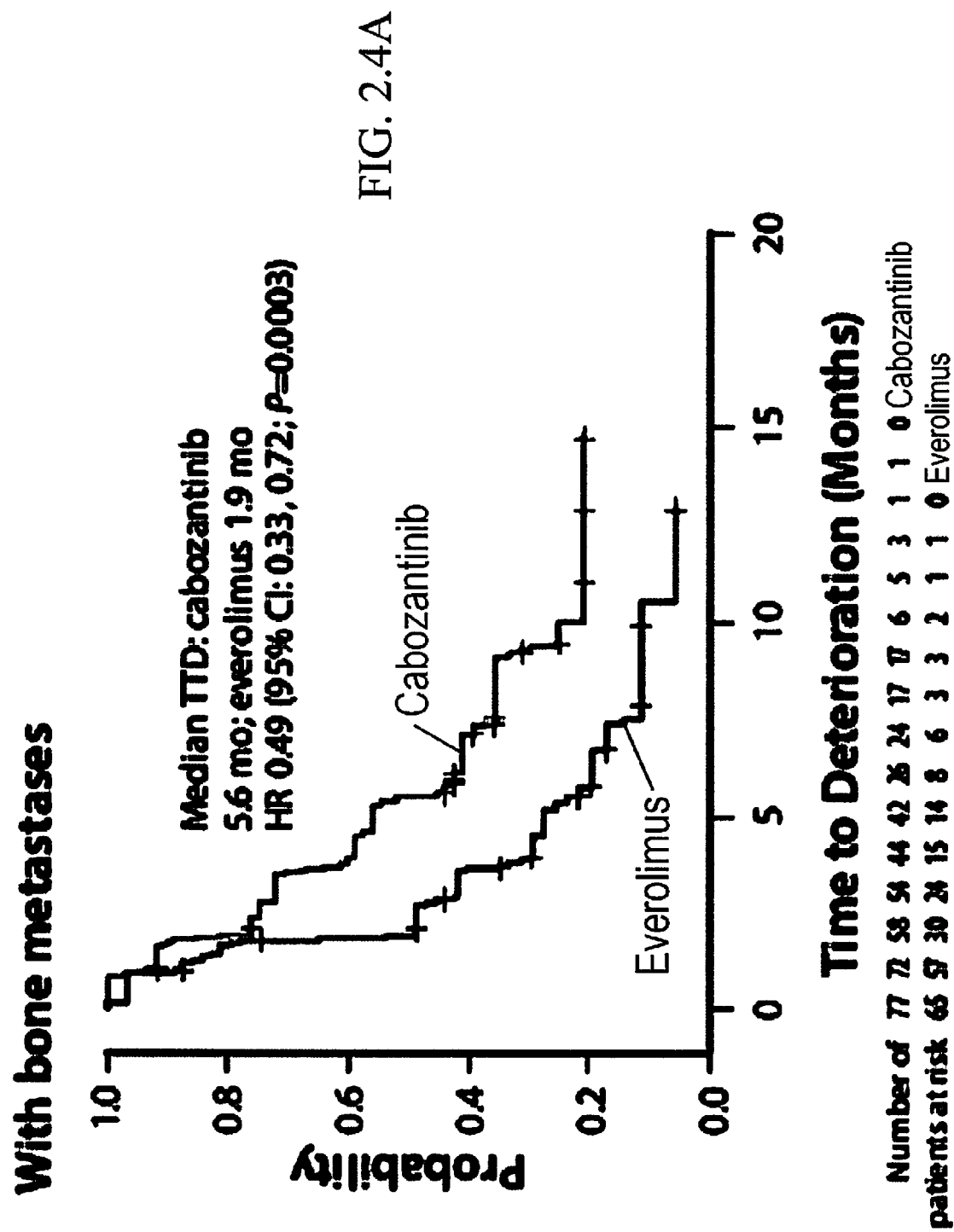
FIG. 2.4A

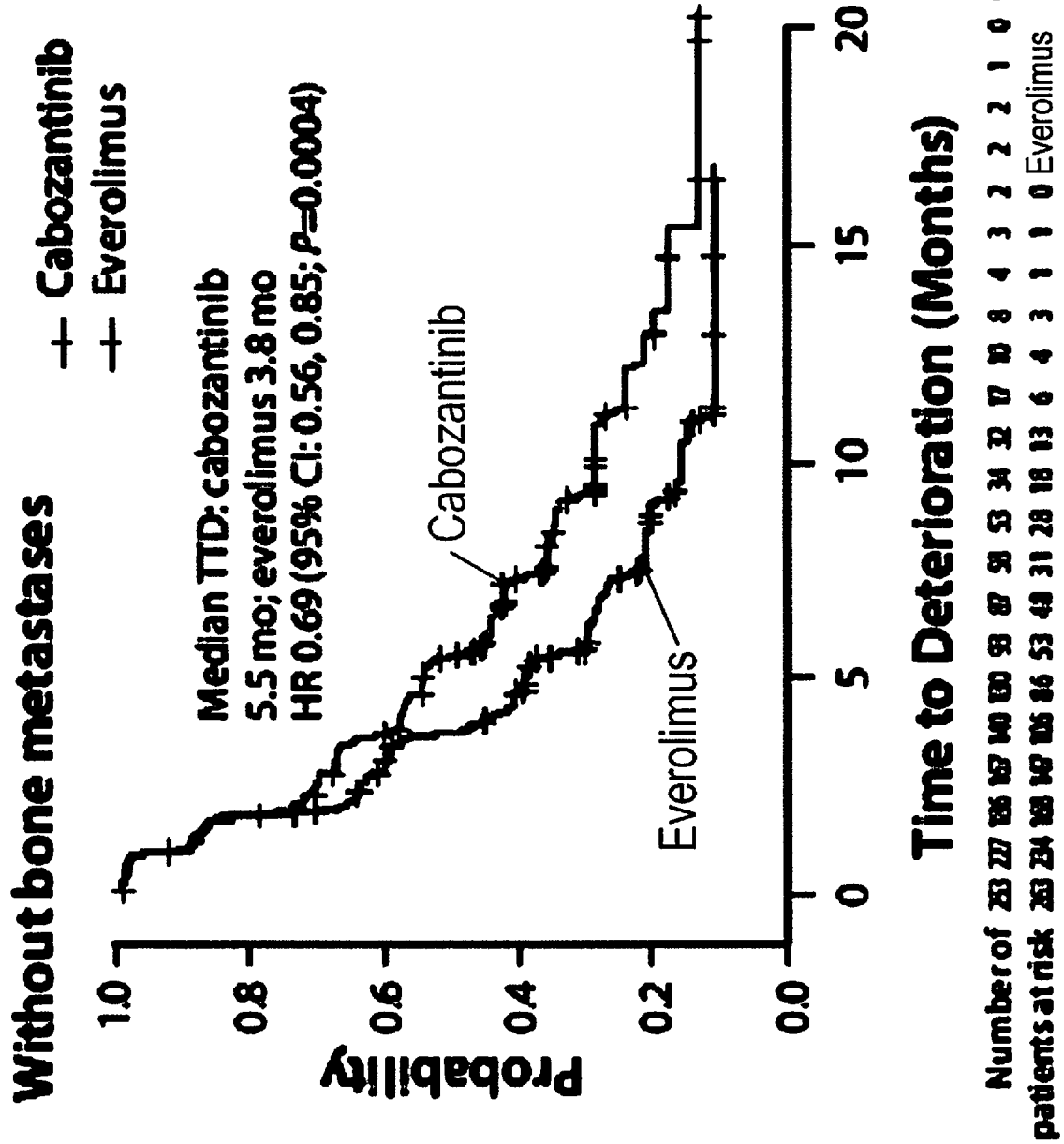
FIG. 2.4B

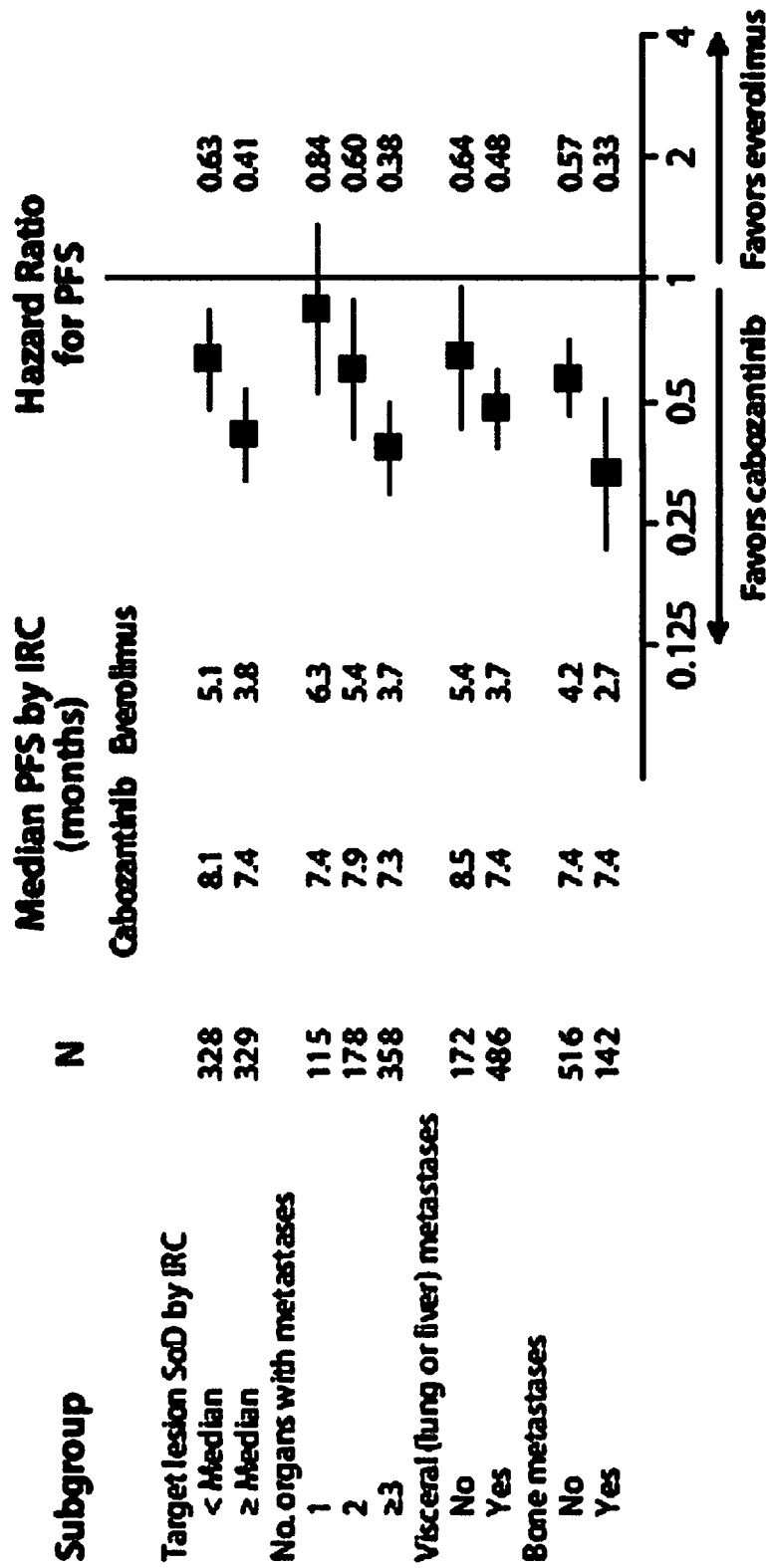
FIG. 3.1
IRC, independent radiology committee; PFS, progression-free survival; SoD, sum of diameters

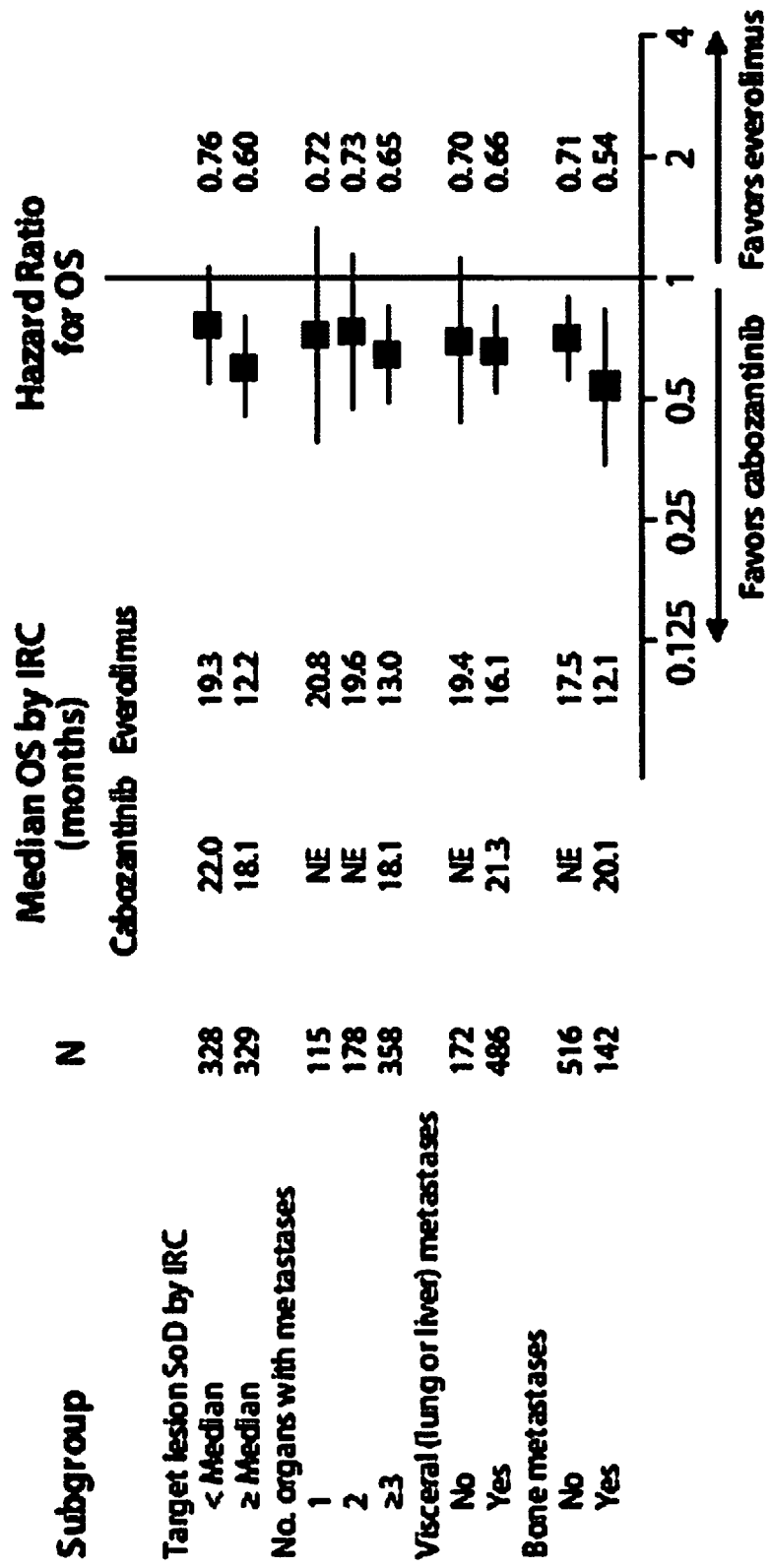
FIG. 3.2
IRC, independent radiology committee; NE, not estimable; OS, overall survival; SoD, sum of diameters

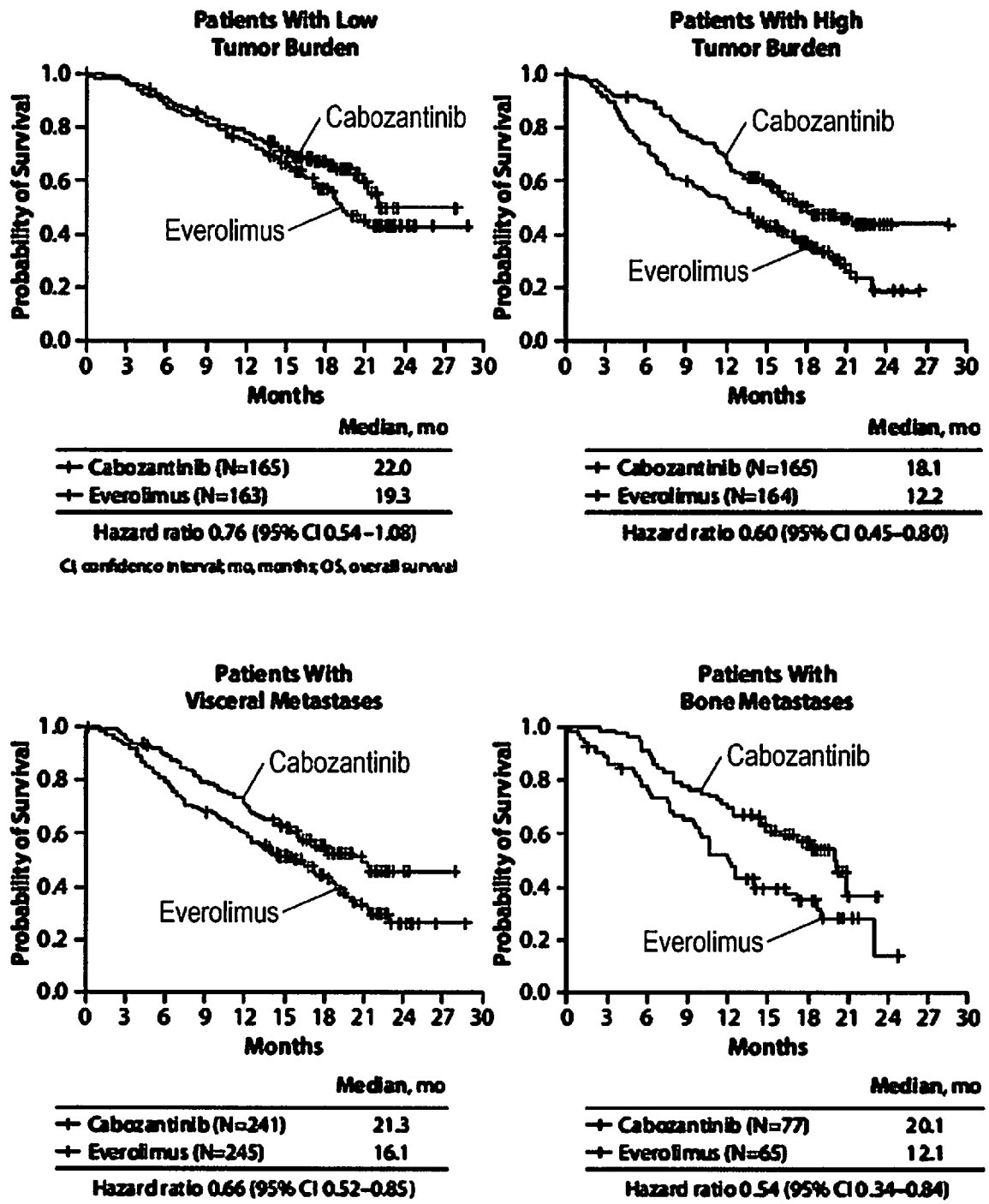
FIG. 3.3

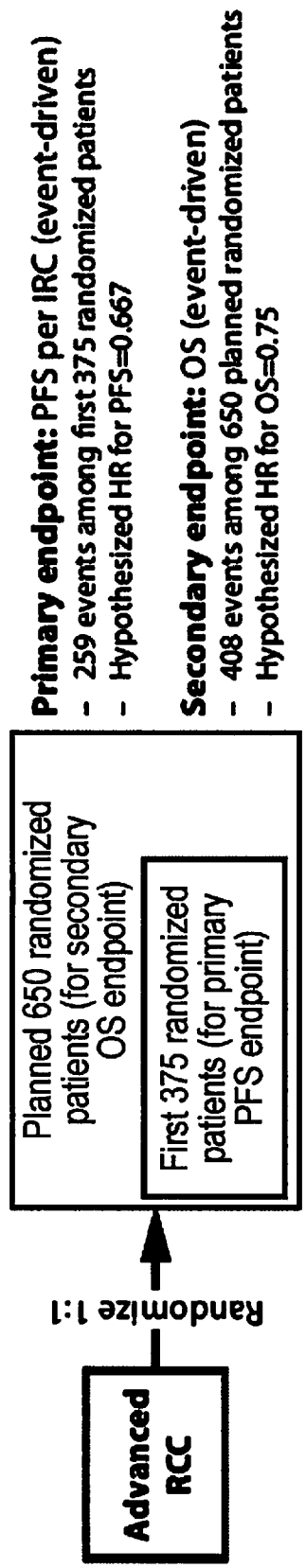
FIG. 4.1
HR, hazard ratio; IRC, independent radiology committee; OS, overall survival; PFS, progression-free survival; RCC, renal cell carcinoma

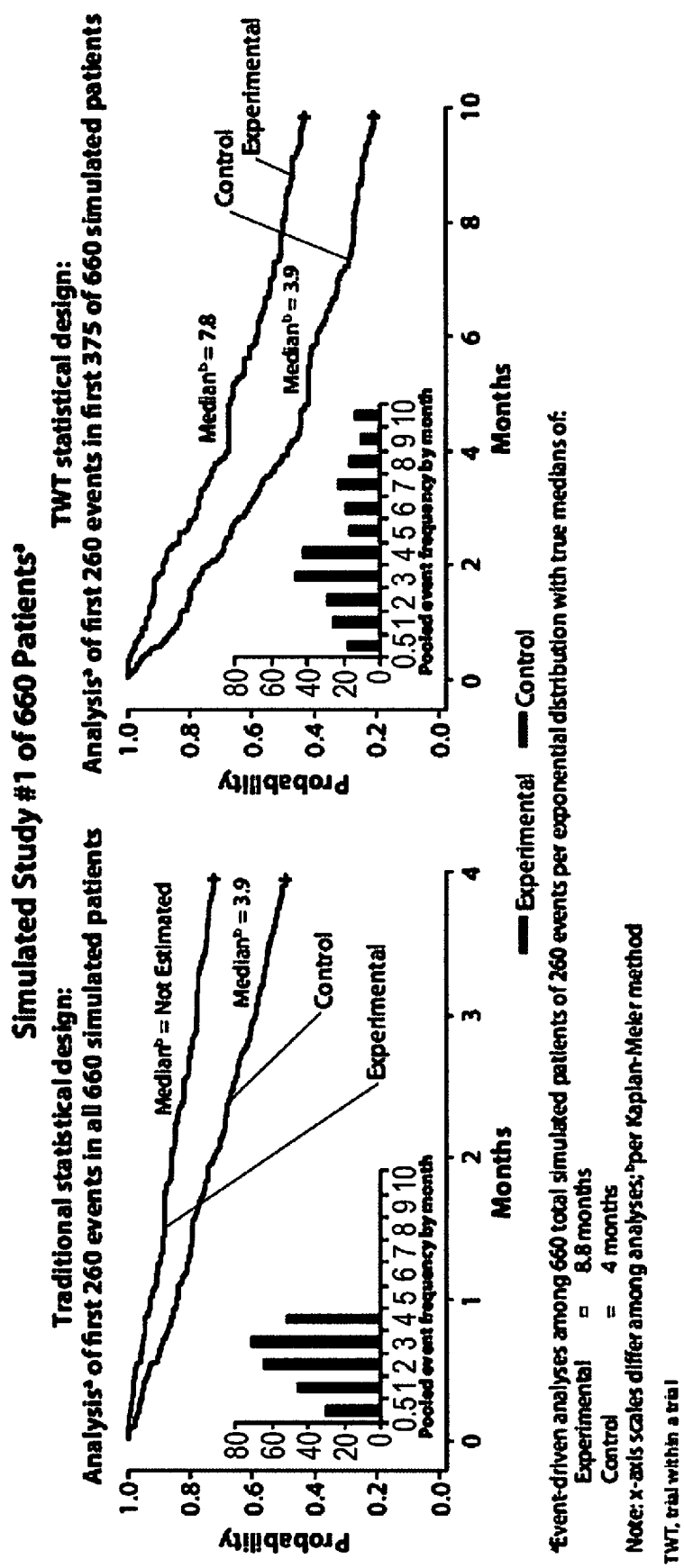
FIG. 4.2A

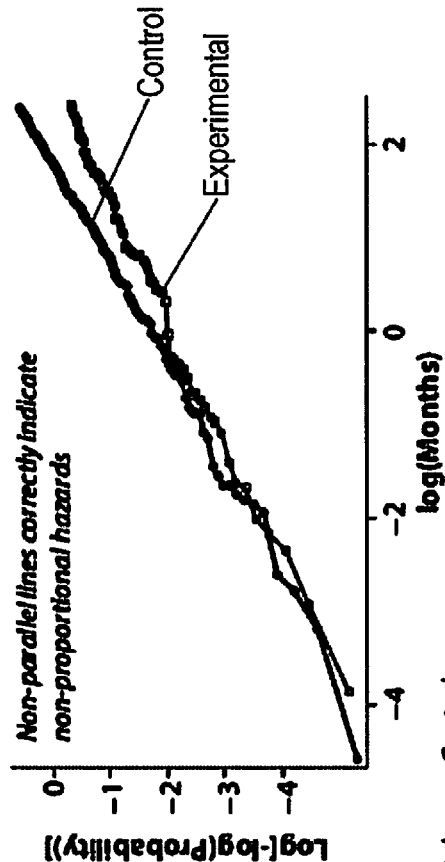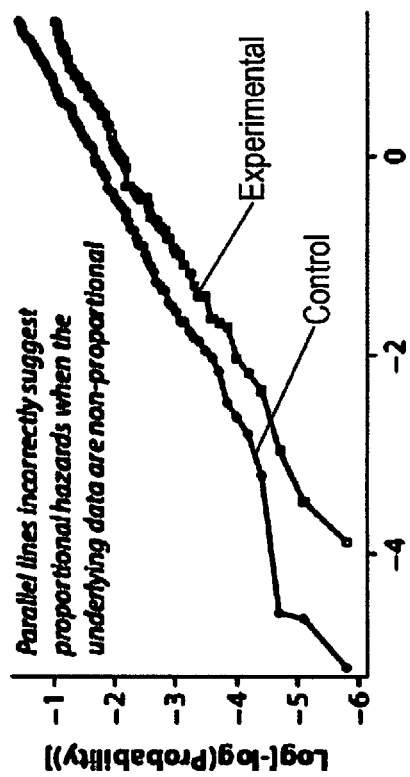
FIG. 4.2B

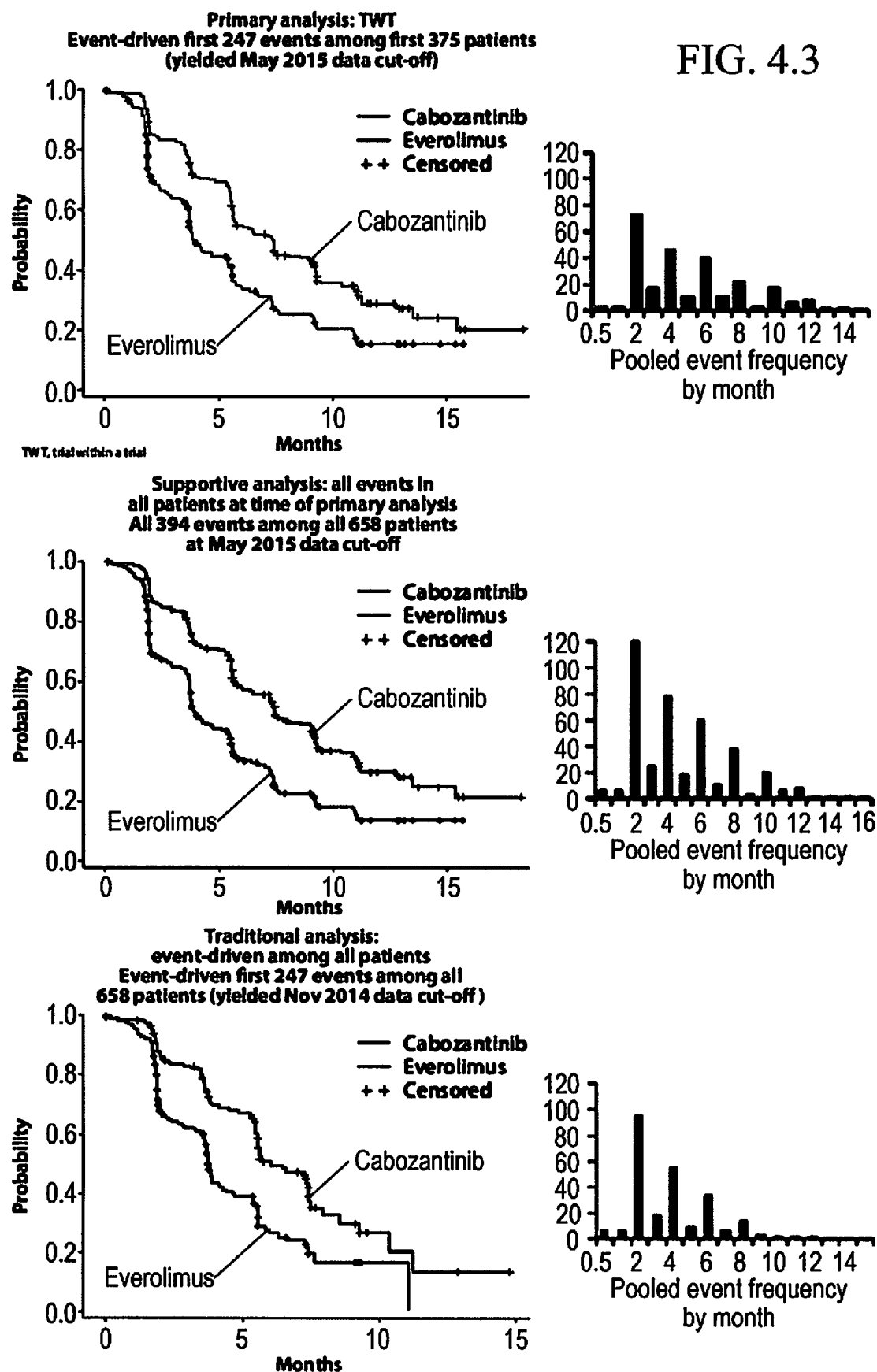
FIG. 4.3

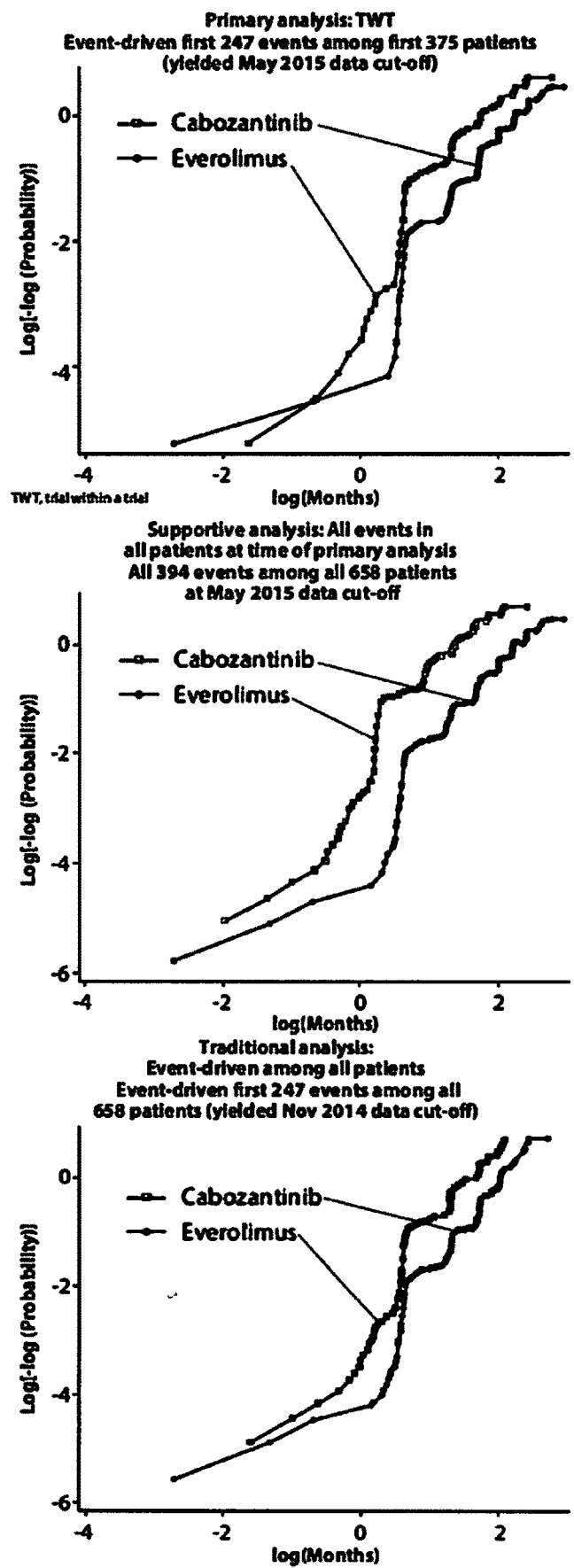
FIG. 4.4

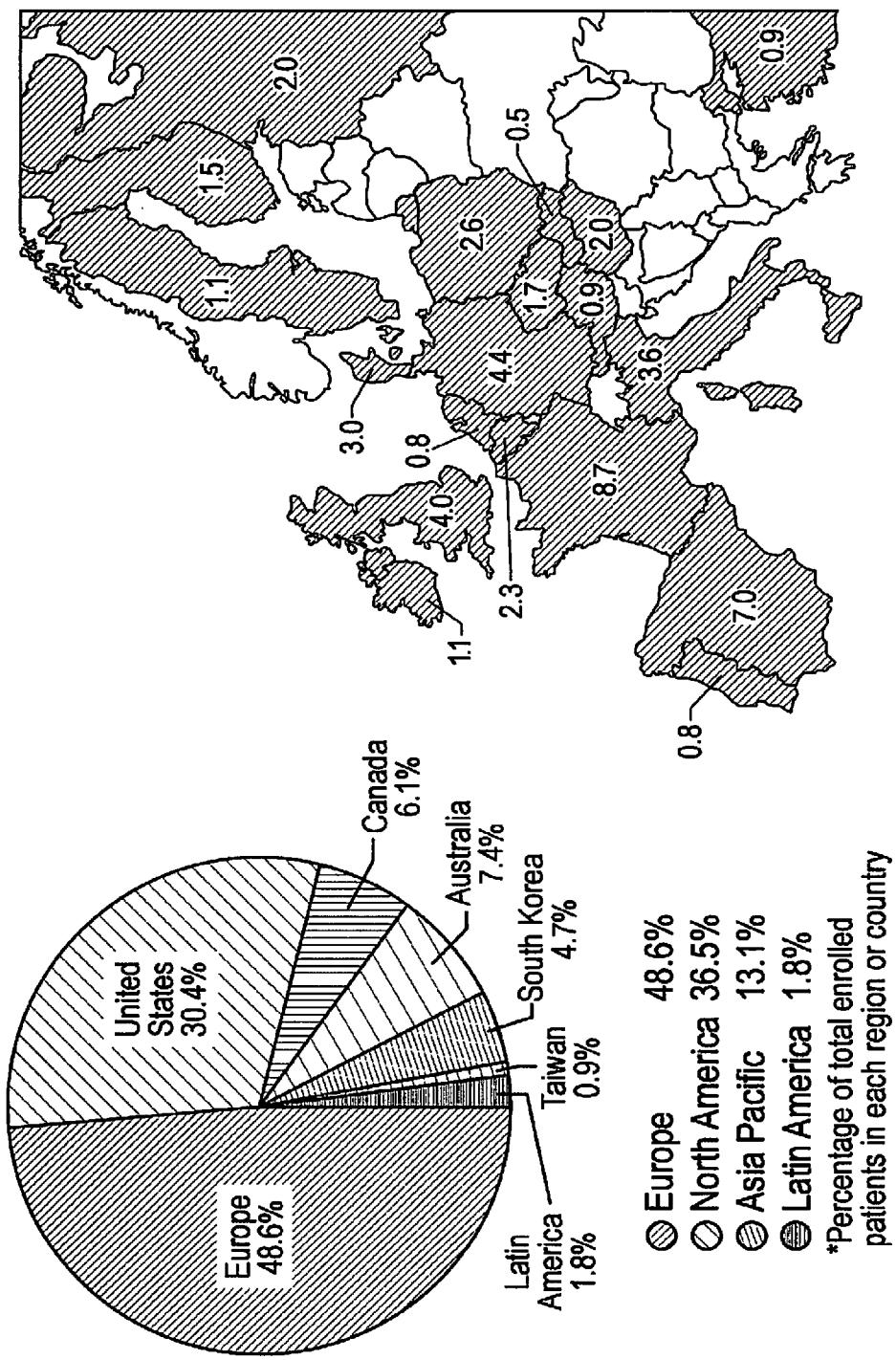
FIG 5.1

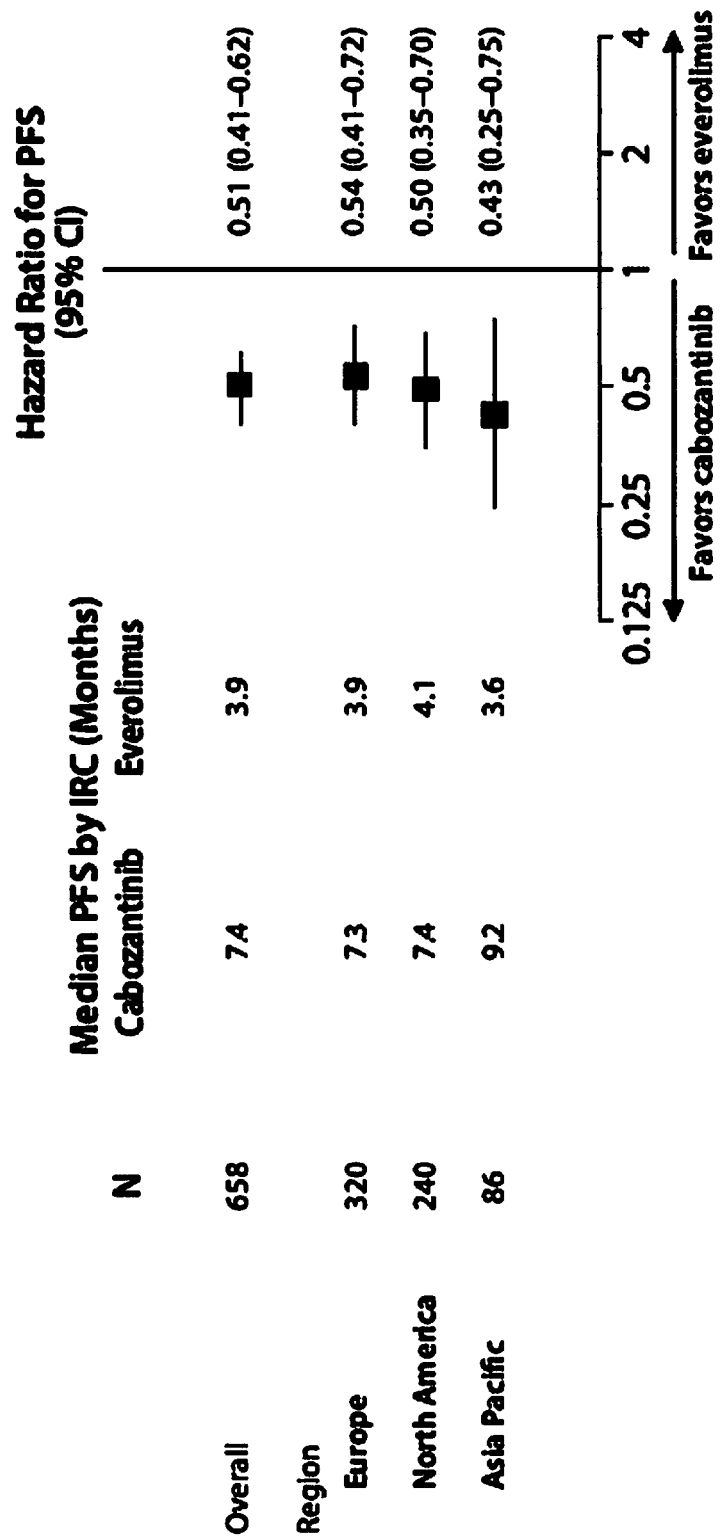
FIG. 5.2

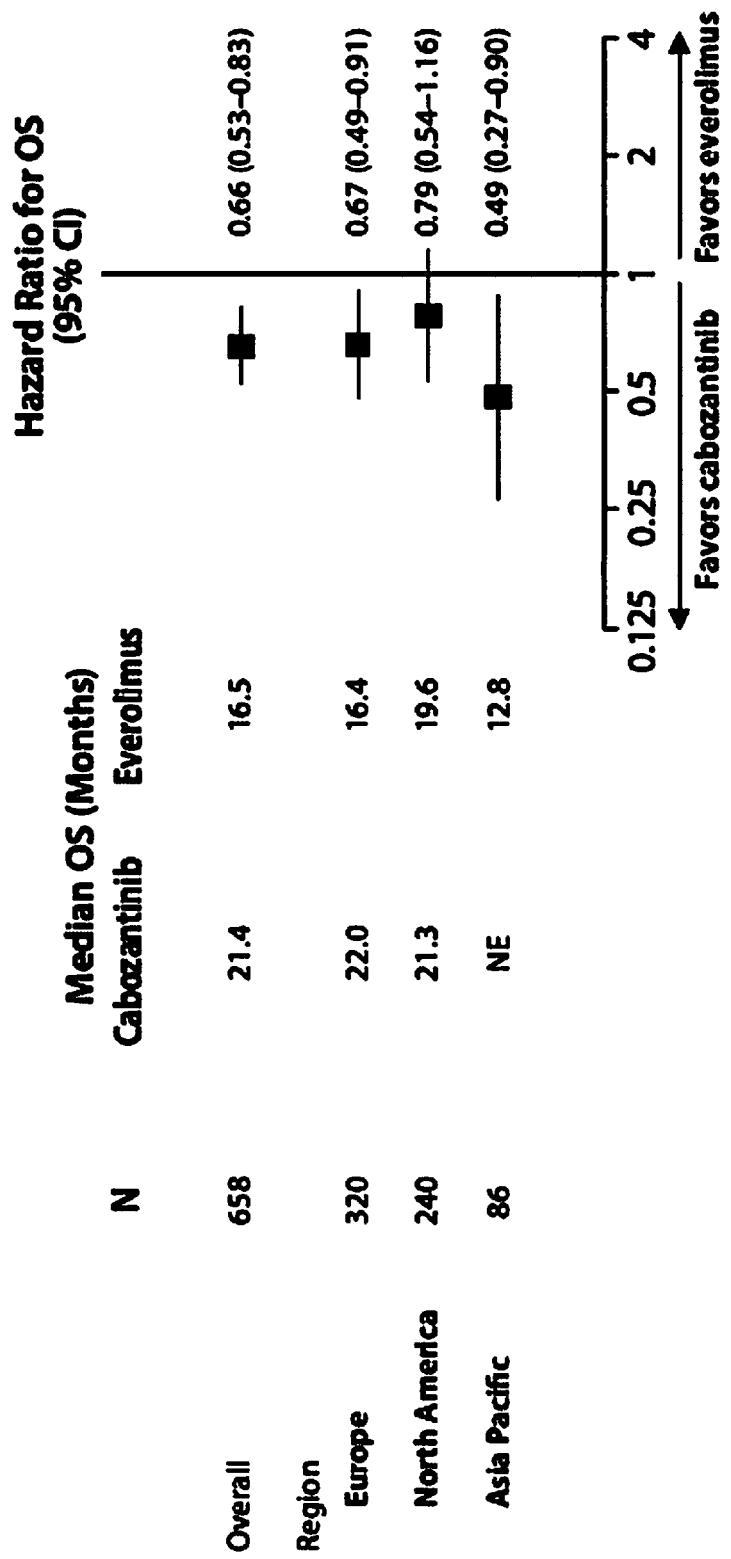
FIG. 5.3

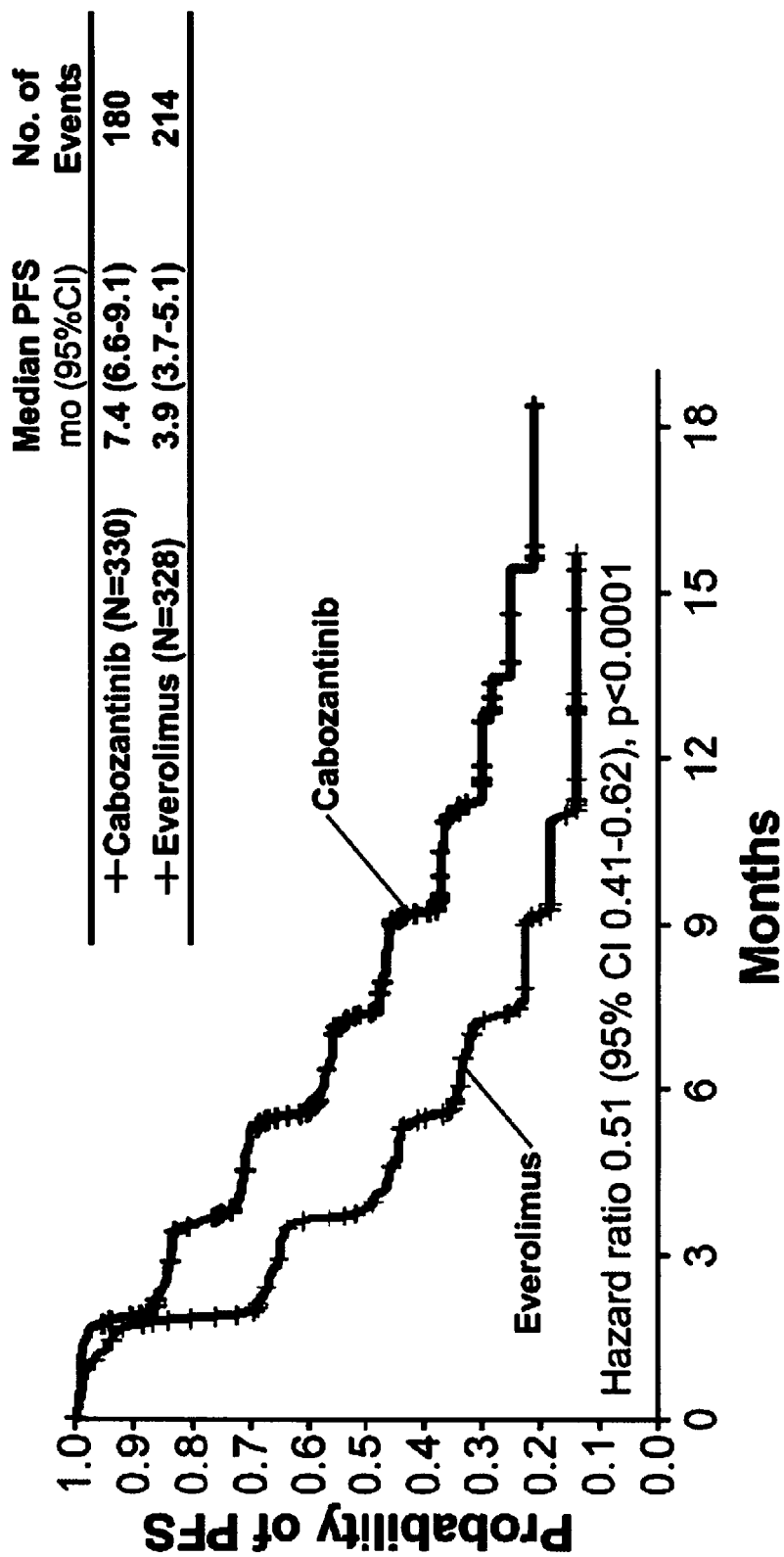
FIG. 8.1

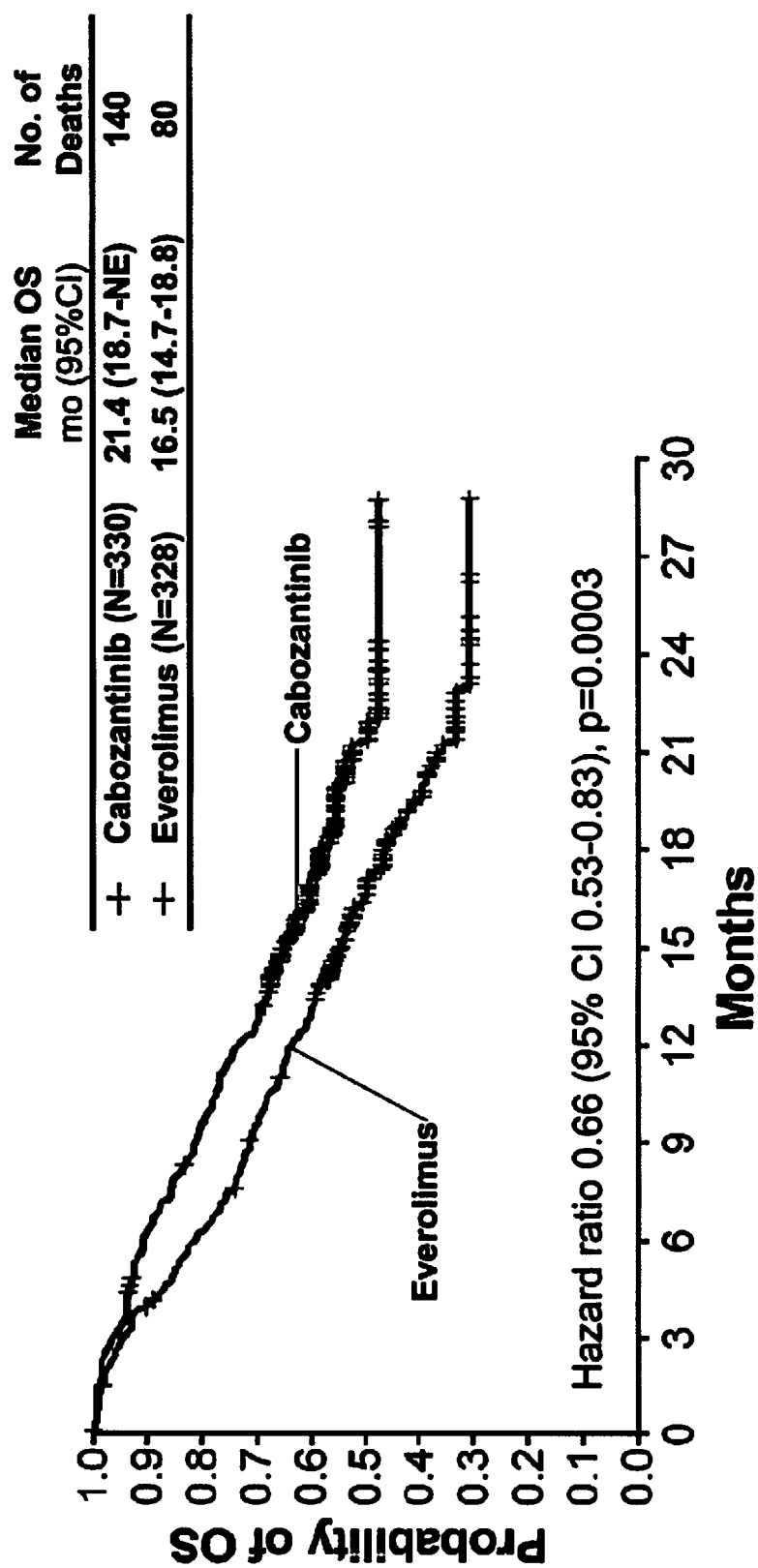
FIG. 8.2

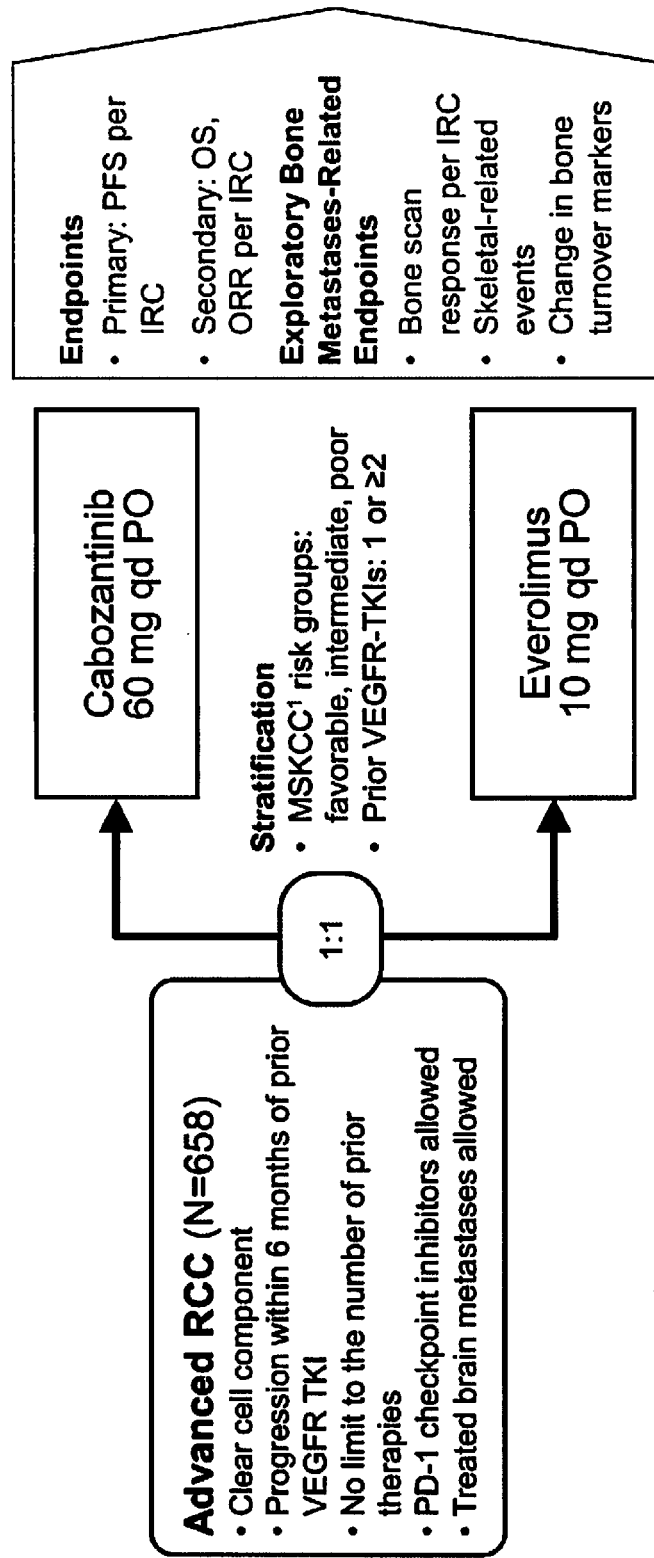
FIG. 8.3

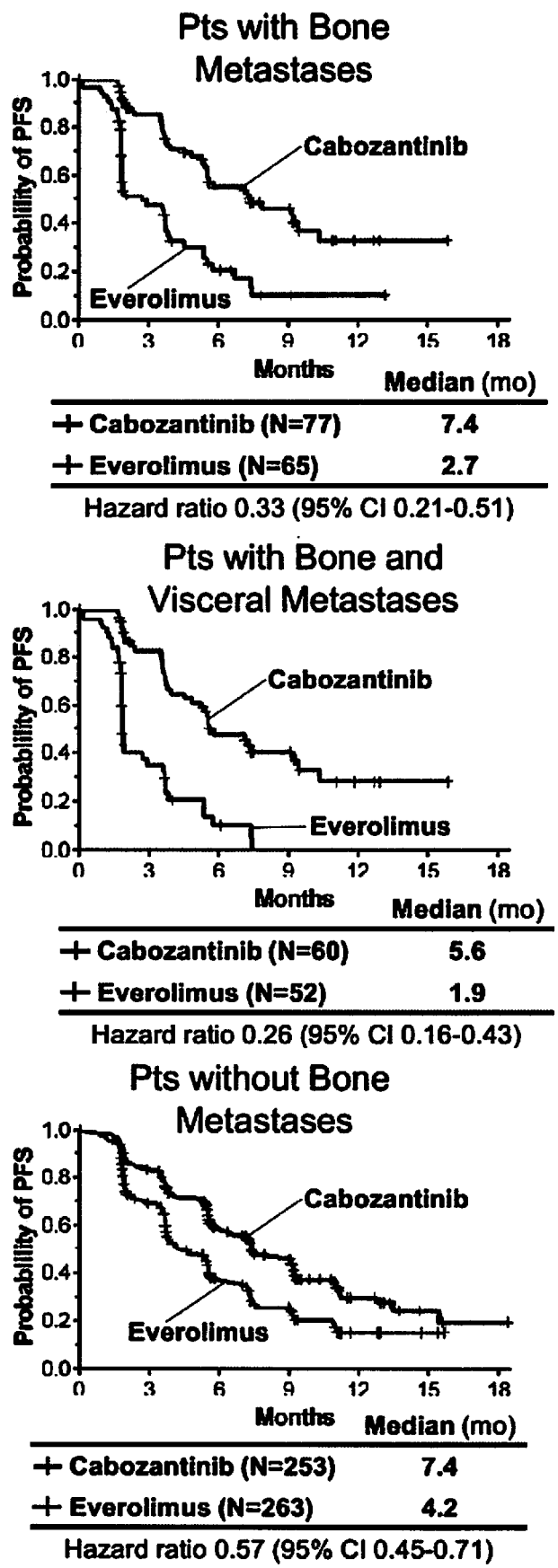
FIG. 8.4

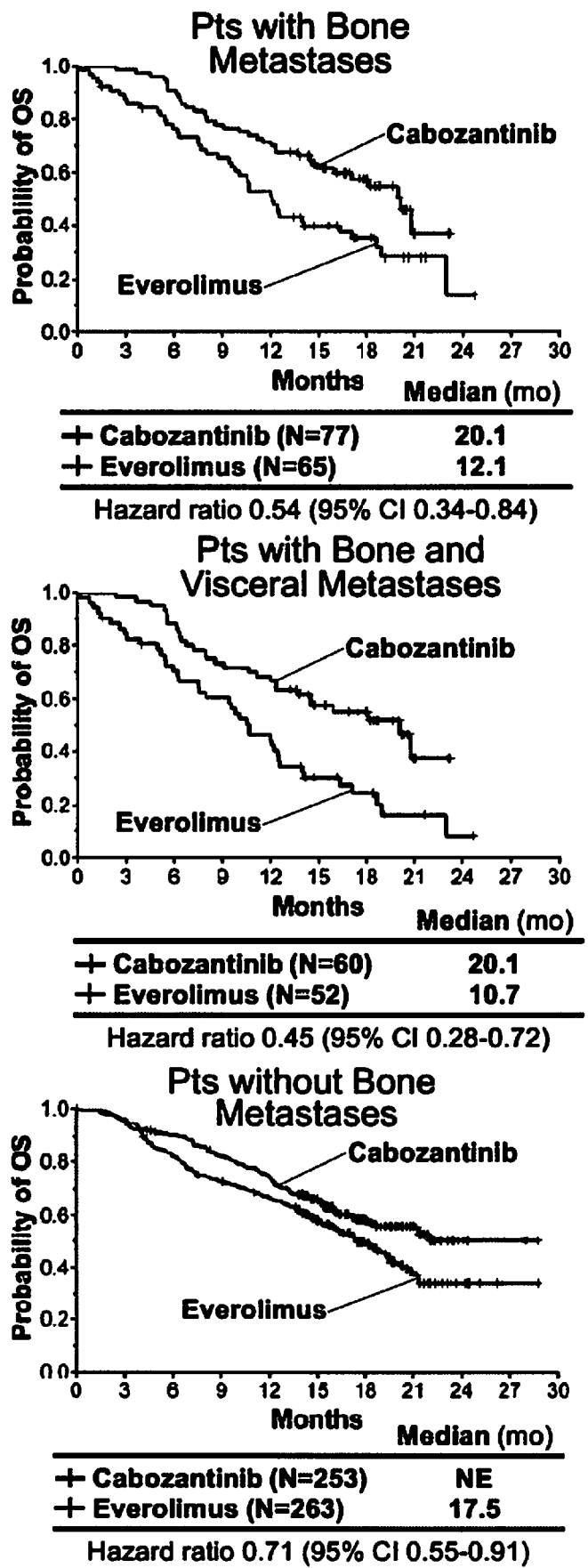
FIG. 8.5

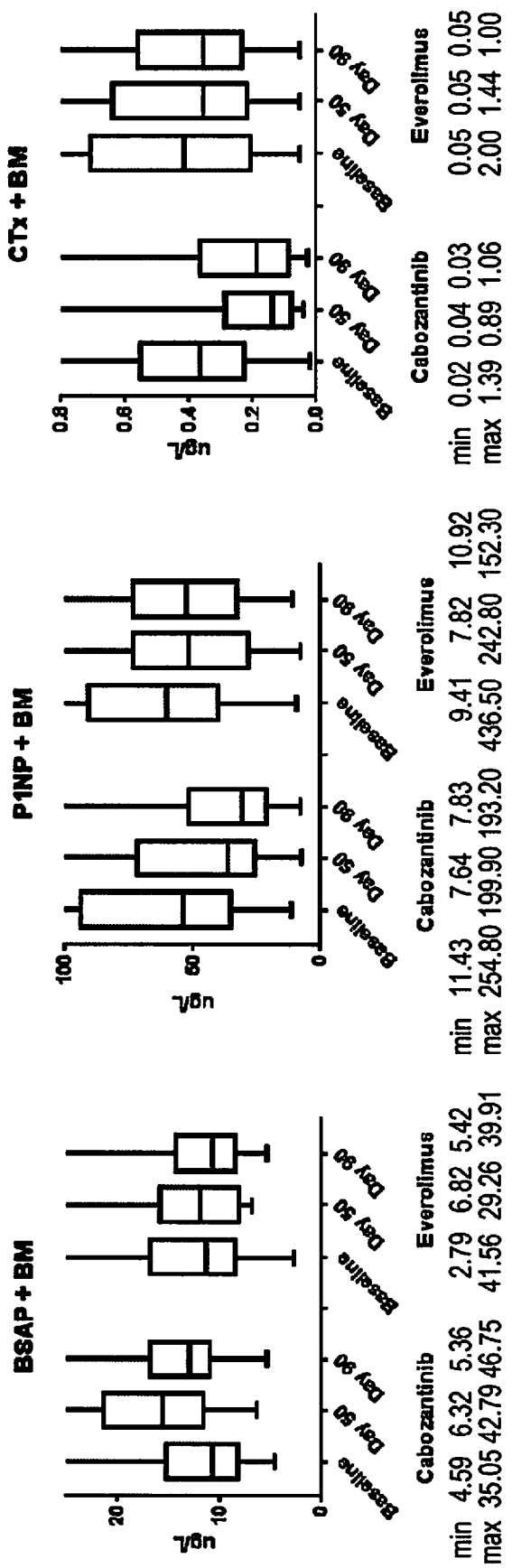
FIG. 8.6

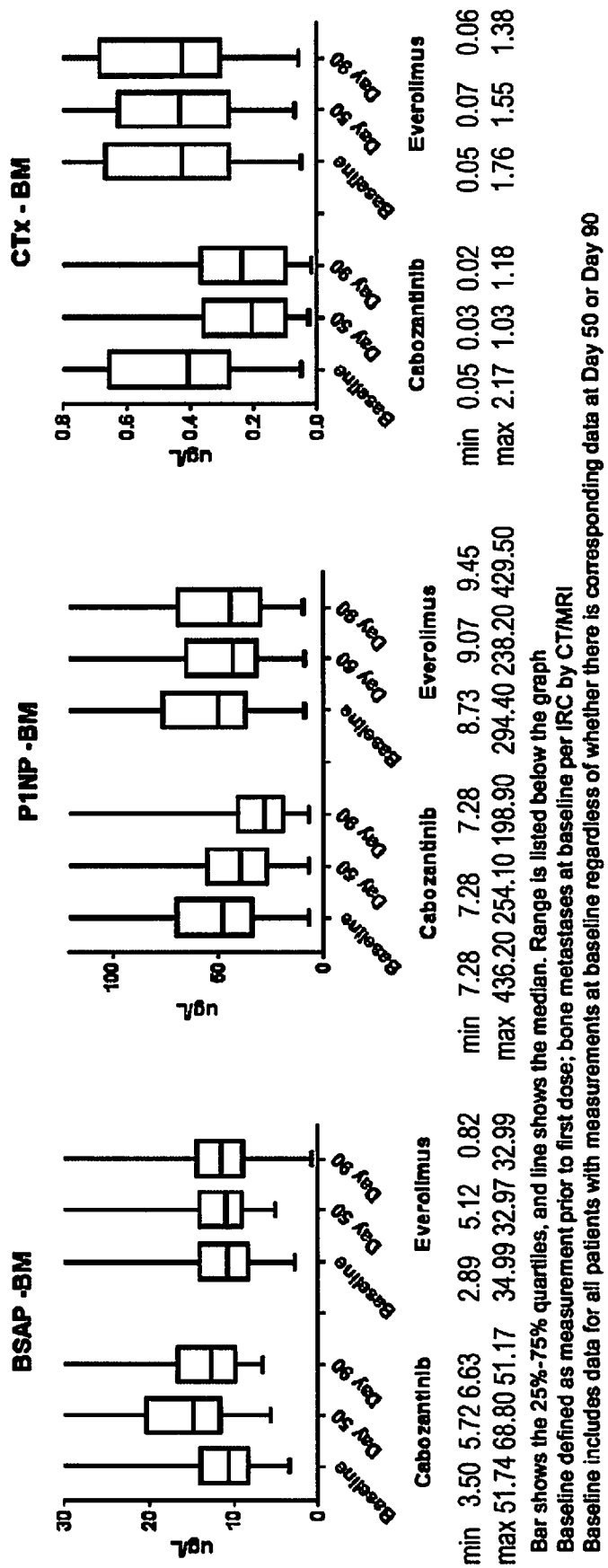
FIG. 8.7

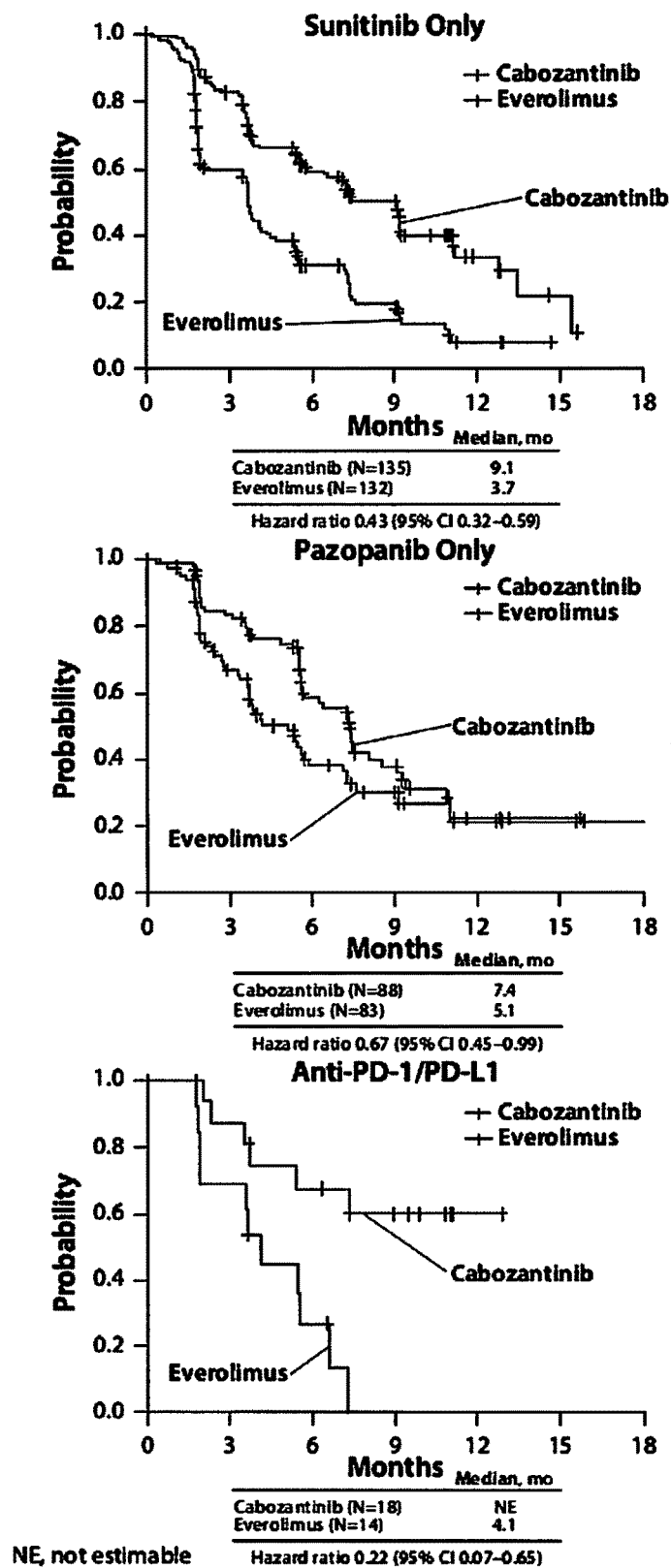
FIG. 9.1

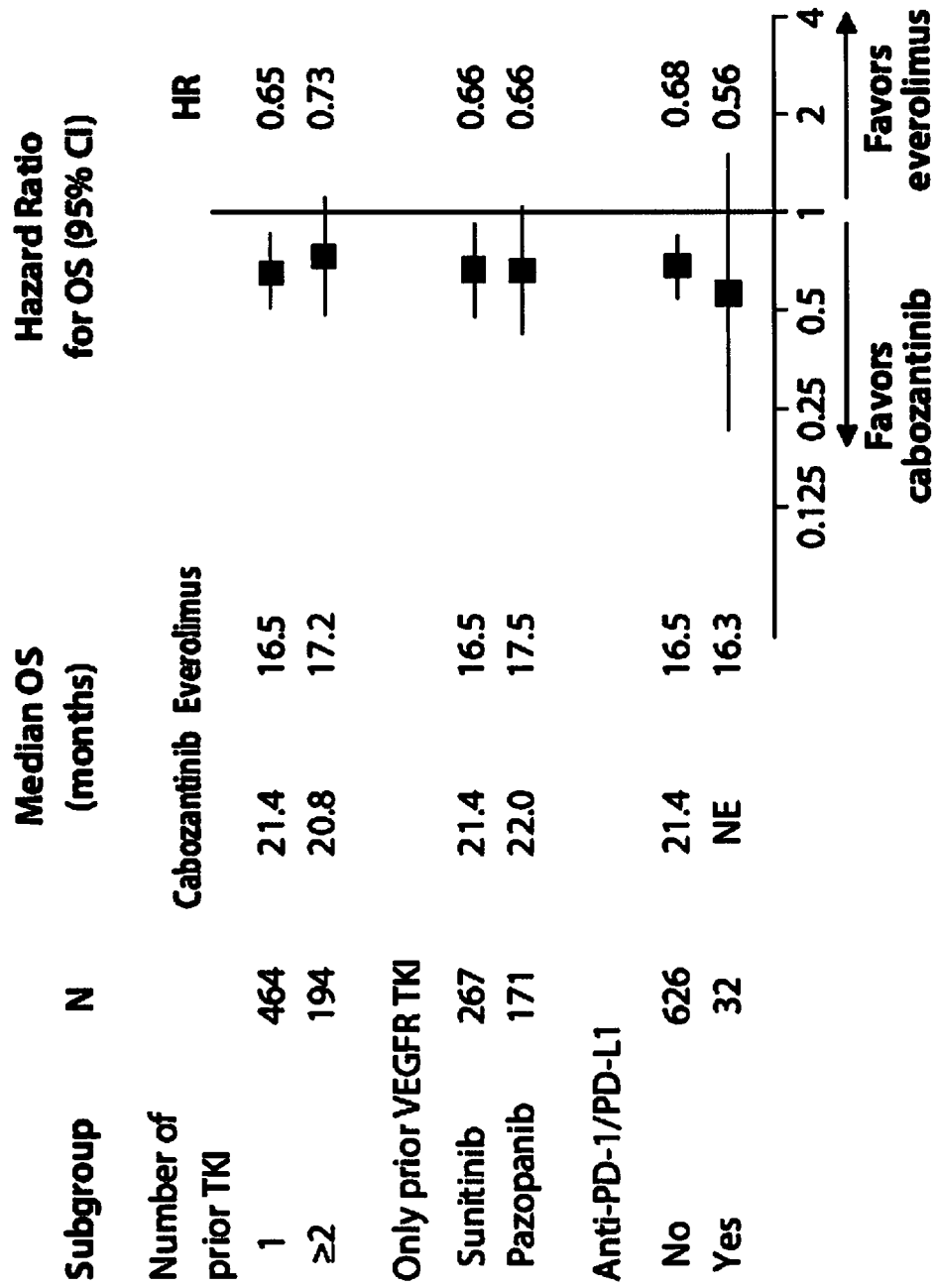
FIG. 9.2

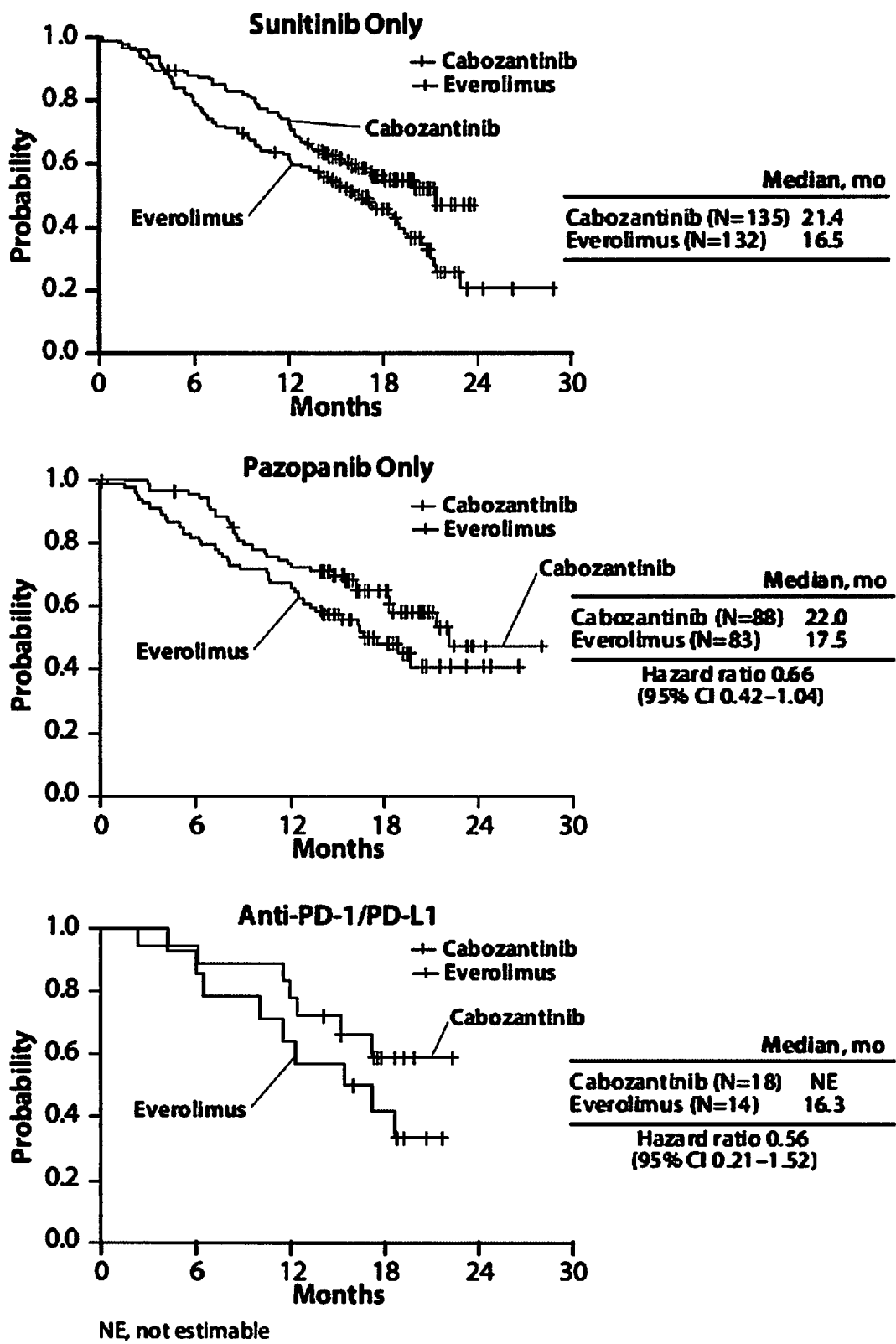
FIG. 9.3

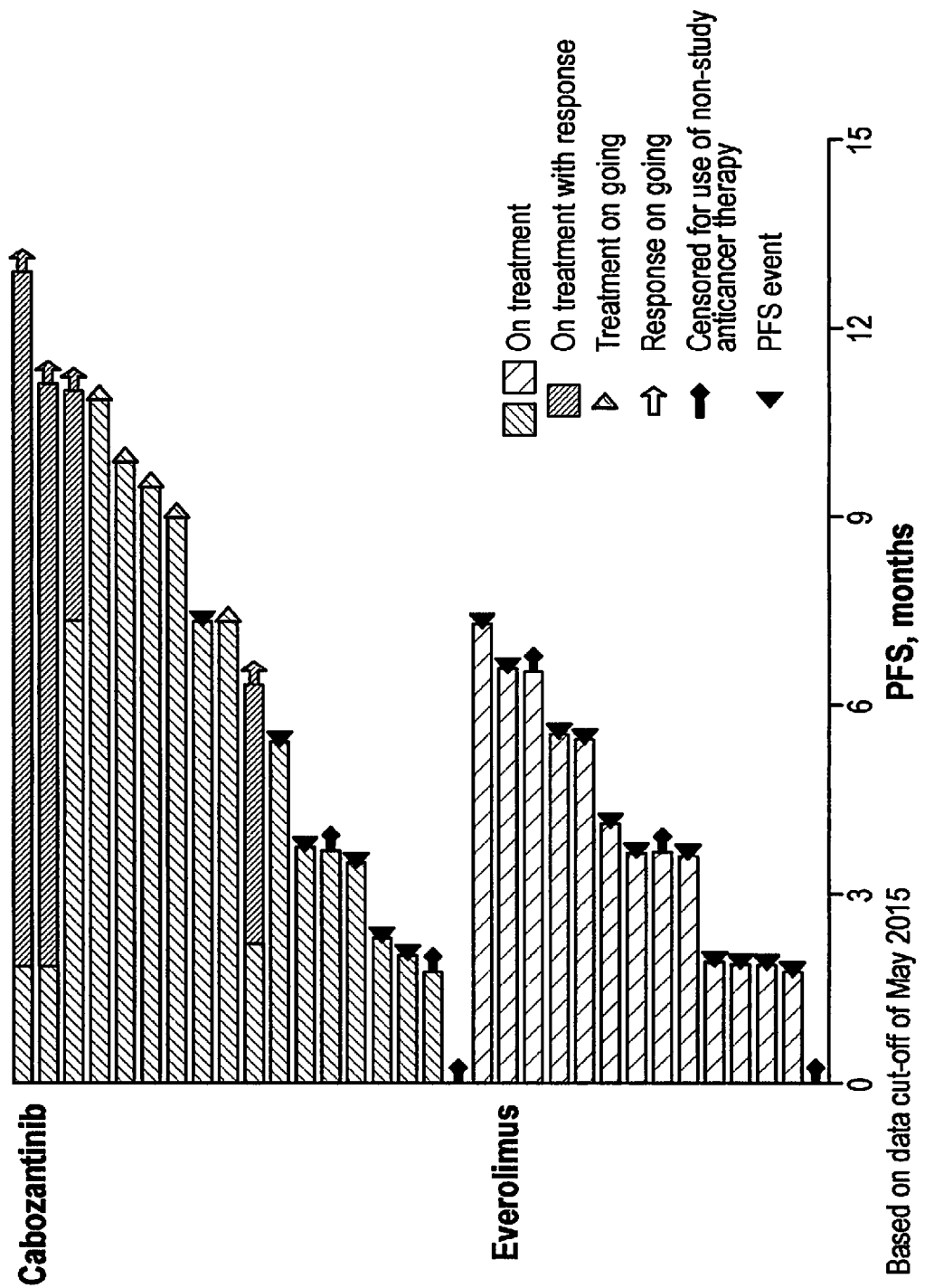
FIG. 9.4

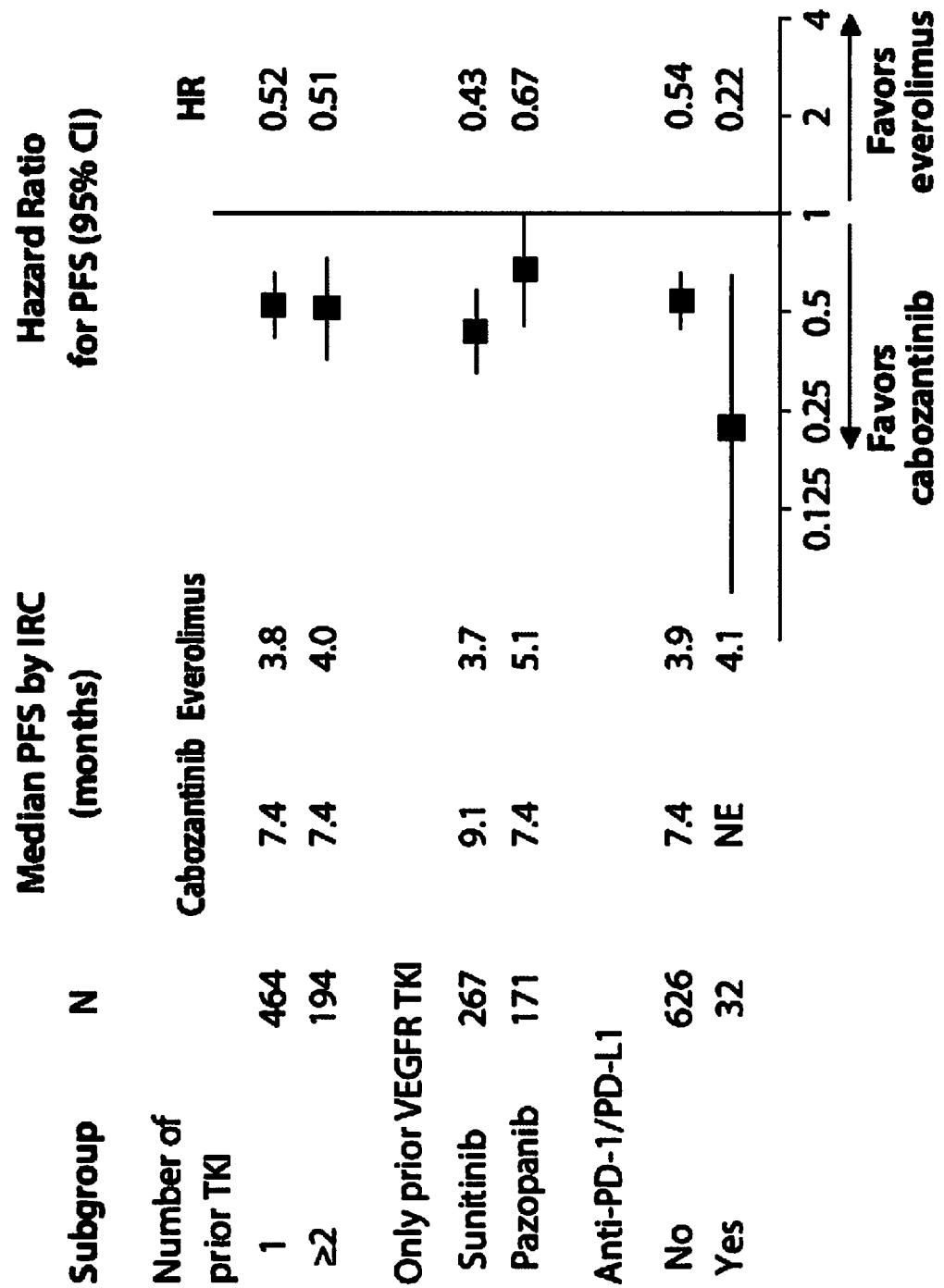
FIG. 9.5

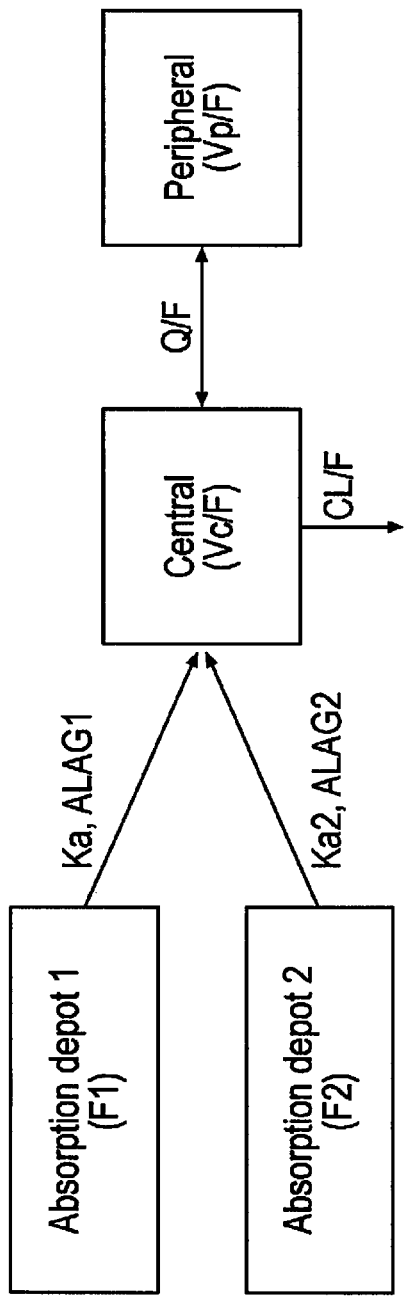

FIG. 10.1

F1 = fraction of dose in the first depot ; F2 = fraction of dose in the second depot; Ka = depot 1 absorption rate constant
Ka2 = depot 2 absorption rate constant; ALAG1 = depot 1 absorption lag time ; ALAG2 = depot 2 absorption lag time
Vc/F = apparent volume of distribution (central compartment); Vp/F = apparent volume of distribution (peripheral compartment)
Q/F = apparent flow between plasma (central) and peripheral compartments ; CL/F = apparent plasma clearance

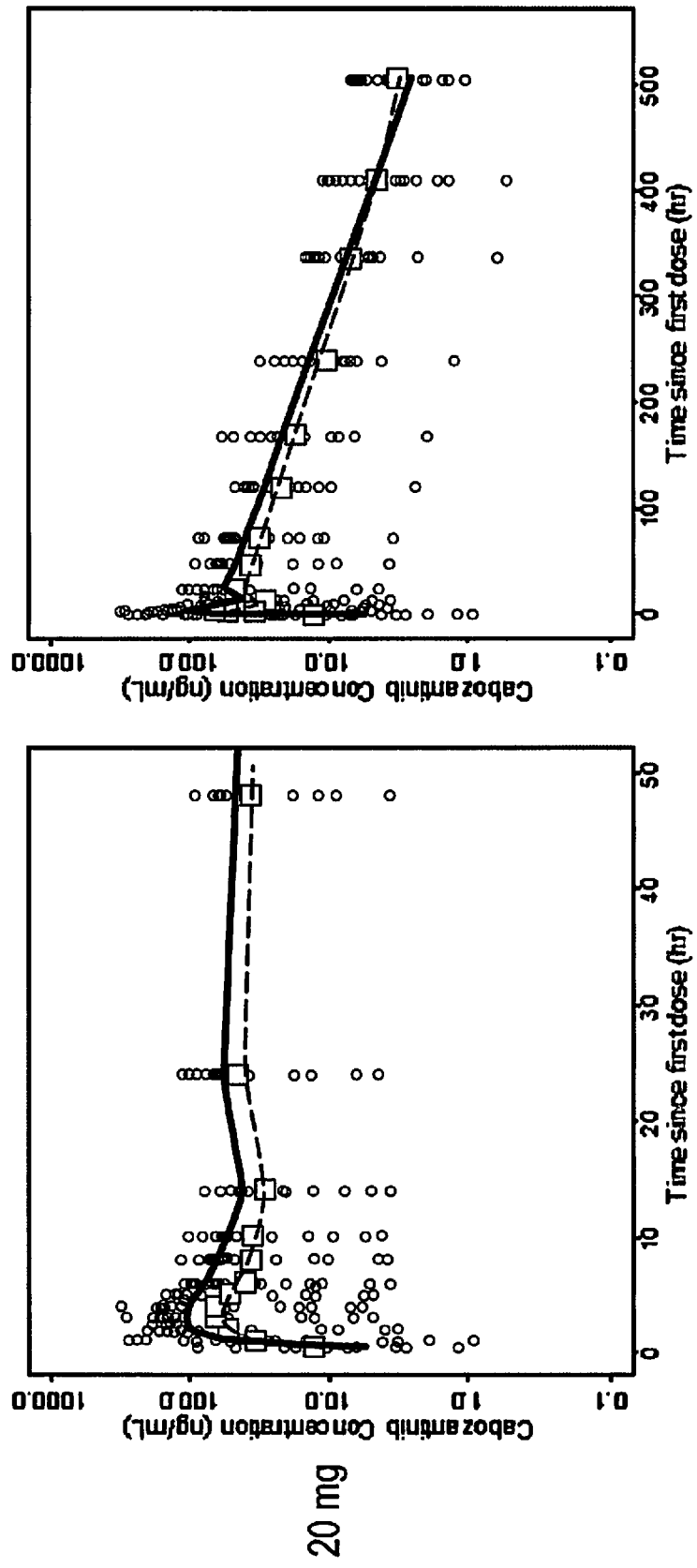
FIG. 10.2A

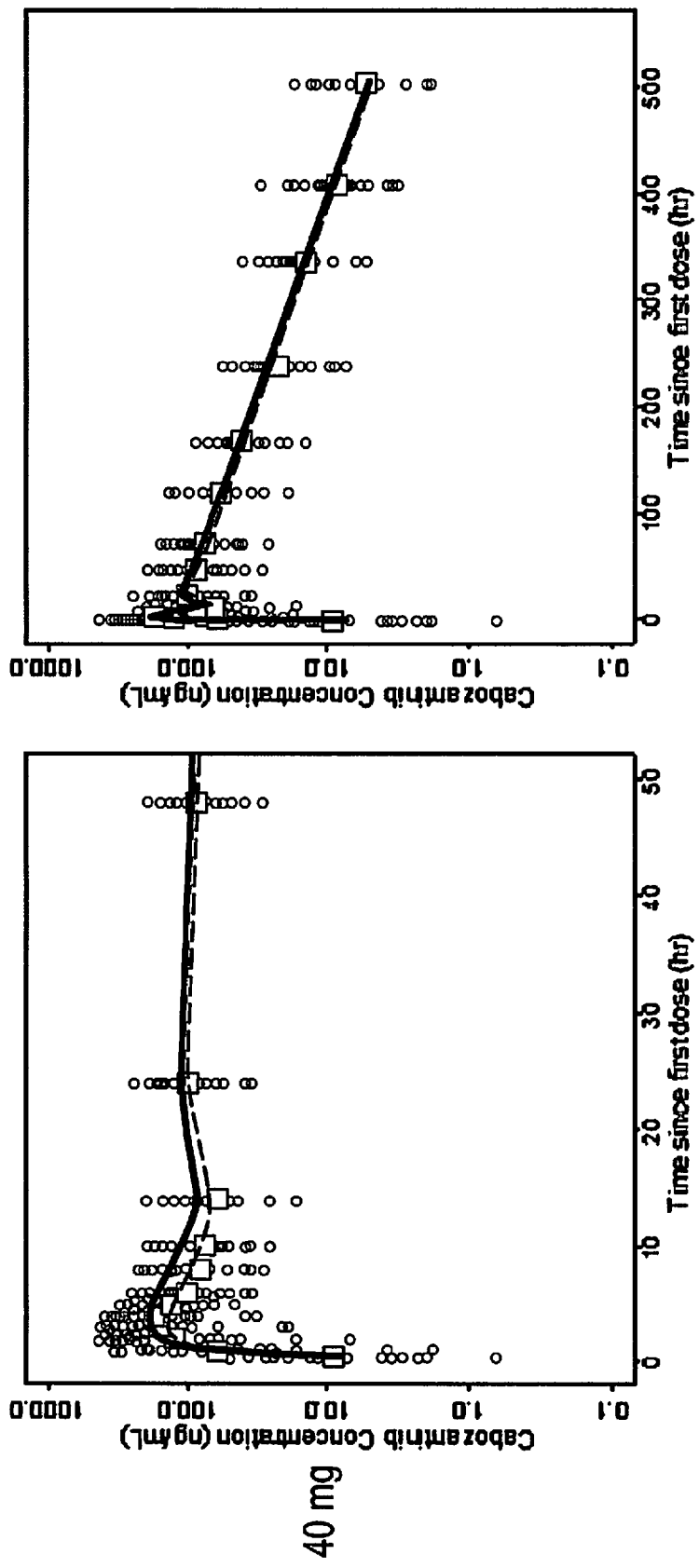
FIG. 10.2B

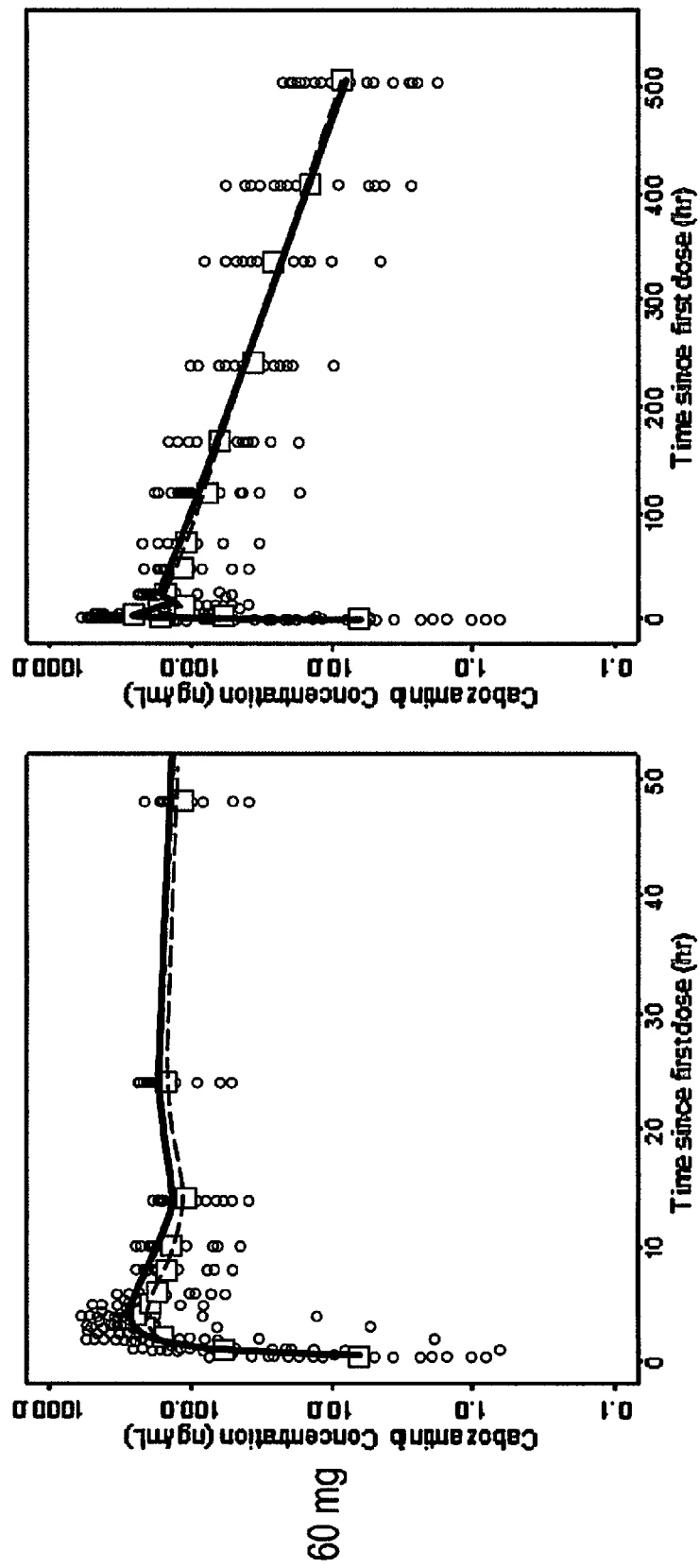
FIG. 10.2C

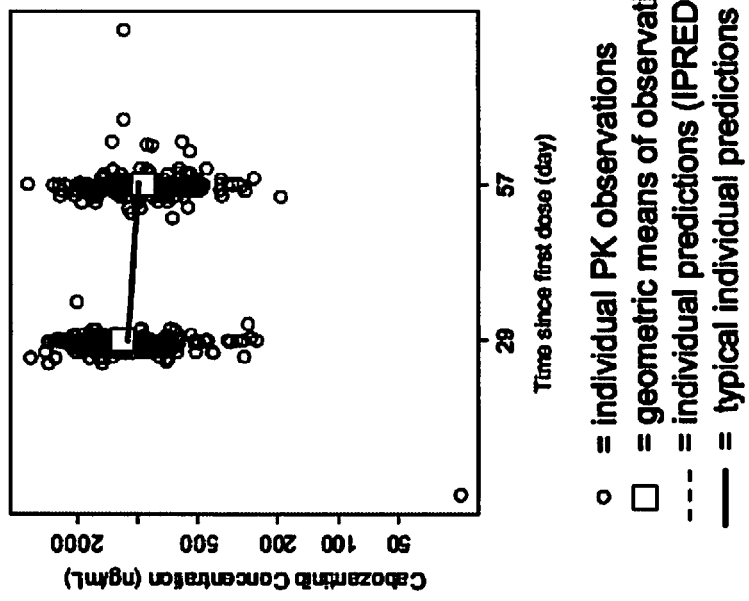
FIG. 10.2D

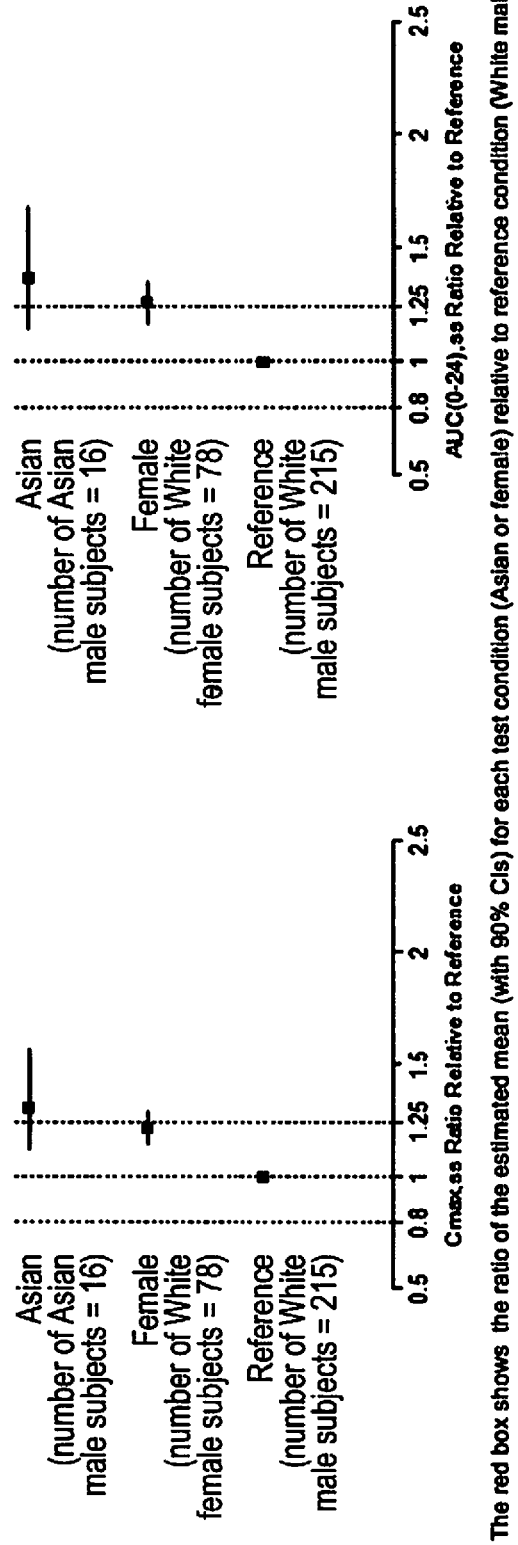
FIG. 10.3

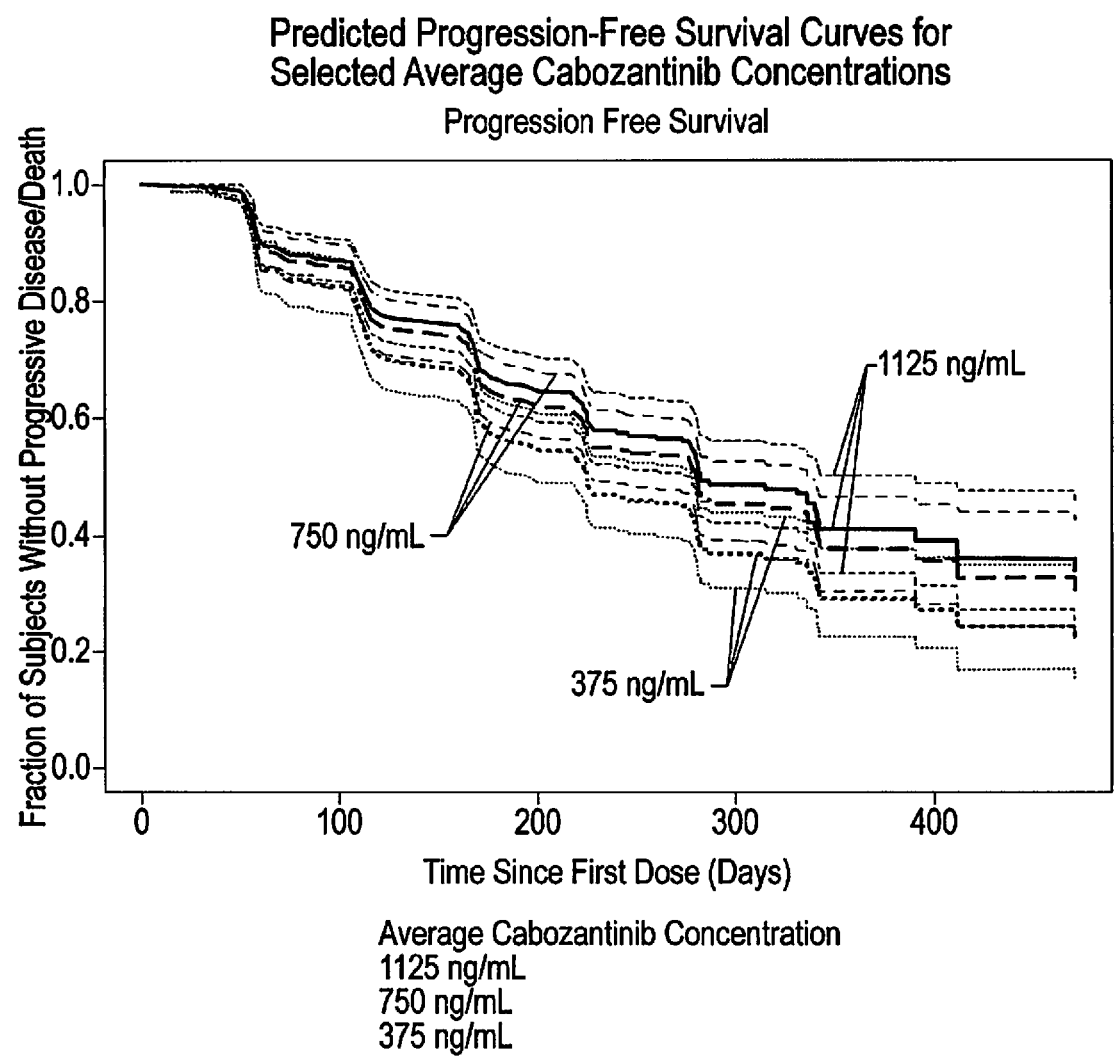
FIG. 10.4

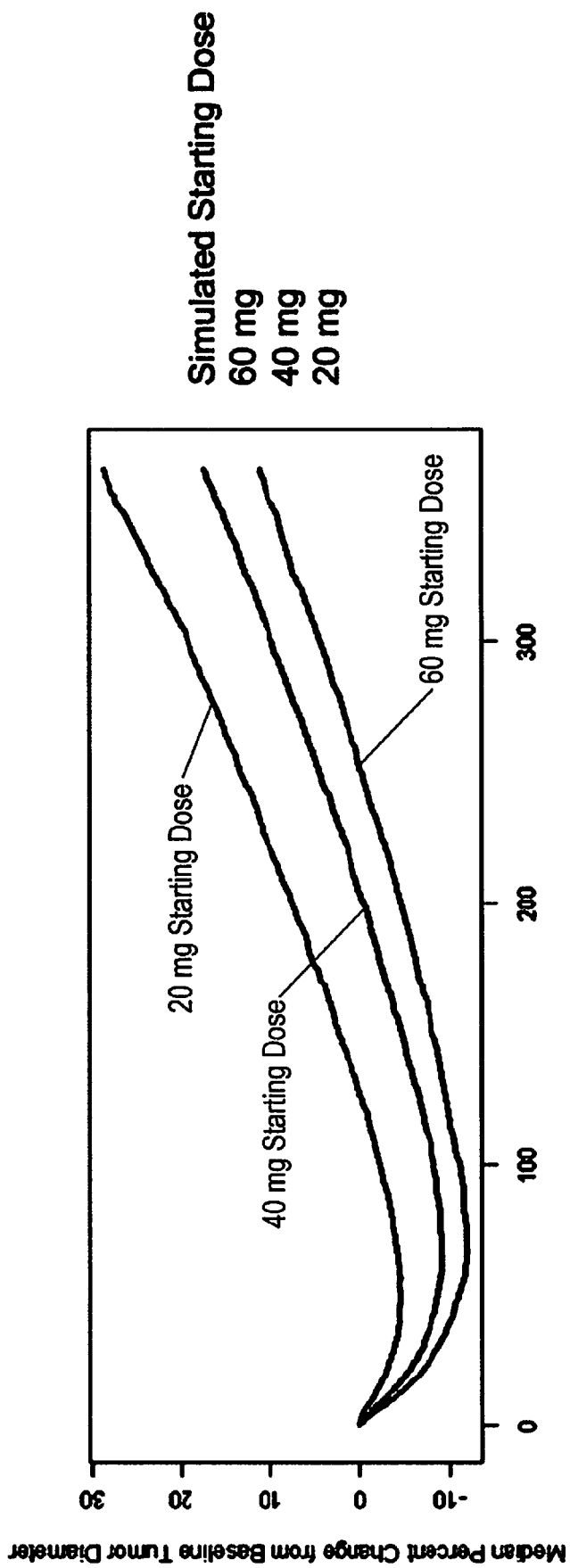
FIG. 10.5
The maximal median reduction in tumor size increased with increasing simulated starting doses of 20 mg (-4.45%), 40 mg (-9.1%), and 60 mg (-11.9%)

METHOD OF TREATING RENAL CELL CARCINOMA USING N-(4-(6,7-DIMETHOXYQUINOLIN-4-YLOXY)PHENYL)-N'-(4-FLUOROPHENYL)CYCLOPROPANE-1,1-DICARBOXAMIDE, (2S)-HYDROXYBUTANEDIOATE

RELATED APPLICATIONS

This application is a United States National Phase filing of PCT/US2017/027965, filed Apr. 17, 2017, which claims the benefit of priority to U.S. Provisional Application Nos. 62/457,613 filed Feb. 10, 2017, 62/457,471 filed Feb. 10, 2017, 62/457,671 filed Feb. 10, 2017, 62/345,652 filed Jun. 3, 2016, 62/338,195 filed May 18, 2016, 62/338,267 filed May 18, 2016, 62/338,240 filed May 18, 2016, 62/338,154 filed May 18, 2016, 62/324,157 filed Apr. 18, 2016, 62/324,158 filed Apr. 18, 2016, 62/324,176 filed Apr. 18, 2016, 62/323,536 filed Apr. 15, 2016, 62/323,548 filed Apr. 15, 2016, and 62/323,556 filed Apr. 15, 2016, the entire contents of which are incorporated herein by reference.

TECHNICAL FIELD

The present disclosure relates to methods of treating renal cell carcinoma (RCC) in human patients who have received prior anti-angiogenic therapy. The method employs cabozantinib, a kinase inhibitor.

BACKGROUND

Advances in the understanding of the molecular pathology of renal cell carcinoma (RCC) have led to the development of agents targeting the vascular endothelial growth receptor (VEGFR) and mTOR signaling pathways. Commonly used first-line therapies in patients with advanced RCC are the VEGFR tyrosine kinase inhibitors (TKIs) sunitinib and pazopanib. Second-line therapies include the VEGFR TKIs axitinib and sorafenib, the mTOR inhibitor everolimus, and the programmed cell death receptor 1 (PD-1) checkpoint inhibitor nivolumab. Motzer R J, Jonasch E, Agarwal N, et al. Kidney cancer, version 3. 2015. *J Natl Compr Canc Netw* 2015; 13: 151-9. Powles T, Staehler M, Ljungberg B, et al. Updated EAU Guidelines for Clear Cell Renal Cancer Patients Who Fail VEGF Targeted Therapy. *Eur Urol* 2016; 69: 4-6. Motzer R J, Escudier B, McDermott D F, et al. Nivolumab versus Everolimus in Advanced Renal-Cell Carcinoma. *N Engl J Med* 2015; 373: 1803-13. Despite a number of available therapies, few have shown a survival benefit, and no agent has demonstrated an improvement in all three efficacy endpoints of progression-free survival (PFS), objective response rate, and overall survival in a randomized phase 3 trial compared to standard therapy in previously-treated RCC patients.

As a result, a need remains for improved therapies for the treatment of renal cell carcinoma and, in particular, therapies that achieve improvement in the three efficacy endpoints of progression-free survival (PFS), objective response rate, and overall survival in the treatment of renal cell carcinoma.

SUMMARY

These and other needs are met by the present invention, which is directed to a method of treating advanced renal cell carcinoma (RCC) in human patients who have received prior anti-angiogenic therapy. The method employs cabozantinib. The invention is also directed to the use of cabozantinib for treating advanced renal cell carcinoma (RCC) in human patients who have received prior anti-angiogenic therapy. The invention is also directed to the use of cabozantinib in the manufacture of a medicament for treating advanced renal cell carcinoma (RCC) in human patients who have received prior anti-angiogenic therapy.

The methods and associated uses disclosed herein employ cabozantinib, which is an oral inhibitor of tyrosine kinases including MET, VEGF receptors, and AXL. Cabozantinib has the structure depicted below.

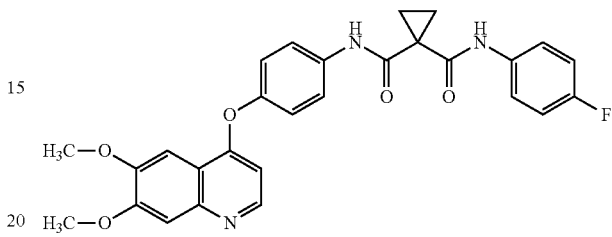

In preferred embodiments, the (S)-malate salt of cabozantinib is administered. Cabozantinib (S)-malate is described chemically as N-(4-(6,7-dimethoxyquinolin-4-yloxy)phenyl)-N'-(4-fluorophenyl)cyclopropane-1,1-dicarboxamide, (2S)-hydroxybutanedioate. The molecular formula is $C_{28}H_{24}FN_3O_5 \cdot C_4H_6O_5$, and the molecular weight is 635.6 Daltons as malate salt. The chemical structure of cabozantinib (S)-malate salt is depicted below.

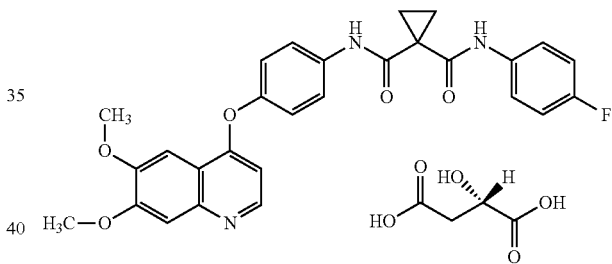

Cabozantinib as a capsule formulation (COMETRIQ®) has been approved for the treatment of medullary thyroid cancer.

In preferred embodiments, the cabozantinib is administered as CABOMETYX®, which is a tablet formulation of the (S)-malate salt of cabozantinib. The tablet formulation (CABOMETYX®) achieved a 19% increase in the $C_{max}$ compared to the capsule formulation (COMETRIQ®) following a single 140 mg dose. A less than 10% difference in the AUC was observed between cabozantinib tablet (CABOMETYX®) and capsule (COMETRIQ®) formulations. Importantly, CABOMETYX® is the first agent to demonstrate an improvement in all three efficacy endpoints of progression-free survival (PFS), objective response rate, and overall survival in a late stage clinical trial for treating advanced renal cell carcinoma (RCC) who have received prior anti-angiogenic therapy, as described in U.S. Ser. No. 62/323,536 filed Apr. 15, 2016, the entire contents of which is incorporated herein by reference.

Thus, in one aspect, the invention is directed to a method of treating advanced renal cell carcinoma with or without bone metastases in a human patient who has received prior anti-angiogenic therapy comprising administering to the patient an amount of cabozantinib or a pharmaceutically acceptable salt thereof wherein progression-free survival (PFS), and one or both of overall survival (OS) and objective response rate (ORR) are extended as compared to patients who have received prior anti-angiogenic therapy. In preferred embodiments of this and other aspects, cabozantinib is administered as cabozantinib (S)-malate.

In another aspect, the invention is directed to a method of treating renal cell carcinoma that has metastasized to bone in a human patient who has received prior anti-angiogenic therapy comprising administering to the patient an amount of cabozantinib or a pharmaceutically acceptable salt thereof wherein progression-free survival (PFS), and one or both of overall survival (OS) and objective response rate (ORR) are extended as compared to patients who have received prior anti-angiogenic therapy. In preferred embodiments of this and other aspects, cabozantinib is administered as cabozantinib (S)-malate.

In another aspect, the invention is directed to a method of treating advanced renal cell carcinoma in a human patient who has received prior anti-angiogenic therapy comprising administering to the patient an amount of cabozantinib (S)-malate sufficient to achieve one or more effects selected from the group consisting of a median time to peak plasma concentration (Tmax) of from approximately 3.2 to 3.8 hours post-dose; and a Cmax of 310 to 350 ng/mL, wherein the median overall survival of the patients are extended as compared to the median overall survival of patients who have received prior anti-angiogenic therapy.

In another aspect, the invention is directed to a method of treating advanced renal cell carcinoma in human patients in need of such treatment who have received prior everolimus therapy, comprising administering to the patients an amount of cabozantinib (S)-malate free base equivalent (FBE) sufficient to achieve one, two, three, four, or five effects selected from the group consisting of:
 a Cmax of 30 to 500 ng/mL;
 an $AUC_{0-24}$ of 500 to 5200 ng*h/mL;
 an $AUC_{0-t}$ of 4500 to 42,000 ng*h/mL;
 an $AUC_{0-\infty}$ of 5000 to 45,000 ng*h/mL;
 a terminal half-life of 90 to 165 h;
 wherein the cabozantinib (S)-malate is administered as a tablet formulation comprising approximately (% w/w):
 31-32 percent by weight of cabozantinib, (S)-malate salt;
 39-40 percent by weight of microcrystalline cellulose;
 19-20 percent by weight of lactose;
 2.5-3.5 percent by weight of hydroxypropyl cellulose;
 5.5-6.5 percent by weight of croscarmellose sodium;
 0.25-0.35 percent by weight of colloidal silicon dioxide;
 0.7-0.8 percent by weight of magnesium stearate; and further comprising:
 3.9-4.1 percent by weight of a film coating material comprising hypromellose, titanium dioxide, triacetin, and iron oxide yellow; and wherein:
 the median overall survival of the patients is extended as compared to the median overall survival of patients taking everolimus; and wherein
 one or both of progression-free survival (PFS) and objective response rate are also extended as compared to patients taking everolimus.

In another aspect, the invention is directed to a method of treating advanced renal cell carcinoma in human patients in need of such treatment who have received prior everolimus therapy, comprising administering to the patients 20 mg, 40 mg, or 60 mg of cabozantinib (S)-malate free base equivalent (FBE) sufficient to achieve one, two, three, four, or five effects selected from the group consisting of:
 a Cmax of 30 to 500 ng/mL;
 an $AUC_{0-24}$ of 500 to 5200 ng*h/mL;
 an $AUC_{0-t}$ of 4500 to 42,000 ng*h/mL;
 an $AUC_{0-\infty}$ of 5000 to 45,000 ng*h/mL;
 a terminal half-life of 90 to 165 h;
 wherein the cabozantinib (S)-malate is administered as a tablet formulation comprising approximately (% w/w):
 31-32 percent by weight of cabozantinib, (S)-malate salt;
 39-40 percent by weight of microcrystalline cellulose;
 19-20 percent by weight of lactose;
 2.5-3.5 percent by weight of hydroxypropyl cellulose;
 5.5-6.5 percent by weight of croscarmellose sodium;
 0.25-0.35 percent by weight of colloidal silicon dioxide;
 0.7-0.8 percent by weight of magnesium stearate; and further comprising: 3.9-4.1 percent by weight of a film coating material comprising hypromellose, titanium dioxide, triacetin, and iron oxide yellow; and wherein:
 the median overall survival of the patients is extended as compared to the median overall survival of patients taking everolimus; and wherein
 one or both of progression-free survival (PFS) and objective response rate are also extended as compared to patients taking everolimus.

In another aspect, the invention is directed to a method of treating advanced renal cell carcinoma in human patients in need of such treatment who have received prior everolimus therapy, comprising administering to the patients an amount of cabozantinib (S)-malate free base equivalent (FBE) sufficient to achieve one, two, three, four, five, six, seven, or eight effects selected from the group consisting of:
 a median time to peak plasma concentration (Tmax) from 2 to 5 hours post-dose;
 a Cmax of 200 to 500 ng/mL;
 an $AUC_{0-24}$ of 2500 to 5200 ng*h/mL;
 an $AUC_{0-t}$ of 18,000 to 42,000 ng*h/mL;
 an $AUC_{0-\infty}$ of 19,000 to 45,000 ng*h/mL;
 an oral volume distribution (Vz/F) of 100 to 600 L;
 a terminal half-life of 90 to 135 h; and
 a clearance at steady state (CL/F) of 0.7 to 3.9 L/h;
 wherein:
the cabozantinib (S)-malate is administered as a tablet formulation comprising approximately (% w/w):
 31-32 percent by weight of cabozantinib, (S)-malate salt;
 39-40 percent by weight of microcrystalline cellulose;
 19-20 percent by weight of lactose;
 2.5-3.5 percent by weight of hydroxypropyl cellulose;
 5.5-6.5 percent by weight of croscarmellose sodium;
 0.25-0.35 percent by weight of colloidal silicon dioxide;
 0.7-0.8 percent by weight of magnesium stearate; and further comprising:
 3.9-4.1 percent by weight of a film coating material comprising hypromellose, titanium dioxide, triacetin, and iron oxide yellow; and wherein:
 the median overall survival of the patients is extended as compared to the median overall survival of patients taking everolimus; and wherein
 one or both of progression-free survival (PFS) and objective response rate are also extended as compared to patients taking everolimus.

In another aspect, the invention is directed to a method of treating renal cell carcinoma in human patients in need of such treatment who have received prior everolimus therapy, comprising administering to the patients 60 mg of cabozantinib (S)-malate free base equivalent (FBE) sufficient to achieve one, two, three, four, five, six, seven, or eight effects selected from the group consisting of:
 a median time to peak plasma concentration (Tmax) from 2 to 5 hours post-dose;
 a Cmax of 200 to 500 ng/mL;
 an $AUC_{0-24}$ of 2500 to 5200 ng*h/mL;

an $AUC_{0-t}$ of 18,000 to 42,000 ng*h/mL;
an $AUC_{0-\infty}$ of 19,000 to 45,000 ng*h/mL;
an oral volume distribution (Vz/F) of 100 to 600 L;
a terminal half-life of 90 to 135 h; and
a clearance at steady state (CL/F) of 0.7 to 3.9 L/h;
wherein:
the cabozantinib (S)-malate is administered as a tablet formulation comprising approximately (% w/w):
31-32 percent by weight of cabozantinib, (S)-malate salt;
39-40 percent by weight of microcrystalline cellulose;
19-20 percent by weight of lactose;
2.5-3.5 percent by weight of hydroxypropyl cellulose;
5.5-6.5 percent by weight of croscarmellose sodium;
0.25-035 percent by weight of colloidal silicon dioxide;
0.7-0.8 percent by weight of magnesium stearate; and
further comprising:
3.9-4.1 percent by weight of a film coating material comprising hypromellose, titanium dioxide, triacetin, and iron oxide yellow; and wherein:
the median overall survival of the patients is extended as compared to the median overall survival of patients taking everolimus; and wherein
one or both of progression-free survival (PFS) and objective response rate are also extended as compared to patients taking everolimus.

In another aspect the invention is directed to a method of treating advanced renal cell carcinoma in patients in need of such treatment who have received prior antiangiogenic therapy selected from the group consisting of sunitinib therapy, pazopanib therapy, and anti-PD-1/PD-L1 immune checkpoint inhibitor therapy, comprising administering cabozantinib

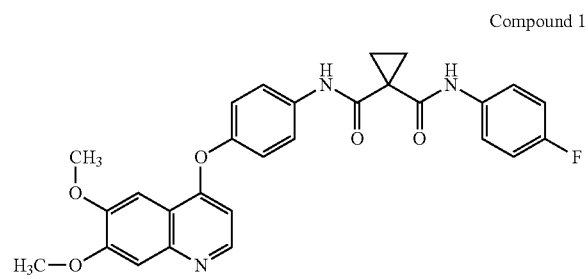

Compound 1 or a pharmaceutically acceptable salt thereof, wherein progression-free survival (PFS), and one or both of overall survival (OS) and objective response rate (ORR) are extended over patients who have received everolimus or another anti-angiogenic therapy. In this and other aspects, cabozantinib is administered as cabozantinib (S)-malate.

In a further aspect, the invention is directed to a method of optimizing the treatment of a renal carcinoma patient with a tyrosine kinase inhibitor (TKI) comprising the step of: quantifying the patient's response to one or more dosing regimens of said TKI inhibitor with a model employing Equation 1:

$$\frac{dY}{dt} = k_{grow} \cdot Y - \frac{(k_{dmax} + k_{dmax_{tol}} \cdot e^{-k_{tol} \cdot t}) \cdot Cavg}{(EC_{50} + Cavg)} \cdot Y \quad \text{Equation 1}$$

where:
dY/dt is the change in tumor diameter per unit time
$k_{grow}$ is the first-order growth rate constant $k_{dmax}$ is the maximum non-attenuating drug induced tumor decay rate
$k_{dmax\_tol}$ is the maximum loss in the decay rate due to resistance
$k_{tol}$ is the rate constant which governs the rate of attenuation
$EC_{50}$ is the cabozantinib concentration yielding one-half of the current tumor decay rate
Cavg is the individual predicted daily average cabozantinib concentration.

In this and other aspects, the TKI is cabozantinib as the S-malate salt.

A further aspect of the present invention is to provide the use of cabozantinib as the S-malate salt for treating advanced renal cell carcinoma in a human patient as described herein. A further aspect of the present invention is to provide the use of cabozantinib as the S-malate salt in the manufacture of a medicament for treating advanced renal cell carcinoma in a human patient as described herein.

Additional embodiments and advantages of the invention will be set forth in part in the description that follows, and will flow from the description, or can be learned by practice of the invention. The embodiments and advantages of the invention will be realized and attained by means of the elements and combinations particularly pointed out in the appended claims.

It is to be understood that both the foregoing summary and the following detailed description are exemplary and explanatory only and are not restrictive of the invention as claimed.

BRIEF DESCRIPTION OF THE DRAWINGS

FIG. 1.1 depicts the progression-free survival rates in Study 1 (First 375 Randomized).

FIG. 1.2 depicts the overall survival in Study 1 (Intent to Treat, ITT).

FIG. 1.3 depicts a flow chart of patient disposition through Dec. 31, 2015.

FIG. 1.4 is a Kaplan-Meier plot of overall survival through Dec. 31, 2015. All 658 randomized patients were included in the analysis.

FIG. 1.5A and FIG. 1.5B depict Forest plots of overall survival and progression-free survival.

FIG. 1.6A and FIG. 1.6B depict Kaplan-Meier Plots of Overall Survival for Subgroups of Tumor MET Expression.

FIG. 1.7 is a Kaplan-Meier plot of progression-free survival as of May 22, 2015.

FIG. 1.8 depicts a schematic view of the METEOR study design.

FIG. 1.9 depicts the statistical design of the METEOR study.

FIG. 1.10 depicts the patient disposition for the METEOR study.

FIG. 1.11 depicts the overall survival of patients by the MSKCC risk group: favorable risk, intermediate risk, and poor risk.

FIG. 1.12 depicts the overall survival of patients by prior VEGFR TKI treatment sunitinib as only prior VEGFR TKI and pazopanib as only prior VEGFR TKI.

FIG. 1.13 depicts the overall survival of patients by presence of bone metastases: bone metastases and bone and visceral metastases.

FIG. 1.14 depicts patient disposition (ITT Population).

FIG. 1.15A and FIG. 1.15B plot absolute FKSI scores over time (IT Population).

FIG. 1.16 depicts the effect of baseline FKSI-DRS on OS (ITT Population). CI, confidence interval; DRS, disease-related symptoms; FKSI, FACT Kidney Symptom Index; HR, hazard ratio; mo, month; OS, overall survival; QoL, quality of life.

FIG. 2.1 depicts the quality of life instruments and quality of life assessment schedule.

FIG. 2.2A and FIG. 2.2B depict FKSI-19 total scores over time.

FIG. 2.3 depicts the time to deterioration (TTD) in the overall population.

FIG. 2.4A and FIG. 2.4B depict the effect of baseline bone metastases on TTD.

FIG. 3.1 depicts progression free survival based on metastatic site and tumor burden.

FIG. 3.2 depicts overall survival based on metastatic site and tumor burden.

FIG. 3.3 depicts the Kaplan-Meier analysis of overall survival.

FIG. 4.1 depicts the METEOR trial within a trial statistical design.

FIG. 4.2A and FIG. 4.2B depict sample plots from statistical studies. Example 1 depicts the potential inability to estimate medians. Example 2 depicts the potential to mask non-proportional hazards.

FIG. 4.3 depicts the Kaplan-Meier analysis of progression free survival.

FIG. 4.4 depicts the evaluation of proportional hazards assumption for progression free survival by log-log plots.

FIG. 5.1 depicts the METEOR enrollment in countries as a percentage of total enrolled patients.

FIG. 5.2 provides Forest plots of progression free survival per IRC by Region.

FIG. 5.3 provides Forest plots of overall survival per IRC by Region.

FIG. 8.1 depicts the progression-free survival per independent radiology committee (IRC) in all 658 randomized patients.

FIG. 8.2 depicts the overall survival over 30 months.

FIG. 8.3. depicts the study design.

FIG. 8.4 shows Kaplan-Meier analyses of progression-free survival in patients with bone metastases, patients with bone and visceral metastases, and patients without bone metastases.

FIG. 8.5 shows Kaplan-Meier analyses of overall survival in patients with bone metastases, patients with bone and visceral metastases, and patients without bone metastases.

FIG. 8.6 depicts the effect of cabozantinib on bone markers for patients with bone metastases at baseline.

FIG. 8.7 depicts the effect of cabozantinib on bone markers for patients without bone metastases at baseline.

FIG. 9.1 depicts the progression free survival of subgroups based on prior therapy (sunitinib, pazopanib, or Anti-PD-1/PD-L1).

FIG. 9.2 depicts the Forest Plot analysis of overall survival.

FIG. 9.3 depicts the overall survival of subgroups based on prior therapy (sunitinib, pazopanib, or Anti-PD-1/PD-L1).

FIG. 9.4 depicts the analysis of progression free survival.

FIG. 9.5 depicts the progression free survival and response in Anti-PD-1/PD-L1 subgroup.

FIG. 10.1 depicts the Cabozantinib PopPK Model.

FIG. 10.2A, FIG. 10.2B, FIG. 10.2C, and FIG. 10.2D depict the PopPK Goodness of Fit by Study and Dose.

FIG. 103 depicts the Impact of Covariates Gender and Asian Race on Steady State Cabozantinib Exposure.

FIG. 10.4 depicts the Predicted Progression-Free Survival Curves for Selected Average Cabozantinib Concentrations.

FIG. 16.5 depicts the Predicted Median Percent Change from Baseline Tumor Diameter for Selected Simulated Starting Doses of Cabozantinib.

DETAILED DESCRIPTION

In preferred embodiments, CABOMETYX® is indicated for the treatment of patients with advanced renal cell carcinoma (RCC) who have received prior anti-angiogenic therapy. Prior anti-angiogenic therapy includes, for instance, a therapy selected from the group consisting of axitinib, pazopanib, sorafenib, sunitinib, everolimus, temsirolimus, bevacizumab, interleukins, interferon-α, peginterferon, nivolumab, AMP-514, and atezolizumab. Dosing information for prior anti-angiogenic therapy is publically available. For example:

axitinib (Inlyta®) is used to treat patients with advanced renal cell carcinoma after failure of one prior systemic therapy. It is administered at a starting dose of 5 mg orally once daily, approximately 12 hours apart, with or without food. Sec www.accessdata.fda.gov/drugsatfda_docs/labc/2012/202324lbl.pdf (last visited Apr. 14, 2017);

pazopanib (Votrient®) is used to treat patients with advanced renal cell carcimona and advanced soft tissue sarcoma who have received prior therapy. It is administered at a dose of 800 mg orally once daily without food. See www.accessdata.fda.gov/drugsatfda_docs/label/2015/022465s020lbledt.pdf (last visited Apr. 14, 2017);

sorafenib (Nexavare) is used to treat patients with unrecectable metastatic carcinoma and advanced renal cell carcinoma. It is administered at a dose of 400 mg (2 tablets) orally twice daily without food. See www.accessdata.fda.gov/drugsatfda_docs/label/2010/021923s008s009lbl.pdf (last visited Apr. 14, 2017);

sunitinib (Sutent®) is used to treat patients with gastrointestinal stromal tumor, advanced renal cell carcinoma, and progressive, well-differentiated pancreatic neuroendocrine tumors in patients with unrectable locally advanced or metastatic disease. It is administered at a dose of 50 mg orally once daily with or without food, four weeks on treatment, followed by two weeks off. See www.accessdata.fda.gov/drugsatfda_docs/label/2011/021938s13s17s18lbl.pdf (last visited Apr. 14, 2017);

everolimus (Afinitor®) is used to treat patients with advanced renal cell carcinoma and subependymal giant cell astrocytoma (SEGA) associated with tuberous sclerosis (TS) who require therapeutic intervention but are not candidates for curative surgical resection. It is administered orally at a dose of 10 mg once daily with or without food. See www.accessdatafda.gov/drugsatfda_docs/label/2010/022334s6lbl.pdf (last visited Apr. 14, 2017);

temsirolimus (Torisel®) (25 mg) is used to treat patients with advanced renal cell carcinoma. It is infused over a 30 to 60 minute period once a week. Treatment is continued until progression or unacceptable toxicity. See www.accessdata.fda.gov/drugsatfda_docs/label/2011/022088s002s004s005s007s010s 012lbl.pdf (last visited Apr. 14, 2017);

bevacizumab (Avastin®) is used to treat patients with metastatic colorectal cancer, with intravenous 5-fluorouracil-based chemotherapy for first- or second-line treatment; metastatic colorectal cancer, with fluoropyrimidine-irinotecan- or fluoropyrimidine-oxaliplatin-based chemotherapy for second-line treatment in patients who have progressed on a first-line Avastin containing regimen; non-squamous non-small cell lung cancer, with carboplatin and paclitaxel for first line treatment of unresectable, locally advanced, recurrent or metastatic disease; glioblastoma, as a single agent for adult patients with progressive disease following prior therapy; and cervical cancer, in combination with paclitaxel and cisplatin or paclitaxel and topotecan in persistent, recurrent, or metastatic disease. It is administered at the recommended dose of 10 mg/kg every 2 weeks in combination with interferon alfa for the treatment of metastatic renal cell carcinoma). Bevacizumab is available in 100 mg/4 mL or 400 mg/16 mL single use vials. See www.accessdata.fda.gov/drugsatfda_docs/label/2014/125085s301lbl.pdf (last visited Apr. 14, 2017);

nivolumab (Opdivo®) is used to treat patients with BRAF V600 wild-type unresectable or metastatic melanoma, as a single agent; BRAF V600 mutation-positive unresectable or metastatic melanoma, as a single agent. This indication is approved under accelerated approval based on progression-free survival. Continued approval for this indication may be contingent upon verification and description of clinical benefit in the confirmatory trials; unresectable or metastatic melanoma, in combination with ipilimumab. This indication is approved under accelerated approval based on progression-free survival. Continued approval for this indication may be contingent upon verification and description of clinical benefit in the confirmatory trials. metastatic non-small cell lung cancer and progression on or after platinum-based chemotherapy. Patients with EGFR or ALK genomic tumor aberrations should have disease progression on FDA-approved therapy for these aberrations prior to receiving OPDIVO; Advanced renal cell carcinoma who have received prior anti-angiogenic therapy; Classical Hodgkin lymphoma that has relapsed or progressed after autologous hematopoietic stem cell transplantation (HSCT) and post-transplantation brentuximab vedotin. This indication is approved under accelerated approval based on overall response rate. Continued approval for this indication may be contingent upon verification and description of clinical benefit in confirmatory trials. It is administered as follows: (i) unresectable or metastatic melanoma—OPDIVO 3 mg/kg every 2 weeks; OPDIVO with ipilimumab: OPDIVO 1 mg/kg, followed by ipilimumab; on the same day, every 3 weeks for 4 doses, then OPDIVO 3 mg/kg every 2 weeks; (ii) metastatic non-small cell lung cancer—OPDIVO 3 mg/kg every 2 weeks; (iii) advanced renal cell carcinoma—OPDIVO 3 mg/kg every 2 weeks; (iv) classical Hodgkin lymphoma—OPDIVO 3 mg/kg every 2 weeks. See www.accessdata.fda.gov/drugsatfda_docs/label/2014/125554lbl.pdf (last visted Apr. 14, 2017); and Atezolizumab (Tecentriq®) is used to treat patients with (i) locally advanced or metastatic urothelial carcinoma who have disease progression during or following platinum-containing chemotherapy; or have disease progression within 12 months of neoadjuvant or adjuvant treatment with platinum-containing chemotherapy. This indication is approved under accelerated approval based on tumor response rate and duration of response. Continued approval for this indication may be contingent upon verification and description of clinical benefit in confirmatory trials; (ii) metastatic non-small cell lung cancer who have disease progression during or following platinum-containing chemotherapy. Patients with EGFR or ALK genomic tumor aberrations should have disease progression on FDA-approved therapy for these aberrations prior to receiving TECENTRIQ. It is administered as an intravenous infusion (1200 mg) over 60 minutes every 3 weeks. It is diluted prior to intravenous infusion. See www.accessdata.fda.gov/drugsatfda_docs/label/2016/761041lbl.pdf (last visited Apr. 14, 2017).

In preferred embodiments, CABOMETYX® tablets should not be substituted with cabozantinib capsules. The recommended daily dose of CABOMETYX® is 60 mg. CABOMETYX® should not be administered with food. Patients should not to eat for at least 2 hours before and at least 1 hour after taking CABOMETYX®. Treatment should be continued until the patient no longer experiences clinical benefit or experiences unacceptable toxicity. CABOMETYX® tablet should be swallowed whole. CABOMETYX® tablet should not be crushed. A missed dose should not be taken within 12 hours of the next dose. Foods (e.g., grapefruit, grapefruit juice) or nutritional supplements that are known to inhibit cytochrome P450 should not be ingested during CABOMETYX® treatment.

In preferred embodiments, treatment with CABOMETYX® should be stopped at least 28 days prior to scheduled surgery, including dental surgery. CABOMETYX® should be withheld for NCI CTCAE Grade 4 adverse reactions, and for Grade 3 or intolerable Grade 2 adverse reactions that cannot be managed with a dose reduction or supportive care. Upon resolution/improvement (i.e., return to baseline or resolution to Grade 1) of an adverse reaction, the dose should be reduced as follows:

If previously receiving 60 mg daily dose, resume treatment at 40 mg daily.

If previously receiving 40 mg daily dose, resume treatment at 20 mg daily.

If previously receiving 20 mg daily dose, resume at 20 mg if tolerated, otherwise, discontinue CABOMETYX®.

In preferred embodiments, CABOMETYX® should be permanently discontinued for any of the following:

development of unmanageable fistula or GI perforation;

severe hemorrhage;

arterial thromboembolic event (e.g., myocardial infarction, cerebral infarction);

hypertensive crisis or severe hypertension despite optimal medical management;

nephrotic syndrome;

reversible posterior leukoencephalopathy syndrome.

In preferred embodiments, in patients concurrently taking a strong CYP3A4 inhibitor, the daily CABOMETYX® dose should be reduced by 20 mg (for example, from 60 mg to 40 mg daily or from 40 mg to 20 mg daily). The dose that was used prior to initiating the CYP3A4 inhibitor should be resumed 2 to 3 days after discontinuation of the strong inhibitor.

In preferred embodiments, in patients concurrently taking a strong CYP3A4 inducer, the daily CABOMETYX® dose should be increased by 20 mg (for example, from 60 mg to 80 mg daily or from 40 mg to 60 mg daily) as tolerated. The dose that was used prior to initiating the CYP3A4 inducer should be resumed 2 to 3 days after discontinuation of the strong inducer. The daily dose of CABOMETYX® should not exceed 80 mg.

In preferred embodiments, in patients with mild or moderate hepatic impairment, the starting dose of CABOMETYX® should be reduced to 40 mg once daily. CABOMETYX® is not recommended for use in patients with severe hepatic impairment.

There are no contraindications for CABOMETYX®.

Cabazaatiaib Tablet Formulations

As indicated previously, the invention relates in part to a method of treating advanced renal cell carcinoma (RCC) in human patients who have received prior anti-angiogenic therapy, wherein progression-free survival (PFS), and one or both of overall survival (OS) and objective response rate (ORR) are extended as compared to patients who have received prior anti-angiogenic therapy.

The invention also relates to a method of treating advanced renal cell carcinoma in a human patient who has received prior anti-angiogenic therapy comprising administering to the patient an amount of cabozantinib (S)-malate sufficient to achieve one or more effects selected from the group consisting of a median time to peak plasma concentration (Tmax) of from approximately 3.2 to 3.8 hours post-dose; and a Cmax of 310 to 350 ng/mL, wherein progression-free survival (PFS), and one or both of overall survival (OS) and objective response rate (ORR) are extended as compared to patients who have received prior anti-angiogenic therapy.

The invention also relates to a method of treating advanced renal cell carcinoma in human patients in need of such treatment who has received prior everolimus therapy, comprising administering to the patients an amount of cabozantinib (S)-malate free base equivalent (FBE) sufficient to achieve one, two, three, four, or five effects selected from the group consisting of:
- a Cmax of 30 to 500 ng/mL;
- an $AUC_{0-24}$ of 500 to 5200 ng*h/mL;
- an $AUC_{0-t}$ of 4500 to 42,000 ng*h/mL;
- an $AUC_{0-\infty}$ of 5000 to 45,000 ng*h/mL;
- a terminal half-life of 90 to 165 h;
- wherein the cabozantinib (S)-malate is administered as a tablet formulation comprising approximately (% w/w):
- 31-32 percent by weight of cabozantinib, (S)-malate salt;
- 39-40 percent by weight of microcrystalline cellulose;
- 19-20 percent by weight of lactose;
- 2.5-3.5 percent by weight of hydroxypropyl cellulose;
- 5.5-6.5 percent by weight of croscarmellose sodium;
- 0.25-035 percent by weight of colloidal silicon dioxide;
- 0.7-0.8 percent by weight of magnesium stearate; and further comprising:
- 3.9-4.1 percent by weight of a film coating material comprising hypromellose, titanium dioxide, triacetin, and iron oxide yellow; and wherein:
- the median overall survival of the patients is extended as compared to the median overall survival of patients taking everolimus; and wherein
- one or both of progression-free survival (PFS) and objective response rate are also extended as compared to patients taking everolimus.

The invention also relates to a method of treating advanced renal cell carcinoma in human patients in need of such treatment who has received prior everolimus therapy, comprising administering to the patients 20 mg, 40 mg or 60 mg of cabozantinib (S)-malate free base equivalent (FBE) sufficient to achieve one, two, three, four, or five effects selected from the group consisting of:
- a Cmax of 30 to 500 ng/mL;
- an $AUC_{0-24}$ of 500 to 5200 ng*h/mL;
- an $AUC_{0-t}$ of 4500 to 42,000 ng*h/mL;
- an $AUC_{0-\infty}$ of 5000 to 45,000 ng*h/mL;
- a terminal half-life of 90 to 165 h;
- wherein the cabozantinib (S)-malate is administered as a tablet formulation comprising approximately (% w/w):
- 31-32 percent by weight of cabozantinib, (S)-malate salt;
- 39-40 percent by weight of microcrystalline cellulose;
- 19-20 percent by weight of lactose;
- 2.5-3.5 percent by weight of hydroxypropyl cellulose;
- 5.5-6.5 percent by weight of croscarmellose sodium;
- 0.25-0.35 percent by weight of colloidal silicon dioxide;
- 0.7-0.8 percent by weight of magnesium stearate; and further comprising:
- 3.9-4.1 percent by weight of a film coating material comprising hypromellose, titanium dioxide, triacetin, and iron oxide yellow; and wherein:
- the median overall survival of the patients is extended as compared to the median overall survival of patients taking everolimus; and wherein
- one or both of progression-free survival (PFS) and objective response rate are also extended as compared to patients taking everolimus.

The invention also relates to a method of treating advanced renal cell carcinoma in a human patient who has received prior anti-angiogenic therapy comprising administering to the patient an amount of cabozantinib (S)-malate FBE sufficient to achieve one, two, three, four, five, six, seven, or eight effects selected from the group consisting of:
- a median time to peak plasma concentration (Tmax) from 2 to 5 hours post-dose;
- a Cmax of 200 to 500 ng/mL;
- an $AUC_{0-24}$ of 2500 to 5200 ng*h/mL;
- an $AUC_{0-t}$ of 18,000 to 42,000 ng*h/mL;
- an $AUC_{0-\infty}$ of 19,000 to 45,000 ng*h/mL;
- an oral volume distribution (Vz/F) of 100 to 600 L;
- a terminal half-life of 90 to 135 h; and
- a clearance at steady state (CL/F) of 0.7 to 3.9 L/h;
- wherein the cabozantinib (S)-malate is administered as a tablet formulation comprising approximately (% w/w):
- 31-32 percent by weight of cabozantinib, (S)-malate salt;
- 39-40 percent by weight of microcrystalline cellulose;
- 19-20 percent by weight of lactose;
- 2.5-3.5 percent by weight of hydroxypropyl cellulose;
- 5.5-6.5 percent by weight of croscarmellose sodium;
- 0.25-035 percent by weight of colloidal silicon dioxide;
- 3.9-4.1 percent by weight of magnesium stearate; and further comprising: 3.9-4.1 percent by weight of a film coating material comprising hypromellose, titanium dioxide, triacetin, and iron oxide yellow;
wherein progression-free survival (PFS), and one or both of overall survival (OS) and objective response rate (ORR) are extended as compared to patients who have received prior anti-angiogenic therapy.

The invention also relates to a method of treating advanced renal cell carcinoma in a human patient who has received prior anti-angiogenic therapy comprising administering to the patient 60 mg of cabozantinib (S)-malate FBE sufficient to achieve one, two, three, four, five, six, seven, or eight effects selected from the group consisting of:
- a median time to peak plasma concentration (Tmax) from 2 to 5 hours post-dose;
- a Cmax of 200 to 500 ng/mL;
- an $AUC_{0-24}$ of 2500 to 5200 ng*h/mL;
- an $AUC_{0-t}$ of 18,000 to 42,000 ng*h/mL;
- an $AUC_{0-\infty}$ of 19,000 to 45,000 ng*h/mL;
- an oral volume distribution (Vz/F) of 100 to 600 L;
- a terminal half-life of 90 to 135 h; and
- a clearance at steady state (CL/F) of 0.7 to 3.9 L/h;

wherein the cabozantinib (S)-malate is administered as a tablet formulation comprising approximately (% w/w):
- 31-32 percent by weight of cabozantinib, (S)-malate salt;
- 39-40 percent by weight of microcrystalline cellulose;
- 19-20 percent by weight of lactose;
- 2.5-3.5 percent by weight of hydroxypropyl cellulose;
- 5.5-6.5 percent by weight of croscarmellose sodium;
- 0.25-0.35 percent by weight of colloidal silicon dioxide;
- 0.7-0.8 percent by weight of magnesium stearate; and further comprising:
- 3.9-4.1 percent by weight of a film coating material comprising hypromellose, titanium dioxide, triacetin, and iron oxide yellow,
- wherein progression-free survival (PFS), and one or both of overall survival (OS) and objective response rate (ORR) are extended as compared to patients who have received prior anti-angiogenic therapy.

Cabozantinib is administered as a tablet comprising cabozantinib (S)-malate, microcrystalline cellulose, anhydrous lactose, hydroxypropyl cellulose, croscarmellose sodium, colloidal silicon dioxide magnesium stearate, and film coating comprising hypromellose, titanium dioxide, triacetin, and iron oxide yellow.

In particular, CABOMETYX® is administered as a tablet comprising cabozantinib (S)-malate, microcrystalline cellulose, anhydrous lactose, hydroxypropyl cellulose, croscarmellose sodium, colloidal silicon dioxide magnesium stearate, and film coating comprising hypromellose, titanium dioxide, triacetin, and iron oxide yellow.

In an embodiment, the cabozantinib (S)-malate is administered as a tablet formulation comprising approximately:
- 30-32 percent by weight of cabozantinib, (S)-malate salt;
- 38-40 percent by weight of microcrystalline cellulose;
- 18-22 percent by weight of lactose;
- 2-4 percent by weight of hydroxypropyl cellulose;
- 4-8 percent by weight of croscarmellose sodium;
- 0.2-0.6 percent by weight of colloidal silicon dioxide;
- 0.5-1 percent by weight of magnesium stearate; and further comprising:
- a film coating material comprising hypromellose, titanium dioxide, triacetin, and iron oxide yellow.

In another embodiment, the cabozantinib (S)-malate is administered as a tablet formulation comprises approximately:
- 31-32 percent by weight of cabozantinib, (S)-malate salt;
- 39-40 percent by weight of microcrystalline cellulose;
- 19-20 percent by weight of lactose;
- 2.5-3.5 percent by weight of hydroxypropyl cellulose;
- 5.5-6.5 percent by weight of croscarmellose sodium;
- 0.25-035 percent by weight of colloidal silicon dioxide;
- 0.7-0.8 percent by weight of magnesium stearate; and further comprising:
- 3.9-4.1 percent by weight of a film coating material comprising hypromellose, titanium dioxide, triacetin, and iron oxide yellow.

In another embodiment the cabozantinib (S)-malate is administered as a tablet formulation selected from the group consisting of:

| Ingredient | Theoretical Quantity (mg/unit dose) | | |
|---|---|---|---|
| | 20-mg Tablet* | 40-mg Tablet* | 60-mg Tablet* |
| Cabozantinib (S)-malate | 25.34 | 50.69 | 76.03 |
| Microcrystalline Cellulose, PH-102 | 31.08 | 62.16 | 93.24 |
| Lactose Anhydrous, 60M | 15.54 | 31.07 | 46.61 |
| Hydroxypropyl Cellulose, EXF | 2.400 | 4.800 | 7.200 |
| Croscarmellose Sodium | 4.800 | 9.600 | 14.40 |
| Colloidal Silicon Dioxide | 0.2400 | 0.4800 | 0.7200 |
| Magnesium Stearate (Non-Bovine) | 0.6000 | 1.200 | 1.800 |
| Opadry ® Yellow (03K92254) | 3.200 | 6.400 | 9.600 |
| Total Tablet weight | 83.20 | 166.4 | 249.6 |

*Free Base Equivalent

In another embodiment, the cabozantinib (S)-malate is administered as a tablet formulation containing 20, 40, or 60 mg of cabozantinib. 60 mg tablets are yellow film-coated, oval shaped with no score, debossed with "XL" on one side and "60" on the other side of the tablet available in bottles of 30 tablet: NDC 42388-023-26. 40 mg tablets are yellow film-coated, triangle shaped with no score, debossed with "XL" on one side and "40" on the other side of the tablet; available in bottles of 30 tablets: NDC 42388-025-26. 20 mg tablets are yellow film-coated, round shaped with no score, debossed with "XL" on one side and "20" on the other side of the tablet; available in bottles of 30 tablets: NDC 42388-024-26.

In another embodiment, CABOMETYX® should be stored at 20° C. to 25° C. (68° F. to 77° F.); excursions are permitted from 15° C. to 30° C. (59° F. to 86° F.) [see USP Controlled Room Temperature].

In a further embodiment, the cabozantinib (S)-malate is administered once daily.

In a further embodiment, the 60 mg of cabozantinib is administered once daily as the CABOMETYX® tablet formulation as described herein.

In a further aspect, the invention described herein relates to a method of treating renal cell carcinoma in a human patient who has received prior anti-angiogenic therapy, comprising administering to the patient 60 mg cabozantinib (S)-malate (free base equivalent) sufficient to achieve one, two, three, four, five, six, seven, or eight effects selected from the group consisting of:
- a median time to peak plasma concentration (Tmax) from 2 to 5 hours post-dose;
- a Cmax of 200 to 500 ng/mL;
- an $AUC_{0-24}$ of 2500 to 5200 ng*h/mL;
- an $AUC_{0-t}$ of 18,000 to 42,000 ng*h/mL;
- an $AUC_{0-\infty}$ of 19,000 to 45,000 ng*h/mL;
- an oral volume distribution (Vz/F) of 100 to 600 L;
- a terminal half-life of 90 to 135 h; and
- a clearance at steady state (CL/F) of 0.7 to 3.9 L/h;
- wherein the cabozantinib (S)-malate is administered as a tablet formulation comprising approximately (% w/w):
- 31-32 percent by weight of cabozantinib, (S)-malate salt;
- 39-40 percent by weight of microcrystalline cellulose;
- 19-20 percent by weight of lactose;
- 2.5-3.5 percent by weight of hydroxypropyl cellulose;
- 5.5-6.5 percent by weight of croscarmellose sodium;
- 0.25-0.35 percent by weight of colloidal silicon dioxide;
- 0.7-0.8 percent by weight of magnesium stearate; and further comprising:
- 3.9-4.1 percent by weight of a film coating material comprising hypromellose, titanium dioxide, triacetin, and iron oxide yellow;

wherein progression-free survival (PFS), and one or both of overall survival (OS) and objective response rate (ORR) are extended as compared to patients who have received prior anti-angiogenic therapy.

In another embodiment, the cabozantinib (S)-malate is administered as a tablet formulation containing 20, 40, or 60 mg of cabozantinib.

In a further embodiment, the cabozantinib (S)-malate is administered in an amount sufficient to achieve one, two, three, four, five, six, seven, or eight effects selected from the group consisting of:
- a median time to peak plasma concentration (Tmax) from 2 to 5 hours post-dose;
- a Cmax of 200 to 500 ng/mL;
- an $AUC_{0-24}$ of 2500 to 5200 ng*h/mL;
- an $AUC_{0-t}$ of 18,000 to 42,000 ng*h/mL;
- an $AUC_{0-\infty}$ of 19,000 to 45,000 ng*h/mL;
- an oral volume distribution (Vz/F) of 100 to 600 L;
- a terminal half-life of 90 to 135 h; and
- a clearance at steady state (CL/F) of 0.7 to 3.9 L/h In a further embodiment, the cabozantinib (S)-malate is administered in an amount sufficient to achieve one, two, three, four, five, six, seven, or eight effects selected from the group consisting of:
- a median time to peak plasma concentration (Tmax) from 2.5 to 4.5 hours post-dose;
- a Cmax of 250 to 450 ng/mL;
- an $AUC_{0-24}$ of 3000 to 4700 ng*h/mL;
- an $AUC_{0-t}$ of 23,000 to 37,000 ng*h/mL;
- an $AUC_{0-\infty}$ of 24,000 to 40,000 ng*h/mL;
- an oral volume distribution (Vz/F) of 150 to 550 L;
- a terminal half-life of 100 to 125 h; and
- a clearance at steady state (CL/F) of 1.2 to 3.2 L/h.

In a further embodiment, the cabozantinib (S)-malate is administered in an amount sufficient to achieve one, two, three, four, five, six, seven, or eight effects selected from the group consisting of:
- a median time to peak plasma concentration (Tmax) from 3 to 4 hours post-dose;
- a Cmax of 300 to 400 ng/mL;
- an $AUC_{0-24}$ of 3500 to 4200 ng*h/mL;
- an $AUC_{0-t}$ of 28,000 to 32,000 ng*h/mL;
- an $AUC_{0-\infty}$ of 29,000 to 35,000 ng*h/mL;
- an oral volume distribution (Vz/F) of 200 to 500 L;
- a terminal half-life of 110 to 115 h; and
- a clearance at steady state (CL/F) of 1.2 to 3.2

In a further embodiment, the cabozantinib (S)-malate is administered in an amount sufficient to achieve one, two, three, four, five, six, seven, or eight effects selected from the group consisting of:
- a median time to peak plasma concentration (Tmax) from 3.2 to 3.8 hours post-dose;
- a Cmax of 310 to 350 ng/mL;
- an $AUC_{0-24}$ of 3700 to 4000 ng*h/mL;
- an $AUC_{0-t}$ of 29,000 to 30,000 ng*h/mL;
- an $AUC_{0-\infty}$ of 30,000 to 33,000 ng*h/mL;
- an oral volume distribution (Vz/F) of 300 to 400 L;
- a terminal half-life of 110 to 114 h; and
- a clearance at steady state (CL/F) of 2 to 3.

Warnings and Precautions

Severe hemorrhage occurred with CABOMETYX®. The incidence of Grade ≥3 hemorrhagic events was 2.1% in CABOMETYX-treated patients and 1.6% in everolimus-treated patients. Fatal hemorrhages also occurred in the cabozantinib clinical program. CABOMETYX® should not be administered to patients that have or are at risk for severe hemorrhage.

In a randomized study in renal cell carcinoma, fistulas were reported in 1.2% (including 0.6% anal fistula) of CABOMETYX-treated patients and 0% of everolimus-treated patients. Gastrointestinal (GI) perforations were reported in 0.9% of CABOMETYX-treated patients and 0.6% of everolimus-treated patients. Fatal perforations occurred in the cabozantinib clinical program. Patients should be monitored for symptoms of fistulas and perforations. CABOMETYX® should be discontinued in patients who experience a fistula which cannot be appropriately managed or a GI perforation.

CABOMETYX® treatment results in an increased incidence of thrombotic events. Venous thromboembolism was reported in 7.3% of CABOMETYX-treated patients and 2.5% of everolimus-treated patients. Pulmonary embolism occurred in 3.9% of CABOMETYX-treated patients and 0.3% of everolimus-treated patients. Events of arterial thromboembolism were reported in 0.9% of CABOMETYX-treated patients and 0.3% of everolimus-treated patients. Fatal thrombotic events occurred in the cabozantinib clinical program. CABOMETYX® should be discontinued in patients who develop an acute myocardial infarction or any other arterial thromboembolic complication.

CABOMETYX® treatment results in an increased incidence of treatment-emergent hypertension. Hypertension was reported in 37% (15% Grade ≥3) of CABOMETYX-treated patients and 7.1% (3.1% Grade ≥3) of everolimus-treated patients. Patients' blood pressure should be monitored prior to initiation and regularly during CABOMETYX® treatment. CABOMETYX® should be withheld for hypertension that is not adequately controlled with medical management; when controlled, CABOMETYX® should be resumed at a reduced dose. CABOMETYX® should be discontinued for severe hypertension that cannot be controlled with anti-hypertensive therapy. CABOMETYX® should be discontinued if there is evidence of hypertensive crisis or severe hypertension despite optimal medical management.

Diarrhea occurred in 74% of patients treated with CABOMETYX® and was Grade 3 in 11% of patients. CABOMETYX® should be withheld in patients who develop intolerable Grade 2 diarrhea or Grade 3-4 diarrhea that cannot be managed with standard antidiarrheal treatments until improvement to Grade 1; upon improvement to Grade 1, CABOMETYX® should be resumed at a reduced dose. Dose modification due to diarrhea occurred in 26% of patients.

Palmar-plantar erythrodysesthesia syndrome (PPES) occurred in 42% of patients treated with CABOMETYX® and was Grade 3 in 8.2% of patients. CABOMETYX® should be withheld in patients who develop intolerable Grade 2 PPES or Grade 3 PPES until improvement to Grade 1; upon improvement to Grade 1, CABOMETYX® should be resumed at a reduced dose. Dose modification due to PPES occurred in 16% of patients.

Reversible Posterior Leukoencephalopathy Syndrome (RPLS), a syndrome of subcortical vasogenic edema diagnosed by characteristic finding on MRI, occurred in the cabozantinib clinical program. An evaluation for RPLS should be performed in any patient presenting with seizures, headache, visual disturbances, confusion or altered mental function. CABOMETYX® should be discontinued in patients who develop RPLS.

Based on data from animal studies and its mechanism of action, CABOMETYX® can cause fetal harm when administered to a pregnant woman. Cabozantinib administration to pregnant animals during organogenesis resulted in embryo-lethality at exposures below those occurring clinically at the recommended dose, and in increased incidences of skeletal variations in rats and visceral variations and malformations in rabbits. Pregnant women should be advised of the potential risk to a fetus. Females of reproductive potential should be advised to use effective contraception during treatment with CABOMETYX® and for 4 months after the last dose.

Adverse Reactions

Adverse Reactions are summarized in Tables A and B. The following serious adverse reactions are discussed elsewhere in the application: hemorrhage; GI perforations and fistulas; thrombotic events; hypertension and hypertensive; crisis diarrhea; palmar-plantar erythrodysesthesia syndrome; reversible posterior leukoencephalopathy syndrome.

Cliaical Trial Experience

Because clinical trials are conducted under widely varying conditions, adverse reaction rates observed in the clinical trials of a drug cannot be directly compared to rates in the clinical trials of another drug and may not reflect the rates observed in practice.

The safety of CABOMETYX® was evaluated in Study 1, a randomized, open-label trial in which 331 patients with advanced renal cell carcinoma received 60 mg CABOMETYX® and 322 patients received 10 mg everolimus administered daily until the patient no longer experienced clinical benefit or experienced intolerable toxicity. The median duration of treatment was 7.6 months (range 0.3-20.5) for patients receiving CABOMETYX® and 4.4 months (range 0.21-18.9) for patients receiving everolimus.

Adverse reactions which occurred in ≥25% of CABOMETYX®-treated patients included, in order of decreasing frequency: diarrhea, fatigue, nausea, decreased appetite, palmar-plantar erythrodysesthesia syndrome (PPES), hypertension, vomiting, weight decreased, and constipation. Grade 3-4 adverse reactions which occurred in ≥5% of patients were fatigue, diarrhea, hypertension, palmar-plantar erythrodysesthesia syndrome, and anemia.

The most common laboratory abnormalities in CABOMETYX-treated patients (≥25%) were: hypophosphatemia, hypomagnesemia, increased lipase, hyponatremia, AST increased, and ALT increased.

The dose was reduced in 60% of patients receiving CABOMETYX® and in 24% of patients receiving everolimus. Twenty percent (20%) of patients received 20 mg CABOMETYX® as their lowest dose. The most frequent adverse reactions leading to dose reduction in patients treated with CABOMETYX® were: diarrhea, PPES, fatigue, and hypertension. Adverse reactions led to study treatment being held in 70% patients receiving CABOMETYX® and in 59% patients receiving everolimus. Adverse reactions led to study treatment discontinuation in 10% of patients receiving CABOMETYX® and in 10% of patients receiving everolimus. The most frequent adverse reactions leading to permanent discontinuation in patients treated with CABOMETYX® were decreased appetite (2%) and fatigue (1%).

TABLE A

Adverse Reactions Occurring in ≥10% Patients Who Received CABOMETYX

| Adverse Reaction | CABOMETYX (n = 331) [1] | | Everolimus (n = 322) | |
|---|---|---|---|---|
| | All Grades[2] | Grade 3-4 | All Grades[2] | Grade 3-4 |
| | Percentage (%) of Patients | | | |
| Gastrointestinal Disorders | | | | |
| Diarrhea | 74 | 11 | 28 | 2 |
| Nausea | 50 | 4 | 28 | <1 |
| Vomiting | 32 | 2 | 14 | <1 |
| Stomatitis | 22 | 2 | 24 | 2 |
| Constipation | 25 | <1 | 19 | <1 |
| Abdominal pain [3] | 23 | 4 | 13 | 2 |
| Dyspepsia | 12 | <1 | 5 | 0 |
| General Disorders and Administration Site Conditions | | | | |
| Fatigue | 56 | 9 | 47 | 7 |
| Mucosal inflammation | 19 | <1 | 23 | 3 |
| Asthenia | 19 | 4 | 16 | 2 |
| Metabolism and Nutrition Disorders | | | | |
| Decreased appetite | 46 | 3 | 34 | <1 |
| Skin and Subcutaneous Tissue Disorders | | | | |
| Palmar-plantar erythro-dysesthesia syndrome | 42 | 8 | 6 | <1 |
| Rash [4] | 23 | <1 | 43 | <1 |
| Dry skin | 11 | 0 | 10 | 0 |
| Vascular Disorders | | | | |
| Hypertension [5] | 39 | 16 | 8 | 3 |
| Investigations | | | | |
| Weight decreased | 31 | 2 | 12 | 0 |
| Nervous System Disorders | | | | |
| Dysgeusia | 24 | 0 | 9 | 0 |
| Headache | 11 | <1 | 12 | <1 |
| Dizziness | 11 | 0 | 7 | 0 |
| Endocrine Disorders | | | | |
| Hypothyroidism | 21 | 0 | <1 | <1 |
| Respiratory, Thoracic, and Mediastinal Disorders | | | | |
| Dysphonia | 20 | <1 | 4 | 0 |
| Dyspnea | 19 | 3 | 29 | 4 |
| Cough | 18 | <1 | 33 | <1 |
| Blood and Lymphatic Disorders | | | | |
| Anemia | 17 | 5 | 38 | 16 |
| Musculoskeletal and Connective Tissue Disorders | | | | |
| Pain in extremity | 14 | 1 | 8 | <1 |
| Muscle spasms | 13 | 0 | 5 | 0 |
| Arthralgia | 11 | <1 | 14 | 1 |
| Renal and Urinary Disorders | | | | |
| Proteinuria | 12 | 2 | 9 | <1 |

[1] One subject randomized to everolimus received cabozantinib.
[2] National Cancer Institute Common Terminology Criteria for Adverse Events Version 4.0
[3] Includes PT terms abdominal pain, abdominal pain upper, and abdominal pain lower
[4] Includes PT terms rash, rash erythematous, rash follicular, rash macular, rash papular, rash pustular, rash vesicular, genital rash, intermittent leg rash, rash on scrotum and penis, rash maculo-papular, rash pruritic, contact dermatitis, dermatitis acneiform
[5] Includes PT terms hypertension, blood pressure increased, hypertensive crisis, blood pressure fluctuation Other clinically important adverse reactions (all grades) that were reported in <10% of patients treated with CABOMETYX® included: wound complications (2%), convulsion (<1%), pancreatitis (<1%), osteonecrosis of the jaw (<1%), and hepatitis cholestatic (<1%).

TABLE B

Laboratory Abnormalities Occurring in ≥25% Patients Who Received CABOMETYX

| Test | CABOMETYX (n = 331) | | Everolimus (n = 322) | |
|---|---|---|---|---|
| | All Grades | Grade 3-4 | All Grades | Grade 3-4 |
| Chemistry | | | | |
| AST increased | 74 | 3 | 40 | <1 |
| ALT increased | 68 | 3 | 32 | <1 |
| Creatinine increased | 58 | <1 | 71 | 0 |
| Triglycerides increased | 53 | 4 | 73 | 13 |
| Hypophosphatemia | 48 | 8 | 36 | 5 |
| Hyperglycemia | 37 | 2 | 59 | 8 |
| Hypoalbuminemia | 36 | 2 | 28 | <1 |
| ALP increased | 35 | 2 | 29 | 1 |
| Hypomagnesemia | 31 | 7 | 4 | <1 |
| Hyponatremia | 30 | 8 | 26 | 6 |
| GGT increased | 27 | 5 | 43 | 9 |
| Hematology | | | | |
| White blood cells decreased | 35 | <1 | 31 | <1 |
| Absolute neutrophil count decreased | 31 | 2 | 17 | <1 |
| Hemoglobin decreased | 31 | 4 | 71 | 17 |
| Lymphocytes decreased | 25 | 7 | 39 | 12 |
| Platelets decreased | 25 | <1 | 27 | <1 |

ALP, alkaline phosphatase;
ALT, alanine aminotransferase;
AST, aspartate aminotransferase;
GGT, gamma glutamyl transferase.
National Cancer Institute Common Terminology Criteria for Adverse Events, Version 4.0

Drug Interactions

Drug interactions are summarized in Table C.

TABLE C

Clinically Significant Drug Interactions Involving Drugs that Affect Cabozantinib

| Strong CYP3A4 Inhibitors | |
|---|---|
| Clinical Implications: | Concomitant use of CABOMETYX ® with a strong CYP3A4 inhibitor increased the exposure of cabozantinib compared to the use of CABOMETYX ® alone. Increased cabozantinib exposure may increase the risk of exposure-related toxicity. |
| Prevention or Management: Examples: | Reduce the dosage of CABOMETYX ® if concomitant use with strong CYP3A4 inhibitors cannot be avoided. Boceprevir, clarithromycin, conivaptan, grapefruit juice[a], indinavir, itraconazole, ketoconazole, lopinavir/ritonavir, nefazodone, nelfinavir, posaconazole, ritonavir, saquinavir, telithromycin, and voriconazole |
| Strong CYP3A4 Inducers | |
| Clinical Implications: | Concomitant use of CABOMETYX ® with a strong CYP3A4 inducer decreased the exposure of cabozantinib compared to the use of CABOMETYX ® alone. Decreased cabozantinib exposure may lead to reduced efficacy. |

TABLE C-continued

Clinically Significant Drug Interactions Involving Drugs that Affect Cabozantinib

| Prevention or Management: Examples: | Increase the dosage of CABOMETYX ® if concomitant use with strong CYP3A4 inducers cannot be avoided. Rifampin, phenytoin, carbamazepine, phenobarbital, rifabutin, rifapentine, and St. John's Wort[b] |
|---|---|

[a]The effect of grapefruit juice varies widely among brands and is concentration-, dose-, and preparation-dependent. Studies have shown that it can be classified as a "strong CYP3A inhibitor" when a certain preparation was used (e.g., high dose, double strength) or as a "moderate CYP3A inhibitor" when another preparation was used (e.g., low dose, single strength).
[b]The effect of St. John's Wort varies widely and is preparation-dependent Use in Specific Populations Pregnancy Based on findings from animal studies and its mechanism of action, CABOMETYX® can cause fetal harm when administered to a pregnant woman.

There are no available data in pregnant women to inform the drug-associated risk. In animal developmental and reproductive toxicology studies administration of cabozantinib to pregnant rats and rabbits during organogenesis resulted in embryofetal lethality and structural anomalies at exposures that were below those occurring clinically at the recommended dose. Pregnant women or women of childbearing potential should be advised of the potential hazard to a fetus.

The estimated background risk of major birth defects and miscarriage for the indicated population is unknown. In the U.S. general population, the estimated background risk of major birth defects and miscarriage in clinically recognized pregnancies is 2-4% and 15-20%, respectively.

In an embryo-fetal development study in pregnant rats, daily oral administration of cabozantinib throughout organogenesis caused increased embryo-fetal lethality compared to controls at a dose of 0.03 mg/kg (approximately 0.12-fold of human AUC at the recommended dose). Findings included delayed ossification and skeletal variations at a dose of 0.1 mg/kg/day (approximately 0.04-fold of human AUC at the recommended dose).

In pregnant rabbits, daily oral administration of cabozantinib throughout organogenesis resulted in findings of visceral malformations and variations including reduced spleen size and missing lung lobe at 3 mg/kg (approximately 1.1-fold of the human AUC at the recommended dose).

In a pre- and postnatal study in rats, cabozantinib was administered orally from gestation day 10 through postnatal day 20. Cabozantinib did not produce adverse maternal toxicity or affect pregnancy, parturition or lactation of female rats, and did not affect the survival, growth or postnatal development of the offspring at doses up to 0.3 mg/kg/day (0.05-fold of the maximum recommended clinical dose).

Lactation

There is no information regarding the presence of cabozantinib or its metabolites in human milk, or their effects on the breastfed infant, or milk production. Because of the potential for serious adverse reactions in a breastfed infant from CABOMETYX, a lactating woman should be advised not to breastfeed during treatment with CABOMETYX® and for 4 months after the final dose.

Females and Males of Reproductive Potential

CABOMETYX® can cause fetal harm when administered to a pregnant woman. Females of reproductive potential should be advised to use effective contraception during treatment with CABOMETYX® and for 4 months after the final dose.

Infertility

Based on findings in animals, CABOMETYX® may impair fertility in females and males of reproductive potential.

Pediatric Use

The safety and effectiveness of CABOMETYX® in pediatric patients have not been studied.

Juvenile Animal Data

Juvenile rats were administered cabozantinib daily at doses of 1 or 2 mg/kg/day from Postnatal Day 12 (comparable to less than 2 years in humans) through Postnatal Day 35 or 70. Mortalities occurred at doses equal and greater than 1 mg/kg/day (approximately 0.16 times the clinical dose of 60 mg/day based on body surface area). Hypoactivity was observed at both doses tested on Postnatal Day 22. Targets were generally similar to those seen in adult animals, occurred at both doses, and included the kidney (nephropathy, glomerulonephritis), reproductive organs, gastrointestinal tract (cystic dilatation and hyperplasia in Brunner's gland and inflammation of duodenum; and epithelial hyperplasia of colon and cecum), bone marrow (hypocellularity and lymphoid depletion), and liver. Tooth abnormalities and whitening as well as effects on bones including reduced bone mineral content and density, physeal hypertrophy, and decreased cortical bone also occurred at all dose levels. Recovery was not assessed at the 2 mg/kg dose level (approximately 0.32 times the clinical dose of 60 mg based on body surface area) due to high levels of mortality. At the low dose level, effects on bone parameters were partially resolved but effects on the kidney and epididymis/testis persisted after treatment ceased.

Geriatric Use

In the Phase 3 study, 41% of RCC patients treated with CABOMETYX® were age 65 years and older, and 8% were age 75 and older. No differences in safety or efficacy were observed between older and younger patients.

Hepatic Impairment

Increased exposure to cabozantinib has been observed in patients with mild to moderate hepatic impairment. The CABOMETYX® dose should be reduced in patients with mild (Child-Pugh score (C-P) A) or moderate (C-P B) hepatic impairment. CABOMETYX® is not recommended for use in patients with severe hepatic impairment Renal Impairment Dosage adjustment is not required in patients with mild or moderate renal impairment. There is no experience with CABOMETYX® in patients with severe renal impairment.

Overdosage

One case of overdosage was reported in the cabozantinib clinical program; a patient inadvertently took twice the intended dose (200 mg daily) of another formulation of cabozantinib product for nine days. The patient suffered Grade 3 memory impairment, Grade 3 mental status changes, Grade 3 cognitive disturbance, Grade 2 weight loss, and Grade 1 increase in BUN. The extent of recovery was not documented.

Description

CABOMETYX® comprises the (S)-malate salt of cabozantinib, a kinase inhibitor. Cabozantinib (S)-malate is described chemically as N-(4-(6,7-dimethoxyquinolin-4-yloxy)phenyl)-N'-(4-fluorophenyl)cyclopropane-1,1-dicarboxamide, (2S)-hydroxybutanedioate. The molecular formula is $C_{28}H_{24}FN_3O_5 \cdot C_4H_6O_5$ and the molecular weight is 635.6 Daltons as malate salt. The chemical structure of cabozantinib (S)-malate salt is:

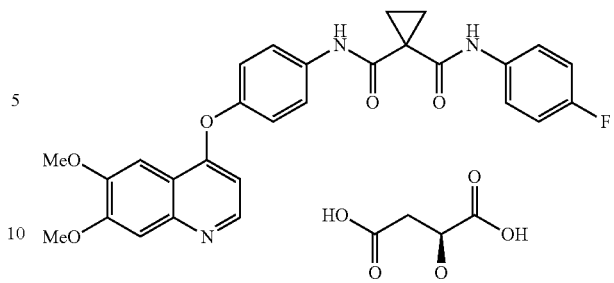

Cabozantinib (S)-malate salt is an white to off-white solid that is practically insoluble in aqueous media.

CABOMETYX® (cabozantinib) tablets are supplied as film-coated tablets containing 20 mg, 40 mg, or 60 mg of cabozantinib, which is equivalent to 25 mg, 51 mg, or 76 mg of cabozantinib (S)-malate, respectively. CABOMETYX® also contains the following inactive ingredients: microcrystalline cellulose, lactose anhydrous, hydroxypropyl cellulose, croscarmellose sodium, colloidal silicon dioxide, and magnesium stearate.

The film coating contains hypromellose, titanium dioxide, triacetin, and iron oxide yellow.

Clinical Pharmacology

Mechanism of Action

In vitro biochemical and/or cellular assays have shown that cabozantinib inhibits the tyrosine kinase activity of MET, VEGFR-1, -2 and -3, AXL, RET, ROS1, TYRO3, MER, KIT, TRKB, FLT-3, and TIE-2. These receptor tyrosine kinases are involved in both normal cellular function and pathologic processes such as oncogenesis, metastasis, tumor angiogenesis, drug resistance, and maintenance of the tumor microenvironment.

Pharmacodynamics

The exposure-response or -safety relationship for cabozantinib is unknown.

Cardiac Electrophysiology

The effect of orally administered cabozantinib on QTc interval was evaluated in a randomized, double-blinded, placebo-controlled study in patients with medullary thyroid cancer administered a dose of 140 mg. A mean increase in QTcF of 10-15 ms was observed at 4 weeks after initiating cabozantinib. A concentration-QTc relationship could not be definitively established. Changes in cardiac wave form morphology or new rhythms were not observed. No cabozantinib-treated patients in this study had a confirmed QTcF>500 ms nor did any cabozantinib-treated patients in the RCC study (at a dose of 60 mg).

Pharmacokinetics

Repeat daily dosing of cabozantinib at 140 mg for 19 days resulted in 4- to 5-fold mean cabozantinib accumulation (based on AUC) compared to a single dose administration; steady state was achieved by Day 15.

Absorption

Following oral administration of cabozantinib, median time to peak cabozantinib plasma concentrations ($T_{max}$) ranged from 2 to 3 hours post-dose.

A 19% increase in the $C_{max}$ of the tablet formulation (CABOMETYX) compared to the capsule formulation (COMETRIQ®) was observed following a single 140 mg dose. A less than 10% difference in the AUC was observed between cabozantinib tablet (CABOMETYX) and capsule (COMETRIQ) formulations.

Cabozantinib $C_{max}$ and AUC values increased by 41% and 57%, respectively, following a high-fat meal relative to fasted conditions in healthy subjects administered a single 140 mg oral dose of an investigational cabozantinib capsule formulation.

Distribution

The oral volume of distribution ($V_z/F$) of cabozantinib is approximately 319 L. Cabozantinib is highly protein bound in human plasma (≥99.7%).

Elimination

The predicted terminal half-life is approximately 99 hours and the clearance (CL/F) at steady-state is estimated to be 2.2 L/hr.

Metabolism

Cabozantinib is a substrate of CYP3A4 in vitro.

Excretion

Approximately 81% of the total administered radioactivity was recovered within a 48-day collection period following a single 140 mg dose of an investigational $^{14}$C-cabozantinib formulation in healthy subjects. Approximately 54% was recovered in feces and 27% in urine. Unchanged cabozantinib accounted for 43% of the total radioactivity in feces and was not detectable in urine following a 72 hour collection.

Specific Populations

The following patient characteristics did not result in a clinically relevant difference in the pharmacokinetics of cabozantinib: age (32-86 years), sex, race (Whites and non-Whites), or mild to moderate renal impairment (eGFR greater than or equal to 30 mL/min/1.73 m$^2$ as estimated by MDRD (modification of diet in renal disease equation)). The pharmacokinetics of cabozantinib is unknown in patients with worse than moderate renal impairment (eGFR less than 29 mL/min/1.73 m$^2$) as estimated by MDRD equation or renal impairment requiring dialysis.

Hepatic Impairment

Cabozantinib exposure ($AUC_{0-inf}$) increased by 81% and 63%, respectively, in patients with mild (C-P A) and moderate (C-P B) hepatic impairment. Patients with severe hepatic impairment have not been studied.

Pediatric Population

The pharmacokinetics of cabozantinib has not been studied in the pediatric population.

Drug Interactions

CYP3A4 Inhibition on Cabozantinib:

Administration of a strong CYP3A4 inhibitor, ketoconazole (400 mg daily for 27 days) to healthy subjects increased single-dose plasma cabozantinib exposure ($AUC_{0-inf}$) by 38%.

CYP3A4 Induction on Cabozantinib:

Administration of a strong CYP3A4 inducer, rifampin (600 mg daily for 31 days) to healthy subjects decreased single-dose plasma cabozantinib exposure ($AUC_{0-inf}$) by 77%.

Cabozantinib on CYP2C8 Substrates:

No clinically-significant effect on single-dose rosiglitazone (a CYP2C8 substrate) plasma exposure ($C_{max}$ and AUC) was observed when co-administered with cabozantinib at steady-state plasma concentrations (≥100 mg/day daily for a minimum of 21 days) in patients with solid tumors.

Gastric pH Modifying Agents on Cabozantinib:

No clinically-significant effect on plasma cabozantinib exposure (AUC) was observed following co-administration of the proton pump inhibitor (PPI) esomeprazole (40 mg daily for 6 days) with a single dose of 100 mg cabozantinib to healthy volunteers.

In Vitro Studies

Metabolic Pathways

Inhibition of CYP3A4 reduced the formation of the oxidative metabolite by >80%. Inhibition of CYP2C9 had a minimal effect on cabozantinib metabolite formation (i.e., a <20% reduction). Inhibition of CYP1A2, CYP2A6, CYP2B6, CYP2C8, CYP2C19, CYP2D6 and CYP2E1 had no effect on cabozantinib metabolite formation.

Although cabozantinib is an inhibitor of CYP2C8 in vitro, a clinical study of this potential interaction concluded that concurrent use did not result in a clinically relevant effect on CYP2C8 substrate exposure. Given this finding, other less sensitive substrates of pathways affected by cabozantinib in vitro (i.e., CYP2C9, CYP2C19, and CYP3A4) were not evaluated in a clinical study because, although a clinically relevant exposure effect cannot be ruled out, it is unlikely. Cabozantinib does not inhibit CYP1A2 and CYP2D6 isozymes in vitro.

Cabozantinib is an inducer of CYP1A1 mRNA; however, the clinical relevance of this finding is unknown. Cabozantinib does not induce CYP1A2, CYP2B6, CYP2C8, CYP2C9, CYP2C19 or CYP3A4.

Drug Transporter Systems

Cabozantinib is an inhibitor, but not a substrate, of P-gp transport activities and has the potential to increase plasma concentrations of co-administered substrates of P-gp. The clinical relevance of this finding is unknown. Cabozantinib is a substrate of MRP2 in vitro and MRP2 inhibitors have the potential to increase plasma concentrations of cabozantinib. The clinical relevance of this finding is unknown.

Nonclinical Toxicology

Carcinogenesis, Mutagenesis, Impairment of Fertility

Cabozantinib was not carcinogenic in a 26-week carcinogenicity study in rasH2 transgenic mice. Cabozantinib was not mutagenic in vitro in the bacterial reverse mutation (Ames) assay and was not clastogenic in both the in vitro cytogenetic assay using human lymphocytes or in the in vivo mouse micronucleus assay. Based on nonclinical findings, male and female fertility may be impaired by treatment with CABOMETYX®. In a fertility study in which cabozantinib was administered to male and female rats at doses of 1, 2.5, and 5 mg/kg/day, male fertility was significantly compromised at doses equal to or greater than 2.5 mg/kg/day (approximately 13-fold of human AUC at the recommended dose), with a decrease in sperm counts and reproductive organ weights. In females, fertility was significantly reduced at doses equal to or greater than 1 mg/kg/day (5-fold of human AUC at the recommended dose) with a significant decrease in the number of live embryos and a significant increase in pre- and post-implantation losses.

Observations effects on reproductive tract tissues in general toxicology studies were supportive effects noted in the dedicated fertility study and included hypospermia and absence of corpora lutea in male and female dogs in a 6-month repeat dose study at plasma exposures (AUC) approximately 0.5-fold (males) and <0.1-fold (females) of those expected in humans at the recommended dose. In addition, female rats administered 5 mg/kg/day for 14 days (approximately 9-fold of human AUC at the recommended dose) exhibited ovarian necrosis.

EMBODIMENTS

The following embodiments are included in the invention.

Embodiment 1

A method of treating advanced renal cell carcinoma with or without bone metastases in a human patient who has received prior anti-angiogenic therapy, comprising administering to the patient an amount of cabozantinib or a pharmaceutically acceptable salt thereof wherein progression-free survival (PFS) and one or both of overall survival (OS) and objective response rate (ORR) are extended as compared to patients who have received prior anti-angiogenic therapy, wherein the prior anti-angiogenic therapy is selected from the group consisting of axitinib, pazopanib, sorafenib, sunitinib, everolimus, temsirolimus, bevacizumab, interleukins, interferon-α, peginterferon, nivolumab, AMP-514, and atezolizumab.

Embodiment 2

The method of embodiment 1, wherein the cabozantinib is administered as cabozantinib (S)-malate.

Embodiment 3

The method of any of embodiments 1-2, wherein cabozantinib (S)-malate is administered in an amount sufficient to achieve a median time to peak plasma concentration (Tmax) of from approximately 2 to 5 hours post-dose; and a Cmax of 200 to 500 ng/mL.

Embodiment 4

The method of any of embodiments 1-3, wherein the prior antiangiogenic therapy is selected from the group consisting of axitinib, pazopanib, sorafenib, sunitinib, everolimus, temsirolimus, bevacizumab, nivolumab, AMP-514, and atezolizumab.

Embodiment 5

The method of any of embodiments 1-4, wherein the prior anti-angiogenic therapy is everolimus.

Embodiment 6

The method of any of embodiments 1-5, wherein cabozantinib (S)-malate is administered as a tablet comprising cabozantinib (S)-malate, microcrystalline cellulose, anhydrous lactose, hydroxypropyl cellulose, croscarmellose sodium, colloidal silicon dioxide magnesium stearate, and film coating comprising hypromellose, titanium dioxide, triacetin, and iron oxide yellow.

Embodiment 7

The method of any of embodiments 1-6, wherein the cabozantinib (S)-malate is administered as a tablet formulation comprising approximately:
  30-32 percent by weight of cabozantinib, (S)-malate salt;
  38-40 percent by weight of microcrystalline cellulose;
  18-22 percent by weight of lactose;
  2-4 percent by weight of hydroxypropyl cellulose;
  4-8 percent by weight of croscarmellose sodium;
  0.2-0.6 percent by weight of colloidal silicon dioxide;
  0.5-1 percent by weight of magnesium stearate; and further comprising:
  a film coating material comprising hypromellose, titanium dioxide, triacetin, and iron oxide yellow.

Embodiment 8

The method of any of embodiments 1-7, wherein the cabozantinib (S)-malate is administered as a tablet formulation comprising approximately (% w/w):
  31-32 percent by weight of cabozantinib, (S)-malate salt;
  39-40 percent by weight of microcrystalline cellulose;
  19-20 percent by weight of lactose;
  2.5-3.5 percent by weight of hydroxypropyl cellulose;
  5.5-6.5 percent by weight of croscarmellose sodium;
  0.25-0.35 percent by weight of colloidal silicon dioxide;
  0.7-0.8 percent by weight of magnesium stearate; and further comprising:
  3.9-4.1 percent by weight of a film coating material comprising hypromellose, titanium dioxide, triacetin, and iron oxide yellow.

Embodiment 9

The method of any of embodiments 1-8, wherein cabozantinib (S)-malate is administered as a tablet formulation containing 20, 40, or 60 mg of cabozantinib (FBE).

Embodiment 10

The method of any of embodiments 1-9, wherein cabozantinib (S)-malate is administered as a tablet formulation selected from the group consisting of:

| Ingredient | Theoretical Quantity (mg/unit dose) | | |
|---|---|---|---|
| | 20-mg Tablet* | 40-mg Tablet* | 60-mg Tablet* |
| Cabozantinib (S)-malate | 25.34 | 50.69 | 76.03 |
| Microcrystalline Cellulose, PH-102 | 31.08 | 62.16 | 93.24 |
| Lactose Anhydrous, 60M | 15.54 | 31.07 | 46.61 |
| Hydroxypropyl Cellulose, EXF | 2.400 | 4.800 | 7.200 |
| Croscarmellose Sodium | 4.800 | 9.600 | 14.40 |
| Colloidal Silicon Dioxide | 0.2400 | 0.4800 | 0.7200 |
| Magnesium Stearate (Non-Bovine) | 0.6000 | 1.200 | 1.800 |
| Opadry ® Yellow (03K92254) | 3.200 | 6.400 | 9.600 |
| Total tablet weight | 83.20 | 166.4 | 249.6 |

*Free Base Equivalent (FBE)

Embodiment 11

The method of any of embodiments 1-10, wherein the cabozantinib (S)-malate is administered once daily.

Embodiment 12

The method of any of embodiments 1-11, wherein the amount of cabozantinib that is administered once daily is 60 mg FBE.

Embodiment 13

The method of any of embodiments 1-12, wherein the amount of cabozantinib (S)-malate is sufficient to achieve a median time to peak plasma concentration (Tmax) from 3.2 to 3.8 hours post-dose; and a mean Cmax of 310 to 350 ng/mL.

Embodiment 14

The method of any of embodiments 1-13, wherein the overall survival of the patient is extended as compared to patients taking everolimus.

Embodiment 15

The method of any of embodiments 1-14, wherein the objective response rate of the patient is extended as compared to patients taking everolimus.

Embodiment 16

The method of any of embodiments 1-15, wherein both the overall survival and the objective response rate of the patient is extended as compared to patients taking everolimus.

Embodiment 17

The method of any of embodiments 1-15 wherein an amount of cabozantinib (S)-malate is sufficient to achieve one, two, three, four, five, six, seven, or eight effects selected from the group consisting of:
  a median time to peak plasma concentration (Tmax) from 2 to 5 hours post-dose;
  a Cmax of 200 to 500 ng/mL;
  an $AUC_{0-24}$ of 2500 to 5200 ng*h/mL;
  an $AUC_{0-t}$ of 18,000 to 42,000 ng*h/mL;
  an $AUC_{0-\infty}$ of 19,000 to 45,000 ng*h/mL;
  an oral volume distribution (Vz/F) of 100 to 600 L;
  a terminal half-life of 90 to 135 h; and
  a clearance at steady state (CL/F) of 0.7 to 3.9 L/h;
wherein the cabozantinib (S)-malate is administered as a tablet formulation comprising approximately (% w/w):
  31-32 percent by weight of cabozantinib, (S)-malate salt;
  39-40 percent by weight of microcrystalline cellulose;
  19-20 percent by weight of lactose;
  2.5-3.5 percent by weight of hydroxypropyl cellulose;
  5.5-6.5 percent by weight of croscarmellose sodium;
  0.25-0.35 percent by weight of colloidal silicon dioxide;
  0.7-0.8 percent by weight of magnesium stearate; and further comprising:
  3.9-4.1 percent by weight of a film coating material comprising hypromellose, titanium dioxide, triacetin, and iron oxide yellow.

Embodiment 18

The method of embodiment 17, wherein cabozantinib (S)-malate is administered as a tablet formulation containing 20, 40, or 60 mg of cabozantinib.

Embodiment 19

The method of any of embodiments 17-18, wherein cabozantinib (S)-malate is administered as a tablet formulation selected from the group consisting of

| Ingredient | Theoretical Quantity (mg/unit dose) | | |
|---|---|---|---|
| | 20-mg Tablet* | 40-mg Tablet* | 60-mg Tablet* |
| Cabozantinib (S)-malate | 25.34 | 50.69 | 76.03 |
| Microcrystalline Cellulose, PH-102 | 31.08 | 62.16 | 93.24 |
| Lactose Anhydrous, 60M | 15.54 | 31.07 | 46.61 |
| Hydroxypropyl Cellulose, EXF | 2.400 | 4.800 | 7.200 |
| Croscarmellose Sodium | 4.800 | 9.600 | 14.40 |
| Colloidal Silicon Dioxide | 0.2400 | 0.4800 | 0.7200 |
| Magnesium Stearate (Non-Bovine) | 0.6000 | 1.200 | 1.800 |
| Opadry ® Yellow (03K92254) | 3.200 | 6.400 | 9.600 |
| Total tablet weight | 83.20 | 166.4 | 249.6 |

*Free Base Equivalent (FBE)

Embodiment 20

The method of any of embodiments 1-19, wherein the cabozantinib (S)-malate is administered in an amount sufficient to achieve one, two, three, four, five, six, seven, or eight effects selected from the group consisting of:
  a median time to peak plasma concentration (Tmax) from 2 to 5 hours post-dose;
  a Cmax of 200 to 500 ng/mL;
  an $AUC_{0-24}$ of 2500 to 5200 ng*h/mL;
  an $AUC_{0-t}$ of 18,000 to 42,000 ng*h/mL;
  an $AUC_{0-\infty}$ of 19,000 to 45,000 ng*h/mL;
  an oral volume distribution (Vz/F) of 100 to 600 L;
  a terminal half-life of 90 to 135 h; and
  a clearance at steady state (CL/F) of 0.7 to 3.9 L/h Embodiment 21 The method of any of embodiments 1-20, wherein the cabozantinib (S)-malate is administered in an amount sufficient to achieve one, two, three, four, five, six, seven, or eight effects selected from the group consisting of:
  a median time to peak plasma concentration (Tmax) from 2.5 to 4.5 hours post-dose;
  a Cmax of 250 to 450 ng/mL;
  an $AUC_{0-24}$ of 3000 to 4700 ng*h/mL;
  an $AUC_{0-t}$ of 23,000 to 37,000 ng*h/mL;
  an $AUC_{0-\infty}$ of 24,000 to 40,000 ng*h/mL;
  an oral volume distribution (Vz/F) of 150 to 550 L;
  a terminal half-life of 100 to 125 h; and
  a clearance at steady state (CL/F) of 1.2 to 3.2 L/h.

Embodiment 22

The method of any of embodiments 1-21, wherein the cabozantinib (S)-malate is administered in an amount sufficient to achieve one, two, three, four, five, six, seven, or eight effects selected from the group consisting of:
  a median time to peak plasma concentration (Tmax) from 3 to 4 hours post-dose;
  a Cmax of 300 to 400 ng/mL;
  an $AUC_{0-24}$ of 3500 to 4200 ng*h/mL;
  an $AUC_{0-t}$ of 28,000 to 32,000 ng*h/mL;
  an $AUC_{0-\infty}$ of 29,000 to 35,000 ng*h/mL;
  an oral volume distribution (Vz/F) of 200 to 500 L;
  a terminal half-life of 110 to 115 h; and
  a clearance at steady state (CL/F) of 1.2 to 3.2

Embodiment 23

The method of any of embodiments 1-19, wherein the cabozantinib (S)-malate is administered in an amount sufficient to achieve one, two, three, four, five, six, seven, or eight effects selected from the group consisting of:

a median time to peak plasma concentration (Tmax) from 3.2 to 3.8 hours post-dose;
a Cmax of 310 to 350 ng/mL;
an $AUC_{0-24}$ of 3700 to 4000 ng*h/mL;
an $AUC_{0-t}$ of 29,000 to 30,000 ng*h/mL;
an $AUC_{0-\infty}$ of 30,000 to 33,000 ng*h/mL;
an oral volume distribution (Vz/F) of 300 to 400 L;
a terminal half-life of 110 to 114 h; and
a clearance at steady state (CL/F) of 2 to 3.

Embodiment 24

A method of treating advanced renal cell carcinoma in human patients who have received prior anti-angiogenic therapy, comprising administering to the patient cabozantinib or a pharmaceutically acceptable salt thereof, wherein the overall survival of the patients are extended as compared to the median overall survival of patients who have received prior anti-angiogenic therapy, wherein the prior anti-angiogenic therapy is selected from the group consisting of axitinib, pazopanib, sorafenib, sunitinib, everolimus, temsirolimus, bevacizumab, interleukins, interferon-α, peginterferon, nivolumab, AMP-514, and atezolizumab.

Embodiment 25

The method of embodiment 24, wherein the cabozanitinib is administered as cabozantinib (S)-malate.

Embodiment 26

The method of any of embodiments 24-25, wherein the overall survival is extended for patients taking cabozantinib (S)-malate as compared to patients who have received axitinib, pazopanib, sorafenib, sunitinib, everolimus, temsirolimus, bevacizumab, nivolumab, AMP-514, and atezolizumab as the prior anti-angiogenic therapy.

Embodiment 27

The method of any of embodiments 24-26, wherein the overall survival is extended for patients taking cabozantinib (S)-malate as compared to patients who have received nivolumab therapy.

Embodiment 28

The method of any of embodiments 24-27, wherein the patients are selected from the group consisting of patients with favorable, intermediate, and poor prognoses on the Memorial Sloan Kettering Cancer Center (MSKCC) Risk Group, patients with bone metastases, patients with visceral metastases, and patients with visceral and bone metastases.

Embodiment 29

The method of any of embodiments 24-28, wherein one or both of progression-free survival (PFS) and objective response rate are also extended over patients who have received prior anti-angiogenic therapy.

Embodiment 30

The method of any of embodiments 24-29 wherein the cabozantinib (S)-malate is administered in an amount sufficient to achieve to achieve a median time to peak plasma concentration (Tmax) from 2 to 5 hours post-dose; and a mean Cmax of 200 to 500 ng/mL; wherein: the overall survival of the patient is extended as compared to a the median overall survival of patients taking who have received prior anti-angiogenic therapy; and wherein one or both of progression-free survival (PFS) and objective response rate are also extended over patients taking who have received prior anti-angiogenic therapy.

Embodiment 31

The method of any of embodiments 24-30, wherein the prior antiangiogenic therapy is selected from the group consisting of axitinib, pazopanib, sorafenib, sunitinib, and everolimus.

Embodiment 32

The method of any of embodiments 24-31, wherein the prior anti-angiogenic therapy is everolimus.

Embodiment 33

The method of any of embodiments 24-32, wherein cabozantinib (S)-malate is administered as a tablet comprising cabozantinib (S)-malate, microcrystalline cellulose, anhydrous lactose, hydroxypropyl cellulose, croscarmellose sodium, colloidal silicon dioxide magnesium stearate, and film coating comprising hypromellose, titanium dioxide, triacetin, and iron oxide yellow.

Embodiment 34

The method of any of embodiments 24-33, wherein the cabozantinib (S)-malate is administered as a tablet formulation comprising approximately:
30-32 percent by weight of cabozantinib, (S)-malate salt;
38-40 percent by weight of microcrystalline cellulose;
18-22 percent by weight of lactose;
2-4 percent by weight of hydroxypropyl cellulose;
4-8 percent by weight of croscarmellose sodium;
0.2-0.6 percent by weight of colloidal silicon dioxide;
0.5-1 percent by weight of magnesium stearate; and further comprising:
a film coating material comprising hypromellose, titanium dioxide, triacetin, and iron oxide yellow.

Embodiment 35

The method of any of embodiments 24-34, wherein the cabozantinib (S)-malate is administered as a tablet formulation comprising approximately (% w/w):
31-32 percent by weight of cabozantinib, (S)-malate salt;
39-40 percent by weight of microcrystalline cellulose;
19-20 percent by weight of lactose;
2.5-3.5 percent by weight of hydroxypropyl cellulose;
5.5-6.5 percent by weight of croscarmellose sodium;
0.25-0.35 percent by weight of colloidal silicon dioxide;
0.7-0.8 percent by weight of magnesium stearate; and further comprising:

3.9-4.1 percent by weight of a film coating material comprising hypromellose, titanium dioxide, triacetin, and iron oxide yellow.

Embodiment 36

The method of any of embodiments 24-35, wherein cabozantinib (S)-malate is administered as a tablet formulation containing 20, 40, or 60 mg of cabozantinib.

Embodiment 37

The method of any of embodiments 24-36, wherein cabozantinib (S)-malate is administered as a tablet formulation selected from the group consisting of

| | Theoretical Quantity (mg/unit dose) | | |
|---|---|---|---|
| Ingredient | 20-mg Tablet* | 40-mg Tablet* | 60-mg Tablet* |
| Cabozantinib (S)-malate | 25.34 | 50.69 | 76.03 |
| Microcrystalline Cellulose, PH-102 | 31.08 | 62.16 | 93.24 |
| Lactose Anhydrous, 60M | 15.54 | 31.07 | 46.61 |
| Hydroxypropyl Cellulose, EXF | 2.400 | 4.800 | 7.200 |
| Croscarmellose Sodium | 4.800 | 9.600 | 14.40 |
| Colloidal Silicon Dioxide | 0.2400 | 0.4800 | 0.7200 |
| Magnesium Stearate (Non-Bovine) | 0.6000 | 1.200 | 1.800 |
| Opadry ® Yellow (03K92254) | 3.200 | 6.400 | 9.600 |
| Total tablet weight | 83.20 | 166.4 | 249.6 |

*Free base Equivalent (FBE)

Embodiment 38

The method of any of embodiments 24-37, wherein the cabozantinib (S)-malate is administered once daily.

Embodiment 39

The method of any of embodiments 24-38, wherein the amount of cabozantinib that is administered once daily is 60 mg FBE.

Embodiment 40

The method of any of embodiments 24-39, wherein the amount of cabozantinib (S)-malate is sufficient to achieve a median time to peak plasma concentration (Tmax) of from approximately 2 to 5 hours post-dose; and a Cmax of 200 to 500 ng/mL.

Embodiment 41

The method of any of embodiments 24-40, wherein the overall survival of the patient are extended as compared to the median overall survival of patients taking everolimus; and wherein the progression-free survival of the patient is extended over patients taking everolimus.

Embodiment 42

The method of any of embodiments 24-41, wherein the overall survival of patients is extended as compared to the median overall survival of patients taking everolimus; and wherein the objective response rate is extended over patients taking everolimus.

Embodiment 43

The method of any of embodiments 24-42, wherein the overall survival of patients is extended as compared to everolimus and both of progression-free survival (PFS) and objective response rate are also extended as compared to patients taking everolimus.

Embodiment 44

A method of treating renal cell carcinoma in a human patient who has received prior anti-angiogenic therapy, comprising administering to the patient an amount of cabozantinib (S)-malate sufficient to achieve one, two, three, four, five, six, seven, or eight effects selected from the group consisting of:
  a median time to peak plasma concentration (Tmax) from 2 to 5 hours post-dose;
  a Cmax of 200 to 500 ng/mL;
  an $AUC_{0-24}$ of 2500 to 5200 ng*h/mL;
  an $AUC_{0-t}$ of 18,000 to 42,000 ng*h/mL;
  an $AUC_{0-\infty}$ of 19,000 to 45,000 ng*h/mL;
  an oral volume distribution (Vz/F) of 100 to 600 L;
  a terminal half-life of 90 to 135 h; and
  a clearance at steady state (CL/F) of 0.7 to 3.9 L/h;
    wherein:
the cabozantinib (S)-malate is administered as a tablet formulation comprising approximately (% w/w):
  31-32 percent by weight of cabozantinib, (S)-malate salt;
  39-40 percent by weight of microcrystalline cellulose;
  19-20 percent by weight of lactose;
  2.5-3.5 percent by weight of hydroxypropyl cellulose;
  5.5-6.5 percent by weight of croscarmellose sodium;
  0.25-035 percent by weight of colloidal silicon dioxide;
  0.7-0.8 percent by weight of magnesium stearate; and
  further comprising:
  3.9-4.1 percent by weight of a film coating material comprising hypromellose, titanium dioxide, triacetin, and iron oxide yellow.

Embodiment 45

The method of embodiment 44, wherein cabozantinib (S)-malate is administered as a tablet formulation containing 20, 40, or 60 mg of cabozantinib FBE.

Embodiment 46

The method of any of embodiments 44-45, wherein cabozantinib (S)-malate is administered as a tablet formulation selected from the group consisting of:

| | Theoretical Quantity (mg/unit dose) | | |
|---|---|---|---|
| Ingredient | 20-mg Tablet* | 40-mg Tablet* | 60-mg Tablet* |
| Cabozantinib (S)-malate | 25.34 | 50.69 | 76.03 |
| Microcrystalline Cellulose, PH-102 | 31.08 | 62.16 | 93.24 |
| Lactose Anhydrous, 60M | 15.54 | 31.07 | 46.61 |
| Hydroxypropyl Cellulose, EXF | 2.400 | 4.800 | 7.200 |
| Croscarmellose Sodium | 4.800 | 9.600 | 14.40 |
| Colloidal Silicon Dioxide | 0.2400 | 0.4800 | 0.7200 |
| Magnesium Stearate (Non-Bovine) | 0.6000 | 1.200 | 1.800 |
| Opadry ® Yellow (03K92254) | 3.200 | 6.400 | 9.600 |
| Total tablet weight | 83.20 | 166.4 | 249.6 |

-continued

| Ingredient | Theoretical Quantity (mg/unit dose) | | |
|---|---|---|---|
| | 20-mg Tablet* | 40-mg Tablet* | 60-mg Tablet* |

*Free base Equivalent (FBE)

Embodiment 47

The method of any of embodiments 44-46, wherein the cabozantinib (S)-malate is administered in an amount sufficient to achieve one, two, three, four, five, six, seven, or eight effects selected from the group consisting of:
a median time to peak plasma concentration (Tmax) from 2 to 5 hours post-dose;
a Cmax of 200 to 500 ng/mL;
an $AUC_{0-24}$ of 2500 to 5200 ng*h/mL;
an $AUC_{0-t}$ of 18,000 to 42,000 ng*h/mL;
an $AUC_{0-\infty}$ of 19,000 to 45,000 ng*h/mL;
an oral volume distribution (Vz/F) of 100 to 600 L;
a terminal half-life of 90 to 135 h; and
a clearance at steady state (CL/F) of 0.7 to 3.9 L/h

Embodiment 48

The method of any of embodiments 44-47, wherein the cabozantinib (S)-malate is administered in an amount sufficient to achieve one, two, three, four, five, six, seven, or eight effects selected from the group consisting of:
a median time to peak plasma concentration (Tmax) from 2.5 to 4.5 hours post-dose;
a Cmax of 250 to 450 ng/mL;
an $AUC_{0-24}$ of 3000 to 4700 ng*h/mL;
an $AUC_{0-t}$ of 23,000 to 37,000 ng*h/mL;
an $AUC_{0-\infty}$ of 24,000 to 40,000 ng*h/mL;
an oral volume distribution (Vz/F) of 150 to 550 L;
a terminal half-life of 100 to 125 h; and
a clearance at steady state (CL/F) of 1.2 to 3.2 L/h.

Embodiment 49

The method of any of embodiments 44-48, wherein the cabozantinib (S)-malate is administered in an amount sufficient to achieve one, two, three, four, five, six, seven, or eight effects selected from the group consisting of:
a median time to peak plasma concentration (Tmax) from 3 to 4 hours post-dose;
a Cmax of 300 to 400 ng/mL;
an $AUC_{0-24}$ of 3500 to 4200 ng*h/mL;
an $AUC_{0-t}$ of 28,000 to 32,000 ng*h/mL;
an $AUC_{0-\infty}$ of 29,000 to 35,000 ng*h/mL;
an oral volume distribution (Vz/F) of 200 to 500 L;
a terminal half-life of 110 to 115 h; and
a clearance at steady state (CL/F) of 1.2 to 3.2

Embodiment 50

The method of any of embodiments 44-49, wherein the cabozantinib (S)-malate is administered in an amount sufficient to achieve one, two, three, four, five, six, seven, or eight effects selected from the group consisting of:
a median time to peak plasma concentration (Tmax) from 3.2 to 3.8 hours post-dose;
a Cmax of 310 to 350 ng/mL;
an $AUC_{0-24}$ of 3700 to 4000 ng*h/mL;
an $AUC_{0-t}$ of 29,000 to 30,000 ng*h/mL;
an $AUC_{0-\infty}$ of 30,000 to 33,000 ng*h/mL;
an oral volume distribution (Vz/F) of 300 to 400 L;
a terminal half-life of 110 to 114 h; and
a clearance at steady state (CL/F) of 2 to 3.

Embodiment 51

The method of any of embodiments 44-50, wherein the overall survival of the patient is extended as compared to the median overall survival of patients taking everolimus; and wherein the progression-free survival of the patient is extended over patients taking everolimus.

Embodiment 52

The method of any of embodiments 44-51, wherein the overall survival of the patient is extended as compared to the median overall survival of patients taking everolimus; and wherein the objective response rate is extended over patients taking everolimus.

Embodiment 53

The method of any of embodiments 44-52, wherein the overall survival of the patient is extended as compared to a the median overall survival of patients taking everolimus; and wherein progression-free survival (PFS) and objective response rate are also extended over patients taking everolimus.

Embodiment 54

A method of treating advanced renal cell carcinoma in patients in need of such treatment who has received prior antiangiogenic therapy selected from the group consisting of sunitinib therapy, pazopanib therapy, and anti-PD-1/PD-L1 immune checkpoint inhibitor therapy, comprising administering cabozantinib Compound 1

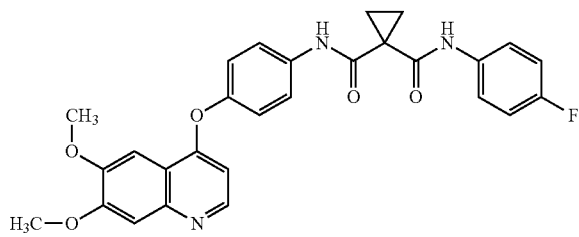 [SMILES: COc1cc2nccc(Oc3ccc(NC(=O)C4(C(=O)Nc5ccc(F)cc5)CC4)cc3)c2cc1OC]

or a pharmaceutically acceptable salt thereof.

Embodiment 55

The method of embodiment 55, wherein the cabozantinib is administered as cabozantinib (S)-malate salt.

Embodiment 56

The method of embodiment 54, wherein the median progression free survival is at least 9.1 months when the prior antiangiogenic therapy is sunitinib therapy only and at least 7.4 months when the prior antiangiogenic therapy is pazopanib only.

Embodiment 57

The method of any of embodiments 54-56, wherein the median overall survival is at least 21.4 months when the prior antiangiogenic therapy was sunitinib only and at least 22.0 months when the prior antiangiogenic therapy was pazopanib only.

Embodiment 58

The method of any of embodiments 54-57, wherein the median progression free survival is at least 9.1 months when the prior antiangiogenic therapy is sunitinib therapy only and at least 7.4 months when the prior antiangiogenic therapy was pazopanib only and the median overall survival is at least 21.4 months when the prior antiangiogenic therapy was sunitinib only and at least 22.0 months when the prior antiangiogenic therapy was pazopanib only.

Embodiment 59

A method of optimizing the treatment of a renal carcinoma patient with a tyrosine kinase inhibitor (TKI) comprising the step of quantifying the patient's response to one or more dosing regimens of said TKI inhibitor with a model employing Equation 1:

$$\frac{dY}{dt} = k_{grow} \cdot Y - \frac{(k_{dmax} + k_{dmax_{tol}} \cdot e^{-k_{tol} \cdot t}) \cdot Cavg}{(EC_{50} + Cavg)} \cdot Y \quad \text{Equation 1}$$

where:
dY/dt is the change in tumor diameter per unit time
$k_{grow}$ is the first-order growth rate constant
$k_{dmax}$ is the maximum non-attenuating drug induced tumor decay rate
$k_{dmax\_tol}$ is the maximum loss in the decay rate due to resistance
$k_{tol}$ is the rate constant which governs the rate of attenuation
$EC_{50}$ is the cabozantinib concentration yielding one-half of the current tumor decay rate
Cavg is the individual predicted daily average cabozantinib concentration.

Embodiment 60

The method of embodiment 59, wherein the target of the TKI is selected from the group consisting of VEGF receptors, MET, and AXL.

Embodiment 61

The method of any of embodiments 59-60, wherein the TKI inhibitor is cabozantinib.

Embodiment 62

A method of adjusting the dosing level of a composition comprising a tyrosine kinase (TKI) inhibitor for administration to a patient, the method comprising:
measuring plasma clearance (CL/F) and apparent volume of distribution of the central compartment (Vd/F) from a patient;
utilizing the measured plasma clearance (CL/F) and apparent volume of distribution of the central compartment ($V_z$/F) to calculate the responsiveness of the patient to the administered composition comprising said TKI inhibitor; and
comparing the calculated responsiveness to a predetermined responsiveness to compositions comprising said TKI inhibitor.

Embodiment 63

The method of embodiment 62, wherein the TKI inhibitor is cabozantinb.

Embodiment 64

A method for treating renal cell carcinoma, comprising administering as a starting dose 60 mg of cabozantinib free base equivalent to a patient in need of such treatment, wherein progression free survival is extended, tumor growth is reduced, and overall response rate is extended as compared to 40 mg or 20 mg starting doses or cabozantinib free base equivalent.

Embodiment 65

The method of claim 64, wherein cabozantinib is administered as cabozantinib (S)-malate salt.

Embodiment 66

A method of treating renal cell carcinoma in a human patient, wherein the method comprises administering cabozantinib or a pharmaceutically acceptable salt thereof daily in an amount of 60 mg of cabozantinib free base equivalent.

Embodiment 67

The method of claim 66, wherein the renal cell carcinoma is advanced renal cell carcinoma.

Embodiment 68

The method of any of claims 66-67, wherein the patient is an adult patient.

Embodiment 69

The method of any of embodiments 66-68, wherein said amount is administered to the patient once daily.

Embodiment 70

The method of any of embodiments 66-69, wherein the cabozantinib is administered as cabozantinib (S)-malate.

Embodiment 71

The method of any of embodiments 66-70, wherein cabozantinib (S)-malate is administered as a tablet comprising cabozantinib (S)-malate, microcrystalline cellulose, anhydrous lactose, hydroxypropyl cellulose, croscarmellose sodium, colloidal silicon dioxide magnesium stearate, and film coating comprising hypromellose, titanium dioxide, triacetin, and iron oxide yellow.

Embodiment 72

The method of any of embodiments 66-71, wherein the cabozantinib (S)-malate is administered as a tablet formulation comprising approximately:

30-32 percent by weight of cabozantinib, (S)-malate salt;
38-40 percent by weight of microcrystalline cellulose;
18-22 percent by weight of lactose;
2-4 percent by weight of hydroxypropyl cellulose;
4-8 percent by weight of croscarmellose sodium;
0.2-0.6 percent by weight of colloidal silicon dioxide;
0.5-1 percent by weight of magnesium stearate; and
further comprising:
a film coating material comprising hypromellose, titanium dioxide, triacetin, and iron oxide yellow.

Embodiment 73

The method of any of embodiments 66-72, wherein the cabozantinib (S)-malate is administered as a tablet formulation comprising approximately (% w/w):
31-32 percent by weight of cabozantinib, (S)-malate salt;
39-40 percent by weight of microcrystalline cellulose;
19-20 percent by weight of lactose;
2.5-3.5 percent by weight of hydroxypropyl cellulose;
5.5-6.5 percent by weight of croscarmellose sodium;
0.25-0.35 percent by weight of colloidal silicon dioxide;
0.7-0.8 percent by weight of magnesium stearate; and
further comprising:
3.9-4.1 percent by weight of a film coating material comprising hypromellose, titanium dioxide, triacetin, and iron oxide yellow.

Embodiment 74

The method of any of embodiments 66-73, wherein the starting dose of 60 mg cabozantinib free base equivalent can be reduced to 40 or 20 mg cabozantinib free base equivalent to minimize adverse side effects.

Embodiment 75

The method of any of embodiments 66-74, wherein cabozantinib (S)-malate is administered as a tablet formulation selected from the group consisting of:

| Ingredient | Theoretical Quantity (mg/unit dose) | | |
| --- | --- | --- | --- |
| | 20-mg Tablet* | 40-mg Tablet* | 60-mg Tablet* |
| Cabozantinib (S)-malate | 25.34 | 50.69 | 76.03 |
| Microcrystalline Cellulose, PH-102 | 31.08 | 62.16 | 93.24 |
| Lactose Anhydrous, 60M | 15.54 | 31.07 | 46.61 |
| Hydroxypropyl Cellulose, EXF | 2.400 | 4.800 | 7.200 |
| Croscarmellose Sodium | 4.800 | 9.600 | 14.40 |
| Colloidal Silicon Dioxide | 0.2400 | 0.4800 | 0.7200 |
| Magnesium Stearate (Non-Bovine) | 0.6000 | 1.200 | 1.800 |
| Opadry ® Yellow (03K92254) | 3.200 | 6.400 | 9.600 |
| Total tablet weight | 83.20 | 166.4 | 249.6 |

*Free Base Equivalent (FBE)

Embodiment 76

The method of any of embodiments 66-75, wherein the patient has received prior anti-angiogenic therapy.

Embodiment 77

The method of embodiment 66-76, wherein the prior anti-angiogenic therapy is selected axitinib, pazopanib, sorafenib, sunitinib, everolimus, temsirolimus, bevacizumab, interleukins, interferon-α, peginterferon, nivolumab, AMP-514, and atezolizumab.

Embodiment 78

The method of embodiments 66-77, wherein the prior anti-angiogenic therapy is everolimus therapy.

Embodiment 79

A method of treating renal cell carcinoma in a human patient, wherein the method comprises administering cabozantinib or a pharmaceutically acceptable salt thereof daily in an amount of 40 mg of cabozantinib free base equivalent.

Embodiment 80

The method of embodiment 79, wherein the renal cell carcinoma is advanced renal cell carcinoma.

Embodiment 81

The method of any of embodiments 79-80, wherein the patient is an adult patient.

Embodiment 82

The method of any of embodiments 79-81, wherein said amount is administered to the patient once daily.

Embodiment 83

The method of any of embodiments 79-82, wherein the cabozantinib is administered as cabozantinib (S)-malate.

Embodiment 84

The method of any of embodiments 79-83, wherein cabozantinib (S)-malate is administered as a tablet comprising cabozantinib (S)-malate, microcrystalline cellulose, anhydrous lactose, hydroxypropyl cellulose, croscarmellose sodium, colloidal silicon dioxide magnesium stearate, and film coating comprising hypromellose, titanium dioxide, triacetin, and iron oxide yellow.

Embodiment 85

The method of any of embodiments 79-84, wherein the cabozantinib (S)-malate is administered as a tablet formulation comprising approximately:
30-32 percent by weight of cabozantinib, (S)-malate salt;
38-40 percent by weight of microcrystalline cellulose;
18-22 percent by weight of lactose;
2-4 percent by weight of hydroxypropyl cellulose;
4-8 percent by weight of croscarmellose sodium;
0.2-0.6 percent by weight of colloidal silicon dioxide;
0.5-1 percent by weight of magnesium stearate; and
further comprising:
a film coating material comprising hypromellose, titanium dioxide, triacetin, and iron oxide yellow.

Embodiment 86

The method of any of embodiments 79-85, wherein the cabozantinib (S)-malate is administered as a tablet formulation comprising approximately (% w/w):
- 31-32 percent by weight of cabozantinib, (S)-malate salt;
- 39-40 percent by weight of microcrystalline cellulose;
- 19-20 percent by weight of lactose;
- 2.5-3.5 percent by weight of hydroxypropyl cellulose;
- 5.5-6.5 percent by weight of croscarmellose sodium;
- 0.25-0.35 percent by weight of colloidal silicon dioxide;
- 0.7-0.8 percent by weight of magnesium stearate; and further comprising:
- 3.9-4.1 percent by weight of a film coating material comprising hypromellose, titanium dioxide, triacetin, and iron oxide yellow.

Embodiment 87

The method of any of embodiments 79-86, wherein cabozantinib (S)-malate is administered as a tablet formulation selected from the group consisting of:

| Ingredient | Theoretical Quantity (mg/unit dose) | | |
|---|---|---|---|
| | 20-mg Tablet* | 40-mg Tablet* | 60-mg Tablet* |
| Cabozantinib (S)-malate | 25.34 | 50.69 | 76.03 |
| Microcrystalline Cellulose, PH-102 | 31.08 | 62.16 | 93.24 |
| Lactose Anhydrous, 60M | 15.54 | 31.07 | 46.61 |
| Hydroxypropyl Cellulose, EXF | 2.400 | 4.800 | 7.200 |
| Croscarmellose Sodium | 4.800 | 9.600 | 14.40 |
| Colloidal Silicon Dioxide | 0.2400 | 0.4800 | 0.7200 |
| Magnesium Stearate (Non-Bovine) | 0.6000 | 1.200 | 1.800 |
| Opadry ® Yellow (03K92254) | 3.200 | 6.400 | 9.600 |
| Total tablet weight | 83.20 | 166.4 | 249.6 |

*Free Base Equivalent (FBE)

Embodiment 88

The method of any of embodiments 79-87, wherein the patient has received prior anti-angiogenic therapy.

Embodiment 89

The method of embodiments 79-88, wherein the prior anti-angiogenic therapy is selected axitinib, pazopanib, sorafenib, sunitinib, everolimus, temsirolimus, bevacizumab, interleukins, interferon-α, peginterferon, nivolumab, AMP-514, and atezolizumab.

Embodiment 90

The method of embodiments 79-89, wherein the prior anti-angiogenic therapy is everolimus therapy.

Embodiment 91

A method of treating renal cell carcinoma in a human patient, wherein the method comprises administering cabozantinib or a pharmaceutically acceptable salt thereof daily in an amount of 20 mg of cabozantinib free base equivalent.

Embodiment 92

The method of embodiment 91, wherein the renal cell carcinoma is advanced renal cell carcinoma.

Embodiment 93

The method of any of embodiments 91-92, wherein the patient is an adult patient.

Embodiment 94

The method of any of embodiments 91-93, wherein said amount is administered to the patient once daily.

Embodiment 95

The method of any of embodiments 91-94, wherein the cabozantinib is administered as cabozantinib (S)-malate.

Embodiment 96

The method of any of embodiments 91-95, wherein cabozantinib (S)-malate is administered as a tablet comprising cabozantinib (S)-malate, microcrystalline cellulose, anhydrous lactose, hydroxypropyl cellulose, croscarmellose sodium, colloidal silicon dioxide magnesium stearate, and film coating comprising hypromellose, titanium dioxide, triacetin, and iron oxide yellow.

Embodiment 97

The method of any of embodiments 91-96, wherein the cabozantinib (S)-malate is administered as a tablet formulation comprising approximately:
- 30-32 percent by weight of cabozantinib, (S)-malate salt;
- 38-40 percent by weight of microcrystalline cellulose;
- 18-22 percent by weight of lactose;
- 2-4 percent by weight of hydroxypropyl cellulose;
- 4-8 percent by weight of croscarmellose sodium;
- 0.2-0.6 percent by weight of colloidal silicon dioxide;
- 0.5-1 percent by weight of magnesium stearate; and further comprising:
- a film coating material comprising hypromellose, titanium dioxide, triacetin, and iron oxide yellow.

Embodiment 98

The method of any of embodiments 91-97, wherein the cabozantinib (S)-malate is administered as a tablet formulation comprising approximately (% w/w):
- 31-32 percent by weight of cabozantinib, (S)-malate salt;
- 39-40 percent by weight of microcrystalline cellulose;
- 19-20 percent by weight of lactose;
- 2.5-3.5 percent by weight of hydroxypropyl cellulose;
- 5.5-6.5 percent by weight of croscarmellose sodium;
- 0.25-0.35 percent by weight of colloidal silicon dioxide;
- 0.7-0.8 percent by weight of magnesium stearate; and further comprising:
- 3.9-4.1 percent by weight of a film coating material comprising hypromellose, titanium dioxide, triacetin, and iron oxide yellow.

Embodiment 99

The method of any of embodiments 91-98, wherein cabozantinib (S)-malate is administered as a tablet formulation selected from the group consisting of:

| | Theoretical Quantity (mg/unit dose) | | |
|---|---|---|---|
| Ingredient | 20-mg Tablet* | 40-mg Tablet* | 60-mg Tablet* |
| Cabozantinib (S)-malate | 25.34 | 50.69 | 76.03 |
| Microcrystalline Cellulose, PH-102 | 31.08 | 62.16 | 93.24 |
| Lactose Anhydrous, 60M | 15.54 | 31.07 | 46.61 |
| Hydroxypropyl Cellulose, EXF | 2.400 | 4.800 | 7.200 |
| Croscarmellose Sodium | 4.800 | 9.600 | 14.40 |
| Colloidal Silicon Dioxide | 0.2400 | 0.4800 | 0.7200 |
| Magnesium Stearate (Non-Bovine) | 0.6000 | 1.200 | 1.800 |
| Opadry ® Yellow (03K92254) | 3.200 | 6.400 | 9.600 |
| Total tablet weight | 83.20 | 166.4 | 249.6 |

*Free Base Equivalent (FBE)

Embodiment 100

The method of any of embodiments 91-99, wherein the patient has received prior anti-angiogenic therapy.

Embodiment 101

The method of embodiments 91-100, wherein the prior anti-angiogenic therapy is selected axitinib, pazopanib, sorafenib, sunitinib, everolimus, temsirolimus, bevacizumab, interleukins, interferon-α, peginterferon, nivolumab, AMP-514, and atezolizumab.

102. The method of embodiments 91-101, wherein prior anti-angiogenic therapy is everolimus therapy.

The invention will now be demonstrated by the following non-limiting examples.

Example 1

Overall Survival Results from a Randomised Phase 3 Trial Comparing Cabozantinib and Everolimus in Advanced Renal Cell Carcinoma This study was a randomized (1:1), open-label, multicenter study of CABOMETYX® versus everolimus conducted in patients with advanced RCC who had received at least 1 prior anti-angiogenic therapy. Patients had to have a Karnofsky Performance Score (KPS)≥70%. Patients were stratified by the number of prior VEGFR tyrosine kinase inhibitors and Memorial Sloan Kettering Cancer Center (MSKCC) Risk Group.

Patients (N=658) were randomized to receive CABOMETYX® (N=330) administered orally at 60 mg daily or everolimus (N=328) administered orally at 10 mg daily. The majority of the patients were male (75%), with a median age of 62 years. Sixty-nine percent (69%) received only one prior anti-angiogenic therapy. Patient distribution by MSKCC risk groups was 46% favorable (0 risk factors), 42% intermediate (1 risk factor), and 13% poor (2 or 3 risk factors). Fifty-four percent (54%) of patients had 3 or more organs with metastatic disease, including lung (63%), lymph nodes (62%), liver (29%), and bone (22%).

The main efficacy outcome measure was progression-free survival (PFS) assessed by a blinded independent radiology review committee among the first 375 subjects randomized. Other efficacy endpoints were objective response rate (ORR) and overall survival (OS) in the Intent-to-Treat (ITT) population. Tumor assessments were conducted every 8 weeks for the first 12 months, then every 12 weeks thereafter. Patients received treatment until disease progression or experiencing unacceptable toxicity. Patients on both arms who had disease progression could continue treatment at the discretion of the investigator.

Statistically significant improvements in PFS, OS, and ORR were demonstrated for CABOMETYX® compared to everolimus (FIG. 1.1, FIG. 1.2, and Tables 1.1 and 1.2).

TABLE 1.1

Progression-Free Survival in Study 1 (First 375 Randomized)

| Endpoint | CABOMETYX N = 187 | Everolimus N = 188 |
|---|---|---|
| Median PFS (95% CI), months | 7.4 (5.6, 9.1) | 3.8 (3.7, 5.4) |
| HR (95% CI), p-value[1] | 0.58 (0.45, 0.74), p < 0.0001 | |

[1]stratified log-rank test with prior VEGFR-targeting TKI therapy (1 vs 2 or more) and MSKCC prognostic criteria for previously treated patients with RCC (0 vs 1 vs 2 or 3) as stratification factors (per IVRS data)

TABLE 1.2

Overall Survival and Objective Response Rate in Study 1 (ITT)

| Endpoint | CABOMETYX N = 330 | Everolimus N = 328 |
|---|---|---|
| Median OS (95% CI), months | 21.4 (18.7, NE) | 16.5 (14.7, 18.8) |
| HR (95% CI), p-value[1] | 0.66 (0.53, 0.83), p = 0.0003 | |
| Confirmed ORR (partial responses only) (95% CI) | 17% (13%, 22%) | 3% (2%, 6%) |
| p-value[2] | p < 0.0001 | |

[1]stratified log-rank test with prior VEGFR-targeting TKI therapy (1 vs 2 or more) and MSKCC prognostic criteria for previously treated patients with RCC (0 vs 1 vs 2 or 3) as stratification factors (per IVRS data)
[2]chi-squared test Advances in the understanding of the molecular pathology of renal cell carcinoma (RCC) have led to the development of agents targeting the vascular endothelial growth receptor (VEGFR) and mTOR signaling pathways. Commonly used first-line therapies in patients with advanced RCC are the VEGFR tyrosine kinase inhibitors (TKIs) sunitinib and pazopanib. Second-line therapies include the VEGFR TKIs axitinib and sorafenib, the mTOR inhibitor everolimus, and the programmed cell death receptor 1 (PD-1) checkpoint inhibitor nivolumab. Motzer R J, Jonasch E, Agarwal N, et al. Kidney cancer, version 3.2015. *J Natl Compr Canc Netw* 2015; 13: 151-9; Powles T, Staehler M, Ljungberg B, et al. Updated EAU Guidelines for Clear Cell Renal Cancer Patients Who Fail VEGF Targeted Therapy. *Eur Urol* 2016; 69: 4-6; Motzer R J, Escudier B, McDermott D F, et al. Nivolumab versus Everolimus in Advanced Renal-Cell Carcinoma. *N Engl J Med* 2015; 373: 1803-13. Despite a number of available therapies, few have shown a survival benefit, and no agent has demonstrated an improvement in all three efficacy endpoints of progression-free survival (PFS), objective response rate, and overall survival in a randomized phase 3 trial compared to standard therapy in previously-treated RCC patients.

Cabozantinib is an oral inhibitor of tyrosine kinases including MET, VEGF receptors, and AXL. Yakes F M, Chen J, Tan J, et al. Cabozantinib (XL184), a novel MET and VEGFR2 inhibitor, simultaneously suppresses metastasis, angiogenesis, and tumor growth. *Mol Cancer Ther* 2011;

10: 2298-308. Up-regulation of MET and AXL in clear cell RCC occurs as a consequence of von Hippel-Lindau protein dysfunction, has been implicated in tumor progression and VEGFR-TKI resistance in preclinical studies, and associated with a poor prognosis in RCC patients. Gibney G T, Aziz S A, Camp R L, et al. c-Met is a prognostic marker and potential therapeutic target in clear cell renal cell carcinoma. *Ann Oncol* 2013; 24: 343-9; Gustafsson A, Martuszewska D, Johansson M, et al. Differential expression of Axl and Gas6 in renal cell carcinoma reflecting tumor advancement and survival. *Clin Cancer Res* 2009; 15: 4742-9; Rankin E B, Fuh K C, Castellini L, et al. Direct regulation of GAS6/AXL signaling by HIF promotes renal metastasis through SRC and MET. *Proc Natl Acad Sci USA* 2014; 111: 13373-8; Zhou L, Liu X D, Sun M, et al. Targeting MET and AXL overcomes resistance to sunitinib therapy in renal cell carcinoma. *Oncogene* 2015 Sep. 14. doi: 10.1038/onc.2015.343; Harshman L C, Choueiri T K. Targeting the hepatocyte growth factor/c-Met signaling pathway in renal cell carcinoma. *Cancer J* 2013; 19: 316-23; Pinato D J, Chowdhury S, Stebbing J. TAMing resistance to multi-targeted kinase inhibitors through Axl and Met inhibition. *Oncogene* 2015 Oct. 5: doi: 10.1038/onc.2015.374. The randomized phase 3 METEOR trial compared the efficacy and safety of cabozantinib with the mTOR inhibitor everolimus in patients with advanced RCC who progressed after prior VEGFR-TKI therapy. Progression-free survival (PFS), the primary endpoint, was significantly improved with cabozantinib compared to everolimus treatment with a median PFS of 7.4 months vs. 3.8 months (HR 0.58, 95% CI 0.45-0.75; p<0.001) as assessed by an independent radiology review committee. Choueiri T K, Escudier B, Powles T, et al. Cabozantinib versus Everolimus in Advanced Renal-Cell Carcinoma. *N Engl J Med* 2015; 373: 1814-23. The primary endpoint analysis was pre-specified to be conducted in the first 375 randomized patients to provide longer follow-up in a smaller population for the event-driven analysis. A planned interim analysis of the secondary endpoint of overall survival in all 658 randomized patients was conducted at the time of the primary PFS analysis and demonstrated a trend for improved survival (49% information fraction: HR 0.67, 95% CI 0.51-0.89; p=0.005) but did not reach the boundary for significance (p≤0.0019) at this information fraction.

We report herein the final overall survival results from the METEOR study based on a second interim analysis. Analyses of PFS and the objective response rate in all patients randomized are reported as well as subgroup analyses to assess the effects of demographics and baseline characteristics on overall survival and progression-free survival. An update of safety data is also provided.

Methods.

658 patients with clear cell RCC, measurable disease, and prior therapy with ≥1 VEGFR tyrosine kinase inhibitor (TKI) were randomized 1:1 via an interactive voice and web response system to receive cabozantinib 60 mg daily or everolimus 10 mg daily. Stratification factors were MSKCC risk group and the number of prior VEGFR TKIs. The primary endpoint was PFS as assessed by an independent radiology review committee in the first 375 randomized patients. Secondary endpoints were overall survival and objective response rate in all randomized patients. The study is closed to enrolment but treatment and follow-up of patients is on-going for long term safety evaluation. This trial is registered at ClinicalTrials.gov, NCT01865747.

Findings.

Median overall survival was 21.4 months (95% confidence interval [CI]18.7 to not estimable) with cabozantinib and 16.5 months (95% CI 14.7-18.8) with everolimus. The hazard ratio (HR) for death was 0.66 (95% CI 0.53-0.83; p=0.0003). Cabozantinib treatment also resulted in improved PFS (HR 0.51, 95% CI 0.41-0.62; p<0.0001) and objective response rate (17% [95% CI 13-2] with cabozantinib vs. 3% [95% CI 2-6] with everolimus; p<0.0001) per independent radiology review among all randomized patients. The most common adverse events (all grades) were diarrhea 249 (75%), fatigue 195 (59%), and nausea 173 (52%) with cabozantinib and fatigue 154 (48%), anemia 126 (39%), and decreased appetite 114 (3-5%) with everolimus. Serious adverse events ≥grade 3 occurred in 130 (40%) of cabozantinib-treated patients and in 129 (40%) of everolimus-treated patients.

Interpretation.

Cabozantinib prolonged overall survival, delayed disease progression, and improved the response rate compared to standard of care everolimus in a large phase 3 trial in previously-treated RCC patients. Patients should be monitored for adverse events that may require dose modifications.

Study Design and Participants.

METEOR is a randomized, open-label, phase 3, international study with patients enrolled at 173 centers in 26 countries. Choueiri T K, Escudier B, Powles T, et al. Cabozantinib versus Everolimus in Advanced Renal-Cell Carcinoma. *N Engl J Med* 2015; 373: 1814-23. FIG. 1.8 depicts the METEOR study design, and FIG. 1.10 shows the patient disposition based on the 922 screened patients. Patients 18 years or older with advanced or metastatic RCC and a clear cell histology were eligible for enrolment provided they had measurable disease per RECIST version 1.1 (See Eisenhauer E A, Therasse P, Bogaerts J, et al. New response evaluation criteria in solid tumors: revised RECIST guideline (version 1.1). *Eur J Cancer* 2009; 45: 228-47), had received at least one prior VEGFR TKI (there was no limit to the number of prior therapies), and had experienced disease progression during or within 6 months of the most recent prior VEGFR-TKI treatment and within 6 months prior to randomization. Patients were required to have a Karnofsky Performance Status score of at least 70% and adequate organ function, based on standard laboratory tests including hematology, serum chemistry, lipids, coagulation, thyroid function, and urinalysis. Patients with brain metastases were allowed provided these were stable and asymptomatic. Patients with prior mTOR inhibitor therapy, including everolimus, were not eligible for the study nor were patients with uncontrolled hypertension or clinically significant cardiovascular, gastrointestinal, wound healing, or infectious comorbidities. The study adhered to the Good Clinical Practice guidelines and the Declaration of Helsinki. The institutional review board or ethics committee of the participating centers approved the study protocol. All patients provided written informed consent.

Randomization and Masking.

Patients were randomized 1:1 to receive either cabozantinib or everolimus. Randomization was stratified by the number of prior VEGFR-TKI therapies (1 or ≥2) and Memorial Sloan Kettering Cancer Center (MSKCC) risk group (favorable, intermediate, or poor) for previously-treated patients (Table 13). Motzer R J, Bacik J, Schwartz L H, et al. Prognostic factors for survival in previously treated patients with metastatic renal cell carcinoma. *J Clin Oncol* 2004; 22: 454-63.

TABLE 1.3

Memorial Sloan-Kettering Cancer Center (MSKCC) Prognostic Criteria for Previously Treated Patients with Renal Cell Carcinoma

| Number of Risk Factors* | Expected Outcome |
|---|---|
| 0 | Favorable |
| 1 | Intermediate |
| 2 or 3 | Poor |

See Motzer R J, Bacik J, Schwartz L H, et al. Prognostic factors for survival in previously treated patients with metastatic renal cell carcinoma. *J Clin Oncol* 2004; 22: 454-63.
*The three risk factors are: Karnofsky performance status score <80%; Hemoglobin <13 g/dL for males or <11.5 g/dL for females; Corrected calcium > upper limit of normal.

The study employed stratified permuted blocks as the randomization schema. Study treatment was assigned centrally using an interactive voice and web response system. Study personnel did not have access to the master list of blocks or block sizes. Patients and investigators were not masked to study treatment to allow appropriate management of adverse events. Aggregate summaries of efficacy data by treatment arm were not performed until the time of the primary PFS analysis.

Procedures.

Cabozantinib was taken orally once daily at 60 mg, and everolimus was taken orally once daily at 10 mg. Treatment modifications, including interruptions and dose reductions, were allowed to manage adverse events. Cabozantinib could be dose-reduced to 40 mg and then 20 mg, and everolimus could be dose-reduced to 5 mg and then 2.5 mg. Patients were allowed to continue study treatment beyond radiographic progression at the discretion of the investigator. On-study crossover between treatment groups was not permitted. Safety evaluations, including physical examination, vital signs, and laboratory assessments, were conducted every 2 weeks for the first 8 weeks and then every 4 weeks thereafter. ECG assessments were performed every 4 weeks for the first 8 weeks and then every 12 weeks. A safety follow-up visit was scheduled 30 days after treatment discontinuation. Adverse events were assessed by investigators and graded according to CTCAE version 4.0. National Cancer Institute. Common Terminology Criteria for Adverse Events (CTCAE) v.4. Posted at evs.nci.nih.gov/ftp1/CTCAE/About.html (accessed Jan. 28, 2015; last visited Apr. 14, 2017).

Radiographic assessments by CT or MRI were conducted at screening and every 8 weeks for the first 12 months and then every 12 weeks thereafter. Tumor response and progression were assessed according to Response Evaluation Criteria in Solid Tumors (RECIST) version 1.1 (Eisenhauer E A, Therasse P, Bogaerts J, et al. New response evaluation criteria in solid tumors: revised RECIST guideline (version 1.1). *Eur J Cancer* 2009; 45: 228-47) by a masked centralized independent radiology review committee. Patients were followed for overall survival every eight weeks.

Tumor tissue (archival or recently biopsied) was obtained at enrollment when available for immunohistochemistry (IHC) analysis of MET. Formalin-fixed paraffin embedded (FFPE) tumor blocks or freshly cut FFPE slides were analyzed by LabCorp using the SP44 antibody (Spring Biosciences, Pleasanton, Calif.). MET expression was defined as high versus low, based on a cutoff of ≥50% of tumor tissue stained with an intensity of 2+ or 3+ by IHC, according to published procedures. Spigel D R, Ervin T J, Ramlau R A, et al. Randomized phase II trial of Onartuzumab in combination with erlotinib in patients with advanced non-small-cell lung cancer. *J Clin Oncol* 2013; 31: 4105-14; Santoro A, Rimassa L, Borbath I, et al. Tivantinib for second-line treatment of advanced hepatocellular carcinoma: a randomized, placebo-controlled phase 2 study. *Lancet Oncol* 2013; 14: 55-63.

Outcomes.

The primary endpoint was PFS by independent radiology review in the first 375 randomized patients. PFS was defined as the time from randomization to radiographic progression per RECIST version 1.1 or death. Secondary endpoint analyses of overall survival and objective response rate (as determined by independent radiology review) were conducted in all randomized patients. Overall survival was defined as the time from randomization to death from any cause, and objective response rate was defined as the proportion of patients experiencing a confirmed complete or partial response per RECIST 1.1. Safety and tolerability were also assessed.

Statistical Analysis.

The study was designed to provide adequate power for both PFS and overall survival. The statistical design of the study is depicted in FIG. 1.9. For the primary endpoint of PFS, the event-driven analysis (at the 2-sided 5% alpha level) required 259 PFS events. The secondary endpoints of overall survival (at the 2-sided 4% alpha level) and objective response rate (at the 2-sided 1% alpha level) were to be tested among all randomized patients (the intention-to-treat (ITT) population) only if the primary PFS endpoint achieved statistical significance. For overall survival, assuming a single interim analysis at the time of the primary endpoint analysis and a subsequent final analysis, 408 deaths were required to provide 80% power to detect a hypothesized HR of 0.75 corresponding to an improvement in median survival from 15 months (Motzer R J, Escudier B, Oudard S, et al. Phase 3 trial of everolimus for metastatic renal cell carcinoma: final results and analysis of prognostic factors. *Cancer* 2010; 116: 4256-65) to 20 months. With a planned average accrual rate of 32 patients per month and using a 1:1 treatment allocation ratio, a total of 650 patients were required to observe 408 deaths within the planned study duration of 36 months. As the total sample size of 650 required to evaluate overall survival was much larger than needed to assess the primary endpoint of PFS, there was the possibility that patients with earlier progression intervals would be overrepresented (and those with longer progression intervals underrepresented) among the planned 259 PFS events. To reduce this potential, the primary analysis of PFS was pre-specified to occur when the required 259 events were observed in the first 375 randomized patients, the size the study would have been without the overall survival endpoint. Supportive analyses of PFS among all randomized patients were also planned.

The planned interim analysis of overall survival (conducted at the time of the primary PFS analysis with a data cutoff of May 22, 2015; minimum follow-up of 6 months) demonstrated a trend for longer survival that at that time did not meet the boundary for significance (49% information fraction: p≤0.0019) defined by the Lan-DeMets O'Brien-Fleming alpha spending function. The results of the planned interim analysis of overall survival were made public in July 2015 and were published in September 2015. Choueiri T K, Escudier B, Powles T, et al. Cabozantinib versus Everolimus in Advanced Renal-Cell Carcinoma. *N Engl J Med* 2015; 373: 1814-23. The decision to conduct an unplanned second interim analysis was made by the sponsor in consultation with regulatory agencies. As a result, the analysis plan was revised in October 2015 to include an unplanned second interim analysis of overall survival with a prospectively-defined cutoff date of Dec. 31, 2015, to provide a minimum of 13 months of follow-up from the last patient enrolled.

Hypothesis testing of duration of overall survival and PFS was performed using the stratified log-rank test with the same stratification factors as for randomization. Median duration of PFS and overall survival, corresponding 95% confidence intervals, and landmark proportions were estimated by the Kaplan-Meier method. Hazard ratios were estimated with a Cox regression model. Hypothesis testing for objective response rate was performed using the 2-sided chi-square test, and confidence intervals for proportions were calculated using exact methods. All subgroup analyses were pre-specified except for the subgroups that had received prior sunitinib and prior pazopanib as their only prior VEGFR TKI. P-values and confidence intervals for subgroup analyses are considered descriptive. Safety analyses were limited to patients who received any amount of study treatment.

All analyses were conducted using SAS® software Version 9.1 or higher (SAS Institute, Inc, Cary, N.C.).

This trial is registered at ClinicalTrials.gov, NCT01865747.

Results

Between Aug. 8, 2013, and Nov. 24, 2014, 658 patients were randomized to receive cabozantinib (n=330) or everolimus (n=328) (FIG. 1.3). As of Dec. 31, 2015, the cutoff for the second interim analysis of overall survival, 74 of 330 patients (22%) in the cabozantinib group and 25 of 328 patients (8%) in the everolimus group remained on study treatment. Demographics and baseline characteristics were typical of patients with advanced RCC and balanced between treatment groups (Table 1.4). Choueiri T K, Escudier B, Powles T, et al. Cabozantinib versus Everolimus in Advanced Renal-Cell Carcinoma. *N Engl J Med* 2015; 373: 1814-23.

TABLE 1.4

Demographics and Baseline Characteristics

|  | Cabozantinib (N = 330) | Everolimus (N = 328) |
|---|---|---|
| Age, median (range) years | 63 (32-86) | 62 (31-84) |
| Sex, n (%) | | |
| Male | 253 (77) | 241 (73) |
| Female | 77 (23) | 86 (26) |
| Not reported | 0 | 1 (<1) |
| Geographic region, n (%) | | |
| Europe | 167 (51) | 153 (47) |
| North America | 118 (36) | 122 (37) |
| Asia-Pacific | 39 (12) | 47 (14) |
| Latin America | 6 (2) | 6 (2) |
| Race, n (%) | | |
| White | 269 (82) | 263 (80) |
| Asian | 21 (6) | 26 (8) |
| Black | 6 (2) | 3 (<1) |
| Other | 19 (6) | 13 (4) |
| Not reported | 15 (5) | 22 (7) |
| Missing data | 0 | 1 (<1) |
| ECOG performance-status score, n (%) | | |
| 0 | 226 (68) | 217 (66) |
| 1 | 104 (32) | 111 (34) |
| MSKCC prognostic risk category, n (%)* | | |
| Favorable | 150 (45) | 150 (46) |
| Intermediate | 139 (42) | 135 (41) |
| Poor | 41 (12) | 43 (13) |

TABLE 1.4-continued

Demographics and Baseline Characteristics

|  | Cabozantinib (N = 330) | Everolimus (N = 328) |
|---|---|---|
| Metastatic site, n (%) | | |
| Lung | 204 (62) | 212 (65) |
| Liver | 88 (27) | 103 (31) |
| Bone | 77 (23) | 65 (20) |
| Lymph node | 206 (62) | 199 (61) |
| Brain | 2 (<1) | 1 (<1) |
| Other | 23 (7) | 21 (6) |
| Sum of lesions diameters, median (range), mm | 65 (0-291) | 65 (0-258) |
| Prior VEGFR tyrosine kinase inhibitors, n (%) | | |
| 1 | 235 (71) | 229 (70) |
| ≥2 | 95 (29) | 99 (30) |
| Previous systemic therapy, n (%) | | |
| Sunitinib | 210 (64) | 205 (62) |
| Pazopanib | 144 (44) | 136 (41) |
| Axitinib | 52 (16) | 55 (17) |
| Sorafenib | 21 (6) | 31 (9) |
| Bevacizumab | 5 (2) | 11 (3) |
| Interleukin-2 | 20 (6) | 29 (9) |
| Interferon alfa | 19 (6) | 24 (7) |
| Nivolumab | 17 (5) | 14 (4) |
| Radiotherapy, n (%) | 110 (33) | 108 (33) |
| Nephrectomy, n (%) | 282 (85) | 279 (85) |

A total of 464 patients (71%) had received only one prior VEGFR TKI, and the most common prior VEGFR TKIs were sunitinib (415 [63%]) and pazopanib (280 [43%]). Thirty-two (5%) had received prior immunotherapy with a PD-1 checkpoint inhibitor, primarily nivolumab. The most frequent reason for treatment discontinuation in both groups was disease progression. The median duration of follow-up for overall survival and safety was 18.7 months (IQR 16.1-21.1) in the cabozantinib group and 18.8 months (IQR 16.0-21.2) in the everolimus group. The data cutoff for PFS and objective response rate analyses among all enrolled patients was the same as for the primary PFS endpoint analysis (May 22, 2015) with a median duration of follow-up of 11.4 months (IQR 8.8-13.7) in the cabozantinib group and 11.5 months (IQR 8.6-13.9) in the everolimus group. Choueiri T K, Escudier B, Powles T, at al. Cabozantinib versus Everolimus in Advanced Renal-Cell Carcinoma. *N Engl J Med* 2015; 373: 1814-23.

The second interim analysis of overall survival included 320 deaths, representing 78% of the 408 deaths planned for the pre-specified final analysis of overall survival. There were 140 deaths out of 330 patients (42%) in the cabozantinib group and 180 deaths out of 328 patients (55%) in the everolimus group. Survival status as of the cutoff date was determined for the majority (98%) of the 658 randomized patients.

Treatment with cabozantinib significantly improved overall survival compared to everolimus in the second interim analysis. FIG. 1.4 is a Kaplan-Meier plot of overall survival through Dec. 31, 2015. All 658 randomized patients were included in the analysis. The number of patients censored is summarized by interval. CI indicates confidence interval, and NE means not estimable. The median overall survival was 21.4 months (95% CI 18.7—not estimable [NE]) in the cabozantinib group compared with 16.5 months (95% CI 14.7-18.8) in the everolimus group. The hazard ratio was 0.66 (95% CI 0.53-0.83; p=0.0003), which met the criterion for significance (p<0.0163) from the pre-specified alpha spending function.

Kaplan-Meier landmark estimates up to 24 months showed that at each time point the proportion of patients estimated to be alive was greater among patients in the cabozantinib group compared to patients in the everolimus group (Table 1.5).

TABLE 1.5

Kaplan-Meier Estimates of Percent of Patients Alive at Selected Landmarks

| | Estimate of % of Patients Alive with 95% CI | |
|---|---|---|
| Landmark | Cabozantinib N = 330 | Everolimus N = 328 |
| 6 Months | 91% (87%, 93%) | 81% (76%, 85%) |
| 12 Months | 73% (68%, 79%) | 63% (58%, 78%) |
| 18 Months | 58% (53%, 64%) | 47% (41%, 52%) |
| 24 Months | 48% (39%, 55%) | 31% (23%, 39%) |

FIG. 1.5A and FIG. 1.5B depict Forest plots of overall survival and progression-free survival. All 658 randomized patients were included in the analyses of overall survival and progression-free survival, which were conducted with a data cutoff of Dec. 31, 2015, and May 22, 2015, respectively. Disease progression was assessed by an independent radiology review committee. Hazard ratios are estimates from the Cox Proportional-Hazards model and are un-stratified with the exception of those for the overall population, which use the stratification factors for randomization. The PFS analysis included 48, 138, and 144 patients with high, low, and unknown MET status, respectively in the cabozantinib group and 48, 151, and 129 patients in the everolimus group, respectively, which was the known MET status of patients as of the May 22, 2015 data cutoff. CI, confidence interval; HR, hazard ratio; IMDC, International Metastatic Renal Cell Carcinoma Database Consortium; MSKCC, Memorial Sloan Kettering Cancer Center; PD-1, programmed cell death protein-1; PD-L, programmed cell death ligand-1; SoD, sum of lesion diameters; TKI, tyrosine kinase inhibitor; VEGFR, vascular endothelial growth factor receptor.

At 12 months estimates of survival were 73% (95% CI 68%, 78%) in the cabozantinib group compared with 63% (58%, 78%) in the everolimus group. At 18 months the estimates were 58% (53%, 64%) in the cabozantinib group compared with 47% (41%, 52%) in the everolimus group.

Subgroup analyses of overall survival were consistent with the results for the overall population with a hazard ratio <1 for all subgroups analyzed (FIG. 1.3). Subgroups defined by MSKCC risk groups of favorable, intermediate, and poor had similar hazard ratios for overall survival ranging from 0.65 to 0.67. These results are depicted in FIG. 1.11. Patients who received sunitinib or pazopanib as their only prior VEGFR-TKI therapy also had a similar overall survival benefit with cabozantinib treatment (hazard ratio of 0.66 for both subgroups). These results are depicted in FIG. 1.12. A marked benefit was observed in patients with bone metastases; the hazard ratio was 0.54 (95% CI 0.34-0.84) for patients with bone metastases and 0.45 (95% CI 0.28-0.72) for those patients with bone metastases who also had visceral metastases. These results are depicted in FIG. 1.13.

FIG. 1.14 depicts patient disposition (ITT Population). FKSI, FACT Kidney Symptom Index; EQ-5D, EuroQoL 5D Utility Score. Baseline FKSI-19 (EQ-5D-5L) data were available for 324 (323) patients in the cabozantinib arm and 313 (314) in the everolimus arm, of whom 319 (317) and 303 (304), respectively, had at least one post-baseline assessment. (a) Five patients randomized to the everolimus arm did not receive study treatment. In addition, one patient randomized to receive everolimus received cabozantinib as study treatment. (b) Includes withdrawals, protocol deviations, lack of efficacy, investigator decision.

FIG. 1.15A and FIG. 1.5B plot absolute FKSI ccores over time (ITT Population). A. FKSI-19 Total. B. 9-item FKSI-DRS. DRS, disease-related symptoms; FKSI, FACT Kidney Symptom Index; PD, progressive disease; rPD, radiographic progressive disease; TRT, treatment; QoL, quality of life; W, week. Higher scores indicate improved QoL status. Peri Last Dose is the closest QoL assessment 2 wks before to 4 wks after last dose. Peri rPD per Inv is the closest QoL assessment 2 wks before to 4 wks after first date of PD per investigator.

FIG. 1.16 depicts the effect of baseline FKSI-DRS on OS (ITT Population). CI, confidence interval; DRS, disease-related symptoms; FKSI, FACT Kidney Symptom Index; HR, hazard ratio; mo, month; OS, overall survival; QoL, quality of life.

Kaplan-Meier plots of overall survival for patients with high and low tumor MET status are shown in the FIG. 1.6A and FIG. 1.6B. For patients with high MET tumor expression, the hazard ratio was 0.55 (95% CI 0.31 to 0.99) and median overall survival was 22.0 months (95% CI 15.4-NE) with cabozantinib and 15.2 months (95% CI 8.7-NE) with everolimus. For patients with low MET tumor expression, the hazard ratio was 0.72 (95% CI, 0.52-1.00), and median overall survival was 20.8 months (95% CI 18.1-NE) with cabozantinib and 18.4 months (95% CI 15.9-19.6) with everolimus.

The proportions of patients continuing study treatment for at least two weeks after radiographic progression were similar between groups (74 [38%] with cabozantinib and 71 [31%] with everolimus). Also, similar proportions of patients in the everolimus group and the cabozantinib group were reported to have received subsequent systemic anti-cancer therapy following study treatment discontinuation (181 [55%] vs. 165 [50%) (Table 1.6).

TABLE 1.6

Subsequent Anticancer Therapies

| | Cabozantinib N = 330 n (%) | Everolimus N = 328 n (%) |
|---|---|---|
| Systemic therapy | 165 (50) | 181 (55) |
| VEGFR-TKI Therapies | 79 (24) | 155 (47) |
| Axitinib | 57 (17) | 90 (27) |
| Cabozantinib[a] | 0 | 7 (2) |
| Pazopanib | 5 (2) | 22 (7) |
| Sorafenib | 9 (3) | 31 (9) |
| Sunitinib | 17 (5) | 33 (10) |
| Other Selected Systemic Therapies | | |
| Everolimus[a] | 96 (29) | 15 (5) |
| Temsirolimus | 6 (2) | 4 (1) |
| Bevacizumab | 8 (2) | 11 (3) |
| Interleukins (Interleukin 2) | 0 | 4 (1) |
| Interferon-α/Peginterferon | 5 (2) | 7 (2) |
| PD-1/PD-L1 targeting agents[b] | 15 (5) | 19 (6) |
| Chemotherapy | 11 (3) | 13 (4) |
| External beam radiotherapy | 61 (18) | 77 (23) |
| Surgery (tumor lesions) | 13 (4) | 9 (3) |

Note:
patients may have received more than one type of anticancer therapy.
[a]Refers to commercial use.
[b]14 patients received nivolumab and one received pembrolizumab. In the everolimus arm, 16 patients received nivolumab, two received AMP-514, and one received MPDL3280A (atezolizumab).
PD-1, programmed cell death protein-1;
PD-L1, programmed cell death ligand-1;
TKI, tyrosine kinase inhibitor;
VEGFR, vascular endothelial growth factor receptor Patients in the everolimus group more frequently received subsequent VEGFR-TKI therapy (155 [47%] vs. 79 [24%]), most frequently axitinib (90 [27%] vs. 57 [17%]), whereas patients in the cabozantinib group more frequently received everolimus (96 [29%] in the cabozantinib group vs. 15 [5%] in the everolimus group). The proportion of patients receiving subsequent therapies targeting PD-1/PD-L was low (about 5%) and balanced in both treatment groups.

FIG. 1.7 is a Kaplan-Meier plot of progression-free survival as of May 22, 2015. Disease progression was assessed by an independent radiology review committee in all 658 randomized patients. The number of patients censored is summarized by interval. CI, confidence interval; No, number, PFS, progression-free survival. The analysis of PFS per independent radiology review conducted in all 658 randomized patients demonstrated improved PFS with cabozantinib: the hazard ratio was 0.51 (95% CI, 0.41-62; p<0.0001). Kaplan-Meier estimates for median duration of PFS were 7.4 months (95% CI 6.6-9.1) in the cabozantinib group versus 3.9 months (95% CI 3.7-5.1) in the everolimus group. Results for PFS per investigator assessment (HR 0.54, 95% CI 0.45-0.66) were similar to those determined by the independent radiology review committee (Table 1.7).

TABLE 1.7

Progression-Free Survival as of the May 22, 2015 Cutoff Date

| | IRC | | Investigator | |
|---|---|---|---|---|
| | Cabozantinib N = 330 | Everolimus N = 328 | Cabozantinib N = 330 | Everolimus N = 328 |
| Event, n (%) | 180 (55) | 214 (66) | 196 (59) | 233 (71) |
| Median duration of progression-free survival (95% confidence interval) (months) | 7.4 (6.6-9.1) | 3.9 (3.7-5.1) | 7.4 (7.3-7.8) | 5.1 (3.9-5.5) |
| Stratified p-value | <0.0001 | | <0.0001 | |
| Hazard ratio (95% confidence interval) | 0.52 (0.42-0.64) | | 0.54 (0.45-0.66) | |

Median is based on Kaplan-Meier survival estimates.
Stratification factors were those used for randomization. The hazard ratio was estimated using the Cox proportional hazard model adjusted for stratification factors. Hazard ratio <1 indicates progression-free survival (PFS) in favor of cabozantinib.
IRC, independent radiology review committee Subgroup analyses of PFS per independent radiology review to assess the effects of demographics and baseline characteristics were consistent with the results for the overall population with all hazard ratios <1 (FIG. 1.5 A and FIG. 1.5B), demonstrating an improvement in PFS with cabozantinib treatment for all subgroups analyzed.

The objective response rate per independent radiology review in all 658 randomized patients was 17% (95% CI 13-22) (57 partial responses) for the cabozantinib group and 3% (95% CI 2-6) (11 partial responses) for the everolimus group (p<0.0001) (Table 1.8).

TABLE 1.8

Tumor Response as of the May 22, 2015 Cutoff Date

| | Cabozantinib N = 330 | | Everolimus N = 328 | |
|---|---|---|---|---|
| | IRC | Investigator | IRC | Investigator |
| Objective response rate (95% confidence interval)[a] | 17 (13-22)[b] | 24 (19-29)[b] | 3 (2-6) | 4 (2-7) |
| Best overall response, n (%) | | | | |
| Confirmed complete response | 0 | 0 | 0 | 0 |
| Confirmed partial response | 57 (17) | 78 (24) | 11 (3) | 14 (4) |
| Stable disease | 216 (65) | 209 (63) | 203 (62) | 205 (63) |
| Progressive disease | 41 (12) | 29 (9) | 88 (27) | 87 (27) |
| Not evaluable or missing[c] | 16 (5) | 14 (4) | 26 (8) | 22 (7) |

[a]The proportion of patients achieving an overall response of confirmed complete response or partial response per RECIST version 1.1.
[b]The p-value from Cochran-Mantel-Haenszel test with stratification factors used for randomization was <0.0001 for both IRC and investigator-determined response compared to everolimus.
[c]No qualifying post-baseline assessment for overall response.
IRC, independent radiology review committee A best response of stable disease was observed for 216 patients (65%) in the cabozantinib group and 203 (62%) in the everolimus group. The incidence of progressive disease as best response was low with cabozantinib ($^{41}/_{330}$ [12%]) compared to everolimus ($^{88}/_{328}$ [27%]). Results for tumor response per investigator assessment were similar to those determined by the independent radiology review committee (Table 1.8); the objective response rate per investigator was 24% (95% CI 19-29) and 4% (95% CI 2-7) for patients in the cabozantinib and everolimus groups, respectively.

As of the Dec. 31, 2015, cutoff for the overall survival analysis, the median duration of exposure was 8.3 months (IQR 4.2-14.6) in cabozantinib-treated patients (n=331) and 4.2 months (IQR 1.9-8.6) in the everolimus-treated patients (n=322). Dose reductions occurred for 206 patients (62%) treated with cabozantinib and 80 patients (25%) treated with everolimus. The median daily dose was 43 mg cabozantinib (IQR 36-56) and 9 mg everolimus (IQR 7-10). Treatment discontinuation due to an adverse event not related to disease progression was 12% ($^{41}/_{330}$) in the cabozantinib group and 10% ($^{34}/_{328}$) in the everolimus group.

The overall incidence of adverse events regardless of causality was 100% (331/331) for the cabozantinib group and >99% (321/322) for the everolimus group. Grade 3 or 4 adverse events were experienced by 235 (71%) and 193 (60%) of cabozantinib- and everolimus-treated patients, respectively (Table 1.9).

TABLE 1.9

Adverse Events

| Event | Cabozantinib (N = 331) n (%) | | | Everolimus (N = 322) n (%) | | |
|---|---|---|---|---|---|---|
| | Grade 1-2 | Grade 3 | Grade 4 | Grade 1-2 | Grade 3 | Grade 4 |
| Any AE | 70 (21) | 210 (63) | 25 (8) | 103 (32) | 167 (52) | 26 (8) |
| Diarrhea | 206 (62) | 43 (13) | 0 | 85 (26) | 7 (2) | 0 |
| Fatigue | 159 (48) | 36 (11) | 0 | 130 (40) | 24 (8) | 0 |
| Nausea | 158 (48) | 15 (5) | 0 | 92 (29) | 1 (<1) | 0 |
| Decreased appetite | 146 (44) | 10 (3) | 0 | 111 (35) | 3 (<1) | 0 |
| Palmar-plantar erythrodysaesthesia syndrome | 115 (35) | 27 (8) | 0 | 16 (5) | 3 (<1) | 0 |
| Vomiting | 106 (32) | 7 (2) | 0 | 44 (14) | 3 (<1) | 0 |
| Weight decreased | 105 (32) | 9 (3) | 0 | 42 (13) | 0 | 0 |
| Constipation | 89 (27) | 1 (<1) | 0 | 64 (20) | 1 (<1) | 0 |
| Dysgeusia | 80 (24) | 0 | 0 | 30 (9) | 0 | 0 |
| Hypothyroidism | 76 (23) | 0 | 0 | 1 (<1) | 1 (<1) | 0 |
| Hypertension | 73 (22) | 49 (15) | 0 | 14 (4) | 12 (4) | 0 |
| Dysphonia | 68 (21) | 2 (<1) | 0 | 16 (5) | 0 | 0 |
| Cough | 67 (20) | 1 (<1) | 0 | 107 (33) | 3 (<1) | 0 |
| Stomatitis | 65 (20) | 8 (2) | 0 | 71 (22) | 7 (2) | 0 |
| Mucosal inflammation | 60 (18) | 5 (2) | 0 | 64 (20) | 10 (3) | 1 (<1) |
| Dyspnoea | 56 (17) | 10 (3) | 0 | 82 (26) | 11 (3) | 3 (<1) |
| Aspartate aminotransferase increased | 55 (17) | 5 (2) | 0 | 19 (6) | 1 (<1) | 0 |
| Back pain | 54 (16) | 8 (2) | 0 | 41 (13) | 7 (2) | 0 |
| Rash | 52 (16) | 2 (<1) | 0 | 92 (29) | 2 (<1) | 0 |
| Asthenia | 49 (15) | 15 (5) | 0 | 46 (14) | 8 (3) | 0 |
| Abdominal pain | 48 (15) | 12 (4) | 0 | 27 (8) | 5 (2) | 0 |
| Alanine aminotransferase increased | 47 (14) | 7 (2) | 1 (<1) | 20 (6) | 1 (<1) | 0 |
| Pain in extremity | 46 (14) | 5 (2) | 0 | 31 (10) | 1 (<1) | 0 |
| Muscle spasms | 45 (14) | 0 | 0 | 17 (5) | 0 | 0 |
| Arthralgia | 43 (13) | 1 (<1) | 0 | 46 (14) | 4 (1) | 0 |
| Headache | 43 (13) | 1 (<1) | 0 | 42 (13) | 1 (<1) | 0 |
| Anemia | 42 (13) | 19 (6) | 0 | 73 (23) | 53 (17) | 0 |
| Dizziness | 41 (12) | 1 (<1) | 0 | 21 (7) | 0 | 0 |
| Dyspepsia | 40 (12) | 1 (<1) | 0 | 15 (5) | 0 | 0 |
| Edema peripheral | 39 (12) | 0 | 0 | 70 (22) | 6 (2) | 0 |
| Hypomagnesaemia | 38 (12) | 6 (2) | 10 (3) | 5 (2) | 0 | 0 |
| Dry skin | 37 (11) | 0 | 0 | 35 (11) | 0 | 0 |
| Proteinuria | 37 (11) | 8 (2) | 0 | 28 (9) | 2 (<1) | 0 |
| Flatulence | 33 (10) | 0 | 0 | 7 (2) | 0 | 0 |
| Insomnia | 32 (10) | 0 | 0 | 33 (10) | 1 (<1) | 0 |
| Pyrexia | 31 (9) | 3 (<1) | 0 | 57 (18) | 2 (<1) | 0 |
| Pruritus | 27 (8) | 0 | 0 | 48 (15) | 1 (<1) | 0 |
| Blood creatinine increased | 17 (5) | 1 (<1) | 0 | 39 (12) | 0 | 0 |
| Hypertriglyceridemia | 17 (5) | 4 (1) | 0 | 31 (10) | 7 (2) | 3 (<1) |
| Hyperglycemia | 15 (5) | 2 (<1) | 1 (<1) | 46 (14) | 16 (5) | 0 |
| Epistaxis | 14 (4) | 0 | 0 | 46 (14) | 0 | 0 |

The most common grade 3 or 4 adverse events with cabozantinib were hypertension (49 [15%]), diarrhea (43 [13%]), and fatigue (36 [11%]) and with everolimus were anemia (53 [17%]), fatigue (24 [7%]), and hyperglycemia (16 [5%]). Among these, no grade 4 adverse events were reported in either treatment group.

Serious adverse events ≥grade 3 occurred in 130 (40%) of cabozantinib-treated patients and in 129 (40%) of everolimus-treated patients. Grade 5 adverse events regardless of causality were reported for 26 patients (7.9%) in the cabozantinib group and 25 (7.8%) in the everolimus group; the majority of these were related to disease progression. One grade 5 adverse event was assessed as treatment-related in the cabozantinib group (death; not otherwise specified) and two in the everolimus group (*aspergillus* infection, pneumonia aspiration).

Discussion

This randomized phase 3 study demonstrated a highly significant overall survival benefit for cabozantinib treatment compared with everolimus in patients with previously-treated advanced RCC. The median overall survival was 21.4 months with cabozantinib as compared with 16.5 months with everolimus (HR 0.66; p=0.0003). PFS was significantly improved, and a higher objective response rate was observed for cabozantinib as compared with everolimus. The median PFS was 7.4 months in the cabozantinib group versus 3.9 months in the everolimus group in all randomized patients, which is consistent with the results previously reported for the first 375 randomized patients (the primary endpoint of the study). Choueiri T K, Escudier B, Powles T, et al. Cabozantinib versus Everolimus in Advanced Renal-Cell Carcinoma. *N Engl J Med* 2015; 373: 1814-23. Objective tumor responses per independent radiology review committee were observed for 17% of patients who received cabozantinib and 3% of patients who received everolimus, which is also consistent with the previously reported results for the first 375 randomized patients.

The updated safety profile of cabozantinib was similar to that previously reported at the earlier data cutoff for this study. The most common adverse events were typical of those observed with other VEGFR TKIs in RCC patients and included diarrhea, fatigue, nausea, decreased appetite, palmar-plantar erythrodysaesthesia syndrome, and hypertension. Eisen T, Steinberg C N, Robert C, et al. Targeted therapies for renal cell carcinoma: review of adverse event management strategies. *J Natl Cancer Inst* 2012; 104: 93-113. The adverse event profile for everolimus was similar to that observed in other clinical studies. Motzer R J, Escudier B, Oudard S, et al. Phase 3 trial of everolimus for metastatic renal cell carcinoma: final results and analysis of prognostic factors. *Cancer* 2010; 116: 4256-65. Adverse events were managed with dose modifications and supportive care in both treatment groups. Although the frequency of dose reductions was higher in the cabozantinib-treated group, the rate of treatment discontinuations due to adverse events were similar in both groups (12% cabozantinib group vs. 10% everolimus group), indicating that dose modifications were effective in minimizing or preventing treatment-associated discontinuations.

Both the overall survival and PFS benefits were consistently observed across all subgroups analyzed including those defined by the pre-specified stratification factors (MSKCC risk group and number of prior VEGFR TKIs), International Metastatic Renal Cell Carcinoma Database Consortium (IMDC) risk group (Ko J J, Xie W, Kroeger N, et al. The International Metastatic Renal Cell Carcinoma Database Consortium model as a prognostic tool in patients with metastatic renal cell carcinoma previously treated with first-line targeted therapy: a population-based study. *Lancet Oncol* 2015; 16: 293-300), duration of prior VEGFR-TKI therapy, and prior treatment with agents targeting PD-1/PD-L1, location and extent of tumor metastases. The most common prior therapies were sunitinib and pazopanib, consistent with standard clinical practice. Motzer R J, Jonasch E, Agarwal N, et al. Kidney cancer, version 3.2015. *J Natl Compr Canc Netw* 2015; 13: 151-9. Patients who received either sunitinib or pazopanib as their only prior VEGFR TKI had an overall survival benefit with cabozantinib treatment that was similar to the overall population. The marked overall survival benefit in patients with bone metastases, which are associated with a poor prognosis (McKay R R, Kroeger N, Xie W, et al. Impact of bone and liver metastases on patients with renal cell carcinoma treated with targeted therapy. *Eur Urol* 2014; 65: 577-84), is consistent with reported effects of cabozantinib on bone metastases in both clinical and preclinical studies (Choueiri T K, Pal S K, McDermott D F, et al. A phase I study of cabozantinib (XL184) in patients with renal cell cancer. *Ann Oncol* 2014; 25: 1603-8; Graham T J, Box G, Tunariu N, et al. Preclinical evaluation of imaging biomarkers for prostate cancer bone metastasis and response to cabozantinib. *J Natl Cancer Inst* 2014; 106: dju033), and warrants further investigation into the mechanisms underlying the activity of cabozantinib in bone.

The proportions of patients continuing study treatment for at least two weeks after radiographic progression were similar between groups. Subsequent anticancer therapy was also balanced between treatment groups after study treatment discontinuation. Therefore, these factors are deemed unlikely to have biased the results overall survival towards one treatment group. In addition, treatment crossover was not allowed after determination of the primary endpoint of PFS enabling robust assessment of overall survival.

Although the study used an open-label design, bias was minimized for the primary endpoint of PFS and secondary endpoint of objective response rate by evaluation of radiographic assessments by a masked central independent radiology review committee. In addition, radiographic assessments were continued beyond investigator-determined progression in order to reduce missing data arising from discordance on the date of progression between the investigator and the independent radiology review committee. An advantage of open-label design is appropriate management of adverse effects in both study groups.

High MET expression in patients with advanced RCC has been associated with both a poor prognosis and prior exposure to VEGFR TKIs, and in preclinical models is associated with resistance to VEGFR TKI treatment. Gibney G T, Aziz S A, Camp R L, et al. c-Met is a prognostic marker and potential therapeutic target in clear cell renal cell carcinoma. *Ann Oncol* 2013; 24: 343-9; Zhou L, Liu X D, Sun M, et al. Targeting MET and AXL overcomes resistance to sunitinib therapy in renal cell carcinoma. *Oncogene* 2015 Sep. 14. doi: 10.1038/onc.2015.343; Harshman L C, Choueiri T K. Targeting the hepatocyte growth factor/c-Met signaling pathway in renal cell carcinoma. *Cancer J* 2013; 19: 316-23; Ciamporcero E, Miles K M, Adelaiye R, et al. Combination strategy targeting VEGF and HGF/c-met in human renal cell carcinoma models. *Mol Cancer Ther* 2015; 14: 101-10. Therefore, because cabozantinib targets receptor tyrosine kinases including MET, MET expression by IHC was investigated as a potentially predictive biomarker for cabozantinib in this study population. However, the hazard ratios for PFS and overall survival suggest that patients experience clinical benefit with cabozantinib treatment regardless of MET expression level, which may reflect the broader target profile of cabozantinib. A limitation of this analysis was that archival tumor tissue was used in most cases rather than a fresh biopsy obtained before study treatment initiation, which may have resulted in MET expression values that were not contemporaneous with the disease state during study treatment. In addition, approximately one third of the randomized patients had an unknown MET status due to the fact that archival tumor tissue was not available.

The study results support the hypothesis that the target profile of cabozantinib, which inhibits MET and AXL in addition to VEGF receptors, may help to overcome resistance to VEGFR inhibition. Gibney G T, Aziz S A, Camp R L, et al. c-Met is a prognostic marker and potential therapeutic target in clear cell renal cell carcinoma. *Ann Oncol* 2013; 24: 343-9; Gustafsson A, Martuszewska D, Johansson M, et al. Differential expression of Axl and Gas6 in renal cell carcinoma reflecting tumor advancement and survival. *Clin Cancer Res* 2009; 15: 4742-9; Rankin E B, Fuh K C, Castellini L, et al. Direct regulation of GAS6/AXL signaling by HIF promotes renal metastasis through SRC and MET. *Proc Nal Acad Sci USA* 2014; 111: 13373-8; Zhou L, Liu X D, Sun M, et al. Targeting MET and AXL overcomes resistance to sunitinib therapy in renal cell carcinoma. *Oncogene* 2015 Sep. 14. doi: 10.1038/onc.2015.343; Harshman L C, Choueiri T K. Targeting the hepatocyte growth factor/c-Met signaling pathway in renal cell carcinoma. *Cancer J* 2013; 19: 316-23; Pinato D J, Chowdhury S, Stebbing J. TAMing resistance to multi-targeted kinase inhibitors through Axl and Met inhibition. *Oncogene* 2015 Oct. 5: doi: 10.1038/onc.2015.374. This is supported by the observed low incidence of refractory disease with only 12% of patients experiencing progressive disease as a best response with cabozantinib treatment. Furthermore, cabozantinib-treated patients benefited regardless of the duration of the first prior VEGFR-TKI therapy. The results also suggest that sequenced VEGFR inhibition can be beneficial for the treatment of advanced RCC which has also been suggested by the report of a phase 2 study with levantinib. Motzer R J, Hutson T E, Glen H, et al. Lenvatinib, everolimus, and the combination in patients with metastatic renal cell carcinoma: a randomized, phase 2, open-label, multi-centre trial. *Lancet Oncol* 2015; 16: 1473-82. Additional studies are necessary to clearly define the roles of MET, AXL, and other targets beyond VEGFR in the clinical activity observed with cabozantinib in patients with advanced RCC. Future studies may also include more detailed evaluation of response to first-line therapy and tumor biopsies at the time of progression to better define the mechanisms of resistance and the benefits of sequenced VEGFR inhibition.

Several VEGFR TKIs have previously been approved for the treatment of metastatic RCC, and these comprise the mainstay of present day treatment Regulatory approval for each of these (sunitinib, sorafenib, pazopanib and axitinib) was based on an improvement in PFS over control arms of cytokine (interferon), placebo, or another TKI (sorafenib) in a randomized phase 3 trial. Motzer R J, Hutson T E, Tomczak P, et al. Sunitinib versus interferon alfa in metastatic renal-cell carcinoma. *N Engl J Med* 2007; 356: 115-24; Escudier B, Eisen T, Stadler W M, et al. Sorafenib for treatment of renal cell carcinoma: Final efficacy and safety results of the phase III treatment approaches in renal cancer global evaluation trial. *J Clin Oncol* 2009; 27: 3312-8; Sternberg C N, Davis I D, Mardiak J, at al. Pazopanib in locally advanced or metastatic renal cell carcinoma: results of a randomized phase III trial. *J Clin Oncol* 2010; 28: 1061-8; Rini B I, Escudier B, Tomczak P, t al. Comparative effectiveness of axitinib versus sorafenib in advanced renal cell carcinoma (AXIS): a randomized phase 3 trial. *Lancet* 2011; 378: 1931-9. The mTOR inhibitor everolimus, which was used as the comparator arm in this study, was also approved based on improved PFS when compared to placebo. Motzer R J, Escudier B, Oudard S, et al. Efficacy of everolimus in advanced renal cell carcinoma: a double-blind, randomized, placebo-controlled phase III trial. *Lancet* 2008; 372: 449-56. None of the pivotal phase 3 trials for these previously approved agents showed a statistically significant benefit in overall survival. Improvement in overall survival remains the gold standard as an endpoint for achieving clinical benefit in patients. It is therefore highly notable that in this study cabozantinib treatment resulted in a benefit in overall survival in addition to improved PFS and objective response rate compared to everolimus in patients who had progressed on these standard VEGFR-TKI therapies. The magnitude of overall survival benefit over everolimus illustrates the high level of clinical activity for cabozantinib in advanced RCC.

Recently, the immune checkpoint inhibitor nivolumab demonstrated an overall survival benefit with an improved response rate compared to everolimus after prior antiangiogenic therapy, but no PFS benefit was observed. Motzer R J, Escudier B, McDermott D F, at al. Nivolumab versus Everolimus in Advanced Renal-Cell Carcinoma. *N Engl J Med* 2015; 373: 1803-13. The hazard ratio for death in the nivolumab study (HR 0.73) was comparable to the hazard ratio with cabozantinib in this study (HR 0.66); however, the median overall survival of the comparator arm everolimus differed (19.6 months in the nivolumab study and 16.5 months in this study), reflecting the challenges of cross-trial comparison. In the current study, the observed median overall survival for everolimus was consistent with that reported in the pivotal RECORD-1 study. Motzer R J, Escudier B, Oudard S, et al. Phase 3 trial of everolimus for metastatic renal cell carcinoma: final results and analysis of prognostic factors. *Cancer* 2010; 116: 4256-65. The median PFS for the respective control arms was similar in both trials (4.4 months in the nivolumab study and 3.9 months in this study). The limits of publically-available data make it difficult to identify any factors to explain the differences in overall survival in the control arms of the two studies.

In this randomized phase 3 study, treatment with cabozantinib, an inhibitor of tyrosine kinases including MET, VEGF receptors, and AXL, was associated with clinically significant improvement in overall survival, PFS, and objective response rate compared with everolimus, a standard of care in second-line advanced RCC. The observed favorable clinical activity of cabozantinib was applicable to patients of all risk categories and regardless of prior therapies and extent of tumor burden. Based on these results, cabozantinib should be considered an important treatment option for previously-treated patients with advanced RCC.

Research in Context

Evidence Before this Study.

In the randomized, phase 3 METEOR trial, cabozantinib, an inhibitor of tyrosine kinases including MET, VEGF receptors, and AXL, significantly improved progression-free survival in previously-treated patients with advanced RCC compared with everolimus. In a literature review up to Mar.

10, 2016, none of the currently approved therapies had demonstrated significant benefit for all three efficacy endpoints of overall survival, progression-free survival, and objective response rate in a pivotal phase 3 trial in previously-treated patients with advanced RCC. Research suggested that increased expression of MET and AXL are associated with a poor prognosis in RCC patients, and that inhibition of these targets may help to overcome resistance to VEGF pathway inhibition.

Added Value of this Study.

In the METEOR phase 3 trial, treatment with cabozantinib was associated with a significant reduction in the risk of death, in addition to improving progression-free survival and the objective response rate compared with everolimus, a standard of care in second-line advanced RCC. All patients had documented radiographic progression during or after prior VEGFR-TKI therapy. The observed clinical benefits were consistent across various subgroups including MSKCC risk groups, number of prior VEGFR-TKI therapies, prior immune checkpoint inhibitor therapy, location and extent of tumor metastases, and tumor MET expression level. The safety profile of cabozantinib was consistent with that previously reported.

Implications of all the Available Evidence.

The observed improvements in progression-free survival, overall survival, and objective response rate indicate that cabozantinib should be considered an important new therapy for previously-treated patients with advanced RCC. Recently, the immune checkpoint inhibitor nivolumab also improved overall survival compared with everolimus in this population, but without improving progression-free survival. Future research on the optimal use of cabozantinib and other available therapies may help to provide maximum benefit to patients with advanced RCC.

Example 2

Quality of Life Outcomes for Cabozantinib vs Everolimus in Patients with Metastatic Renal Cell Carcinoma: METEOR Phase I Randomized Trial Purpose:

In the Phase 3 METEOR trial, 658 previously-treated patients with advanced renal cell carcinoma (RCC) were randomly assigned 1:1 to receive cabozantinib or everolimus. The cabozantinib arm had improved progression-free survival (PFS), overall survival (OS), and objective response rate (ORR) compared with everolimus. Quality of life (QoL) results, an additional endpoint, are reported here.

Patients and Methods:

Patients completed the 19-item Functional Assessment of Cancer Therapy-Kidney Symptoms Index (FKSI-19) and the 5-level EuroQoL-5 Dimensions (EQ-5D-5L) questionnaires at baseline and throughout the study. The 9-item FKSI-Disease Related Symptoms (FKSI-DRS) is a subset of FKSI-19. Data were summarized descriptively and by mixed-effects repeated-measures analysis (clinically relevant difference was an effect size ≥0.3). Time to deterioration (TTD) was defined as earlier of death, radiographic progressive disease or ≥4-point decrease from baseline in FKSI-DRS.

Results:

Questionnaire completion rates remained ≥75% through Week 48 in each arm for both instruments. There was no treatment difference over time for FKSI-19 Total, FKSI-DRS, or EQ data. Among the individual FKSI-19 items, the only differences were lower cabozantinib scores for diarrhea, nausea; lower everolimus scores for shortness of breath. These differences reflect the AE profile of each drug. Cabozantinib improved TTD overall, with a notable improvement in patients with bone metastases at baseline.

Conclusions:

Cabozantinib maintains QoL (FKSI-19 Total, FKSI-DRS, and EQ-5D) over time in patients with advanced RCC to a similar extent to everolimus. Compared with everolimus, cabozantinib extended TTD overall, with a notable improvement in patients with bone metastases.

Introduction

Renal cell carcinoma (RCC) is diagnosed in approximately 330,000 individuals worldwide (North America 64,000; Europe 115,000) (Ferlay J, Soerjomataram I, Dikshit R, Eser S, Mathers C, Rebelo M, et al. Cancer incidence and mortality worldwide: sources, methods and major patterns in GLOBOCAN 2012. Int J Cancer. 2015; 136(5): E359-86) and has generally increased in recent years. See Znaor A, Lortet-Tieulent J, Laversanne M, Jemal A, Bray F. International Variations and Trends in Renal Cell Carcinoma Incidence and Mortality. *Eur Urol.* 2015; 67(3):519-530; Cells D. Quality of life in patients with metastatic renal cell carcinoma: the importance of patient-reported outcomes. *Cancer Treat Rev.* 2009; 35(8):733-7. It affects more men than women; peak incidence occurs between 60-70 years of age. Many patients present with advanced or unresectabk disease at initial diagnosis. QoL in patients with advanced RCC is impacted by frequent disease-related symptoms (such as fatigue, weakness, bone pain, hematuria, weight loss, and shortness of breath) and treatment-related side effects (Cella D. Quality of life in patients with metastatic renal cell carcinoma: the importance of patient-reported outcomes. Cancer Treat Rev. 2009; 35(8):733-7; Palapattu G S, Kristo B, Rajfer J. Paraneoplastic syndromes in urologic malignancy: the many faces of renal cell carcinoma. Rev Urol. 2002; 4(4):163-70).

First-line systemic standard-of-care treatments for patients with advanced clear cell RCC are the VEGF receptor tyrosine kinase inhibitors (VEGFR-TKIs) sunitinib and pazopanib. Second-line standard-of-care therapies include the VEGFR-TKIs cabozantinib, axitinib, and sorafenib; the mTOR inhibitor everolimus; and the PD-1 checkpoint inhibitor nivolumab (NCCN. National Comprehensive Cancer Network Guidelines in Oncology. Kidney Cancer. Version 2 2016. Nov. 24, 2015; Ljungberg B, Bensalah K, Canfield S, Dabestani S, Hofmann F, Hora M, et al. EAU guidelines on renal cell carcinoma: 2014 update. Eur Urol. 2015; 67(5):913-24; Powles T, Staehler M, Ljungberg B, Bensalah K, Canfield S E, Dabestani S, et al. Updated EAU Guidelines for Clear Cell Renal Cancer Patients Who Fail VEGF Targeted Therapy. Eur Urol. 2016; 69(1):4-6; Signorovitch J E, Vogelzang N J, Pal S K, Lin P L, George D J, Wong M K et al. Comparative effectiveness of second-line targeted therapies for metastatic renal cell carcinoma: synthesis of findings from two multi-practice chart reviews in the United States. Curr Med Res Opin. 2014; 30(11):2343-53).

Cabozantinib is an oral inhibitor of tyrosine kinases, including MET, VEGFR, and AXL (Yakes F M, Chen J, Tan J, Yamaguchi K, Shi Y, Yu P, et al. Cabozantinib (XL184), a Novel MET and VEGFR2 Inhibitor, Simultaneously Suppresses Metastasis, Angiogenesis, and Tumor Growth. Mol Cancer Ther. 2011; 10:2298-308). Upregulation of MET and AXL in clear-cell RCC is a consequence of von Hippel-Lindau protein dysfunction and has been implicated in tumor progression and VEGFR-TKI resistance in preclinical studies and has been associated with a poor prognosis in patients with advanced RCC (Gibney G T, Aziz S A, Camp R L, Conrad P, Schwartz B E, Chen C R, et al. c-Met is a prognostic marker and potential therapeutic target in clear cell renal cell carcinoma. Ann Oncol. 2013; 24(2):343-9; Gustafsson A, Martuszewska D, Johansson M, Ekman C, Hafizi S, Ljungberg B, t al. Differential expression of Axl and Gas6 in renal cell carcinoma reflecting tumor advancement and survival. Clin Cancer Res. 2009; 15(14):4742-9; Rankin E B, Fuh K C, Castellini L, Viswanathan K, Finger E C, Diep A N, et al. Direct regulation of GAS6/AXL signaling by HIF promotes renal metastasis through SRC and MET. *Proc Natl Acad Sci USA*. 2014; 111(37):13373-8; Zhou L, Liu X D, Sun M, Zhang X, German P, Bai S, at al. Targeting MET and AXL overcomes resistance to sunitinib therapy in renal cell carcinoma. Oncogene. 2016; 35(21): 2687-97; Harshman L C, Choueiri T K. Targeting the hepatocyte growth factor/c-Met signaling pathway in renal cell carcinoma. *Cancer J*. 2013; 19(4):316-23; Pinato D J, Chowdhury S, Stebbing J. TAMing resistance to multi-targeted kinase inhibitors through Axl and Met inhibition. Oncogene. 2016; 35(21):2684-6). Cabozantinib gained regulatory approval in the US and in Europe as a second-line treatment for patients with advanced RCC after prior therapy with an antiangiogenic drug based on improvements in the randomized Phase 3 METEOR trial against everolimus for progression-free survival (PFS; primary endpoint) and the two secondary endpoints of overall survival (OS) and objective response rate (ORR) (Choueiri T K, Escudier B, Powles T, Mainwaring P N, Rini B I, Donskov F, et al. Cabozantinib versus Everolimus in Advanced Renal-Cell Carcinoma. *N Engl J Med.* 2015; 373(19):1814-23; Choueiri T K, Escudier B, Powles T, Tannir N M, Mainwaring P N, Rini B I, et al. Cabozantinib versus everolimus in advanced renal cell carcinoma (METEOR): final results from a randomized, open-label, phase 3 trial. *Lancet Oncol.* 2016; 17(7):917-27). Median PFS was 7.4 months in the cabozantinib arm vs 3.8 months in the everolimus arm (hazard ratio [HR] 0.58 [95% confidence intervals (CI): 0.45, 0.74]; p<0.0001) and ORR was 17% vs 3% (p<0.0001), both endpoints per independent radiology review. Median O S was 21.4 months (95% CI: 18.7, not estimable) vs 16.5 months (95% CI: 14.7, 18.8) (HR 0.66 [95% CI: 0.53, 0.83]; p=0.0003). Quality of life was an additional endpoint in this study and these results are reported below.

Patients and Methods

Eligibility and Study Treatments.

METEOR is a randomized, open-label, Phase 3 study with patients enrolled at 173 hospital and outpatient clinics in 26 countries. Patients 18 years or older with advanced or metastatic RCC and a clear-cell histology were eligible for enrollment if they had measurable disease per Response Evaluation Criteria in Solid Tumors (RECIST version 1.1) (Eisenhauer et al 2011) had received at least one previous VEGFR-TKI (there was no limit to the number of previous treatments), and had disease progression during or within 6 months of the most recent VEGFR-TKI treatment and within 6 months before randomization. Patients were required to have a Karnofsky performance status score of ≥70% and adequate organ function, based on standard laboratory tests including hematology, serum chemistry, lipids, coagulation, thyroid function, and urinalysis. Asymptomatic patients with stable brain metastases were eligible. Patients with previous mTOR inhibitor therapy, including everolimus, were not eligible for the study nor were patients with uncontrolled hypertension or clinically significant cardiovascular, gastrointestinal, wound healing, or infectious comorbidities. The study adhered to the Good Clinical Practice guidelines and the Declaration of Helsinki. The institutional review board or ethics committee of the participating centers approved the study protocol. All patients provided written informed consent.

Patients were randomized (1:1) to receive either cabozantinib or everolimus. Randomization was stratified by the number of prior VEGFR-TKI treatments (1 or ≥2) and Memorial Sloan Kettering Cancer Center (MSKCC) risk groups (favorable, intermediate, or poor) for previously-treated RCC (Motzer R J, Bacik J, Schwartz L H, Reuter V, Russo P, Marion S, et al. Prognostic Factors for Survival in Previously Treated Patients With Metastatic Renal Cell Carcinoma. *J Clin Oncol*. 2004; 22:454-463). Study treatment was assigned centrally with an interactive voice and web response system. Patients and investigators were not masked to study treatment to allow appropriate management of adverse events (AEs).

Cabozantinib was given orally 60 mg once-daily (qd) and everolimus was given orally 10 mg qd. Treatment interruptions and reductions were allowed to manage AEs. Cabozantinib could be dose reduced to 40 mg and then 20 mg; everolimus could be dose reduced to 5 mg and then 2.5 mg. Patients with clinical benefit could continue study treatment beyond radiographic progression at the discretion of the investigator. On-study crossover between treatment arms was not permitted.

Radiographic tumor imaging assessments occurred regularly every 8-12 weeks throughout the study. Assessment of AEs were performed throughout the study. Patients had a 30-day post-treatment visit with subsequent survival follow-up every 8 weeks. Efficacy and safety evaluations in this study have been previously described (Choueiri T K, Escudier B, Powles T, Mainwaring P N, Rini B I, Donskov F, et al. Cabozantinib versus Everolimus in Advanced Renal-Cell Carcinoma. *N Engl J Med.* 2015; 373(19):1814-23; Choueiri T K, Escudier B, Powles T, Tannir N M, Mainwaring P N, Rini B I, ct al. Cabozantinib versus everolimus in advanced renal cell carcinoma (METEOR): final results from a randomized, open-label, phase 3 trial. *Lancet Oncol.* 2016; 17(7):917-27).

QoL Assessments.

QoL was measured by using two validated patient self-reported instruments: the Functional Assessment of Cancer Therapy-Kidney Symptom Index-19 item (FKSI-19) and EuroQol Group's EQ-5D-5L questionnaires. Patients were required to complete the QoL questionnaires before any assessments at each clinic visit prior to the first dose, every 4 weeks through Week 25, every 8 weeks thereafter for the first year, then every 12 weeks thereafter. The QoL assessments were conducted per protocol prior to the patient knowing the results of their next tumor assessment. These assessments were performed regardless of whether study treatment was given, reduced, interrupted, or discontinued until the date of the last tumor imaging assessment. Questionnaires were provided on paper in the patient's own language.

FKSI-19.

The FKSI-19 instrument is a 19-item self-reported questionnaire with a total score and four subscales that assesses disease-related symptoms (DRS), treatment side effects, and function/well-being associated with advanced kidney cancer. It queries symptom severity and interference in activity and general health perceptions (Rao D, Butt Z, Rosenbloom S, Robinson D Jr, Von Roenn J, Kuzel T M, Cella D. A Comparison of the Renal Cell Carcinoma-Symptom Index (RCC-SI) and the Functional Assessment of Cancer Therapy-Kidney Symptom Index (FKSI). J Pain Symptom Manage. 2009; 38(2):291-8; Rothrock N E, Jensen S E, Beaumont J L, Abernethy A P, Jacobsen P B, Syrjala K, Cella D. Development and initial validation of the NCCN/FACT symptom index for advanced kidney cancer. Value Health. 2013; 16(5):789-96). The FKSI-19 comprises four sub-scales (DRS-Physical, DRS-Emotional, Treatment Side Effects, and Function/Well Being; Table 2.1). Each of the items is scored on a 5-point scale from 0 (not at all) to 4 (very much). Higher FKSI-19 scores indicate improvement. The FKSI-19 ensures content validity congruent with FDA Guidance (FDA. Guidance for Industry. Patient-Reported Outcome Measures: Use in Medical Product Development to Support Labeling Claims. December 2009). and was developed from a previous 9-item DRS version (FKSI-DRS; lack of energy, pain, losing weight, fatigue, short of breath, fevers, bone pain, coughing, blood in urine). The FKSI-19 includes selected treatment side effects that are important to the patient and physician.

TABLE 2.1

Treatment Differences in FKSI-19 and four subscales, FKSI-DRS, EQ-5D-VAS, and EQ-Index, Repeated Measures Change from Baseline Analysis (ITT Population)

| | LSMean | | Effect |
|---|---|---|---|
| | Cabozantinib | Everolimus | Size[a] |
| DRS-Physical | −1.093 | −1.386 | 0.046 |
| Lack of energy | −0.244 | −0.207 | −0.033 |
| Pain | 0.125 | 0.067 | 0.052 |
| Losing weight | −0.533 | −0.301 | −0.21 |
| Fatigued | −0.325 | −0.305 | −0.017 |
| Short of breath | 0.029 | −0.271 | 0.30 |
| Fevers | 0.056 | −0.021 | 0.13 |
| Bone pain | 0.049 | 0.057 | −0.008 |
| Coughing | 0.237 | −0.059 | 0.28 |
| Weak all over | −0.281 | −0.265 | −0.015 |
| Blood in my urine | 0.005 | −0.001 | 0.023 |
| Good appetite | −0.166 | 0.181 | −0.23 |
| Sleeping well | 0.018 | −0.152 | 0.12 |
| DRS-Emotional | 0.398 | 0.393 | 0.004 |
| Worry condition worsen | 0.398 | 0.393 | 0.004 |
| Treatment Side Effects | −2.416 | −0.814 | −0.62 |
| Nausea | −0.236 | 0.069 | −0.34 |
| Diarrhea | −1.280 | −0.326 | −0.77 |
| Side effects of treatment | −0.850 | −0.523 | −0.24 |
| Function/Well-Being | −0.230 | −0.169 | −0.019 |
| Able to work | −0.151 | −0.101 | −0.037 |
| Enjoy life | −0.017 | −0.014 | −0.002 |
| Content with quality life | −0.035 | −0.017 | −0.014 |
| FKSI-19 (19-item) Total Score | −3.483 | −2.214 | −0.13 |
| FKSI-DRS (9-item) | −0.52 | −0.93 | 0.087 |
| EQ-VAS | −1.32 | −1.27 | −0.003 |
| EQ-Index | −0.02 | −0.02 | −0.009 |

DRS, disease-related symptoms;
EQ-VAS, EuroQol Visual Analogue Scale;
FKSI, Functional Assessment of Cancer Therapy-Kidney Cancer Symptom Index;
ITT, intent-to-treat;
LSMean, least squares mean.
A positive mean change (higher score) indicates improved quality of life status.
[a]Effect size = treatment difference in mean change from baseline scores/pooled SD for both groups for baseline values. Effect sizes ≥ 0.3 for treatment arm comparisons were regarded as likely to be clinically relevant. Positive effect size values favor cabozantinib.

FIG. 2.1 depicts the quality of life instruments and quality of life assessment schedule. The items from the earlier FKSI-DRS (9-item) version are included within the FACT Kidney Symptom Index (FKSI-19). FKSI-19 evaluates kidney cancer specific quality of life. A total of 19 items are grouped into four sub-classes and each item is scored on a four-point scale from 0 (not at all) to 4 (very much). Higher scores indicate better quality of life.

The quality of life assessment schedule is a questionnaire completed by a patient prior to assessment.

FKSI-19 norms for the general US population have been calculated (Butt Z, Peipert J, Webster K, Chen C, Cella D. General population norms for the Functional Assessment of Cancer Therapy-Kidney Symptom Index (FKSI). Cancer. 2013; 119(2):429-37). The FKSI instrument has been utilized in other pivotal studies in RCC (Cella D, Grlnwald V, Nathan P, Doan J, Dastani H, Taylor F, et al. Quality of life in patients with advanced renal cell carcinoma given nivolumab versus everolimus in CheckMate 025: a randomized, open-label, phase 3 trial. Lancet Oncol. 2016; 17(7): 994-1003; Motzer R J, Hutson T E, Cella D, Reeves J, Hawkins R, Guo J, at al. Pazopanib versus sunitinib in metastatic renal-cell carcinoma. N Engl J Med. 2013; 369 (8):722-31; Motzer R J, Escudier B, Tomczak P, Hutson T E, Michaelson M D, Negrier S, t al Axitinib versus sorafenib as second-line treatment for advanced renal cell carcinoma: overall survival analysis and updated results from a randomized phase 3 trial. Lancet Oncol 2013; 14:552-562; Motzer R J, Escudier B, Oudard S, Hutson T E, Porta C, Bracarda S, et al. Efficacy ofeverolimus in advanced renal cell carcinoma: a double-blind, randomized, placebo-controlled phase III trial. Lancet. 2008; 372(9637):449-56; Cella D, Michaelson M D, Bushmakin A G, Cappelleri J C, Charbonneau C, Kim S T, at al. Health-related quality of life in patients with metastatic renal cell carcinoma treated with sunitinib vs interferon-αlpha in a phase II trial: final results and geographical analysis. Br J Cancer. 2010; 102(4):658-64).

EQ-5D-5L.

The standardized measure of health status EQ-5D-5L, developed by the EuroQol, was also used in this study in order to measure generic health status (Herdman M, Gudex C, Lloyd A, Janssen M, Kind P, Parkin D, t al. Development and preliminary testing of the new five-level version of EQ-5D (EQ-5D-5L). Qual Life Res. 2011; 20(10):1727-36). It comprises five functional and symptom dimensions: mobility, self-care, usual activities, pain/discomfort, and anxiety/depression. Levels indicate increasing severity from Level 1 (no problem) to Levels 2 through 5 (mild problem to extreme problem). The digits from the 5 dimensions were converted into a single population-based index value normalized across the nine countries in the study for which index value sets were available (van Hout B, Janssen M F, Feng Y S, Kohlmann T, Busschbach J, Golicki D, et al. Interim scoring for the EQ-5D-5L: mapping the EQ-5D-5L to EQ-5D-3L value sets. Value Health. 2012; 15(5):708-15). Index values range from 0 to 1 and a higher index score indicates better health. Patients also completed a 20-cm vertical visual assessment scale (VAS) scored from 0 ("worst health you can imagine") to 100 ("best health you can imagine"). A prior (3-level) version of the EQ-5D instrument had been evaluated in a study of pazopanib vs placebo (Cella D, Pickard A S, Duh M S, Guerin A, Mishagina N, Antràs L, et al. Health-related quality of life in patients with advanced renal cell carcinoma receiving pazopanib or placebo in a randomized phase III trial. Eur J Cancer. 2012; 48(3):311-23) and in the NCT83889 study of sunitinib vs interferon (Cella D. Quality of life in patients with metastatic renal cell carcinoma: the importance of patient-reported outcomes. Cancer Treat Rev. 2009; 35(8): 733-7).

Statistical Analysis.

The QoL analyses were performed on the intention-to-treat (ITT) population with the same data cutoff date (May 22, 2015) as the primary PFS endpoint (Choueiri T K, Escudier B, Powles T, Mainwaring P N, Rini B I, Donskov F, et al. Cabozantinib versus Everolimus in Advanced Renal-Cell Carcinoma. N Engl J Med. 2015; 373(19):1814-23; Choueiri T K, Escudier B, Powles T, Tannir N M, Mainwaring P N, Rini B I, at al. Cabozantinib versus everolimus in advanced renal cell carcinoma (METEOR): final results from a randomized, open-label, phase 3 trial. Lancet Oncol. 2016; 17(7):917-27). OS analyses used a Dec. 31, 2015 cutoff date. All available data were included in the analyses, no data were imputed. The questionnaire completion rate was calculated as number completed/number expected at that timepoint.

Descriptive statistics were used to summarize QoL scores over time for each treatment arm. In addition, a pre-specified repeated-measures mixed effects model was used to compare changes from baseline between the two treatment arms. The model included the outcome variable of QoL score change from baseline. The predictors (fixed effects) were the baseline scores, treatment arms, and visit. The individual subject nested within the planned treatment arm was the random effect. No adjustment was made for multiplicity. Effect sizes in the range 0.2 to <0.5 are generally considered to be small, for this study an effect size for treatment arm comparisons of ≥0.3 was regarded as likely to be clinically relevant (Sloan J A, Cella D, Hays R D. Clinical significance of patient-reported questionnaire data: another step toward consensus. J Clin Epidemiol. 2005; 58(12):1217-9; Yost K J, Eton D T. Combining distribution- and anchor-based approaches to determine minimally important differences: the FACIT experience. Eval Health Prof. 2005; 28(2):172-91).

To assess the effect of patient dropout, post-hoc piecewise linear growth curve sensitivity analyses were undertaken using a mixed-effect regression model. Fixed effects included baseline score, randomization stratification factors, treatment arm, time (a continuous variable) and the interaction between treatment arm and time. Random effects included intercept and slope. The mean trajectory of each arm based on Early (before Week 25), Median (Weeks 25-33), and Late (Week 41 and after) dropout tertiles was estimated. Dropout was defined as the last available analyzable score.

Time to deterioration (TTD; the earlier of death, radiographic disease progression (rPD), or ≥4-point decrease from baseline in the 9-item FKSI-DRS) was a post-hoc analysis. The TTD was repeated as a sensitivity analysis using a ≥3-point decrease.

Finally, a post-hoc analysis of the effect of FKSI-DRS scores on OS was performed in two groups of patients (≥, <median FKSI-DRS at baseline). The same Kaplan-Meier method was used as in a previous OS analysis (Choueiri T K, Escudier B, Powles T, Tannir N M, Mainwaring P N, Rini B I, at al. Cabozantinib versus everolimus in advanced renal cell carcinoma (METEOR): final results from a randomized, open-label, phase 3 trial. Lancet Oncol. 2016; 17(7):917-27).

Results

Baseline Characteristics.

A total of 658 patients were randomly assigned and included in the intent-to-treat (ITT) analysis (FIG. 1.14). At the cutoff date for the QoL analysis 40% of patients in the cabozantinib arm and 21% in the evcrolimus arm were still on study treatment. The incidence of discontinuation due to a primary reason of AE (excluding disease progression) was similar (10%) in each arm.

Baseline characteristics were similar in each arm (Table 2.2). Mean age was 62 years in the cabozantinib arm and 61 in the everolimus arm; approximately 75% of patients were male. FKSI-19 and FKSI-DRS (9-item) mean scores in each arm were similar to the US Adult Population values of 59.8 and 29.5, respectively (Butt Z, Peipert J, Webster K, Chen C, Cella D. General population norms for the Functional Assessment of Cancer Therapy-Kidney Symptom Index (FKSI). Cancer. 2013; 119(2):429-37).

TABLE 2.2

Patient Demographics and Baseline Characteristics (ITT Population)

| Patient Characteristic | Cabozantinib N = 330 | Everolimus N = 328 |
|---|---|---|
| Age, mean (range), years | 61.7 (32, 86) | 61.1 (31, 84) |
| Sex, n (%)[a] | | |
| Male | 253 (77) | 241 (73) |
| Female | 77 (23) | 86 (26) |
| Race, n (%)[a] | | |
| White | 269 (82) | 263 (80) |
| Asian | 21 (6.4) | 26 (7.9) |
| Black or African American | 6 (1.8) | 3 (0.9) |
| Other | 19 (5.8) | 13 (4.0) |
| Not reported | 15 (4.5) | 22 (6.7) |
| Enrollment per geographic region, n (%) | | |
| Europe | 167 (51) | 153 (47) |
| North America | 118 (36) | 122 (37) |
| Asia Pacific | 39 (12) | 47 (14) |
| Latin America | 6 (1.8) | 6 (1.8) |
| Karnofsky Performance Status, n (%) | | |
| ≥80 | 301 (91) | 306 (93) |
| 70 | 29 (8.8) | 22 (6.7) |
| Randomization stratification factors, n (%) | | |
| Prior VEGFR-TKI | | |
| 1 | 233 (71) | 231 (70) |
| ≥2 | 97 (29) | 97 (30) |
| MSKCC risk group[Motzer et al 2004] | | |
| Favorable | 150 (45) | 150 (46) |
| Intermediate | 137 (42) | 136 (41) |
| Poor | 42 (13) | 42 (13) |
| Bone metastases per IRC | 77 (23) | 65 (20) |
| FKSI-19 Total score, mean (SD) | n = 324 | n = 313 |
|  | 56.7 (10.51) | 57.1 (10.17) |
| FKSI-DRS (9-item) score, mean (SD) | n = 324 | n = 313 |
|  | 29.1 (5.08) | 29.3 (4.92) |
| EQ-Index (in countries in which index was validated), mean (SD) | n = 188 | n = 181 |
|  | 0.77 (0.240) | 0.80 (0.184) |
| EQ-VAS, mean (SD) | n = 323 | n = 314 |
|  | 73.6 (18.62) | 74.1 (17.50) |

Abbreviations:
DRS, disease-related symptoms;
EQ-VAS, EuroQol Visual Analogue Scale;
FKSI-19, Functional Assessment of Cancer Therapy-Kidney Symptom Index-19 item;
IRC, Independent Review Committee;
MSKCC, Memorial Sloan-Kettering Cancer Center;
SD, standard deviation;
VEGFR, vascular endothelial growth factor receptor;
TKI, tyrosine kinase inhibitor
[a]Sex and race were missing for one patient. Patients could report more than one race.

Efficacy outcomes for the study are depicted in Table 2.3.

TABLE 2.3

| Outcome | Cabozantinib (N = 30) | Everolimus (N = 328) | Hazard Ratio[a] | P-Value[b] |
|---|---|---|---|---|
| PFS per IRC,[c] mo Median (95% CI) | 7.4 (6.6, 9.1) | 3.9 (3.7, 5.1) | 0.51 (0.41, 0.62) | <0.0001 |
| OS,[d] mo Median (95% CI) | 21.4 (18.7, NE) | 16.5 (14.7, 18.8) | 0.66 (0.53, 0.83) | <0.00026 |
| ORR per IRC,[c] mo Median (95% CI) | 17 (13, 22) | 3 (2, 6) | NA | <0.0001 |

CI, confidence interval;
IRC, independent radiology committee;
ITT, intent to treat;
mo, months;
NA, not applicable;
NE, notestimable;
ORR, objective response rate;
OS, overall survival;
PFS, progression free survival
[a]Estimated using Cox proportional hazard model adjusted for stratification factors;
[b]P-value determined using stratified log-rank test (PFS and OS) and chi squared test (ORR);
[c]May 22, 2015 cutoff date;
[d]Dec. 31, 2015 cutoff date.

Questionnaire Completion Rate.

The questionnaire completion rates (number completed/expected at each timepoint) were high and similar in each treatment arm for both instruments. At baseline the rates for the FKSI-19 (EQ-5D) were 98% (96%) and 95% (95%) in the cabozantinib and everolimus arms, respectively, and remained ≥75% through Week 49 in each arm for both instruments.

FKSI Assessments.

FKSI-19 total scores over time are depicted in FIG. 2.2A and FIG. 2.2B. There were no apparent differences over time between the two treatment arms based on descriptive summaries for the FKSI-19 Total or 9-item FKSI-DRS or for the EQ instrument (data not shown). There was also no treatment difference (i.e., effect size <0.3) based on a repeated-measures mixed effect model change from baseline analysis for FKSI-19 Total or 9-item FKSI-DRS (Table 2.3). Among the 19 individual items, the only differences based on effect size were lower scores in cabozantinib arm for diarrhea and nausea and lower scores in the everolimus arm for shortness of breath.

EQ-5D-5L Assessments.

There were no apparent differences over time between the two treatment arms (ie, effect size <0.3) based on a repeated-measures change from baseline analysis for EQ-Index or EQ-VAS (Table 2.3). There was no apparent treatment difference based on descriptive summaries over time for EQ-Index or EQ-VAS (data not shown).

Sensitivity Analyses.

Post-hoc growth curve sensitivity analyses in Table 2.4 show that there was an inconsistent effect primarily for the intercept (which represents the initial treatment difference at Week 4) across the three tertiles (Early, Median, and Late Dropout). Additional analyses are planned to further explore this observation.

TABLE 2.4

Growth Curve Analysis: Estimated Treatment Difference in Change from Baseline By Dropout Tertile (ITT Population)

| Parameter | Early Dropout (before Week 24) | Median Dropout (Weeks 25-33) | Late Dropout (Week 41 or later) |
|---|---|---|---|
| FKSI-19 Total | | | |
| Cabo vs Evero Slope | 0.131 | 0.141 | 0.082 |
| Cabo vs Evero Intercept[a] | 0.241 | -2.003 | -5.141 |
| Evero Intercept[a] | -3.643 | -1.838 | 1.105 |
| FKSI-DRS (9-item) | | | |
| Cabo vs Evero Slope | 0.037 | 0.094 | 0.046 |
| Cabo vs Evero Intercept[a] | 1.445 | -0.313 | -1.307 |
| Evero Intercept[a] | -2.002 | -0.843 | 0.453 |
| EQ-Index | | | |
| Cabo vs Evero Slope | 0.005 | 0.003 | 0.003 |
| Cabo vs Evero Intercept[a] | 0.020 | -0.033 | -0.090 |
| Evero Intercept[a] | -0.046 | -0.018 | 0.033 |
| EQ-VAS | | | |
| Cabo vs Evero Slope | 0.498 | 0.146 | 0.134 |
| Cabo vs Evero Intercept[a] | -1.933 | -0.352 | -4.749 |
| Evero Intercept[a] | -2.474 | -1.181 | 1.012 |

Cabo, cabozantinib;
evero, everolimus.
Positive treatment differences favor cabozantinib.
[a]Change at Week 4 (first post-baseline timepoint). For everolimus intercept data, positive values indicate better quality of life and negative values indicate worse quality of life.

Table 2.5 summarizes changes from baseline in QOL outcomes by repeated measurement analysis.

TABLE 2.5

Changes from Baseline In Qol Outcomes, Repeated Measures Analysis

| Scale (range) Subscale Items which met effect size criterion | Least Squares Mean | | Effect Size* |
|---|---|---|---|
| | Cabozantinib | Everolimus | |
| FKSI-19 Total Score (0-76) | -3.483 | -2.214 | -0.13 |
| DRS-Physical (0-48) | -1.093 | -1.386 | 0.046 |
| Short of breath (0-4) | 0.029 | -0.271 | 0.30[b] |
| DRS-Emotional (0-4) | 0.398 | 0.393 | 0.004 |
| Treatment Side Effects (0-12) | -2.416 | -0.814 | -0.62[b] |
| Nausea (0-4) | -0.236 | 0.069 | -0.34[b] |
| Diarrhea (0-4) | -1.28 | -0.326 | -0.77[b] |
| Function/Well-being (0-12) | -0.230 | -0.169 | -0.019 |
| FKSI-DRS (9-item) (0-36) | -0.52 | -0.93 | 0.087 |
| EQ VAS (0-100) | -1.32 | -1.27 | -0.003 |
| EQ Index (0-1) | -0.02 | -0.02 | -0.009 |

DRS, disease-related symptoms;
EQ, EuroQol;
FKSI, FACT Kidney Symptom Index;
Qol, quality of life;
SD, standard deviation;
VAS, visual analogue scale.
Higher scores indicated improved QOL status.
[a]Effect size = treatment difference in mean change from baseline scores/pooled SD for both groups for baseline values. Positive effect size values favor cabozantinib.
[b]Effect sizes ≥ 0.3 for treatment arm comparisons were regarded as likely to be clinically relevant.

Time to Deterioration (TTD).

There was a notable decrease in QoL scores compared with baseline at the time of rPD per investigator. Progressive disease was the most frequent reason for study treatment discontinuation. Cabozantinib treatment improved TD (earlier of death, rPD, ≥4-point decrease from baseline in FKSI-DRS) compared with everolimus: median TTD 5.5 vs 3.7 mo (p<0.0001; FIG. 2.3 (and Table 2.6). In a subgroup analysis, there was a pronounced TTD improvement with cabozantinib treatment in patients with bone metastases: median TTD 5.6 vs 1.9 mo (p=0.0003; FIG. 2.4 and Table 2.6).

TABLE 2.6

Time to Deterioration (ITT Population)

| | Cabozantinib Median (mo) | Everolimus Median (mo) | HR (95% CI)$^a$ | p-value$^b$ |
|---|---|---|---|---|
| Overall (earlier of death, rPD, ≥4-point FKSI-DRS decrease from BL) | 5.5 | 3.7 | 0.65 (0.54, 0.78) | <0.0001 |
| Bone metastases per IRC at BL | | | | |
| Yes | 5.6 | 1.9 | 0.49 (0.33, 0.72) | 0.0003 |
| No | 5.5 | 3.8 | 0.69 (0.56, 0.85) | 0.0004 |

BL, baseline;
CI, confidence interval;
HR, hazard ratio;
IRC, Independent Review Committee;
rPD, radiographic progressive disease
$^a$Unstratified HRs are from the Cox Proportional Hazards model
$^b$Unstratified log-rank test QoL as a Prognostic Factor for OS.

Baseline FKSI-DRS (9-item) scores higher than the median population values were associated with improved OS in both treatment arms, as depicted in FIG. 1.16). HRs for OS favored the cabozantinib arm regardless of baseline QoL.

Discussion

As previously reported (Choueiri T K, Escudier B, Powles T, Mainwaring P N, Rini B I, Donskov F, et al. Cabozantinib versus Everolimus in Advanced Renal-Cell Carcinoma. N Engl J Med. 2015; 373(19):1814-23; Choueiri T K, Escudier B, Powles T, Tannir N M, Mainwaring P N, Rini B I, et al. Cabozantinib versus everolimus in advanced renal cell carcinoma (METEOR): final results from a randomized, open-label, phase 3 trial. Lancet Oncol. 2016; 17(7):917-27) the METEOR Phase 3 trial demonstrated that cabozantinib, an oral inhibitor of tyrosine kinases including MET, VEGFR, and AXL, improved key clinical endpoints of PFS, OS, and ORR compared with everolimus in patients with advanced RCC who had received a prior VEGFR-TKI. The improved efficacy for cabozantinib was demonstrated across all pre-specified subgroups. We now report the QoL, an additional endpoint in this trial, which was assessed using standardized instruments (FKSI-19 and EQ-5D-5L). This is the first head-to-head QoL assessment against an mTOR inhibitor comparator in a Phase 3 setting of advanced RCC patients eligible for second-line treatment.

The FKSI-19 instrument was developed to allow the impact of specific treatment-related side effects to be assessed. There was no clinically meaningful difference between treatment arms in FKSI-19 Total scores. Among the 19 individual items, the observed treatment differences (worse diarrhea and nausea for cabozantinib, worse shortness of breath for everolimus) reflect the different safety profiles of each agent. Management of treatment-related AEs in this study may be considered to be reflective of real-world conditions in that this was an open-label trial. Physicians should aim to proactively manage side effects, for example by administration of antidiarrheal agents at the first sign of diarrhea. Tolerability of study treatment, based on the low proportion of patients who discontinued study treatment due to AEs (~10% of patients in each arm), was similar for each study treatment and supports the role of early management of AEs. Of note, there was a low rate of study treatment discontinuation due to diarrhea (0.9% of patients in each arm).

The earlier developed (9-item) FKSI-DRS instrument was intended to examine the effect of study treatment on disease-related symptoms rather than treatment-related adverse effects. Consistent with the 19-item scale, no clinically meaningful treatment difference in QoL was seen for cabozantinib as compared with everolimus. Of note, the previous placebo-controlled study for everolimus showed no difference in FKSI-DRS over time (Beaumont J L, Butt Z, Baladi J, Motzer R J, Haas T, Hollaender N, et al. Patient-reported outcomes in a phase iii study of everolimus versus placebo in patients with metastatic carcinoma of the kidney that has progressed on vascular endothelial growth factor receptor tyrosine kinase inhibitor therapy. Oncologist. 2011; 16(5): 632-40).

QoL decreased notably in both treatment arms at the time of investigator-determined rPD highlighting the negative impact of disease progression on QoL, and the benefit of extending PFS. The prolongation of TTD further supports the overall clinical benefit of cabozantinib treatment in addition to improving PFS, ORR, and OS. The majority of patients in the cabozantinib arm (75%, compared with 48% in the everolimus arm) experienced reduction in measurable tumor lesion size which may be reflected in the improvement in TTD with cabozantinib treatment. The results of the generic EQ-5D (health index and patient-based VAS) instrument support the findings from the overall FKSI-19 and FKSI-DRS scales of no clinically relevant treatment difference between the two study arms. Finally, the effect of baseline QoL on OS has been demonstrated in this study: higher baseline QoL was associated with improved OS in both treatment arms. A similar correlation has been observed in another RCC study (Celia D, Grlnwald V, Nathan P, Doan J, Dastani H, Taylor F, et al. Quality of life in patients with advanced renal cell carcinoma given nivolumab versus everolimus in CheckMate 025: a randomized, open-label, phase 3 trial. Lancet Oncol. 2016; 17(7):994-1003).

The study used an open-label design so patients and caregivers were aware of their study treatment allocation which could potentially lead to an impact on QoL evaluations. However, this may be more of a concern with unequal randomization whereas this trial had equal randomization to active treatments. In addition, QoL assessments were scheduled per protocol prior to the patient knowing the results of their most recent radiographic tumor assessment. This was also a multinational trial with no adjustment for by-country differences. However, this is unlikely to be important in a randomized trial, and key efficacy outcomes (PFS, OS) have been shown to be similar by region (Choueiri T K, Escudier B, Powles T, Mainwaring P N, Rini B I, Donskov F, et al. Cabozantinib versus Everolimus in Advanced Renal-Cell Carcinoma. N Engl J Med. 2015; 373(19):1814-23; Choueiri T K, Escudier B, Powles T, Tannir N M, Mainwaring P N, Rini B I, t al. Cabozantinib versus everolimus in advanced renal cell carcinoma (METEOR): final results from a randomized, open-label, phase 3 trial. Lancet Oncol. 2016; 17(7):917-27).

Use of a mixed effect repeated measures model reduces the potential for bias resulting from dropouts i.e., all available data are used: if a score is missing, it has no effect on other scores from that same patient. In terms of validity of study results, a lack of treatment difference has been demonstrated in both unadjusted and the pre-specified mixed effects repeated measures modelled data. However, post-hoc growth curve sensitivity analyses suggest heterogeneity of the treatment difference (primarily in the intercept, which represents the initial treatment difference at Week 4) across the Early, Median, and Late Dropout tertiles. Of note, results adjusting for non-random dropouts using a technique such as pattern mixture modeling which identifies a weighted average effect across dropout groups may be challenging to interpret due to these time-based differences. Based on these results additional analyses are planned to further explore this observation.

In conclusion, the METEOR trial showed that QoL was maintained over time to a similar extent in both the cabozantinib and everolimus arms. The totality of results for PFS, OS, and ORR shows that cabozantinib has a favorable clinical benefit compared with everolimus and is considered a new standard of care for previously treated patients with advanced RCC.

Example 3

Efficacy of Cabozantinib (Cabo) Vs Everolimus (Eve) by Metastatic Site and Tumor Burden in Patients (Pts) with Advanced Renal Cell Carcinoma (RCC) in the Phase 3 METEOR Trial Background:

High tumor burden (TB) in pts with RCC is associated with poor prognosis (Iacovelli BJU Int 2012). In the Phase 3 METEOR trial (NCT01865747) in advanced RCC after prior vascular endothelial growth factor receptor (VEGFR) tyrosine kinase inhibitor (TKI) therapy (Choueiri NEJM 2015/ASCO 2016 abstr 4506), cabozantinib significantly improved progression-free survival (PFS; HR 0.58, 95% CI 0.45-0.74; P<0.0001), overall survival (OS; HR 0.66, 95% CI 0.53-0.83, P-0.0003) and objective response rate (ORR; 17% vs 3%; P<0.0001) compared with everolimus.

Methods:

658 pts were randomized 1:1 to cabozantinib (60 mg qd) or eve (10 mg qd). Stratification factors were MSKCC risk group and number of prior VEGFR TKIs. Endpoints included PFS, OS and ORR. Subgroup analyses by metastatic site and low and high TB (<median and ≥median sum of target lesion diameters [SoD] at baseline) are presented.

Results:

Baseline Characteristics are summarized in Table 3.1. In the overall population represented in Table 3.1, median target lesion SoD at baseline was 65 mm (range 0-291) in the cabozantinib arm and 65 mm (range 0-258) in the everolimus arm.

TABLE 3.1

Baseline Characteristics

|  | Patients With Low Tumor Burden | | Patients With High Tumor Burden | |
| --- | --- | --- | --- | --- |
|  | Cabozantinib (N = 165) | Everolimus (N = 163) | Cabozantinib (N = 165) | Everolimus (N = 164) |
| Median age, years (range) | 62 (32-81) | 62 (33-81) | 63 (36-86) | 61 (31-84) |
| Male, % | 72 | 69 | 82 | 77 |
| Enrollment region, % | | | | |
| Europe | 47 | 45 | 54 | 49 |
| North America | 39 | 40 | 33 | 34 |
| Asia Pacific + Latin America | 14 | 15 | 13 | 17 |
| Median time since diagnosis to randomization, years (range) | 2.7 (0-23) | 2.6 (0-33) | 2.8 (0-30) | 2.4 (0-23) |
| ECOG performance status, % | | | | |
| 0 | 73 | 70 | 64 | 62 |
| 1 | 27 | 30 | 36 | 38 |
| MSKCC risk group,[4] % | | | | |
| Favorable | 59 | 56 | 32 | 36 |
| Intermediate | 37 | 35 | 47 | 47 |
| Poor | 4 | 9 | 21 | 17 |
| Tumor Burden | | | | |
| Median target lesion SoD, mm (range) | 37 (0-65) | 41 (0-65) | 105 (66-291) | 111 (65-258) |
| Number of organs with metastatic disease per IRC, % | | | | |
| 1 | 30 | 29 | 5 | 5 |
| 2 | 30 | 29 | 31 | 18 |
| ≥3 | 38 | 39 | 64 | 77 |
| Metastatic sites per IRC, % | | | | |
| Visceral (lung or liver) | 70 | 67 | 76 | 82 |
| Lung | 59 | 58 | 64 | 71 |
| Liver | 21 | 25 | 33 | 38 |

TABLE 3.1-continued

| | Baseline Characteristics | | | |
|---|---|---|---|---|
| | Patients With Low Tumor Burden | | Patients With High Tumor Burden | |
| | Cabozantinib (N = 165) | Everolimus (N = 163) | Cabozantinib (N = 165) | Everolimus (N = 164) |
| Lymph node | 55 | 53 | 70 | 69 |
| Bone | 21 | 15 | 26 | 24 |
| Kidney | 14 | 13 | 28 | 27 |

ECOG, Eastern Cooperative Oncology Group;
IRC, independent radiology committee;
MSKCC, Memorial Sloan Kettering Cancer Center;
SoD, sum of diameters Prior therapies are summarized in Table 3.2

TABLE 3.2

| | Prior Therapies | | | |
|---|---|---|---|---|
| | Patients With Low Tumor Burden | | Patients With High Tumor Burden | |
| | Cabozantinib (N = 165) | Everolimus (N = 163) | Cabozantinib (N = 165) | Everolimus (N = 164) |
| Number of VEGFR TKIs, % | | | | |
| 1 | 73 | 77 | 69 | 62 |
| 2 or more | 27 | 23 | 31 | 38 |
| VEGFR TKI, % | | | | |
| Sunitinib | 63 | 61 | 64 | 64 |
| Pazopanib | 42 | 41 | 45 | 42 |
| Axitinib | 15 | 10 | 17 | 23 |
| Sorafenib | 8 | 8 | 5 | 11 |
| Other therapy, % | | | | |
| Interleukins | 5 | 7 | 7 | 10 |
| Interferons | 4 | 4 | 7 | 10 |
| Nivolumab | 2 | 4 | 8 | 5 |
| Bevacizumab | 1 | 4 | 2 | 2 |
| Radiotherapy | 32 | 33 | 35 | 32 |
| Nephrectomy | 90 | 92 | 82 | 78 |

TKI, tyrosine kinase inhibitor

FIG. 3.1 depicts progression free survival based on metastatic site and tumor burden.

FIG. 3.2 depicts overall survival based on metastatic site and tumor burden.

FIG. 3.3 depicts the Kaplan-Meier analysis of overall survival.

Table 3.3 summarizes subsequent anticancer therapy.

TABLE 3.3

| | Subsequent Anti-Cancer Therapy | | | |
|---|---|---|---|---|
| | Patients With Low Tumor Burden | | Patients With High Tumor Burden | |
| | Cabozantinib (N = 165) | Everolimus (N = 163) | Cabozantinib (N = 165) | Everolimus (N = 164) |
| Systemic therapy, % | 46 | 59 | 54 | 51 |
| VEGFR TKI therapies | 19 | 49 | 28 | 46 |
| Axitinib | 13 | 33 | 20 | 23 |
| Cabozantinib | 0 | 1 | 0 | 4 |
| Pazopanib | 1 | 6 | 2 | 8 |
| Sorafenib | 3 | 10 | 2 | 9 |
| Sunitinib | 4 | 10 | 7 | 10 |
| Everolimus | 27 | 6 | 30 | 1 |
| Bevacizumab | 3 | 4 | 2 | 3 |
| PD-1/PD-L1 targeting agents* | 3 | 8 | 6 | 3 |

PD-1, programmed cell death-1;
PD-L1, programmed cell death ligand-1;
TKI, tyrosine kinase inhibitor
*The majority (29 out of 33 patients) received nivolumab Table 3.4 summarizes the best overall tumor response per RECIST Version 1.1.

TABLE 3.4

Best Overall Tumor Response per RECIST Version 1.1

| | Patients With Low Tumor Burden | | Patients With High Tumor Burden | |
|---|---|---|---|---|
| | Cabozantinib (N = 165) | Everolimus (N = 163) | Cabozantinib (N = 165) | Everolimus (N = 164) |
| IRC, % | | | | |
| Confirmed ORR[a] (95% CI) | 17 (12-24) | 7 (3-12) | 18 (12-24) | 0 |
| Stable disease | 62 | 60 | 68 | 64 |
| Progressive disease | 16 | 28 | 8 | 26 |
| Investigator assessed, % | | | | |
| Confirmed ORR[a], % (95% CI)[2] | 27 (20-34) | 7 (4-13) | 21 (15-28) | 1 (0-4) |
| Stable disease | 59 | 64 | 67 | 62 |
| Progressive disease | 10 | 27 | 7 | 27 |

CI confidence internal,
IRC, independent radiology committee,
ORR, objective response rate,
RECIST, Response Evaluation Criteria in Solid Tumors
[a]All responses were partial responses.

Table 3.5 summarizes all causality Grade 3 or 4 adverse events.

TABLE 3.5

All Causality Grade 3 or 4 Adverse Events[a]

| | Patients With Low Tumor Burden | | Patients With High Tumor Burden | |
|---|---|---|---|---|
| | Cabozantinib (N = 166) | Everolimus (N = 161) | Cabozantinib (N = 165) | Everolimus (N = 160) |
| Any, % | 73 | 58 | 69 | 62 |
| Hypertension | 17 | 4 | 12 | 4 |
| Diarrhea | 13 | 2 | 13 | 2 |
| Fatigue | 11 | 7 | 10 | 8 |
| PPES | 7 | 1 | 9 | 1 |
| Anemia | 5 | 11 | 7 | 23 |
| Hyperglycemia | 2 | 4 | 0 | 5 |

PPES palmar-plantar erythrodysesthesia Syndrome
*Events that occurred at a 50% frequency in either treatment arm in the overall safety population are summarized.
The most common adverse events in patients with high and low tumor burden were consistent with the safety profile in the overall population.

At baseline, 74% of pts had visceral (lung or liver) metastases (mets); 63% had lung mets and 29% had liver mets. Median SoD at baseline was 65 mm (range 0-291) in the cabozantinib arm and 65 mm (0-258) in the eve arm. Subgroups by metastatic site and TB generally had similar baseline characteristics on both arms. High compared to low TB was associated with fewer favorable (34% vs 57%) and more intermediate (47% vs 36%) and poor risk (19% vs 7%) pts per MSKCC criteria. For pts with visceral mets, the HRs favored cabozantinib (PFS HR 0.48, 95% CI 0.38-0.60; OS HR 0.66, 95% CI 0.52-0.85). These benefits with cabozantinib were consistent across the metastatic sites analyzed (liver and lung). For pts with low TB, HRs for cabozantinib vs eve were 0.63 (95% CI 0.47-0.84) for PFS and 0.76 (95% CI 0.54-1.08) for OS vs 0.41 (95% CI 0.31-0.54) for PFS and 0.60 (95% CI 0.45-0.80) for OS for pts with high TB. Median O S with cabozantinib was 22.0 mo for low TB and 18.1 mo for high TB pts vs 19.3 mo and 12.2 mo with eve, respectively. The most common grade 3 or 4 adverse events in these subgroups were consistent with the safety profile in the overall study population.

Conclusions:
Treatment with cabozantinib was associated with improved PFS and OS compared to eve in pts irrespective of tumor burden or metastatic sites. Pts with high tumor burden appeared to have a stronger relative benefit with cabozantinib compared to eve for both OS and PFS.

Example 4

Evaluation of the Novel "Trial within a Trial" Design of METEOR, a Randomized Phase 3 Trial of Cabozantinib Versus Everolimus in Patients (Pts) with Advanced Renal Cell Carcinoma (RCC)

Background: Comparative studies of time-to-event endpoints should be designed to yield a wide range of event times to accurately characterize the hazard function (HF) relationship and ensure valid hazard ratio (HR) estimates. The total sample size (N) is ideally small relative to the required number of events. The primary endpoint of progression-free survival (PFS) in METEOR (NCT01865747) required 259 events; the secondary overall survival (OS)

endpoint required 408. As a result, the planned total N (650) was much larger than required to evaluate PFS. Shorter PFS times would be overrepresented if an event-driven analysis was conducted among all 650 pts, potentially undermining the ability to assess the proportional hazards assumption. To address this, METEOR employed a novel "trial within a trial" design: PFS was analyzed in the first 375 randomized pts (PFS Pop); OS was analyzed in all 658 randomized pts (ITT Pop). Both populations follow the intention-to-treat principle.

Methods:

To assess the impact of the design, PFS was reanalyzed at the date of the 247th event in the ITT Pop (minimum follow-up [min f/up] 2 days) and compared to both the primary endpoint results for 247 events in the PFS Pop (min fup 11 mo) and supportive results for 394 events in the ITT Pop (min f/up 6 mo).

Results:

FIGS. 4.1-4.4 summarize the findings of Example 4.

FIG. 4.1 depicts the METEOR trial within a trial statistical design.

FIG. 4.2 depicts sample plots from statistical studies. FIG. 4.2A is a simulated study of 260 events among 660 total patients that demonstrates the potential inability to estimate medians. The example illustrates the risk that medians cannot be estimated with a traditional statistical design when the total sample size is large relative to the number of events required for an endpoint. The trial within a trial statistical design of limiting the primary endpoint analysis to the first 375 patients mitigates this risk.

FIG. 4.2B demonstrates the potential to mask non-proportional hazards. Non-proportional hazards arise when the relative treatment effect is inconsistent over time. In this condition, a single HR is not an appropriate representation of the treatment effect. Non-proportional hazards are detected by non-parallel lines in a log-log plot. This example of a simulated study of 260 events among 660 total patients illustrates the risk that the condition of non-proportional hazards may be masked with a traditional statistical design when the total sample size is large relative to the number of events required for an endpoint. The trial within a trial statistical design of limiting the primary endpoint analysis to the first 375 patients mitigates this risk.

The impact of the trial within a trial design on the actual METOR data, the results of the primary progression free survival analysis were compared to the results of two alternative analyses. The results are summarized in Table 4.1.

TABLE 4.1

Primary and Alternative Progression-Free Survival Analyses

| | Primary PFS Analysis TWT event-driven analysis | Alternative Analyses | |
|---|---|---|---|
| | | Supportive Analysis All events in all patients at time of 1º analysis | Traditional Analysis Traditional event-driven analysis |
| No. of events, population | First 247[a] events among first 375 randomized | All 394 events among all 658[b] randomized | First 247 events among all 658 randomized |
| Data cut-off data | May 2015 | May 2015 | November 2014 |
| Minimum follow-up | 11 months | 6 months | 2 days |

PFS, progression-free survival;
TWT, trial within a trial
[a]259 planned events 247 events included in primary analysis;
[b]650 planned patients, 658 randomized
For all analyses:
The proportional hazards assumption was evaluated using log-log plots
Medians were estimated using the Kaplan-Meier (KM) method
HRs were estimated using the Cox proportional hazards model Table 4.2 summarizes the hazard ratios and median estimates in primary and alternative progression free survival analysis.

TABLE 4.2

Hazard Ratios and Median Estimates in Primary and Alternative Progression-Free Survival Analyses

| Analysis (Population) | Cut-off Date | N | Min Follow-up | Median Follow-up | No. of PFS Events | HR | Median, Cabo | Median, Everol |
|---|---|---|---|---|---|---|---|---|
| Primary TWT (first 375) | May 2015 | 375 | 11 mo | 13 mo | 247 | 0.58 | 7.4 mo | 3.8 mo |
| Supportive, all events (all 658) | May 2015 | 658 | 6 mo | 11 mo | 394 | 0.51 | 7.4 mo | 3.9 mo |
| Traditional (all 658) | November 2014 | 656[a] | 2 days | 5 mo | 247 | 0.48 | 6 mo | 3.7 mo |

HR, hazard ratio;
mo, months;
PFS, progression-free survival;
TWT, trial within a trial
[a]Data cut-off before all subjects are randomized.

FIG. 4.3 depicts the Kaplan-Meier analysis of progression free survival.

FIG. 4.4 depicts the evaluation of proportional hazards assumption for progression free survival by log-log plots. Lines are parallel if the proportional hazards assumption is met. For METOER, the PH assumption generally holds after the first scheduled tumor assessment approximately 0.68 on x-axis, with a "step pattern" arising from the periodic nature of tumor assessments. In all analyses, there is slightly more separation early versus later in the parallel section, suggestion that a slightly larger difference between arms among patients with early progression. This is consistent with the largest relative drop in the K M curve for the everolimus arm at the first tumor assessment.

The HFs were reasonably proportional between arms in all analyses. The HR and median estimate for the cabozantinib arm in the primary analysis of 247 events in the PFS Pop (0.58, 7.4 mo) are close to the estimates in the larger analysis of 394 events in the ITT Pop (0.52, 7.4 mo) using the same cutoff date. Despite the similar relationship among HFs, an analysis using an earlier cutoff based upon 247 events in the ITY Pop is biased, overestimating the treatment benefit as represented by the HR and underestimating the median PFS in the cabozantinib arm (0.49, 6 mo). A traditional design would have been biased in terms of overestimating the treatment benefit as represented by the HR and underestimating the median PFS in the cabozantinib arm (HR=0.48, median 6 months).

Conclusions:

The "trial within a trial" design provided critical data required to characterize the HF relationship in METEOR and demonstrate robust results. This design should be considered when the HF relationship is unknown and the total N is large relative to the number of events needed for a time-to-event endpoint.

Example 5

Analysis of Regional Differences in the Phase 3 METEOR Study of Cabozantinib (Cabo) Versus Everolimus (Eve) in Advanced Renal Cell Carcinoma (RCC)

Background: In the METEOR study (NCT01865747), patients (pts) with advanced RCC and prior treatment with an antiangiogenic therapy were randomized to receive cabozantinib or eve. Improved progression-free survival (PFS), overall survival (OS) and objective response rate (ORR) were demonstrated in the cabozantinib arm vs the eve arm (Choueiri 2016 JCO suppl abstr 4506). Baseline characteristics and clinical outcomes were evaluated in pts enrolled in three regions: Europe (EU; 19 countries), North America (NA; US, Canada) and Asia Pacific (AP; Australia, South Korea, Taiwan).

Methods:

658 pts were randomized 1:1 to receive cabozantinib (60 mg qd) or eve (10 mg qd). Stratification factors were MSKCC risk group and number of prior vascular endothelial growth factor receptor (VEGFR) tyrosine kinase inhibitors (TKIs).

Results:

Table 5.1 summarizes the baseline characteristics of the enrolled patients.

TABLE 5.1

| | Baseline Characteristics | | | | | |
|---|---|---|---|---|---|---|
| | Europe | | North America | | Asia Pacific | |
| | Cabozantinib (N = 167) | Everolimus (N = 153) | Cabozantinib (N = 118) | Everolimus (N = 122) | Cabozantinib (N = 39) | Everolimus (N = 47) |
| Median age, years (range) | 63.0 (32-86) | 63.0 (33-84) | 63.0 (36-83) | 61.5 (37-84) | 59.0 (38-78) | 60.0 (31-81) |
| Male, % | 73 | 75 | 81 | 79 | 82 | 55 |
| Median time from diagnosis to randomization, years (range) | 3.0 (0-30) | 2.6 (0-19) | 2.8 (0-20) | 2.7 (0-33) | 2.1 (0-23) | 2.3 (0-16) |
| ECOG performance status, % | | | | | | |
| 0 | 66 | 68 | 68 | 62 | 77 | 64 |
| 1 | 34 | 32 | 32 | 38 | 23 | 36 |
| MSKCC risk group, % | | | | | | |
| Favorable | 47 | 48 | 42 | 40 | 41 | 51 |
| Intermediate | 38 | 37 | 47 | 49 | 49 | 36 |
| Poor | 15 | 15 | 10 | 11 | 10 | 13 |
| Race, % | | | | | | |
| White | 83 | 80 | 89 | 91 | 49 | 51 |
| Asian | 1 | 1 | 2 | 3 | 46 | 45 |
| Black | 0 | 0 | 5 | 2 | 0 | 0 |
| Other | 8 | 7 | 3 | 2 | 5 | 2 |
| Not reported | 8 | 13 | 1 | 2 | 0 | 2 |
| Metastatic sites per IRC, % | | | | | | |
| Lung | 62 | 65 | 56 | 61 | 74 | 72 |
| Liver | 25 | 37 | 31 | 26 | 26 | 30 |
| Bone | 22 | 22 | 27 | 19 | 21 | 15 |

ECOG, Eastern Cooperative Oncology Group;
IRC, independent radiology committee;
MSKCC, Memorial Sloan Kettering Cancer Center FIG. 5.1 depicts the METEOR enrollment in countries as a percentage of total enrolled patients.

Table 5.2 summarizes prior therapies.

TABLE 5.2

| | Baseline Prior Therapies | | | | | |
|---|---|---|---|---|---|---|
| | Europe | | North America | | Asia Pacific | |
| | Cabozantinib (N = 167) | Everolimus (N = 153) | Cabozantinib (N = 118) | Everolimus (N = 122) | Cabozantinib (N = 39) | Everolimus (N = 47) |
| | Number of VEGFR TKIs, % | | | | | |
| 1 | 68 | 71 | 70 | 64 | 85 | 81 |
| 2 | 29 | 28 | 25 | 31 | 15 | 19 |
| 3 or more | 2 | 1 | 6 | 5 | 0 | 0 |
| | VEGFR TKI, % | | | | | |
| Sunitinib | 71 | 66 | 58 | 60 | 62 | 64 |
| Pazopanib | 35 | 35 | 51 | 47 | 49 | 43 |
| Axitinib | 16 | 18 | 22 | 21 | 0 | 2 |
| Sorafenib | 8 | 8 | 4 | 11 | 5 | 11 |
| | Other therapy, % | | | | | |
| Interleukins | 5 | 6 | 9 | 16 | 0 | 2 |
| Interferons | 10 | 14 | 2 | 2 | 0 | 2 |
| Anti-PD-1/PD-L1 | 4 | 4 | 9 | 6 | 3 | 2 |
| Bevacizumab | 1 | 5 | 3 | 3 | 0 | 2 |
| Radiotherapy | 31 | 29 | 39 | 40 | 31 | 26 |
| Nephrectomy | 84 | 86 | 88 | 86 | 85 | 81 |

PD-1, programmed cell death -1;
PD-L1, programmed cell death ligand-1;
TKI, tyrosine kinase inhibitor FIG. 5.2 provides Forest plots of progression free survival per IRC by Region.

FIG. 5.3 provides Forest plots of overall survival per IRC by Region.

Table 5.3 summarizes the best overall tumor response per RECIST Version 1.1 by region.

TABLE 5.3

| | Best Overall Tumor Response per RECIST Version 1.1 by Region[a] | | | | | |
|---|---|---|---|---|---|---|
| | Europe | | North America | | Asia Pacific | |
| | Cabozantinib (N = 167) | Everolimus (N = 153) | Cabozantinib (N = 118) | Everolimus (N = 122) | Cabozantinib (N = 39) | Everolimus (N = 47) |
| | IRC, % | | | | | |
| ORR[b] (95% CI) | 15 (10-21) | 4 (1-8) | 16 (10-24) | 2 (1-7) | 28 (15-45) | 2 (0-11) |
| Stable disease | 69 | 65 | 62 | 59 | 62 | 60 |
| Progressive disease | 10 | 24 | 17 | 30 | 10 | 28 |
| | Investigator assessed, % | | | | | |
| ORR[b] (95% CI) | 22 (16-29) | 4 (1-8) | 20 (13-29) | 3 (1-8) | 36 (21-53) | 4 (1-15) |
| Stable disease | 65 | 66 | 62 | 62 | 64 | 60 |
| Progressive disease | 8 | 25 | 13 | 29 | 0 | 26 |

CI, confidence interval;
IRC, independent radiology committee;
ORR, objective response rate;
RECIST, Response Evaluation Criteria in Solid Tumors
[a]The sum of responses is less than 100% because there were patients with not evaluable or missing assessments in both arms.
[b]All responses were confirmed partial responses.

Table 5.5 summarizes subsequent anticancer therapy.

TABLE 5.4

Subsequent Anti-Cancer Therapy

| Subsequent Therapy | Europe | | North America | | Asia Pacific | |
|---|---|---|---|---|---|---|
| | Cabozantinib (N = 167) | Everolimus (N = 153) | Cabozantinib (N = 118) | Everolimus (N = 122) | Cabozantinib (N = 39) | Everolimus (N = 47) |
| Any systemic anti-cancer therapy, % | 50 | 55 | 53 | 66 | 44 | 34 |
| Any VEGFR TKI | 25 | 50 | 29 | 57 | 5 | 21 |
| Axitinib | 17 | 28 | 22 | 38 | 3 | 2 |
| Sorafenib | 4 | 14 | 3 | 6 | 0 | 6 |
| Sunitinib | 4 | 11 | 8 | 9 | 3 | 11 |
| Pazopanib | 2 | 8 | 2 | 7 | 0 | 4 |
| Cabozantinib | 0 | 1 | 0 | 6 | 0 | 0 |
| Everolimus | 30 | 4 | 28 | 4 | 33 | 9 |
| Anti-PD-1/PD-L1 | 2 | 2 | 9 | 13 | 3 | 0 |

PD-1, programmed cell death-1;
PD-L1, programmed cell death ligand-1;
TKI, tyrosine kinase inhibitor Table 5.5 summarizes study treatment exposure and dose reductions.

TABLE 5.5

Study Treatment Exposure and Dose Reductions

| | Europe | | North America | | Asia Pacific | |
|---|---|---|---|---|---|---|
| | Cabozantinib (N = 167) | Everolimus (N = 153) | Cabozantinib (N = 118) | Everolimus (N = 122) | Cabozantinib (N = 39) | Everolimus (N = 47) |
| Median duration of exposure, wks | 33 | 21 | 39 | 16 | 56 | 24 |
| Patients receiving dose reductions, % | 62 | 27 | 58 | 26 | 72 | 13 |
| Median average daily dose, mg | 43.6 | 9.1 | 43.3 | 8.7 | 41.0 | 9.4 |
| Median time to first dose reduction, days | 55 | 64 | 59 | 64 | 57 | 51 |

Wks, weeks

Table 5.6 summarizes all causality Grade 3 or 4 adverse events.

TABLE 5.6

All Causality Grade 3 or 4 Adverse Events[a]

| | Europe | | North America | | Asia Pacific | |
|---|---|---|---|---|---|---|
| | Cabozantinib (N = 167) | Everolimus (N = 153) | Cabozantinib (N = 118) Any, % | Everolimus (N = 122) | Cabozantinib (N = 39) | Everolimus (N = 47) |
| Hypertension | 17 | 7 | 14 | 1 | 5 | 2 |
| Diarrhea | 13 | 2 | 14 | 2 | 10 | 4 |
| Fatigue | 11 | 6 | 13 | 10 | 5 | 4 |
| PPES | 9 | 1 | 7 | 1 | 8 | 0 |
| Anemia | 5 | 17 | 7 | 13 | 5 | 26 |
| Hyperglycemia | 1 | 1 | 2 | 10 | 0 | 4 |

AE, adverse event;
PPES, palmar-plantar erythrodysesthesia syndrome
[a]AEs that occurred at ≥5.0% frequency in either treatment arm of the overall safety population are summarized.

Of pts enrolled in METEOR, 320, 240 and 86 came from EU, NA and AP, respectively. Baseline demographic characteristics other than race were similar between regions. Pts with 2 or more prior TKIs were more frequent in EU and NA (31% and 33%) than AP (17%). Prior use of axitinib was rare in AP (1%) compared to EU and NA (17% and 22%). PFS and OS in the cabozantinib arm were prolonged vs eve in all regions, with PFS hazard ratios (HR) of 0.54, 0.50 and 0.43 and OS HRs of 0.67, 0.79 and 0.49 for EU, NA and AP, respectively. The cabozantinib arm ORRs (% [95% CI]) for EU, NA and AP regions were 15% (10-21), 16% (10-24) and 28% (15-45). Adverse event (AE) rates were generally similar across regions. Subsequent treatment with VEGFR-TKI and anti-PD-1/L1 agents was most frequent in NA and least frequent in AP, and at higher frequency in the eve arm versus the cabozantinib arm. Post trial use of eve in the cabozantinib arm was similar across regions.

Conclusions:

Improvements in PFS, OS and ORR for cabozantinib vs eve were measured across all regions in the METEOR trial despite differences in subsequent treatment. No differences in safety were reported.

Example 6

Clinical Outcomes for Canadian Patients in the Phase 3 METEOR Study of Cabozantinib (Cabo) Versus Everolimus (Eve) in Advanced Renal Cell Carcinoma (RCC)

Background:

In the METEOR study (NCT01865747), patients (pts) with advanced RCC and prior treatment with vascular endothelial growth factor receptor (VEGFR) tyrosine kinase inhibitor (TKI) therapy were randomized to receive cabo or eve. Cabo demonstrated improved progression-free survival (PFS) (median 7.4 vs 3.8 mo; HR 0.58, 95% CI 0.45-0.74; P<0.0001), overall survival (OS) (median 21.4 vs 16.5 mo; HR 0.66, 95% CI 0.53-0.83, P=0.0003), and objective response rate (ORR) (17% vs 3%; P<0.0001) compared with eve (Choueiri NEJM 2015, Lancet Oncol 2016). Here we evaluate clinical outcomes for patients enrolled in Canada.

Methods:

658 pts were randomized 1:1 to receive cabo (60 mg qd) or eve (10 mg qd) with stratification by MSKCC risk group and number of prior VEGFR TKI therapies.

Results:

Forty pts were enrolled at 11 sites in Canada, 23 pts in the cabo arm and 17 pts in the eve arm. Median PFS was 7.4 mo (95% CI, 4.3-NE) with cabo and 3.7 mo (95% CI, 1.7-4.7) with eve (HR 0.40; 95% CI, 0.17-0.89). Median O S was 20.8 mo (95% CI, 13.1-NE) with cabo and 12.8 mo (95% CI, 5.5-15.9) with eve (HR 0.33; 95% CI, 0.14-0.75). ORR for the cabo arm was 17% (95% CI, 0.14-0.75) vs 0% for the eve arm. The median duration of exposure was 9.2 mo with cabo and 3.7 mo with eve. The proportion of pts who received subsequent systemic anticancer therapy was 39% in the cabo arm vs 59% in the eve arm.

Conclusions:

These results from Canadian patients with advanced RCC enrolled in METEOR are consistent with the overall study population, with observed improvements with cabo compared to eve in the 3 key efficacy endpoints of PFS, OS, and ORR.

Example 7

Overall Survival (OS) and Subgroup Analysis Results from ALLIANCE A031203 Trial: Cabozantinib Versus Sunitinib (CABOSUN) as Initial Targeted Therapy for Patients (Pts) with Metastatic Renal Cell Carcinoma (mRCC)

Background:

Cabozantinib (Cabo) is an oral, potent inhibitor of MET, AXL and VEGFR2 that increases progression free-survival (PFS) and overall response rate (ORR) compared to Sunitinib (Sun) as front-line targeted therapy in patients (pts) with mRCC of poor or intermediate risk (Choueiri et al, JCO 2016). Overall survival (OS) results will be presented.

Methods:

Eligible pts had untreated clear-cell mRCC, ECOG performance status 0-2, and intermediate or poor risk disease, per the International mRCC Database Consortium Criteria (IMDC, Heng J C O 2009). Pts were randomized 1:1 to receive Cabo (60 mg QD) or Sun (50 mg QD, 4 weeks on/2 weeks off). Pts were stratified by the IMDC risk groups (intermediate vs. poor risk) and bone metastasis (yes, no). The primary endpoint was PFS. With 123 events, the log-rank statistic has 85% power to detect a hazard ratio of 0.67 for PFS assuming a one-sided type I error of 0.12. Secondary endpoints included OS, investigator-assessed overall response rate (ORR), and toxicity. The Kaplan-Meier product-limit estimator was used to estimate the OS between treatment arms.

Results:

See previous Examples, including Examples 1, 3, and 5 and Example 9. Compared with sunitinib, cabozantinib treatment significantly increased median PFS (8.2 v 5.6 months) and was associated with a 34% reduction in rate of progression or death (adjusted hazard ratio, 0.66; 95% CI, 0.46 to 0.95; one-sided P=0.012). ORR was 46% (95% CI, 34 to 57) for cabozantinib versus 18% (95% CI, 10 to 28) for sunitinib. All-causality grade 3 or 4 adverse events were 67% for cabozantinib and 68% for sunitinib and included diarrhea (cabozantinib, 10% v sunitinib, 11%), fatigue (6% v 15%), hypertension (28% v 22%), palmar-plantar erythrodysesthesia (8% v 4%), and hematologic adverse events (3% v 22%). Median O S with cabozantinib was 30.3 months (95% CI, 14.6 to 35.0 months) versus 21.8 months (95% CI, 16.3 to 27.0 months) with sunitinib (adjusted HR, 0.80; 95% CI, 0.50 to 1.26.

Example 8

Efficacy of Cabozantinib (C) Vs Everolimus (E) in Patients with Advanced Renal Cell Carcinoma (RCC) and Bone Metastases from the Phase 3 METEOR Study In patients with metastatic RCC, bone metastases are prognostic for poor outcomes and represent an unmet medical need. The Phase 3 METEOR trial (NCT01865747) assessed the efficacy and safety of cabozantinib vs everolimus in patients with RCC and ≥1 prior VEGFR TKI. The trial met its primary endpoint of improving progression-free survival (PFS; HR 0.58, 95% CI 0.45-0.75; P<0.001) (Choueiri NEJM 2015). As cabozantinib has shown clinical activity in bone metastases in prostate cancer patients (Smith J C O 33 2015 abs 139), we evaluated clinical outcomes in RCC patients with bone metastases in METEOR.

In the METEOR Phase 3 study, treatment with cabozantinib resulted in statistically significant improvements in progression-free survival (PFS), overall survival (OS), and objective response rate (ORR) compared with everolimus in advanced RCC patients. FIG. 8.1 depicts the progression-free survival per independent radiology committee (IRC) in all 658 randomized patients. FIG. 8.2 depicts the overall survival over 30 months.

Methods:

658 patients were randomized (stratified by MSKCC risk group and number of prior VEGFR TKIs) 1:1 to receive cabozantinib (60 mg qd) or everolimus (10 mg qd). The study design in depicted in FIG. 8.3. Clinical outcome measures included PFS, ORR, overall survival (OS), and safety. Exploratory endpoints included bone scan response (BSR) in patients with bone scan lesions at baseline (Brown Nucl Med Commun 2012 33:384), incidence of skeletal-related events (SRE), and changes in bone turnover markers. Table 8.1 depicts the baseline characteristics of the patients. The subgroup of patients with bone metastases (N=142) was defined by the presence of bone metastases at baseline by CT or MRI per IRC. Bone scan response (BSR) was evaluated for patients who had bone lesions detected by technetium bone scans at baseline (N=178).

TABLE 8.1

| Baseline Characteristics | | | | |
|---|---|---|---|---|
| | Pts with Bone Metastases[1] | | Pts without Bone Metastases | |
| | Cabozantinib (N = 77) | Everolimus (N = 65) | Cabozantinib (N = 253) | Everolimus (N = 263) |
| Median age, years (range) | 61.0 (32-84) | 64.0 (34-84) | 63.0 (35-86) | 61.0 (31-81) |
| Male, % | 83 | 82 | 75 | 71 |
| Enrollment Region, % | | | | |
| Europe | 47 | 52 | 52 | 45 |
| North America | 42 | 35 | 34 | 38 |
| Asian Pacific + Latin American | 11 | 13 | 14 | 17 |
| ECOG Performance Status, % | | | | |
| 0 | 83 | 92 | 94 | 94 |
| 1 | 17 | 8 | 6 | 6 |
| MSKCC risk group[1], % | | | | |
| Favorable | 36 | 45 | 48 | 46 |
| Intermediate | 45 | 42 | 41 | 41 |
| Poor | 18 | 14 | 11 | 13 |
| Visceral metastases per IRC, % | 78 | 80 | 72 | 73 |

[1] 22% (142/858) of randomized patients had bone metastases by CT or MRI at baseline.
2. Motzer R. et al., J Clin Oncol. 2004

The prior therapies for both patients with bone metastases and without bone metastases are shown in Table 8.2. The concomitant use of bone-targeted therapies in patients with bone metastases at baseline is shown in Table 8.3. Table 8.3 includes patients who initiated bone-targeted therapy prior to randomization.

TABLE 8.2

| Prior Therapies | | | | |
|---|---|---|---|---|
| | Pts with Bone Metastases | | Pts without Bone Metastases | |
| | Cabozantinib (N = 77) | Everolimus (N = 65) | Cabozantinib (N = 253) | Everolimus (N = 263) |
| Number of VEGFR TKIs, % | | | | |
| 1 | 65 | 66 | 73 | 71 |
| 2 or more | 35 | 34 | 27 | 29 |
| VEGFR-TKI, % | | | | |
| Sunitinib | 61 | 59 | 64 | 64 |
| Pazopanib | 46 | 48 | 43 | 40 |
| Axitinib | 22 | 23 | 14 | 15 |
| Sorafenib | 7 | 11 | 6 | 9 |
| Other systemic therapy, % | | | | |
| Interleukins | 8 | 5 | 6 | 10 |
| Interferon alfa | 4 | 9 | 6 | 6 |
| Nivolumab | 5 | 6 | 5 | 4 |
| Bevacizumab | 3 | 6 | 1 | 3 |
| Radiotherapy, % | 56 | 62 | 27 | 26 |
| Nephrectomy, % | 87 | 72 | 85 | 88 |

TABLE 8.3

Concomitant use of Bone-Targeted Therapies in
Patients with Bone Metastases at Baseline

|  | Cabozantinib (n = 77) | Everolimus (n = 65) |
|---|---|---|
| Bone-targeted therapy at baseline, n (%) | | |
| Bisphosphonate | 18 | 11 |
| Denosumab | 12 | 9 |
| Bone-targeted therapy post-randomization,* n (%) | | |
| Bisphosphonate | 23 | 20 |
| Denosumab | 13 | 12 |

Assessments:

Participants were screened via CT or MRI every 8 weeks for the first 12-months post-randomization, and then every 12 weeks thereafter. Technetium bone scans were performed at screening (all patients), every 16 weeks for the first 12 months post-randomization (only in patients with bone lesions at baseline), and then every 23 weeks thereafter. Skeletal-related events (SREs) were assessed and consisted of pathological fractures, spinal cord compression, surgery to bone, and external radiation therapy to bone. Serum bone marker analyses consisted on N-terminal propeptide of type I collagen (PINP), and the bone resorption marker c-terminal cross-lined telopeptides of type I collagen (CTx), which were collected prior to the first dose at week 1, at week 5, and at week 9.

Results:

142 patients had bone metastases at baseline; of these, 112 had visceral metastases also. MSKCC risk groups in patients with bone metastases were consistent with the overall study population. PFS HRs of cabozantinib vs everolimus were 0.33 (bone; 95% CI 0.21-0.51) and 0.26 (bone+visceral; 95% CI 0.16-0.43). Median PFS with cabozantinib was 7.4 mo in patients with bone metastases and 5.6 mo in patients with bone and visceral metastases compared to 2.7 mo and 1.9 mo with everolimus respectively. The ORR with cabozantinib was 17% and 20%, respectively. BSR by IRC was 18% (cabozantinib) vs 10% (everolimus). 12% (cabozantinib) and 14% (everolimus) of randomized patients had at least one SRE, including 4 (cabozantinib) and 8 (everolimus) cases of spinal cord compression. For patients with an SRE pre-randomization, the incidence of post-randomization SREs was 16% (cabozantinib) and 34% (everolimus) and included 0 (cabozantinib) and 5 (everolimus) cases of spinal cord compression (Tables 8.4 and 8.6). Reductions in bone markers were greater with cabozantinib vs everolimus (Table 8.9). The most common adverse events (AE) in patients with bone metastases were consistent with the safety profile in the overall study population (Table 8.6).

TABLE 8.4

Post-Randomization Skeletal-Relates Events (SREs)

|  | Pts with Bone Metastases | | Pts without Bone Metastases | |
|---|---|---|---|---|
|  | Cabozantinib N = 77 | Everolimus N = 65 | Cabozantinib N = 253 | Everolimus N = 263 |
| Post-Randomization SREs, n (%) | 16 (21) | 19 (29) | 22 (9) | 27 (10) |
| Pathologic fractures | 9 (12) | 3 (5) | 7 (3) | 8 (3) |
| Spinal cord compression | 2 (3) | 4 (6) | 2 (1) | 4 (2) |
| Surgery to bone | 6 (8) | 5 (8) | 5 (2) | 5 (2) |
| External radiation therapy to bone | 7 (9) | 16 (25) | 18 (7) | 19 (7) |
| Time to first SRE, median (95% CI), months | 3.45 (0.4-10.5) | 2.53 (0.3-7.3) | 3.93 (0.5-11.3) | 4.27 (0.7-13.4) |

TABLE 8.5

Post-Randomization Skeletal-Related Events (SREs) in Patients with a Prior History of SREs

| | Patients with a prior history of SREs | | | |
|---|---|---|---|---|
|  | Pts with Bone Metastases | | Pts without Bone Metastases | |
|  | Cabozantinib N = 43 | Everolimus N = 43 | Cabozantinib N = 48 | Everolimus N = 47 |
| SREs in patients with a prior history of SREs, n (%) | 10 (23) | 14 (33) | 5 (10) | 17 (36) |
| Pathologic fractures | 6 (14) | 2 (5) | 3 (6) | 6 (13) |
| Spinal cord compression | 0 | 2 (5) | 0 | 3 (6) |
| Surgery to bone | 4 (9) | 3 (7) | 2 (4) | 4 (9) |
| External radiation therapy to bone | 4 (9) | 12 (28) | 4 (8) | 11 (23) |
| Time to first SRE, median (95% CI), months | 3.25 (0.4-10.5) | 2.41 (0.3-7.3) | 2.76 (0.7-7.6) | 4.27 (0.7-11.5) |

TABLE 8.6

| | All Casualty Grade 3 or 4 Adverse Events | | | |
|---|---|---|---|---|
| | Pts with Bone Metastases | | Pts without Bone Metastases | |
| | Cabozantinib N = 77 | Everolimus N = 65 | Cabozantinib N = 254 | Everolimus N = 257 |
| Any, n (%) | 52 (68) | 32 (49) | 174 (69) | 154 (60) |
| Fatigue | 10 (13) | 3 (5) | 20 (8) | 19 (7) |
| Diarrhea | 9 (12) | 0 | 29 (11) | 7 (3) |
| PPES | 6 (8) | 0 | 21 (8) | 3 (1) |
| Hypertension | 5 (6) | 1 (2) | 44 (17) | 9 (4) |
| Anemia | 4 (5) | 9 (14) | 14 (6) | 41 (16) |
| Hypomagnesaemia | 3 (4) | 0 | 12 (5) | 0 |
| Hyperglycemia | 0 | 5 (8) | 2 (1) | 11 (4) |
| Hypokalaemia | 4 (5) | | 11 (4) | 5 (2) |
| Event of interest | | | | |
| Hypercalcemia | 0 | 2 (3) | 2 (1) | 4 (2) |

Events that occured at 25% frequency in either treatment arm in the overall safety population and the incidence of grade 3or 4 hypercalcemia are summarized.
The most common AEs in pts with and without bone metastases were consistent with the safety profile in the overall population.
Grade 5 (related) AEs in pts with bone metastases everolimus (n = 1; pneumonia aspiration).
Grade 5 (related) AEs in pts without bone metastases cabozantinib (n = 1; death not otherwise specified), everolimus (n = 1; *aspergillus* infection).

The objective response rates are outlined in Table 8.7.

TABLE 8.7

| | Objective Response Rate per RECIST version 1.1 | | | | | |
|---|---|---|---|---|---|---|
| | Pts with Bone Metastases | | Pts with Bone and Visceral[1] Metastases | | Pts without Bone Metastases | |
| | Cabozantinib n = 77 | Everolimus n = 65 | Cabozantinib n = 60 | Everolimus n = 52 | Cabozantinib n = 253 | Everolimus n = 263 |
| | IRC | | | | | |
| Confirmed responses, % (95% CI)[3] | 17 (9-27) | 0 | 20 (11-32) | 0 | 17 (13-23) | 4 (2-7) |
| Stable disease, (%) | 70 | 54 | 65 | 44 | 64 | 64 |
| Progressive disease, (%) | 13 | 37 | 15 | 44 | 12 | 24 |
| | Investigator assessed | | | | | |
| Confirmed responses, % (95% CI)[3] | 27 (18-39) | 0 | 30 (19-43) | 0 | 23 (18-28) | 5 (3-9) |
| Stable disease, (%) | 64 | 63 | 60 | 59 | 83 | 63 |
| Progressive disease, (%) | 9 | 26 | 10 | 29 | 9 | 26 |

[1]Visceral metastases were defined as lung or liver metastase.
[3]All responses were partial responses.

FIG. 8.4 shows Kaplan-Meier analyses of progression-free survival in patients with bone metastases, patients with bone and visceral metastases, and patients without bone metastases. FIG. 8.5 shows Kaplan-Meier analyses of overall survival in patients with bone metastases, patients with bone and visceral metastases, and patients without bone metastases.

Bone scan responses per IRC in patients with bone scan lesions were performed using computer-assisted detection of bone scan lesions. An IRC was used to quantitate bone scan tumor burden using computer-assisted detection (CAD) to measure lesions and defined criteria for response. Bone scan lesion area (BSLA), which represents the number of pixels with radiotracer uptake above the threshold for normal bone, was also calculated. BSR was defined as greater than or equal to 30% decrease in BSLA. The bone scan response is shown in Table 8.8.

TABLE 8.8

| Bone Scan Response per IRC in Patients with Bone Scan Lesions | | |
|---|---|---|
| | Pts with bone lesions at baseline by bone scan | |
| | Cabozantinib N = 105 | Everolimus N = 73 |
| Bone scan response, % (95% CI) | 18 (11, 27) | 10 (4, 19) |

FIG. 8.6 and Table 8.9 depict the effect of cabozantinib on bone markers for patients with bone metastases at baseline. FIG. 8.7 depicts the effect of cabozantinib on bone markers for patients without bone metastases at baseline.

TABLE 8.9

|  | Cabozantinib | | Everolimus | |
| --- | --- | --- | --- | --- |
|  | Baseline* | Week 5* | Baseline* | Week 5* |
| N-terminal propeptide of type 1 collagen (P1NP) | 48.5 | 38.9 | 49.9 | 44.1 |
| C-terminal cross-lined telopeptides of type 1 collagen (CTx) | 0.40 | 0.19 | 0.43 | 0.43 |

*Median, ug/L

Conclusions:

Treatment with cabozantinib was associated with improved PFS, OS, and ORR in patients with or without bone metastases as compared to everolimus. This clinical benefit was supported by the outcomes of bone metastasis-related endpoints.

Example 9

Outcomes Based on Prior VEGF TKI and PD-1 Checkpoint Inhibitor Therapy is METEOR, a Randomized Phase 3 Tiral of Cabozantinib Vs Everolimus in Advanced Renal Cell Carcinoma Background Optimizing the sequence of systemic therapy to improve outcomes in patients with advanced renal cell carcinoma (RCC) remains a clinical question. Cabozantinib, a tyrosine kinase inhibitor (TKI), was recently evaluated in patients with RCC and ≥1 prior vascular endothelial growth factor receptor (VEGFR) TKI therapies in the Phase 3 METEOR trial (NCT01865747) (FIG. 4). 658 patients were randomized 1:1 to receive cabozantinib (60 mg once daily [qd]) or everolimus (10 mg qd). Stratification was by Memorial Sloan Kettering Cancer Center (MSKCC) risk group (favorable, intermediate, poor) and number of prior VEGFR TKIs (1, ≥2)

Eligibility criteria included: RCC with clear cell component; Prior treatment with at least 1 VEGFR TKI; Radiographic progression during treatment or within 6 months after most recent TKI regimen; Prior treatment with anti-PD-1/PD-L1 agents was allowed.

Progression-free survival (PFS) by independent radiology committee (IRC), overall survival (OS), and objective response rate (ORR) by IRC were significantly improved compared with everolimus (FIGS. 3 and 4), providing a Median PFS of 7.4 vs 3.9 months, HR=0.51, 95% CI: 0.41-0.62; P<0.0001; a Median O S of 21.4 vs 16.5 months, HR=0.66, 95% CI: 0.53-0.83; P-0.0003; and an ORR of 17% for cabozantinib vs 3% for everolimus (P<0.0001)

The goal of this study was to better understand efficacy outcomes by prior VEGFR TKI.

Methods.

Demographics, efficacy, and safety endpoints were evaluated in subgroups defined by prior anticancer therapy.

Sunitinib only: patients with sunitinib as the only prior VEGFR TKI therapy

Pazopanib only: patients with pazopanib as the only prior VEGFR TKI therapy

Anti-PD-1/PD-L1: patients with prior exposure to immune checkpoint inhibitors targeting PD-1 or PD-L Clinical outcome measures included PFS (primary endpoint), OS, ORR, and safety. Tumor assessment was by IRC and utilized Response Evaluation Criteria in Solid Tumors, (RECIST) v1.1. Adverse events were reported according to National Cancer Institute Common Terminology Criteria for Adverse Events, v4.0

Data cut-off: All data are as of May 22, 2015 except for the OS analyses which are as of Dec. 31, 2015.

The prior therapy subgroups and baseline characteristics are summarized in Tables 9.1 and 9.2.

TABLE 9.1

Prior Therapy Subgroups

| Prior Anticancer Regimens, n(%) | Cabozantinib (N = 330) | Everolimus (N = 328) |
| --- | --- | --- |
| 1 prior VEGFR TKI | 235 (71) | 229 (70) |
| Sunitinib only | 135 (41) | 132 (440) |
| Pazopanib only | 88 (27) | 83 (25) |
| ≥2 prior VEGFR TKI | 95 (29) | 99 (30) |
| Anti-PD-1/PD-L1* | 18 (5) | 14 (4) |

*31 patients received nivolumab,
1 patient received atezolizumab

TABLE 9.2

Baseline Characteristics

| | Sunitinib Only | | Pazopanib Only | | Anti-PD-1/PD-L1 | |
| --- | --- | --- | --- | --- | --- | --- |
| | Cabozantinib N = 135 | Everolimus N = 132 | Cabozantinib N = 88 | Everolimus N = 83 | Cabozantinib N = 18 | Everolimus N = 14 |
| Median age, years (range) | 62.0 (37-79) | 62.0 (31-81) | 63.0 (38-86) | 61.0 (36-84) | 63.5 (47-81) | 61.0 (37-84) |
| Male, % | 79 | 72 | 77 | 77 | 72 | 79 |
| Enrollment region, % | | | | | | |
| Europe | 53 | 50 | 39 | 41 | 33 | 43 |
| North America | 33 | 33 | 40 | 39 | 61 | 50 |
| Asia Pacific | 13 | 17 | 15 | 16 | 6 | 7 |
| Latin America | 0 | 1 | 7 | 5 | 0 | 0 |
| ECOG Performance Status*, % | | | | | | |
| 0 | 70 | 66 | 75 | 59 | 67 | 64 |
| 1 | 30 | 34 | 25 | 41 | 33 | 36 |

TABLE 9.2-continued

| | Sunitinib Only | | Pazopanib Only | | Anti-PD-1/PD-L1 | |
|---|---|---|---|---|---|---|
| | Cabozantinib N = 135 | Everolimus N = 132 | Cabozantinib N = 88 | Everolimus N = 83 | Cabozantinib N = 18 | Everolimus N = 14 |
| Baseline Characteristics | | | | | | |
| MSKCC risk group[4], % | | | | | | |
| Favorable | 41 | 45 | 45 | 42 | 28 | 43 |
| Intermediate | 47 | 44 | 44 | 45 | 50 | 50 |
| Poor | 13 | 11 | 10 | 13 | 22 | 7 |
| Metastatic sites per IRC, % | | | | | | |
| Lung | 59 | 67 | 70 | 65 | 56 | 79 |
| Liver | 32 | 42 | 25 | 19 | 33 | 29 |
| Bone | 20 | 17 | 23 | 22 | 28 | 29 |
| Prior Therapy VEGFR TKI, % | | | | | | |
| Sunitinib | 100 | 100 | — | — | 67 | 64 |
| Pazopanib | — | — | 100 | 100 | 61 | 43 |
| Axitinib | — | — | — | — | 28 | 21 |
| Sorafenib | — | — | — | — | 6 | 14 |
| Other therapy, % | | | | | | |
| Interleukins | 5 | 5 | 5 | 8 | 11 | 0 |
| Interferon-alfa | 3 | 5 | 7 | 6 | 6 | 0 |
| Nivolumab | 4 | 4 | 1 | 4 | 94 | 100 |
| Bevacizumab | 0 | 2 | 1 | 4 | 6 | 7 |
| Radiotherapy | 29 | 31 | 40 | 31 | 33 | 36 |
| Nephrectomy | 86 | 85 | 86 | 78 | 89 | 79 |

*Based on Karnofsky Performance Status score

Results.

The results are summarized in FIGS. 9.1-9.5 and Tables 93 and 9.4.

FIG. 9.1 depicts the progression free survival of subgroups based on prior therapy (sunitibib, pazopanib, or Anti-PD-1/PD-L).

FIG. 9.2 depicts the Forest Plot analysis of overall survival.

FIG. 9.3 depicts the overall survival of subgroups based on prior therapy (sunitibib, pazopanib, or Anti-PD-1/PD-L1).

FIG. 9.4 depicts the analysis of progression free survival.

Table 9.3 summarizes the objective response rate among prior therapy subgroups.

TABLE 9.3

| | Sunitinib Only | | Pazopanib Only | | Anti-PD-1/PD-L1 | |
|---|---|---|---|---|---|---|
| | Cabozantinib N = 135 | Everolimus N = 132 | Cabozantinib N = 88 | Everolimus N = 83 | Cabozantinib N = 18 | Everolimus N = 14 |
| Tumor response by IRC (%) | | | | | | |
| Confirmed ORR* (95% CI) | 16 (11-24) | 3 (1-8) | 19 (12-29) | 4 (1-10) | 22 (6-48) | 0 |
| Stable disease | 66 | 57 | 65 | 66 | 50 | 64 |
| Progressive disease | 12 | 35 | 14 | 22 | 11 | 29 |
| Tumor response by investigator (%) | | | | | | |
| Confirmed ORR* (95% CI) | 23 (16-31) | 4 (1-9) | 31 (21-41) | 4 (1-10) | 22 (6-48) | 0 |
| Stable disease | 60 | 63 | 64 | 64 | 56 | 86 |
| Progressive disease | 11 | 29 | 3 | 27 | 11 | 14 |

*All partial responses

FIG. 9.5 depicts the progression free survival and response in Anti-PD-1/PD-L1

Table 9.4 summarizes grade 3 and 4 adverse events per prior therapy.

TABLE 9.4

|  | Sunitinib Only | | Pazopanib Only | | Anti-PD-1/PD-L1 | |
| --- | --- | --- | --- | --- | --- | --- |
|  | Cabozantinib N = 135 | Everolimus N = 132 | Cabozantinib N = 88 | Everolimus N = 83 | Cabozantinib N = 18 | Everolimus N = 14 |
| Any, n (%) | 86 (64) | 77 (59) | 62 (70) | 50 (62) | 15 (83) | 8 (57) |
| Hypertension | 22 (16) | 5 (4) | 14 (16) | 1 (1) | 4 (22) | 0 |
| Diarrhea | 19 (14) | 4 (3) | 8 (9) | 0 | 2 (11) | 0 |
| Fatigue | 14 (10) | 8 (6) | 3 (3) | 8 (10) | 5 (28) | 2 (14) |
| Palmar-plantar erythrodysesthesia | 11 (8) | 0 | 9 (10) | 2 (2) | 3 (17) | 1 (7) |
| Anemia | 11 (8) | 22 (17) | 2 (2) | 7 (9) | 2 (11) | 2 (14) |
| Hypomagnesemia | 8 (6) | 0 | 3 (3) | 0 | 0 | 0 |
| Hypokalemia | 7 (5) | 2 (2) | 2 (2) | 3 (4) | 1 (6) | 0 |
| Hyperglycemia | 0 | 6 (5) | 1 (1) | 3 (4) | 0 | 0 |

*Events that occulted at >5% frequency in either treatment arm in the overall safety population Conclusion.

Efficacy outcomes by prior VEGFR TKI therapy consistently favored cabozantinib over everolimus. The Median PFS in the cabozantinib arm was 9.1 months for sunitinib only and 7.4 months for pazopanib only. The Median OS in the cabozantinib arm was 21.4 months for sunitinib only and 22.0 months for pazopanib only. The prior anti-PD-1/PD-L1 subgroup was small. However, preliminary data suggest that the clinical benefit of cabozantinib is maintained in these patients as well. Adverse events in subgroups were similar to the overall study population.

We therefore conclude that cabozantinib is a new standard of care for patients with advanced RCC after prior anti-angiogenic therapy.

Example 10

Population Pharmacokinetic (PopPK) and Exposure-Response (ER) Modeling of Cabozantinib (C) in Patients (Pts) with Renal Cell Carcinoma (RCC) in the Phase 3 METEOR Study Population pharmacokinetic (PopPK) and exposure-response (ER) modeling of cabozantinib (C) in patients (pts) with renal cell carcinoma (RCC) in the phase 3 METEOR study Summary.

PopPK and ER models were developed to characterize the C concentration-time profile and the relationship between C exposure and efficacy endpoints in patients with RCC.

Background.

Cabozantinib is a tyrosine kinase inhibitor (TKI) which targets VEGF receptors, MET, and AXL. In the phase 3 METEOR trial, cabozantinib treatment significantly improved progression-free survival (PFS), overall response rate (ORR) and overall survival (OS) compared to everolimus in patients with advanced renal cell carcinoma (RCC) who had received prior VEGFR inhibitor therapy Because of variability in pharmacokinetics (PK) of TKIs such as cabozantinib, drug concentrations/exposure can vary from patient to patient despite treatment at the same dose. In the METEOR study, all patients started at a daily cabozantinib tablet dose of 60 mg, but could dose reduce to 40 mg or 20 mg to achieve a tolerated exposure as specified in the protocol. Dose reductions/modifications are frequently used with TKIs to manage adverse events (AEs) and individualize treatment.

To better understand factors affecting cabozantinib PK variability in RCC patients, a population pharmacokinetic (PopPK) model was developed to characterize the cabozantinib concentration-time profile and to identify statistically significant covariates for cabozantinib clearance.

To better understand the impact of cabozantinib exposure on efficacy in RCC patients, exposure-response (ER) models were developed to characterize the relationship between cabozantinib exposure and efficacy endpoints (PFS, tumor regression) at plasma concentrations associated with the cabozantinib doses that patients received in the METEOR study (60 mg, 40 mg, 20 mg qd).

Methods.

The PopPK model was developed using nonlinear mixed effects modeling methodology (NONMEM v7.3) that incorporated 1650 measurable PK concentrations from 345 subjects (Table 10.1).

TABLE 10.1

| Study Number | Phase | Description | Cabozantinib Treatment[a] | Population | PK Samples | Tumor Diameter Measurements[b] |
| --- | --- | --- | --- | --- | --- | --- |
| XL184-020 | 1 | Pharmacokinetic study in healthy adult subjects | Single dose po (20, 40 or 60 mg) | Healthy subjects (63 subjects) | Pre-dose and 0.5, 1, 2, 3, 4, 5, 6, 8, 10, 14, 24, 48, 72, 120, 168, 240, 288, 336, 408, and 504 hours post-dose | NA |

TABLE 10.1-continued

| Study Number | Phase | Description | Cabozantinib Treatment[a] | Population | PK Samples | Tumor Diameter Measurements[b] |
|---|---|---|---|---|---|---|
| XL184-308 (METEOR) | 3 | Cabozantinib vs Everolimus in patients with advanced RCC who had progressed after prior VEGFR inhibitor therapy | 60 mg po qd (dose reductions to 40 or 20 mg qd allowed) | RCC Patients (approximately 325 cabozantinib arm patients with on-treatment PK samples) | One sample ~8 or more hours after the prior evening dose on the Day 29 and Day 57 visits | Screening and every 8 weeks for the first 12 months, and every 12 weeks thereafter |

PK, pharmacokinetic;
po, oral;
qd, once daily;
RCC, renal cell carcinoma;
NA, not applicable
[a]cabozantinib tablet dose in free base equivalents;
[b]determined by independent radiology committee Two-hundred eighty two (282) RCC pts received 60 mg cabozantinib qd (single steady-state sample on Days 29 and 57). Sixty three (63) healthy volunteers received a single 20, 40 or 60 mg cabozantinib dose (21 samples over 21 days post-dose).

Covariates were evaluated for effects on apparent plasma clearance (CL/F) and apparent volume of distribution of the central compartment (VF) (Table 10.2).

TABLE 10.2

| | Study | XL184-020 | XL184-308 | Pooled |
|---|---|---|---|---|
| | Number of Subjects | 63 | 318[a,b] | 381[a,b] |
| Age (years) | Median | 38 | 62.5 | 60 |
| | Range (Min-Max) | (19-54) | (32-86) | (19-86) |
| Baseline BMI (kg/m$^2$)[a] | Median | 27.7 | 26.5 | 26.7 |
| | Range (Min-Max) | (20.6-32.9) | (17.1-57.7) | (17.1-57.7) |
| Baseline Albumin (g/L) | Median | 47 | 38 | 39 |
| | Range (Min-Max) | (41-53) | (17-48) | (17-53) |
| Baseline ALT (U/L) | Median | 23 | 17 | 18 |
| | Range (Min-Max) | (9-59) | (5-115) | (5-115) |
| Baseline Hemoglobin (g/L) | Median | 149 | 122.5 | 127 |
| | Range (Min-Max) | (119-174) | (84-181) | (84-181) |
| Baseline Creatinine Clearance (mL/min) | Median | 135.5 | 72.6 | 78.3 |
| | Range (Min-Max) | (86.4-246.7) | (20.8-183.6) | (20.8-246.7) |
| Baseline Total Bilirubin (μmol/L)[b] | Median | 10.3 | 7 | 7 |
| | Range (Min-Max) | (3.4-30.8) | (3-21) | (3-30.8) |
| Sex | No. Male (%) | 33 (52.4) | 247 (77.7) | 280 (73.5) |
| | No. Female (%) | 30 (47.6) | 71 (22.3) | 101 (26.5) |
| Race | No. White (%) | 62 (98.4) | 257 (80.8) | 319 (83.7) |
| | No. Black (%) | 1 (1-6) | 6 (1.9) | 7 (1.8) |
| | No. Asian (%) | 0 (0) | 21 (6.6) | 21 (5.5) |
| | No. Other (%) | 0 (0) | 19 (6.0) | 19 (5.0) |
| | No. Unknown (%) | 0 (0) | 15 (4.7) | 15 (3.9) |

[a]18 subjects from Study XL184-308 had missing baseline BMI
[b]14 subjects from Study XL184-308 had missing baseline total bilirubin
N = number of subjects;
BMI = body mass index;
ALT = alanine aminotransferase ER models (time-to-event Cox proportional hazard) were developed to characterize the relationship between various predicted cabozantinib exposure measures and the relative hazard for progression-free survival (PFS) based on 172 events in 315 RCC patients from the METEOR study with at least one measureable cabozantinib concentration. PFS was modeled for cabozantinib concentrations of 375, 750, and 1125 ng/mL which correspond to predicted steady-state average concentrations at dose levels of 20 mg, 40 mg, and 60 mg, respectively. A tumor growth model was developed to simulate median longitudinal percent change from baseline tumor diameter at plasma concentrations associated with 20 mg, 40 mg and 60 mg simulated starting dose treatments.

Results.

As provided in FIG. 10.1, a 2-compartment model with first-order elimination and two parallel (fast and slow), lagged first-order absorption processes adequately described the cabozantinib concentration data. In FIG. 10.1:

F1=fraction of dose in the first depot;
F2=fraction of dose in the second depot;
Ka=depot 1 absorption rate constant
Ka2=depot 2 absorption rate constant;
ALAG1=depot 1 absorption lag time;
ALAG2=depot 2 absorption lag time
Vc/F=apparent volume of distribution (central compartment);
Vp/F=apparent volume of distribution (peripheral compartment);

Q/F=apparent flow between plasma (central) and peripheral compartments;

CL/F=apparent plasma clearance

FIG. 10.2A, FIG. 10.2B, FIG. 10.2C, and FIG. 10.2D depict the cabozantinib PopPK goodness of fit plots by study and dose. The model predicted good fit to exposure data. The final model parameter estimates are summarized in the Table 10.3. The CL/F, $V_c$/F and terminal half-life values for a White male were estimated to be 2.23 L/hr, 81.5 L, and 99 hours, respectively. The estimated inter-individual variability of CL/F (% CV)=46%.

TABLE 10.3

| Parameter | Estimate (90% CI) |
|---|---|
| Ka (hr$^{-1}$) | 0.568 (0.471, 0.684) |
| Ka2 (hr$^{-1}$) | 0.102 (0.068, 0.154) |
| CL/F (L/hr) | 2.23 (2.12, 2.34) |
| Vc/F (L) | 81.5 (66.0, 101) |
| Q/F (L/hr) | 14.2 (12.4, 16.2) |
| Vp/F (L) | 213 (200, 226) |
| ALAG1 (hr) | 0.459 (0.443, 0.476) |
| ALAG2 (hr) | 16.8 (15.3, 18.4) |

The covariates listed in Table 103 were evaluated for effects on apparent plasma clearance (CL/F) and apparent volume of distribution of the central compartment ($V_c$/F) and the results are depicted in FIG. 103. In FIG. 103, Female gender and Asian race were statistically-significant covariates on CL/F. Female subjects had 21% lower CL/F compared with male subjects. Asian subjects had 27% lower CL/F compared with White subjects. No other covariate evaluated had a significant effect on cabozantinib CL/F (Table 10.3).

An Exposure-Response analysis of Progression Free Survival was performed based on 172 events in 315 RCC patients from the METEOR study with at least one measurable cabozantinib concentration. PFS was modeled for cabozantinib concentrations of 375, 750, and 1125 ng/mL which correspond to predicted steady-state average concentrations at dose levels of 20 mg, 40 mg, and 60 mg respectively. The results are depicted in FIG. 10.4. In FIG. 10.4, exposure values for calculating PFS were a time-varying average concentration over the previous 3 weeks (updated daily). The solid line represents the fraction over time of subjects at each modeled dose level without PD or death. The dashed lines represent 95% confidence intervals. A statistically significant relationship was identified between the rate of PFS (PD or death) and the time-varying average daily cabozantinib concentration. Increases in cabozantinib concentration were predicted to decrease the rate of PD or death in a nonlinear manner. The best $E_{max}$ (maximal efficacy) model was nonlinear (p<0.001) with $EC_{50}$ (half maximal effective concentration) equal to 100 ng/mL. The predicted steady-state average cabozantinib concentrations for the modeled 20 mg, 40 mg, and 60 mg dose levels were all above the $EC_{50}$. The confidence intervals overlap for the predicted steady-state concentrations at all three dose levels, although a dose-related trend was observed.

A tumor growth model was developed to simulate median longitudinal percent change from baseline tumor diameter at plasma concentrations associated with simulated 20 mg, 40 mg and 60 mg starting dose treatments. Objective responses (per RECIST version 1.1) were computed at baseline and every 8 weeks for 1 year for 1000 simulated subjects using the longitudinal sum of tumor diameter predictions. The best fitting model among those tested for the change in tumor diameter over time is defined in Equation 1. The initial condition for this system is an estimated parameter for baseline tumor diameter. Simulations assume no patients dropped out of the study.

$$\frac{dY}{dt} = k_{grow} \cdot Y - \frac{(k_{dmax} + k_{dmax_{tol}} \cdot e^{-k_{tol} \cdot t}) \cdot Cavg}{(EC_{50} + Cavg)} \cdot Y \quad \text{Equation 1}$$

where:
dY/dt=the change in tumor diameter per unit time
$k_{grow}$=the first-order growth rate constant
$k_{dmax}$=the maximum non-attenuating drug induced tumor decay rate
$k_{dmax\_tol}$=the maximum loss in the decay rate due to resistance
$k_{tol}$=the rate constant which governs the rate of attenuation
$EC_{50}$=the cabozantinib concentration yielding one-half of the current tumor decay rate
Cavg=the individual predicted daily average cabozantinib concentration FIG. 10.4 depicts the predicted progression free survival curves for selected average cabozantinib concentrations.

FIG. 10.5 depicts the median percent change from baseline tumor diameter for selected simulated starting doses of cabozantinib. The maximal median reduction in tumor size increased with increasing simulated starting doses of 20 mg (−4.45%), 40 mg (−9.1%), and 60 mg (−11.9%).

Table 10.4 summarizes the best overall response rates for selected simulated doses of cabozantinib. Responses (per RECIST version 1.1) were computed at baseline and every 8 weeks for 1 year for 1000 simulated subjects using the longitudinal sum of tumor diameter predictions. A higher percentage of subjects achieved an objective response and a lower percentage of subjects had progressive disease in the simulated 60 mg dose group relative to the simulated 40 mg and 20 mg dose groups.

TABLE 10.4

| | Simulated Starting Dose | | |
|---|---|---|---|
| Best Overall Response Rate | 20 mg | 40 mg | 60 mg |
| Objective Response (%) | 8.7 | 15.6 | 19.1 |
| Complete Response (%) | 0.10 | 0.0 | 0.0 |
| Partial Response (%) | 8.6 | 15.6 | 19.1 |
| Stable Disease (%) | 81.1 | 76.3 | 73.4 |
| Progressive Disease (%) | 10.2 | 8.1 | 7.5 |

Conclusions.

The oral clearance, terminal phase volume of distribution, and terminal half-life were estimated to be 2.23 L/hr, 319 L, and 99 hours, respectively, for a White male subject. Inter-individual variability of CL/F was estimated to be 46% CV. A statistically significant relationship was identified between the rate of progressive disease (PD) or death and the time-varying average daily C concentration. Increases in C concentration were predicted to decrease the rate of PD or death in a nonlinear manner. The best $E_{max}$ model (p<0.001) was achieved with $EC_{50=100}$ ng/mL, a value below the typical individual predicted steady-state average concentration at 60 (1125 ng/mL) or 20 (375 ng/mL) mg/day. In addition, female gender and Asian race were statistically-significant covariates on CL/F, but the small magnitude of effect was not considered to be clinically-significant.

In ER models, a 60 mg simulated starting dose resulted in improved PFS, reduced tumor growth and increased ORR compared to 40 mg or 20 mg simulated starting doses. ER analysis indicates that cabozantinib would be effective at the 60 mg starting dose evaluated in METEOR as well as dose levels of 40 mg and 20 mg resulting from dose reduction. Thus, based on the ER analysis, C was efficacious at all doses evaluated in METEOR, including those resulting from dose reductions, with higher exposures predicted to correlate with improved PFS.

Example 11

Cabozantinib (C) Exposure-Response (ER) Modeling of Safety Endpoints in Patients (Pts) with Renal Cell Carcinoma (RCC) in the Phase 3 METEOR Study Background:
ER models were previously developed to characterize the relationship between C exposure and efficacy endpoints in RCC pts in the phase 3 METEOR study (J Clin Oncol 34, 2016 [suppl; abstr 2565]). Higher C exposure correlated with decreased tumor size and improved progression-free survival and objective response rate. Model-based predictions showed that C would be effective at the 60 mg starting dose evaluated in METEOR as well as dose levels of 40 and 20 mg resulting from dose reduction. In the current study, ER models were developed to characterize the relationship between C exposure and safety endpoints in RCC pts.

Methods:
The ER analysis included 318 RCC pts who had received at least one C dose and had at least one measurable C concentration. Time-to-event Cox proportional hazard ER models were developed to characterize the relationship between various individual predicted C exposure measures and the likelihood of dose modification and 6 specific adverse events (AEs): fatigue/asthenia, palmar-plantar erythrodysesthesia (PPE), nausea/vomiting, diarrhea, hypertension, and stomatitis.

Results:
A statistically significant relationship was identified between individual predicted C clearance (CL/F) and the rate of dose modification (p<0.0001), with the risk of dose modification decreasing with increasing CUF. An increase in average C concentration was associated with increased risk of fatigue/asthenia (Grade ≤3), PPE (Grade ≤1), hypertension (systolic blood pressure [BP]>160 mmHg or diastolic BP>100 mmHg), and diarrhea (Grade ≤3). The predicted hazard ratios for these AEs were 2.01, 2.21, 1.85, and 1.78, respectively, based on the predicted steady-stage average C concentration for a 60 mg dose relative to a 20 mg dose. Statistically significant ER relationships were not identified for nausea/vomiting (Grade ≤3) or stomatitis (Grade ≤3).

Conclusions:
Based on the ER analysis, higher C exposures resulting from lower C CL/F are predicted to increase the dose modification rate. Reduced C exposures resulting from dose reduction are predicted to decrease the risk of fatigue/asthenia, PPE, hypertension, and diarrhea while maintaining clinical benefit.

Other Embodiments

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The invention claimed is:

1. A method of treating advanced renal cell carcinoma with or without bone or visceral metastases in a human patient who has received prior anti-angiogenic therapy, comprising administering to the patient an amount of cabozantinib or a pharmaceutically acceptable salt thereof, wherein progression-free survival (PFS) and one or both of overall survival (OS) and objective response rate (ORR) are extended as compared to patients who have received prior anti-angiogenic therapy, wherein the prior anti-angiogenic therapy is selected from the group consisting of axitinib, pazopanib, sorafenib, sunitinib, everolimus, temsirolimus, bevacizumab, interleukins, interferon-α, and peginterferon.

2. The method of claim 1, wherein the cabozantinib is administered as cabozantinib (S)-malate.

3. The method of claim 2, wherein cabozantinib (S)-malate is administered in an amount sufficient to achieve a median time to peak plasma concentration (Tmax) of from approximately 2 to 5 hours post-dose; and a Cmax of 200 to 500 ng/mL.

4. The method of claim 1, wherein the prior antiangiogenic therapy is selected from the group consisting of axitinib, pazopanib, sorafenib, sunitinib, everolimus, temsirolimus, and bevacizumab.

5. The method of claim 4, wherein the prior anti-angiogenic therapy is everolimus.

6. The method of claim 2, wherein cabozantinib (S)-malate is administered as a tablet comprising cabozantinib (S)-malate, microcrystalline cellulose, anhydrous lactose, hydroxypropyl cellulose, croscarmellose sodium, colloidal silicon dioxide magenisum stearate, and film coating comprising hypromellose, titanium dioxide, triacetin, and iron oxide yellow.

7. The method of claim 2, wherein the cabozantinib (S)-malate is administered as a tablet formulation comprising approximately:
   30-32 percent by weight of cabozantinib, (S)-malate salt;
   38-40 percent by weight of microcrystalline cellulose;
   18-22 percent by weight of lactose;
   2-4 percent by weight of hydroxypropyl cellulose;
   4-8 percent by weight of croscarmellose sodium;
   0.2-0.6 percent by weight of colloidal silicon dioxide;
   0.5-1 percent by weight of magnesium stearate; and further comprising:
   a film coating material comprising hypromellose, titanium dioxide, triacetin, and iron oxide yellow;
or wherein the cabozantinib (S)-malate is administered as a tablet formulation comprising approximately (% w/w):
   31-32 percent by weight of cabozantinib, (S)-malate salt;
   39-40 percent by weight of microcrystalline cellulose;
   19-20 percent by weight of lactose;
   2.5-3.5 percent by weight of hydroxypropyl cellulose;
   5.5-6.5 percent by weight of croscarmellose sodium;
   0.25-0.35 percent by weight of colloidal silicon dioxide;

0.7-0.8 percent by weight of magnesium stearate; and further comprising:
3.9-4.1 percent by weight of a film coating material comprising hypromellose, titanium dioxide, triacetin, and iron oxide yellow.

8. The method of claim 2, wherein cabozantinib (S)-malate is administered as a tablet formulation containing 20, 40, or 60 mg of cabozantinib.

9. The method of claim 8, wherein cabozantinib (S)-malate is administered as a tablet formulation selected from the group consisting of:

| Ingredient | Theoretical Quantity (mg/unit dose) | | |
|---|---|---|---|
| | 20-mg Tablet* | 40-mg Tablet* | 60-mg Tablet* |
| Cabozantinib (S)-malate | 25.34 | 50.69 | 76.03 |
| Microcrystalline Cellulose, PH-102 | 31.08 | 62.16 | 93.24 |
| Lactose Anhydrous, 60M | 15.54 | 31.07 | 46.61 |
| Hydroxypropyl Cellulose, EXF | 2.400 | 4.800 | 7.200 |
| Croscarmellose Sodium | 4.800 | 9.600 | 14.40 |
| Colloidal Silicon Dioxide | 0.2400 | 0.4800 | 0.7200 |
| Magnesium Stearate (Non-Bovine) | 0.6000 | 1.200 | 1.800 |
| Opadry ® Yellow (03K92254) | 3.200 | 6.400 | 9.600 |
| Total tablet weight | 83.20 | 166.4 | 249.6. |

*Free Base Equivalent (FBE)

10. The method of claim 2, wherein the cabozantinib (S)-malate is administered once daily.

11. The method of claim 10, wherein the amount of cabozantinib that is administered once daily is 60 mg.

12. The method of claim 2, wherein the amount of cabozantinib (S)-malate is sufficient to achieve a median time to peak plasma concentration (Tmax) from 3.2 to 3.8 hours post-dose; and a mean Cmax of 310 to 350 ng/mL.

13. The method of claim 1, wherein the overall survival of the patient is extended as compared to patients taking everolimus, or the objective response rate of the patient is extended as compared to patients taking everolimus, or both the overall survival and the objective response rate of the patient are extended as compared to patients taking everolimus.

14. The method of claim 2, wherein an amount of cabozantinib (S)-malate is sufficient to achieve one, two, three, four, five, six, seven, or eight effects selected from the group consisting of:
a median time to peak plasma concentration (Tmax) from 2 to 5 hours post-dose;
a Cmax of 200 to 500 ng/mL;
an $AUC_{0-24}$ of 2500 to 5200 ng*h/mL;
an $AUC_{0-t}$ of 18,000 to 42,000 ng*h/mL;
an $AUC_{0-\infty}$ of 19,000 to 45,000 ng*h/mL;
an oral volume distribution (Vz/F) of 100 to 600 L;
a terminal half-life of 90 to 135 h; and
a clearance at steady state (CL/F) of 0.7 to 3.9 L/h;
wherein the cabozantinib (S)-malate is administered as a tablet formulation comprising approximately (% w/w):
31-32 percent by weight of cabozantinib, (S)-malate salt;
39-40 percent by weight of microcrystalline cellulose;
19-20 percent by weight of lactose;
2.5-3.5 percent by weight of hydroxypropyl cellulose;
5.5-6.5 percent by weight of croscarmellose sodium;
0.25-0.35 percent by weight of colloidal silicon dioxide;
0.7-0.8 percent by weight of magnesium stearate; and further comprising:
3.9-4.1 percent by weight of a film coating material comprising hypromellose, titanium dioxide, triacetin, and iron oxide yellow.

15. The method of 14, wherein cabozantinib (S)-malate is administered as a tablet formulation containing 20, 40, or 60 mg of cabozantinib.

16. The method of claim 2, wherein the cabozantinib (S)-malate is administered in an amount sufficient to achieve one, two, three, four, five, six, seven, or eight effects selected from the group consisting of:
a median time to peak plasma concentration (Tmax) from 2 to 5 hours post-dose;
a Cmax of 200 to 500 ng/mL;
an $AUC_{0-24}$ of 2500 to 5200 ng*h/mL;
an $AUC_{0-t}$ of 18,000 to 42,000 ng*h/mL;
an $AUC_{0-\infty}$ of 19,000 to 45,000 ng*h/mL;
an oral volume distribution (Vz/F) of 100 to 600 L;
a terminal half-life of 90 to 135 h; and
a clearance at steady state (CL/F) of 0.7 to 3.9 L/h.

17. The method of claim 2, wherein the cabozantinib (S)-malate is administered in an amount sufficient to achieve one, two, three, four, five, six, seven, or eight effects selected from the group consisting of:
a median time to peak plasma concentration (Tmax) from 2.5 to 4.5 hours post-dose;
a Cmax of 250 to 450 ng/mL;
an $AUC_{0-24}$ of 3000 to 4700 ng*h/mL;
an $AUC_{0-t}$ of 23,000 to 37,000 ng*h/mL;
an $AUC_{0-\infty}$ of 24,000 to 40,000 ng*h/mL;
an oral volume distribution (Vz/F) of 150 to 550 L;
a terminal half-life of 100 to 125 h; and
a clearance at steady state (CL/F) of 1.2 to 3.2 L/h.

18. The method of claim 2, wherein the cabozantinib (S)-malate is administered in an amount sufficient to achieve one, two, three, four, five, six, seven, or eight effects selected from the group consisting of:
a median time to peak plasma concentration (Tmax) from 3 to 4 hours post-dose;
a Cmax of 300 to 400 ng/mL;
an $AUC_{0-24}$ of 3500 to 4200 ng*h/mL;
an $AUC_{0-t}$ of 28,000 to 32,000 ng*h/mL;
an $AUC_{0-\infty}$ of 29,000 to 35,000 ng*h/mL;
an oral volume distribution (Vz/F) of 200 to 500 L;
a terminal half-life of 110 to 115 h; and
a clearance at steady state (CL/F) of 1.2 to 3.2 L/h.

19. The method of claim 2, wherein the cabozantinib (S)-malate is administered in an amount sufficient to achieve one, two, three, four, five, six, seven, or eight effects selected from the group consisting of:
a median time to peak plasma concentration (Tmax) from 3.2 to 3.8 hours post-dose;
a Cmax of 310 to 350 ng/mL;
an $AUC_{0-24}$ of 3700 to 4000 ng*h/mL;
an $AUC_{0-t}$ of 29,000 to 30,000 ng*h/mL;
an $AUC_{0-\infty}$ of 30,000 to 33,000 ng*h/mL;
an oral volume distribution (Vz/F) of 300 to 400 L;
a terminal half-life of 110 to 114 h; and
a clearance at steady state (CL/F) of 2 to 3 L/h.

20. A method of treating advanced renal cell carcinoma in human patients who have received prior anti-angiogenic therapy, comprising administering to the patient cabozantinib or a pharmaceutically acceptable salt thereof, wherein the overall survival of the patients are extended as compared to the median overall survival of patients who have received prior anti-angiogenic therapy, wherein the prior anti-angiogenic therapy is selected from the group consisting of axitinib, pazopanib, sorafenib, sunitinib, everolimus, temsirolimus, bevacizumab, interleukins, interferon-α, and peginterferon.

21. A method of treating advanced renal cell carcinoma with bone or visceral metastases in a human patient who has received prior anti-angiogenic therapy, comprising administering to the patient an amount of cabozantinib or a pharmaceutically acceptable salt thereof, wherein progression-free survival (PFS) and one or both of overall survival (OS) and objective response rate (ORR) are extended as compared to patients who have received prior anti-angiogenic therapy, wherein the prior anti-angiogenic therapy is selected from the group consisting of axitinib, pazopanib, sorafenib, sunitinib, everolimus, temsirolimus, bevacizumab, interleukins, interferon-α, and peginterferon.

* * * * *